US007427397B2

(12) United States Patent
Adams et al.

(10) Patent No.: US 7,427,397 B2
(45) Date of Patent: Sep. 23, 2008

(54) PROBIOTIC PROPIONIBACTERIUM

(75) Inventors: Michelle Catherine Adams, Hamilton (AU); Yang Huang, Marsfield (AU)

(73) Assignee: University of Newcastle Research Associates (TUNRA) Ltd., Callaghan, New South Wales (AU)

( * ) Notice: Subject to any disclaimer, the term of this patent is extended or adjusted under 35 U.S.C. 154(b) by 179 days.

(21) Appl. No.: 11/018,911

(22) Filed: Dec. 21, 2004

(65) Prior Publication Data
US 2005/0180963 A1 Aug. 18, 2005

Related U.S. Application Data

(63) Continuation of application No. PCT/AU03/000775, filed on Jun. 20, 2003.

(30) Foreign Application Priority Data

Jun. 21, 2002 (AU) ................ PS3124
Jun. 24, 2002 (AU) ................ PS3152
Nov. 18, 2002 (AU) ............ 2002952793

(51) Int. Cl.
*A01N 63/00* (2006.01)
*A23L 1/30* (2006.01)
*C12Q 1/00* (2006.01)
(52) U.S. Cl. .................. 424/93.4; 426/72; 435/4
(58) Field of Classification Search ............ None
See application file for complete search history.

(56) References Cited

U.S. PATENT DOCUMENTS

| 4,210,720 | A |   | 7/1980 | Kojima et al. |
| 4,981,705 | A | * | 1/1991 | Tomes ................ 426/53 |
| 5,639,659 | A | * | 6/1997 | Barefoot et al. ........ 435/252.1 |
| 5,989,612 | A | * | 11/1999 | King et al. .............. 426/335 |
| 6,019,985 | A |   | 2/2000 | Brown et al. |
| 6,080,401 | A |   | 6/2000 | Reddy et al. |
| 6,262,019 | B1 |   | 7/2001 | Keller et al. |
| 6,455,063 | B1 | * | 9/2002 | Rehberger et al. ........ 424/438 |
| 7,270,994 | B2 |   | 9/2007 | Jiang et al. |
| 7,279,320 | B1 |   | 10/2007 | Parker et al. |
| 2003/0129165 | A1 | * | 7/2003 | Rehberger et al. ........ 424/93.4 |
| 2004/0028689 | A1 |   | 2/2004 | Borody |

FOREIGN PATENT DOCUMENTS

| AU | 58612/86 | 12/1986 |
| EP | 0914778 | 5/1999 |
| EP | 1060745 | 12/2000 |
| EP | 1308506 | 5/2003 |
| EP | 1374878 | 1/2004 |
| WO | WO-9804275 | 2/1998 |
| WO | WO-0020013 | 4/2000 |

OTHER PUBLICATIONS

Adams et al, Proceedings of the Nutrition Society of Australia (2002), vol. 26, p. S261.*
Ball, G.F.M., "Bioavailability and Analysis of Vitamins in Foods", 1998, Chapter 14, pp. 497-515.*
Rowland, Ian R., Probiotics: The Scientific Basis, 1992, "Metabolic Interactions in the Gut", Chapter 3, pp. 29-53.*
Carmel, Ralph,"Current Concepts in Cobalamin Deficiency," Annu. Rev. Med. vol. 51, 2000, pp. 357-375.
Brooker et al, "Adhesion of Lactobacilli to the Chicken Crop epithelium," Journal of Ultrastructure Research vol. 52, 1975, pp. 21-31.
Schaible et al, "Confrontation between Intracellular Bacteria and the Immune System," Advances in Immunology vol. 71, pp. 267-377.
Sato et al, "Differential Potentiation of Anti-Mycobacterial Activity and Reactive Nitrogen Intermediate Producing Ability of Murine Peritoneal Macrophages Activated by Interferon-Gamma (IFN-γ) and Tumour Necrosis Factor-Alpha (TNF-α)," Clin Exp. Immunol. vol. 112, 1998, pp. 63-68.
Sarem et al, "Comparison of the Adherence of Three Lactobacillus Strains to Caco-2 and Int-407 Human Intestinal Cell Lines," Letters in Applied Microbiology vol. 22, 1996, pp. 439-442.
Salminen et al, "Clinical Applications of Probiotic Bacteria," Int. Dairy Journal vol. 8, 1998, pp. 563-572.
Salminen et al, "Demonstration of Safety of Probiotics—A Review," International Journal of Food Microbiology vol. 44, 1998, pp. 93-106.
Salminen et al, "Probiotics: How They Should be Defined?" Trends in Food Science & Technology vol. 10, 1999, pp. 107-110.
Wang et al, "The Protective Effects of High Amylose Maize (Amylomaize) Starch Granules on the Survival of *Bifidobacterium* spp. in the Mouse Intestinal Tract," Journal of Applied Microbiology vol. 87, 1999, pp. 631-639.
van der Griend et al, "Hyperhomocysteinaemia as a Cardiovascular Risk Factor: an Update," The Netherlands Journal of Medicine vol. 56, 2000, pp. 119-130.
Tuomola et al, "Adhesion of Some Probiotic and Dairy *Lactobacillus* Strains to Caco-2 Cell Cultures," International Journal of Food Microbiology vol. 41, 1998, pp. 45-51.

(Continued)

*Primary Examiner*—Leon B. Lankford, Jr.
*Assistant Examiner*—Laura Schuberg
(74) *Attorney, Agent, or Firm*—Fulbright & Jaworski, LLP

(57) ABSTRACT

The present invention relates to probiotic *Propionibacterium* strains and their use in the preparation of probiotic supplements and foods. The invention relates to the provision of Vitamin $B_{12}$, propionic acid, folacin and bacteriocins by probiotic strains, stimulation of bifidobacteria growth, production of favourable effects on the lipid metabolism and on the immune system of hosts through immunostimulation, immunomodulation or use of a probiotic strain as an adjuvant, reduction of homocysteine and β glucuronidase and the prevention, treatment or amelioration of conditions associated with a need for these activities. The probiotic bacteria of the invention can be used in humans or other animals. In at least some applications, the bacteria can be used dead and parts rather than whole cells may be used. The present invention also relates to the preparation of vaccines for use in protecting patients from infectious diseases, in particular tuberculosis.

9 Claims, 15 Drawing Sheets

OTHER PUBLICATIONS

Tuomola et al, "Human Ileostomy Glycoproteins as a Model for Small Intestinal Mucus to Investigate Adhesion of Probiotics," Letters in Applied Microbiology vol. 28, 1999, pp. 159-163.
Toy et al, "Basic and Clinical Overview of the Mucosal Immune System," Seminars in Gastrointestinal Disease vol. 7, No. 1, Jan. 1996, pp. 2-11.
Taylor et al, "Effects of Probiotics and Prebiotics on Blood Lipids," British Journal of Nutrition vol. 80, Suppl. 2, 1998, pp. S225-S230.
Tascon et al, "Protection against Mycobacterium Tuberculosis Infection by CD8+ T Cells Requires the Production of Gamma Interferon," Infection and Immunity, Feb. 1998, pp. 830-834.
Takeda et al, "Mitogenic Activity of Whole Cells and Cell Wall Components of *Lactobacillus acidophilus* Group Lactic acid Bacteria on Murine Spleen and Peyer's Patch Cells," Milchwissenschaft vol. 52 No. 1, 1997, pp. 21-25.
Sutter, Vera, "Anaerobes as Normal Oral Flora," Reviews of Infectious Diseases vol. 6 Supplemental 1, Mar.-Apr. 1984, pp. S62-S66.
Steffen et al, "Relationship between Cecal Population Levels of Indigenous Bacteria and Translocation to the Mesenteric Lymph Nodes," Infection and Immunity, Mar. 1983, pp. 1252-1259.
Somkuti et al, "Cholesterol Uptake by *Propionibacterium freudenreichii*," Current Microbiology vol. 20, 1990, pp. 305-309.
Silva et al, "Cytotoxic T Cells and Mycobacteria," FEMS Microbiology Letters vol. 197, 2001, pp. 11-18.
Sieling et al, "CD1-Restricted T Cell Recognition of Microbial Lipoglycan Antigens," Science vol. 269, Jul. 14, 1995, pp. 227-230.
Shaw et al, "Plasma Homocysteine Levels in indigenous Australians," MJA vol. 170, Jan. 4, 1999, pp. 19-22.
Scott, John, "Folate and Vitamin B12," Proceedings of the Nutrition Society vol. 58, 1999, pp. 441-448.
Scheinbach, Saul, "Probiotics: Functionality and Commercial Status," Biotechnology Advances vol. 16, No. 3, 1998, pp. 581-608.
Hess et al, "Live Antigen Carriers as Tools for Improved Anti-tuberculosis Vaccines," FEMS Immunology and Medicine Microbiology vol. 23, 1999, pp. 165-173.
Herbert, Victor, "Vitamin B-12: Plant Sources Requirements and Assay," Am J Clin Nutr vol. 48, 1988, pp. 852-858.
Havlir et al, "Human Immune Response to Mycobacterium tuberculosis Antigens," infection and Immunity, Feb. 1991, pp. 665-670.
Havenaar et al, "Selection of Strains for Probiotic Use," Probiotics: The Scientific Basis Chapter Nine.
Harrigan, Wilkie, "A Scheme for the Identification of Gram-positive Bacteria," Laboratory Methods in Food Microbiology, Third Edition, Chapter 39.
Guerin, N., "Evaluation of BCG and New Vaccines against Tuberculosis," Pediatric Pulmonology Supplement 16, 1997, pp. 286-287.
Grant et al, "The Potential of *Propionibacterium* spp. as Probiotics," Chapter 18, pp. 589-601.
Gilliland et al, "Importance of Bile Tolerance of *Lactobacillus acidophilus* Used as a Dietary Adjunct," J Dairy Sci vol. 67, 1984, pp. 3045-3051.
Harrigan, Wilkie, "Isolation of *Propionibacteria* from Swiss Cheese," Laboratory Methods in Food Microbiology Third Edition, p. 266.
Gautier et al, "DNA Fingerprinting of Dairy Propionibacteria Strains by Pulsed-Field Gel Electrophoresis," Current Microbiology vol. 32, 1996, pp. 17-24.
Gariballa, S.E., "Review Article: Nutritional Factors in Stroke," British Journal of Nutrition vol. 84, 2000, pp. 5-17.
Gadelle et al, "β-Glucuronidase Activities of Intestinal Bacteria Determined Both in Vitro and In Vivo in Gnotobiotic Rats," Applied Environmental Microbiology, Mar. 1985, pp. 682-685.
Fujisawa et al, "Influence of Bile Salts on β-Glucuronidase Activity of Intestinal Bacteria," Letters in Applied Microbiology vol. 22, pp. 271-274.
Fooks et al, "Prebiotics, Probiotics and Human Gut Microbiology," International Dairy Journal vol. 9, 1999, pp. 53-61.
Finegold et al, "Normal Indigenous Intestinal Flora," Human Intestinal Microflora in Health and Disease Chapter 1, 1983, pp. 3-31.
Fessler et al, "Rapid Identification of Dairy Propionibacterium Species by Restriction Analysis of the Insertion within the 23S rRNA Gene," Lait vol. 78, 1998, pp. 203-216.
Feng et al, "Increase in Gamma Interferon-Secreting CD8+, as Well as CD4+, T Cells in Lungs following Aerosol Infection with Mycobacterium tuberculosis," Infection and Immunity, Jul. 1999, pp. 3242-3247.
Fatkenheuer et al, "The Return of Tuberculosis," Diagn Microbiol infect Dis vol. 34, 1999, pp. 139-146.
Fang et al, "Modulation of Humoral Immune Response through Probiotic Intake," FEMS Immunology and Medical Microbiology vol. 29, Issue 1, Sep. 2000. pp. 47-52.
Famularo et al, "Stimulation of Immunity by Probiotics," Probiotics 2: Applications and Practical Aspects Chapter 6, 1997, pp. 133-161.
Stine et al, "Measuring Toxicity and Assessing Risk," Principles of Toxicology Chapter 1. pp. 1-10.
Falero-Diaz et al, "Intranasal Vaccination of Mice Against infection with Mycobacterium tuberculosis," Vaccine vol. 18, 2000, pp. 3223-3229.
Erickson et al, "Probiotic Immunomodulation in Health and Disease," American Society of Nutritional Sciences Symposium: Probiotic Bacteria: Implications for Human Health 2000, pp. 403S-409S.
Donohue et al, "Safety of Probiotic Bacteria," Chapter 13, pp. 369-383.
Zhou et al, "Acute Oral Toxicity and Bacterial Translocation Studies on Potentially Probiotic Strains of Lactic Acid Bacteria," Food and Chemical Toxicology vol. 38, 2000, pp. 153-161.
Memoranda, "Tuberculosis Control and Research Strategies for the 1990s: Memorandum from a WHO meeting," Bulletin of the World Health Organization vol. 70 No. 1, 1992, pp. 17-21.
Ozkan et al, "Plasma Total Homocysteine and Cysteine Levels as Cardiovascular Risk Factors in Coronary Heart Disease," International Journal of Cardiology vol. 82, 2002, pp. 269-277.
Niaid, "Strategies for Developing a Tuberculosis Vaccines," http://www.niaid.nih.gov/publications/blueprint, Aug. 3, 2002.
Niaid News, "Tuberculosis," http://www.niaid.nih.gov/newsroom/releases, Mar. 22, 1996.
Rossi et al, "Genus- and Species-Specific PCR-Based Detection of Dairy Propionibacteria in Environmental Samples by Using Primers Targeted to the Genes Encoding 16S rRNA," Applied and Environmental Microbiology, Sep. 1999, pp. 4241-4244.
Riedel et al, "Justification of the "Classical" Propionibacterium Species Concept by Restriction Analysis of the 16S Ribosomal RNA Gnes," Aytem Appl. Microbiol. vol. 17, 1994, pp. 536-542.
Richter et al, "Transgenic Plants as Edible Vaccines," pp. 159-176.
Richardson et al, "Application of a Commercial Radioassay Test Kit to the Determination of Vitamin B12 in Food," Analyst vol. 103, Aug. 1978, pp. 865-868.
Russell-Jones, G.J., "Oral Vaccine Delivery," Journal of Controlled Release vol. 65, 2000, pp. 49-54.
Rowland et al, "A Comparison of the Activity of Five Microbial Enzymes in Cecal Content from Rats, Mice and Hamsters and Response to Dietary Pectin," Toxicology and Applied Pharmacology vol. 69, 1983, pp. 143-148.
Rowland, Ian R., "Metabolic Interactions in the Gut," Probiotics: The Scientific Basis Chapter 3, pp. 29-53.
Mann et al, "The Effect of Diet on Plasma Homocysteine Concentrations in Healthy Male Subjects," European Journal of Clinical Nutrition vol. 53, 1999, pp. 895-899.
Ravn et al, "Human T Cell Responses Induced by Vaccination with *Mycobacterium bovis Bacillus* Calmette-Guerin," The Journal of Immunology vol. 158, 1997, pp. 1949-1955.
Pulvere et al, "Combined Immunomodulation (*Propionibacteium avidum* KP-40) and Lectin Blocking (D-Galactose) Prevents Liver Tumor Colonization in BALB/C-Mice," Zbl. Bakr., vol. 281, 1994, pp. 491-494.
Puuwels et al, "Lactic Acid Bacteria as Antigen Delivery Vehicles for Oral Immunization Purposes," International Journal of Food Microbiology vol. 41, 1998, pp. 155-167.
Poston et al, "Cobalamins and Cobalamin-Dependent Enzymes in *Candida utilis*," Journal of Bacteriology vol. 140, No. 3, Dec. 1979, pp. 1013-1016.

Pizza et al, "Mucosal Vaccines: Non Toxic Derivatives of LT and CT as Mucosal Adjuvants," Vaccine vol. 19, 2001, pp. 2534-2541.

Pinto et al, "Enterocyte-like Differentiation and Polarization of the Human Colon Carcinoma Cell Line Caco-2 in Culture," Biol. Cell. vol. 47, 1983, pp. 323-330.

Kaufmann et al, "Immunity to Mycobacteria with Emphasis on tuberculosis: Implications for Rational Design of an Effective Tuberculosis Vaccine," Immunology of Intracellular Parasitism Chem Immunol Basel, Karger vol. 70, 1998, pp. 21-59.

Kankaanpaa et al, "Influence of Probiotic Supplemental Infant Formula on Composition of Plasma Lipids in Atopic Infants," Journal of Nutritional Biochemistry vol. 13, 2002, pp. 364-369.

Kaneko et al, "Growth Stimulator for Bifidobacteria Produced by *Propionibacterium freudenreichii* and Several Intestinal Bacteria," J Dairy Sci, vol. 77, 1994, pp. 393-404.

Johnson, John L.,"Bacterial Classification III: Nucleic Acids in Bacterial Classification," pp. 972-975.

Jones et al, "Serology and Chemotazonomy," Bacterial Classification V, pp. 979-983.

Table 15.1 in Bergey's Manual of Systematic Bacteriology vol. 2, p. 1263.

Hood et al, "Effect of Low pH on the Ability of *Lactobacillus acidophilus* to Survive and Adhere to Human Intestinal Cells," Journal of Food Science vol. 53, No. 5, 1988, pp. 1514-1516.

Hill, M.J., "Intestinal Flora and Endogenous Vitamin Synthesis," European Journal of Cancer Prevention vol. 6, Suppl 1, 1997, pp. S43-S45.

Hettinga et al, "The Propionic-Acid Bacteria-A Review: III Miscellaneous Metabolic Activities," J. Milk Food Technology vol. 35, No. 7, 1972, pp. 436-447.

Hettinga et al, "The Propionic-Acid Bacteria-A Review: II Metabolism," J. Milk Food Technol. vol. 35, No. 6, 1972, pp. 358-372.

Mahairas et al, "Molecular Analysis of Genetic Differences between *Mycobacterium bovis* BCG and Virulent *M. bovis*," Journal of Bacteriology, Mar. 1996, pp. 1274-1282.

Macfarlane et al, "Protein Degradation by Human Intestinal Bacteria," Journal of Genereak Microbiology vol. 132, 1986, pp. 1647-1656.

Lowrie et al, "Genetic Vaccination against Tuberculosis," Springer Semin Immunopathol vol. 19, 1997, pp. 161-173.

Lindbland et al, "Adjuvant Modulations of immune Responses to Tuberculosis Subunit Vaccines," Infection and Immunity vol. 65, No. 2, Feb. 1997, pp. 623-629.

Lilly et al, "Probiotics: Growth-Promoting Factors Produced by Microorganisms," Science vol. 147, Feb. 12, 1965, pp. 747-748.

Langridge et al, "Edible Vaccines," Scientific American vol. 283, Issue 3, Sep. 2000, p. 66-72.

Flaminio et al, "Immunologic Function in Horses after Non-Specific Immunostimulant Administration," Veterinary Immunology and Immunopathology, vol. 63, 1998, pp. 303-315.

Kitazawa et al, "Interferon Induction in Murine Peritoneal Macrophage by Stimulation with *Lactobacillus acidophilus*," Microbiol Immunol. vol. 36 No. 3, 1992, pp. 311-315.

Kenney et al, "2nd Meeting on novel Adjuvants Currently in/close to Human Clinical testing: World Health Organization—Organization Mondiale de la Sante Fondation Merieux, Annecy France Jun. 5-7, 2000," Vaccine vol. 20, pp. 2155-2163.

Kawata et al, "Effect of Vitamin $B_{12}$ Deficiency on testicular Tissue in Rats Fed by Pair-Feeding," Internat J. Vit. Nutr. Res 67, 1997, pp. 17-21.

Kaur et al, "Probiotics: Potential Pharmaceutical Applications," European Journal of Pharmaceutical Science vol. 15, 2002, pp. 1-9.

NIAID Fact Sheet, "Tuberculosis," www.niaid.nih.gov/factsheets/tb.htm. Aug. 3, 2002.

Murray et al, "Modeling the Impact of Global Tuberculosis Control Strategies," Proc. Natl. Acad. Sci, vol. 95, Nov. 1998, pp. 13881-13886.

Muhammad et al, "The Appropriateness of Using Cyanocobalamin as Calibration Standards in *Lactobacillus leichmanii* A.T.C.C. 7830 assay of Vitamin $B_{12}$," Food Chemistry vol. 48, 1993, pp. 427-429.

Muhammad et al, "Comparison of a Competitive Binding Assay with *Lactobacillus Leichmanni* A.T.C.C. 7830 Assay for the Determination of Vitamin B12 in Foods," Food Chemistry vol. 48, 1993, pp. 431-434.

Muhammad et al, "The Appropriateness of Using Cyanocobalamin as Calibration Standards in Competitive Binding Assays of Vitamin B12," Food Chemistry vol. 48, 1993, pp. 423-425.

"Tuberculosis," Bulletin of the World Health Organization vol. 76, 1998, pp. 141-143.

Meile et al, "Classification of Propionic Acidic Bacteria and Approaches to Applied Genetics," Lait vol. 79, 1999, pp. 71-78.

Medina et al, "Modulation of Immune Responses Following Antigen administration by Mucosal Route," FEMS Immunology and Medical Microbiology vol. 27, 2000, pp. 305-311.

Makinen et al, "The Adherence of Latic Acid Bacteria to the Column Epithelial Cells of Pigs and Calves," Journal of Applied Bacteriology vol. 55, 1983, pp. 241-245.

Matsuzaki et al, "Special Feature: Modulating Immune Responses with Probiotic Bacteria," Immunology and Cell Biology vol. 78, 2000, pp. 67-73.

Marteau et al, "Survival of Lactic Acid Bacteria in A Dynamic Model of the Stomach and Small Instestine: Validation and the Effect of Bile," J. Dairy Sci. vol. 80, 1997, pp. 1031-1037.

Mantere-Alhonen, S., "On the Survival of a Propionibacterium Freudenrechii-Culture During In Vitro Gastric Digestion," Meijeritieteellinen Aikakauskirja XLI, No. 2, 1983, pp. 19-23.

Pieters et al, "Hijacking the Host: Survival of Pathogenic Mycobacteria Inside Macrophages," Trends in Microbiology vol. 10 No. 3, Mar. 2002, pp. 142-146.

Chaia et al, "The Probiotic Properties of Propionibacteria," Lait vol. 79, 1999, pp. 175-185.

Chaia et al, "The Propionibacteria in the Gut: Effect on Some Metabolic Activities of the Host," Lait vol. 75, 1995, pp. 435-445.

Orme, Ian M., "Beyond BCG: the Potential for a More Effective TB Vaccine," Molecular Medicine Today vol. 5, Nov. 1999, pp. 487-492.

Sun et al, "Cholera Toxin B Subunit: An Efficient Transmucosal Carrier—Delivery System for Induction of Peripheral Immunological Tolerance," Proc. Natl. Acad. Sci. vol. 91, Nov. 1994, pp. 10795-10799.

Swift et al, "Scanning Electron Microscopy of Rat Intestinal Microvilli," Letters to the Editor The Lancet, Oct. 26, 1968, p. 915.

Tsuyuguchi, Izuo, "Regulation of the Human Immune Response in Tuberculosis," Infectious Agents and Disease, vol. 5, 1996, pp. 82-97.

Broker, Michael, "New Approaches to Vaccines Against Tuberculosis: Where We Stand and Where we Want to Go, Introductory Remarks to the Symposium," FEMS Immunology and Medical Microbiology vol. 23, 1999, pp. 147-148.

Britz et al, "Propionibacterium Species Diversity in Leerdammer Cheese," International Journal of Food Microbiology vol. 22, 1994, pp. 257-267.

Bougle et al, "Effect of Propionibacteria Supplementation on Fecal Bifodobacteria and Segmental Colonic Transit Time in Healthy Human Subjects," Scand J Gastroenterol vol. 34, 1999, pp. 144-148.

Boom, W. Henry, "γδ T Cells and Mycobacterium Tuberculosis," Microbes and Infection vol. 1, 1999, pp. 187-195.

Bjorkegren et al, "Serum Cobalamin, Folate, Methylmalonic Acid Total Homocysteine as Vitamin B12 and Folate Tissue Deficiency Markers Amongst Elderly Swedes—a Population-based Study," Journal of Internal Medicine vol. 249, 2001, pp. 423-432.

Bermudez et al, "Cellular and Molecular Mechanisms of Internalization of Mycobacteria by host Cells," Microbes and Infection vol. 3, 2001, pp. 37-42.

Barnes et al, "Patterns of Cytokine Production by Mycobacterium-Reactive Human T-Cell Clones," Infection and Immunity, Jan. 1993, pp. 197-203.

Ball, G.F.M., "Bioavailability and Analysis of Vitamins in Foods," Chapter 14, pp. 497-515.

Baer, A., "Identification and Differentiation of Propionibacteria by Electrophoresis of Their Proteins," Michwissenschaft vol. 42, No. 7, 10987, pp. 431-433.

Berry et al., "Use of Cheese Whey for Vitamin B12 Production: II Cobalt, Precursor, and Aeration Levels," Applied Microbiology, vol. 14, No. 3, May 1996, pp. 356-360.

Brandtzaeg, Per, "History of Oral Tolerance and Mucosal Immunity," Annals of New York Academy of Sciences, pp. 1-27.

Lau et al, "Measurement of Serum Vitamin B12 Level Using Radioisotope Dilution and Coated Charcoal," Blood vol. 26, No. 2, Aug. 1965, pp. 202-214.

Riedel et al, "Differentiation of "Classical" Propionibacterium Species by Numerical Analysis of Electrophoretic Protein Profiles," System Appl. Microbiol. vol. 15, 1992, pp. 567-572.

Sarkar et al, "Recent Trends in Utilization of Propionibacterium—A Review," J. Dairying Foods & Home Sci, vol. 14, No. 1, 1995, pp. 1-16.

Tsakalidou et al, "The Combined Use of Whole-Cell Protein Extracts for the Identification (SDS-PAGE) and Enzyme Activity Screening of Lactic Acid Bacteria Isolated from Traditional Greek Dairy Products," System Appl. Microbiol. vol. 17, 1994, pp. 444-458.

O'Sullivan, Daniel J., "Methods for Analysis of the Intestinal Microflora," Probiotics: A Critical Review, Chapter 3, Ed. Tannock G.W.

Tripathy et al, "Fifteen-year Follow-Up of the Indian BCG Prevention Trial," XXVIth IUAT World Conference, pp. 69-72.

Balaji et al, "Processing of Mycobacterium Tuberculosis Bacille by Human Monocytes for CD4+ $\alpha\beta$ and $\gamma\delta$T Cells: Role of Particulate Antigen," Infection and Immunity vol. 66, No. 1, Jan. 1998, pp. 98-106.

Baik et al, "Vitamin B12 Deficiency in the Elderly," Annu. Rev. Nutr., 1999, pp. 357-377.

Attanasio et al, "Immunogenicity and Safety of *Mycobacterium tuberculosis* Culture Filtrate Proteins in Non-Human Primates," Clin exp Immunol vol. 119, 2000, pp. 84-91.
"Microbiological Methods: AOAC Offical Method 960.46 Vitamin Assays—Microbiological Methods Final Action," AOAC Official Methods of Analysis, Vitamins and Other Nutrients Chapter 45, 1995, pp. 41-44.
Andersen, Peter, "Effective Vaccination of Mice Against Mycobacterium Tuberculosis Infection with a Soluble Mixture of Secreted Mycrobacterial Proteins," Infection and Immunity vol. 62, Jun. 1993, pp. 2536-2544.
Andersen, Peter, "TB VAccines: Progress and Problems," TRENDS in Immunology vol. 22, No. 3, Mar. 2001, pp. 160-168.
Allison et al, "studies on Mixed Populations of Human Instestinal Bacteria Grown in Single-Stage and Multistage Continuous Culture Systems," Applied and Environmental Microbiology, Mar. 1989, pp. 672-678.
Donohue et al, "Safety of Probiotic Bacteria," Asia Pacific J. Clin Nutr, vol. 5, 1996, pp. 25-28.
Delva, M. Dianne, "Vitamin B12 Replacement," Canadian Family Physician vol. 43, May 1997, pp. 917-922.
Cummins et al, "Genus Propionibacterium Orla-jensen 1909, 337 AI," Bergey's Manual of Systematic Bacteriology vol. 2, pp. 1346-1353.
Crociani et al, "Adhesion of Different Bifidobacteria Strains to Human Enterocyte-like Caco-2 Cells and Comparison with In Vivo Study," Letters in Applied Microbiology vol. 21, 1995, pp. 146-148.
Costas et al, "Interlaboratory Comparative Study of the Numerical Analysis of One-Dimensional Sodium Dodecyl Sulphate-Polyacrylamide Gel Electrophoretic Protein Patterns of Campylobacter Strains.," Electrophoresis, vol. 11, 1990, pp. 467-474.
Costas, Menelaos, "Numerical Ananlysis of Sodium Dodecyl Sulphate-Polyacrylamide Gel Electrophoretic Protein Patterns for the Classification, Identification and Typing of Medically Important Bacteria," Electrophoresis vol. 11, 1990, pp. 382-391.
Cooper et al, "The Role of Onterleukin-12 in Acquired Immunity to Mycobacterium tuberculosis Infection," Immunology vol. 84, 1995, pp. 423-432.
Conway et al, "Survival of Lactic Acid Bacteria in the Human Stomach and Adhesion to Intestinal Cells," Jurnal of Dairy Science vol. 70, No. 1, 1987, pp. 1-12.
Collins, Desmond M., "New Tuberculosis Vaccines Based on Attenuated Strains of the Mycobacterium tuberculosis Complex," Immunology and Cell Biology vol. 78, 2000, pp. 342-348.
Clark et al, "Selection of Bifidobacteria for Use as Dietary Adjuncts in Cultured Dairy Foods: III—Tolerance to Simulated Bile Concentrations of Human Small Intestines," Cultured Dairy Products Journal vol. 29, 1994, pp. 18-21.
Clarkk et al, "Selection of Bifidobacteria for Use as Dietary Adjuncts in Cultured Dairy Foods: II—Tolerance to Simulated pH of Human Stomachs," Cultured Dairy Products Journal, Nov. 1993, pp. 11-14.
Chung et al, "Screening and Selection of Acid and Bile Resistant Bifidobacteria," International Journal of Food Microbiology, vol. 47, 1999, pp. 25-32.
Chou et al, "Isolation and Characterization of Acid- and Bile- Tolerant Isolates from Strains of *Lactobacillus acidophilus*," J Dairy Sci, vol. 82, 1999, pp. 23-31.
Choi, Sang-Woon, "Brief Critical Review: Vitamin B12 Deficiency: A New Risk Factor for Breast Cancer?" Nutrition Reviews vol. 57, No. 8, Aug. 1999, pp. 250-260.
Charteris et al, "development and Application of an In Vitro Methodology to Determine the Transit Tolerance of Potentially Probiotic Lactobacillus and Bifidobacterium species in the Upper Human Gastrointestinal tract," Journal of Applied Microbiology vol. 84, 1998, pp. 759-768.
Casey et al, "Vitamins and Other Nutrients: Radioisotope Dilution Technique for Determination of Vitamin B12 in Foods," J. Assoc of Anal. Chem. vol. 65, No. 1, 1982, pp. 85-88.
Caruso et al, "Mice Deficient in CD4 T Cells Have Only Transiently Dimished Levels of IFN-γ, Yet Succumb to Tuberculosis," The Journal of immunology vol. 162, 1999, pp. 5407-5416.
Feng et al, "CD4+ and CD8+ Cells Mediate Adoptive Immunity to Aersol Infection of *Mycobacterium bovis Bacillus* Calmette-Guerin," The Journal of Infectous Diseases vol. 181, 2000, pp. 1846-1849.
Fessler et al, "Propionibacterial Flora in Swiss Raw Milk," Lait 79. 1999, pp. 201-209.
Flynn, J.L., "Why is IFN-γ Insufficient to Control Tuberculosis?" Trends in Microbiloigy vol. 7, No. 12, Dec. 1999, pp. 477-478.
Gleeson et al, "Salivary IgA Subclasses and Infection Risk in Elite Swimmers," Imunology and Cell biology vol. 77, 1999, pp. 351-355.
Gleissberg, V., "The Threat of Multidrug Resistance: Is Tuberculosis Ever Untreatable or uncontrollable?" Lancet vol. 353, 1999, pp. 998-999.
Ibrahim et al, "Survival of Bifodobacteria in the Presence of Bile Salt," J Sci Food Agric, vol. 62, 1993, pp. 351-354.
Jan et al, "Acid Stress Susceptibilty and Acid Adaptation of Propionibacterium Freudenreichii Subsp, Shermanii," Lait vol. 80, 2000, pp. 325-336.
Kaufmann et al, "Immune Response Against Mycobacterium tuberculosis: Immplications for Vaccine Development," journal of Biotechnology vol. 83, 2000, pp. 13-17.
Kawata et al, "Utilization of Dietary Protein in the Vitamin B12—Deficient Rats," Internat. j. Vit. Nutr. Res. vol. 65, 1995, pp. 248-254.
Lehto et al, "Adhesion of Two Lactobacillus Strains, One *Lactococcus* and One *Propionibacterium* Strain to Cultured human Intestinal Caco-2 Cell Line," Bioscience Microflora vol. 16, No. 1, 1997, pp. 13-17.
Quesada-Chanto et al, "Effect of the Oxygen Supply on Pattern of Growth and Corrinoid and Organic Acid Production of *Propionibacterium shermanii*," Appl Microbiol Biotechnol vol. 49, 1998, pp. 732-736.
Riedel et al, "Identification of Classical *Propionibacterium* Species Using 16S rDNA—Restriction Fragment Length Polymorphisms," System Appl. Microbiol. vol. 21, 1998, pp. 419-428.
Rossi et al, "Identification and Clustering of dairy *Propionibacteria* by RAPD=PCR and CGE-REQ methods," Journal of Applied Microbiology vol. 85, 1998, pp. 956-964.
Quesada-Chanto et al, "Optimization of a *Propionibacterium acidipropionici* Continuous Culture Utilizing Sucrose," Appl. Microbiol Biotechnol vol. 42, 1994, pp. 16-21.

Quesada-Chanto et al, "Microbial Production of Propionic Acid and Vitamin B12 Using Molasses or Sugar," Appl microbiol Biotechnolog, vol. 41, 1994, pp. 378-383.

Elhay etal, "Immunological Requirements for a Subunit Vaccine Against tuberculosis," Immunology and Cell Biology vol. 75, 1997, pp. 595-603.

Ehlers, S., "Immunity to Tuberculosis: A Delicate Balance Between Protection and Pathology," FEMS Immunology and Medical Microbiology vol. 23, 1999, pp. 149-158.

Wilcken et al, "B Vitamins and Homocysteine in Cardiovascular Disease and Aging," Annals of New York Academy of Sciences 954, 1998, pp. 361-370.

Ye et al, "Efficient Production of Vitamin B12 from Propionic Acid Bacteria under Periodic Variation of Dissolved Oxygen Concentration," Journal of Fermentation and Bioengineering vol. 82, No. 5, 1996, pp. 484-491.

Weldingh et al, "Immunological Evaluation of Novel Mycobacterium tuberculosis Culture Filtrate Porteins," FEMS Immunology and Medical Microbiology vol. 23, 1999, pp. 159-164.

Bouvet et al, "Stimulation of Local Antibody Production: Parental or Mucosal Vaccination?" Trends in Immunology vol. 23, No. 4, Apr. 2002, pp. 209-213.

Brandt et al, "Failure of the *Mycobacterium bovis* BCG Vaccine: Some Species of Environmental *Mycobacteria* Block Multiplication of BCG and induction of Protective Immunity to Tuberculosis," Infection and Immunity vol. 70, No. 2, 2002, pp. 672-678.

Brandtzaeg, Per, "Development and Basic Mechansims of human Gut Immunity," Nutrition Review vol. 56, No. 1, Jan. 1998, pp. S5-S18.
Del Giudice et al, "What are the Limits of Adjuvanticity?" Vaccine vol. 20, 2002, pp. S38-S41.
Collins etal, "Prospects for Better Tuberculosis Vaccines," The Lancet Infectious Diseases vol. 1, Aug. 2001. pp. 21-28.
Demangel et al, "Interaction of Dendritic Cells with Mycobacteria,: where the Action Starts," Immunology and Cell Biology vol. 78, 2000, pp. 318-324.
Albert et al, "Vitamin B12 Synthesis by Human Small Intestinal Bacteria," Nature vol. 283, Feb. 21, 1980, pp. 781-782.
Agger et al, "Tuberculosis Subunit Vaccine Development: On the Role of Interferon-γ," Vaccine vol. 19, 2001, pp. 2298-2302.
Saunders et al, "Restraining *Mycobacteria*: Role of granulomas in mycobacterial Infections," Immunology and Cell Biology vol. 78, 2000, pp. 334-341.
Stenger et al, "T Cell Mediated Immunity to Mycobacterium tuberculosis," Current Opinions in Microbiology vol. 2, 1999, pp. 89-93.
Nanno et al, "Mutagenic Activation of Biliary Metabolites of Benzo (a) pyrene by β-Glucuronidase—Positive Bacteria in Human Faeces," J. Med. Microbiol. vol. 22, 1986, pp. 351-355.
Mustafa, A.S., "Development of New Vaccines and Diagnostic Reagents Against Tuberculosis," Molecular Immunology vol. 1121, 2002, pp. 1-7.
marth et al, "Oral Tolerance and its modulation by Anti-Cytokines," 72nd Forum in Immunology, pp. 554-561.
Wynn et al, "The Danger of B12 Deficiency in the Elderly," Nutrition and Health vol. 12, 1998, pp. 215-226.
Huang et al, "An In Vitro Model for Investigating Intestinal Adhesion of Potential Dairy *Propionibacteria* Probiotic Strains Using Cell Line C2BBe1," Letters in Applied Microbiology vol. 36, Issues 4, Apr. 2003, p. 213.
Analysis of ISR Citations.
Stambas et al, "Oxidised Mannan as a Novel Adjuvant Inducing Mucosal IgA Production," Vaccine 20, 2002, pp. 1068-1078.
Doherty et al, "Oral Vaccination with Subunit Vaccines Protects Animals Against Aerosol Infection with Mycobacterium tuberculosis," Infection and Immunity vol. 70, No. 6, 2002, pp. 3111-3121.
Barefoot et al, "Antibiosis Revisted: Bacteriocins Produced by Dairy Starter Cultures," J. Dairy Sci vol. 76, 1993, pp. 2366-2379.
Vogel, F.R., "Improving Vaccine Performance with Adjuvants," Clinical Infectious Diseases vol. 30, Suppl. 3, 2000, pp. S266-S270.
Babuchowski et al, "*Propionibacteria* in Fermented Vegetables," Lait vol. 79, 1999, pp. 113-124.
Hugenholtz, J., et al., Nutraceutical production by *Propionibacteria*, LAIT, vol. 82, Mar. 2002, pp. 103-112.
Ouwehand, A. C., et al., "In vitro adhesion of propionic acid bacteria to human intestinal mucus." LAIT, vol. 82, Mar. 2002, pp. 123-130.
Huang, Y., et al., "The in vivo assessment of safety and gastrointestinal survival of an orally administered novel probiotic, *Propionibacterium jensenii* 702, in a male Wistar rat model," Food and Chemical Toxicology, vol. 41, No. 12, Dec. 2003, pp. 1781-1787.
Supplementary European Search Report issued for EP 03 72 9709, dated Apr. 28, 2006.
Agger et al., "Tuberculosis Subunit Vaccine Development: On the Role of Interfron-γ", Vaccine, 2001, pp. 2298-2302, vol. 19(17-19).
Albert et al., "Vitamin B12 synthesis by human small intestinal bacteria", Nature, Feb. 21, 1980, pp. 781-782, vol. 283(5749).
Allison et al., "Studies on mixed populations of human intestinal bacteria growth in single-stage and multistage continuous culture systems", Applied and Environmental Microbiology, Mar. 1989, pp. 672-678, vol. 55(33).
Analysis of ISR Citations of PCT/AU03/00775 2004 p. 1-5.
Andersen, "Effective Vaccination of Mice Against Mycobacterium tuberculosis Infection with a Soluble Mixture of Secreted *Mycobacterium* Proteins", Infection and Immunity, 1994, pp. 2536-2544, vol. 62.
Andersen, "TB Vaccines: Progress and Problems", Trends in Immunology, Mar. 2001, pp. 160-168, vol. 22(3).
"AOAC Official Method 960.46 Vitamin Assays: Microbiological Methods, Final Action", Microbiological Methods, AOAC Official Methods of Analysis, Vitamins and Other Nutrients Chapter 45, Subchapter 2, 1995, pp. 41-44.
Attanasio et al., "Immunogenicity and Safety of Mycobacterium tuberculosis Culture Filtrate Proteins in Non-Human Primates", Clin Exp Immunol, 2000, pp. 84-91, vol. 119(1).
Babuchowski et al., "*Propionibacteria* in Fermented Vegetables", Lait, 1999, pp. 113-124, vol. 79.
Baer, A., "Identification and Differentiation of *Propionibacteria* by Electrophoresis of Their Proteins", Michwissenschaft, 1987, pp. 431-433, vol. 41.
Baik et al., "Vitamin B12 Deficiency in the Elderly", Annu. Rev. Nutr., 1999, pp. 357-377, vol. 19.
Balaji et al., "Processing of Mycobactarium tuberculosis bacilli by human monocytes for CD4+ alphabeta and gammadelta T cells: role of particulate antigen", Infection and Immunity, Jan. 1998, pp. 98-106, vol. 66(1).
Barefoot et al., "Antibiosis Revisted: Bacteriocins Produced by Dairy Starter Cultures", J. Dairy Sci, 1993, pp. 2366-2379, vol. 76(8).
Barnes et al., "Patterns of Cytokine Production by *Mycobacterium*-Reactive Human T-Cell Clones", Infection and Immunity, Jan. 1993, pp. 197-203, vol. 61(1).
Bermudez et al., "Cellular and Molecular Mechanisms of Internalization of *Mycobacteria* by host Cells", Microbes and Infection, 2001. pp. 37-42, vol. 3(1).
Berry et al., "Use of Cheese Whey for Vitamin B12 Production: II Cobalt, Precursor, and Aeration Levels", Appl. Environ Microbiol., May 1966; 356-357, vol. 14(3).
Bjorkegren et al., "Serum Cobalamin, Folate, Methylmalonic Acid Total Homocysteine as Vitamin B12 and Folate Tissue Deficiency Markers Amongst Elderly Swedes—a Population-based Study", Journal of Internal Medicine, 2001, pp. 423-432, vol. 249.
Boom, "γδ T Cells and Mycobacterium tuberculosis", Microbes and Infection, 1999, pp. 187-195, vol. 1(3).
Bougle et al., "Effect of *Propionibacteria* supplementation on fecal bifidobacteria and segmental colonic transit time in healthy human subjects", Scand J Gastroenetrol, 1999, pp. 144-148, vol. 34
Bouvet et al., "Stimulation of Local Antibody Production: Parental or Mucosal Vaccination?", Trends in Immunology, Apr. 2002, pp. 209-213, vol. 23(4).
Brandt et al., "Failure of the *Mycobacterium bovis* BCG Vaccine: Some Species of Environmental *Mycobacteria* Block Multiplication of BCG and induction of Protective Immunity to Tuberculosis", Infection and Immunity, 2002, pp. 672-678, vol. 70(2).
Brandtzaeg, "Development and Basic Mechanisms of human Gut Immunity ", Nutrition Review, Jan. 1998, pp. S5-S1B, vol. 56(1).
Brandtzaeg, Per, "History of Oral Tolerance and Mucosal Immunity", Annals of New York Acadmey of Sciences. 1996, pp. 1-27, vol. 778(1).

Britz et al., "*Propionibacterium* Species Diversity in Leerdammer Cheese", International Journal of Food Microbiology, 1994, pp. 257-267, vol. 22(4).

Broker, Michael, "New Approaches to Vaccines Against Tuberculosis: Where We Should and Where we Want to Go. Introductory Remarks to the Symposium", FEMS Immunology and Medical Microbiology, 1999, pp. 147-148, vol. 23(2).

Brooker et al., "Adhesion of Lactobacilli to the Chicken Crop epithelium", Journal of Ultrastructure Research, 1975, pp. 21-31, vol. 52(1).

Carmel, "Current Concepts in Cobalamin Deficiency", Annu. Rev. Med., 2000, pp. 357-375, vol. 51.

Caruso et al., "Mice Deficient in CD4 T Cells Have Only Transiently Diminished Levels of IFN-γ, Yet Succumb to Tuberculosis". The Journal of immunology, 1999, pp. 5407-5416, vol. 162.

Casey et al., "Vitamins and Other Nutrients: Radioisotope Dilution Technique for Determination of Vitamin B12 in Foods", Assoc of Anal. Chem., 1982, pp. 85-88, vol. 65(1).

Chaia et al., "The Probiotic Properties of *Propionibacteria*", Lait, 1999, pp. 175-185, vol. 79.

Chaia et al., "Propionibacteria in the Gut: Effect on Some Metabolic Activities of the Host", Lait, 1995, pp. 435-445, vol. 75.

Charteris et al., "Development and Application of an In Vitro Methodology to Determine the Transit Tolerance of Potentially Probiotic *Lactobacillus* and *Bifidobacterium* species in the Upper Human Gastrointestinal tract", Journal of Applied Microbiology, 1998, pp. 759-768, vol. 84(5).

Choi, Sang-Woon. "Brief Critical Review: Vitamin B12 Deficiency: A New Risk Factor for Breast Cancer?", Nutrition Reviews, Aug. 1999, pp. 250-253, vol. 57(8).

Chou et al., "Isolation and Characterization of Acid- and Bile- Tolerant Isolates from Strains of *Lactobacillus acidophilus*" J. Dairy Sci, 1999, pp. 23-31, vol. 82(1).

Chung et al., "Screening and Selection of Acid and Bile Resistant Bifidobacteria", International Journal of Food Microbiology, 1999, pp. 25-32. vol. 47(1).

Clark et al., "Selection of Bifidobacteria for Use as Dietary Adjuncts in Cultured Dairy Foods: III—Tolerance to Simulated Bile Concentrations of Human Small Instestines", Cultured Dairy Products Journal, 1994, pp. 18, 20-21, vol. 29(3).

Clark et al., "Selection of Bifidobacteria for Use as Dietary Adjuncts in Cultured Dairy Foods: II—Tolerance to Simulated pH of Human Stomachs", Cultured Dairy Products Journal., Nov. 1993, pp. 11-14, vol. 28(4).

Collins et al., "New Tuberculosis Vaccines Based on Attenuated Strains of the Mycobacterium tuberculosis Complex", Immunology and Cell Biology, 2000, pp. 342-348., vol. 78.

Collins et al., "Prospects for Better Tuberculosis Vaccines", The Lancet Infectious Diseases, Aug. 2001, pp. 21-28, vol. 1(1).

Conway et al., "Survival of Lactic Acid Bacteria in the Human Stomach and Adhesion to Intestinal Cells", Journal of Dairy Science, 1987, pp. 1-12, vol. 70(1).

Cooper et al., "The role of interleukin-12 in acquired immunity to Mycobacterium tuberculosis infection", Immunology, 1995, pp. 423-432, vol. 84(3).

Costas et al., "Interlaboratory Comparative Study of the Numerical Analysis of One-Dimensional Sodium Dodecyl Sulphate-Polyacrylamide Gel Electrophoretic Protein Patterns of Campylobacter Strains", Electrophoresis, 1990, pp. 467-474, vol. 11(6).

Costas, "Numerical Ananlysis of Sodium Dodecyl Sulphate-Polyacrylamide Gel Electrophoretic Protein Patterns for the Classification, Identification and Typing of Medically Important Bacteria", Electrophoresis, 1990, pp. 382-391, vol. 11(5).

Crociani et al., "Adhesion of Different Bifidobacteria Strains to Human Enterocyte-like Caco-2 Cells and Comparison with In Vivo Study", Letters in Applied Microbiology, 1995, pp. 146-148, vol. 21(3).

Cummins et al., "Genus *Propionibacterium* Orla-jensen 1909, 337 Al.". Bergey's Manual of Systematic Bacteriology, 1986, pp. 1346-1353, vol. 2.

Del Giudice et al., "What are the Limits of Adjuvanticity?", Vaccine, 2002, pp. S38-S41, vol. 20(Suppl 1).

Delva, M. Dianne, "Vitamin B12 Replacement", Canadian Family Physician, May 1997, pp. 917-922, vol. 43.

Demangel et al., "Interaction of Dendritic Cells with *Mycobacteria*,: where the Action Starts", Immunology and Cell Biology, 2000, pp. 318-324, vol. 78.

Doherty et al., "Oral Vaccination with Subunit Vaccines Protects Animals Against Aerosol Infection with Mycobacterium Tuberculosis", Infection and Immunity, 2002, pp. 3111-3121, vol. 70(6).

Donohue et al., "Safety of Probiotic Bacteria", Asia Pacific J. Clin Nutr, 1996, pp. 25-28. vol. 5.

Donohue et al., "Safety of Probiotic Bacteria", Lactic Acid Bacteria, Microbiology and Functional Aspects, 1998, Chapter 13, pp. 369-383, New York, USA, Marcel Dekker Inc., ISBN: 0-8247-0133-X.

Ehlers, S., "Immunity to Tuberculosis: A Delicate Balance Between Protection and Pathology", FEMS Immunology and Medical Microbiology, 1999, pp. 149-158, vol. 23(2).

Elhay etal., "Immunological requirements for a subunit vaccine against tuberculosis", Immunology and Cell Biology, 1997, pp. 595-603, vol. 75(6).

Erickson et al., "Probiotic Immunomodulation in Health and Disease", American Society of Nutritional Sciences Symposium: Probiotic Bacteria: Implications for Human Health, Journal of Nutrition, 2000, 403S-409S, vol. 130.

Falero-Diaz et al., "Intranasal Vaccination of Mice Against infection with Mycobacterium tuberculosis", Vaccine, 2000, pp. 3223-3229, vol. 18(28).

Famularo et al., "Stimulation of Immunity by Probiotics", Probiotics 2: Applications and Pratical Aspects, Chapter 6, 1997, pp. 133-161.

Fang et al., "Modulation of Humoral Immune Response through Probiotic Intake", FEMS Immunology and Medical Microbiology, Sep. 2000. pp. 47-52, vol. 29(1).

Fatkenheuer et al., "The Return of Tuberculosis", Diagn Microbiol infect Dis, 1999, pp. 139-146, vol. 34(2).

Feng et al., "CD4+ and CD8+ T Cells Mediate Adoptive Immunity to Aersol Infection of *Mycobacterium bovis Bacillus* Calmette-Guerin", The Journal of Infectous Diseases. 2000, pp. 1846-1849, vol. 181.

Feng et al., "Increase in Gamma Interferon-Secreting CD8+, as Well as CD4+, T Cells in Lungs following Aerosol Infection with Mycobacterium tuberculosis", Infection and Immunity, Jul. 1999, pp. 3242-3247, vol. 67(7).

Fessler et al., "Rapid Identification of Dairy *Propionibacterium* Species by Restriction Analysis of the Insertion within the 23S rRNA Gene", Lait, 1998, pp. 203-216, vol. 78.

Fessler et al., "*Propionibacteria flora* in Swiss raw milk from lowlands and Alps", Lait, 1999, pp. 201-209, vol. 29.

Finegold et al., "Normal indigenous intestinal Flora", Human Intestinal Microflora in Health and Disease, Chapter 1, 1983, pp. 3-31.

Flaminio et al., "Immunologic Function in Horses after Non-Specific Immunostimulant Administration", Veterinary Immunology and Immunopathology, 1998, pp. 303-315, vol. 63(4).

Flynn, "Why is IFN-γ Insufficient to Control Tuberculosis?", Trends in Microbiology, Dec. 1999, pp. 477-478, vol. 7(12).

Fooks et al., "Prebiotics, Probiotics and Human Gut Microbiology", International Dairy Journal 1999, pp. 53-61, vol. 9(1).

Fujisawa et al., "Influence of Bile Salts on β-Glucuronidase Activity of Intestinal Bacteria", Letters in Applied Microbiology, pp. 271-274, vol. 22, Apr. 1996.

Gadelle et al., "β-Glucuronidase Activities of Intestinal Bacteria Determined Both in Vitro and In Vivo in Gnotobiotic Rats", Applied Environmental Microbiology, Mar. 1985, pp. 682-685, vol. 49(3).

Gariballa, S.E., "Review Article: Nutritional Factors in Stroke", British Journal of Nutrition, 2000. pp. 5-17, vol. 84(1).

Gautier et al., "DNA Fingerprinting of Dairy Propionibacteria Strains by Pulsed-Field Gel Electrophoresis", Current Microbiology, 1996, pp. 17-24, vol. 32(1).

Gilliland et al., "Importance of Bile Tolerance of *Lactobacillus acidophilus* Used as a Dietary Adjunct", J Dairy Sci; 1984, pp. 3045-3051, vol. 67(12).

Gleeson et al., "Salivary IgA Subclasses and Infection Risk in Elite Swimmers", Imunology and Cell biology, 1999, pp. 351-355, vol. 77(4).

Gleissberg, "The Threat of Multidrug Resistance: Is Tuberculosis Ever Untreatable or uncontrollable?", Lancet, 1999, pp. 998-999, vol. 353(9157).

Grant et al., "The Potential of *Propionibacterium* spp. as Probiotics", Chapter 18, Lactic acid bacteria: microbiology and functional aspects, New York, N.Y: Marcel Dekker, Inc.; 1998, pp. 589-601.

Guerin, "Evaluation of BCG and New Vaccines against Tuberculosis", Pediatric Pulmonology, Supplemental 18, 1997, pp. 286-287.

Harrigan, "Isolation of *Propionibacteria* from Swiss Cheese", Laboratory Methods in Food Microbilogy, Third Edition, 1998, pg. Academic Press, San Diego, p. 266.

Havenaar et al., "Selection of Strains for Probiotic Use", Probiotics: The Scientific Basis Chapter Nine, 1992, p. 210-224.

Havlir et al., "Human Immune Response to Mycobacterium tuberculosis Antigens", Infection and Immunity, Feb. 1991, pp. 665-670, vol. 59(2).

Herbert, "Vitamin B-12: Plant Sources, Requirements. and Assay", Am J Clin Nutr, 1988, pp. 852-858, vol. 48(3 Supp).

Hess et al., "Live Antigen Carriers as Tools for Improved Anti-tuberculosis Vaccines", FEMS Immunology and Medical Microbiology, 1999, pp. 165-173, vol. 23(2).

Hettinga et al., "The Propionic-Acid Bactera—A Review: II Metabolism", J. Milk Food Technol., 1972, pp. 358-372, vol. 35(6).

Hettinga et al., "The Propionic-Acid Bacteria—A Review: III Miscellaneous Metabolic Activities", J. Milk Food Technology, 1972, pp. 436-447, vol. 35(7).

Hill, "Intestinal Flora and Endogenous Vitamin Synthesis", European Journal of Cancer Prevention, 1997, pp. S43-S45, vol. 6(Suppl 1).

Hood et al., "Effect of Low pH on the Ability of *Lactobacillus acidophilus* to Survive and Adhere to Human Intestinal Cells", Journal of Food Science, 1988, pp. 1514-1516, vol. 53(5).

Huang et al., "An In Vitro Model for Investigating Intestinal Adhesion of Potential Dairy *Propionibacteria* Probiotic Strains Using Cell Line C2BBe1", Letters in Applied Microbiology, Apr. 2003, p. 213-216, vol. 36(4).

Ibrahim et al., "Survival of *Bifidobacteria* in the Presence of Bile Salt", J Sci Food Agric, 1993, pp. 351-354. vol. 62.

Jan et al., "Acid stress susceptibility and acid adaptation of *Propionibacterium freudenreichii* subsp. *shermanii*", Lait, 2000, pp. 325-336, vol. 80.

Johnson, "Bacterial Classification III: Nucleic Acids in Bacterial Classification", Bergey's manual of systematic bacteriology, 1986, 972-975.

Kaneko et al., "Growth Stimulator for *Bifidobacteria* Produced by *Propionibacterium freudenreichil* and Several Intestinal Bacteria", J Dairy Sci, 1994, pp. 393-404, vol. 77(2).

Kankaanpaa et al., "Influence of Probiotic Supplemented Infant Formula on Composition of Plasma Lipids in Atopic Infants", Journal of Nutritional Biochemistry, 2002, pp. 364-369, vol. 13.

Kaufmann et al., "Immunity to *Mycobacteria* with Emphasis on tuberculosis: Implications for Rational Design of an Effective Tuberculosis Vaccine", Immunology of Intracellular Parasitism Chem Immunol Basel, Karger, 1998, pp. 21-59, vol. 70.

Kaufmann et al., "Immune response against Mycobacterium tuberculosis: implications for vaccine development", Journal of Biotechnology, 2000, pp. 13-17, vol. 83(1).

Kaur et al., "Probiotics: Potential Pharmaceutical Applications". European Journal of Pharmaceutical Science, 2002, pp. 1-9, vol. 15(1).

Kawata et al., "Effect of Vitamin B12 Deficiency on testicular Tissue in Rats Fed by Pair-Feeding", Internat J. Vit. Nutr. Res, 1997, pp. 17-21, vol. 67(1).

Kawata et al., "Utilization of Dietary Protein in the Vitamin B12—Deficient Rats", Internat. J. Vit. Nutr. Res., 1995, pp. 248-254, vol. 65(4).

Kenney et al., "2nd Meeting on novel Adjuvants Currently in/close to Human Clinical testing: World Health Organization—Organization Mondiale de la Santa Fondation Menieux, Annecy France, Jun. 5-7, 2000", Vaccine, pp. 2155-2163, vol. 20.

Kitazawa et al., "Interferon Induction in Murine Peritoneal Macrophage by Stimulation with *Lactobacillus acidophilus*", Microbiol Immunol., 1992, pp. 311-315, vol. 36(3).

Langridge et al., "Edible Vaccines", Scientific American, Sep. 2000, p. 66-71, vol. 283(3).

Lau et al., "Measurement of Serum Vitamin B12 Level Using Radio-isotope Dilution and Coated Charcoal", Blood, Aug. 1965, pp. 202-214, vol. 26(2).

Lehto et al., "Adhesion of Two *Lactobacillus* Strains, One *Lactococcus* and One *Propionibacterium* Strain to Cultured human intestinal Caco-2 Cell Line", Bioscience Microflore, 1997, pp. 13-17, vol. 16(1).

Lilly et al., "Probiotics: Growth-Promoting Factors Produced by Microorganisms", Science, Feb. 12, 1965, pp. 747-748, vol. 147(3659).

Lindbland et al., "Adjuvant Modulations of immune Responses to Tuberculosis Subunit Vaccines", Infection and Immunity, Feb. 1997, pp. 623-629, vol. 65, No. 2.

Lowrie et al., "Genetic Vaccination against Tuberculosis", Springer Semin Immunopathol, 1997, pp. 161-173, vol. 19(12).

Macfarlane et al., "Protein Degradation by Human Intestinal Bacteria", Journal of Gen Microbiology, 1986, pp. 1647-1656, vol. 132(6).

Mahairas et al., "Molecular Analysis of Genetic Differences between *Mycobacterium bovis* BCG and Virulent *M. bovis*", Journal of Bacteriology, Mar. 1996, pp. 1274-1282, vol. 178(5).

Makinen et al., "The Adherence of Lactic Acid Bacteria to the Column Epithelial Cells of Pigs and Calves", Journal of Applied Bacteriology, 1983, pp. 241-245, vol. 55.

Mann et al., "The Effect of Diet on Plasma Homocysteine Concentrations in Healthy Male Subjects", European Journal of Clinical Nutrition, 1999, pp. 895-899, vol. 53(11).

Mantere-Alhonen, "On the survival of a *Propionibacterium freudenreichii*-culture during in vitro gastric digestion", Meijeritieteellinan Aikakauskirja XLI. 1983, pp. 19-23, vol. 41(2).

Marteau et al., "Survival of Lactic Acid Bacteria in A Dynamic Model of the Stomach and Small Intestine: Validation and the Effect of Bile", J. Dairy Sci. 1997, pp. 1031-1037, vol. 80(6).

Marth et al., "Oral Tolerance and its modulation by Anti-Cytokines", 72nd Forum in Immunology, Research in Immunology, Oct. 12, 1997, pp. 554-561(8), vol. 148 (8).

Matsuzaki et al., "Special Feature: Modulating Immune Responses with Probiotic Bacteria", Immunology and Cell Biology, 2000, pp. 67-73, vol. 78.

Medina et al., "Modulation of Immune Responses Following Antigen administration by Mucosal Route", FEMS Immunology and Medical Microbiology, 2000, pp. 305-311, vol. 27.

Meile et al., "Classification of Propionic Acid Bacteria and Approaches to Applied Genetics", Lait, 1999, pp. 71-78, vol. 79.

Memoranda, "Tuberculosis Control and Research Strategies for the 1990s: Memorandum from a WHO meeting", Bulletin of the World Health Organization, 1992, pp. 17-21, vol. 70(1).

Miller et al., "Tuberculosis", Bulletin of the World Health Organization, 1998, pp. 141-143, vol. 76(Suppl. 2).

Muhammad et al., "Comparison of a competitive binding assay with *Lactobacillus leichmanni* A.T.C.C. 7830 assay for the determination of vitamine B12 in foods", Food Chemistry 93, pp. 431-434, vol. 48(4), 1993.

Muhammad et al., "The Appropriateness of Using Cyanocobalamin as Calibration Standards in Competitive Binding Assays of Vitamin B12", Food Chemistry, 1993, pp. 423-425, vol. 48(4).

Muhammad et al., "The appropriateness of using cyanocobalamin as calibration standards in *Lactobacillus leichmannii* A.T.C.C. 7830 assay of vitamin B12", Food Chemistry, 1993, pp. 427-429. vol. 48(4).

Murray et al., "Modeling the Impact of Global Tuberculosis Control Strategies", Proc. Natl. Acad. Sci. Nov. 1998, pp. 13881-13886, vol. 95(23).

Mustafa, A.S., "Development of New Vaccines and Diagnostic Reagents Against Tuberculosis", Molecular Immunology, 2002, pp. 113-119, vol. 39(1).

Nanno et al., "Mutagenic Activation of Biliary Metabolites of Benzo (a) pyrene by β-Glucuronidase—Positive Bacteria in Human Faeces", J. Med. Microbiol., 1986, pp. 351-355, vol. 22(4).

NIAID Fact Sheet, "Tuberculosis", www.niaid.nih.gov/factsheets/tb.htm. Aug. 3, 2002, p. 1-10.

NIAID News "Tuberculosis", http://www.niaid.nih.gov/newsroom/releases, Mar. 22, 1996, p. 1-5.
Niaid, "Strategies for Developing a Tuberculosis Vaccines", http://www.niaid.nih.gov/publications/blueprint, Jun. 3, 2002, p. 1-6.
Orme, Ian M., "Beyond BCG: the Potential for a More Effective TB Vaccine", Molecular Medicine Today, Nov. 1999, pp. 487-492, vol. 5(11).
O'Sullivan, "Methods for Analysis of the Intestinal Microflora", Probiotics: A Critical Review, Chapter 3, Ed. Tannock G.W., Curr. Issues Intestinal. Microbiol., 2000, 39.-50. vol. 1(2).
Ozkan et al., "Plasma Total Homocysteine and Cysteine Levels as Cardiovascular Risk Factors in Coronary Heart Disease", International Journal of Cardiology, 2002, pp. 269-277, vol. 82(3).
Pieters et al., "Hijacking the Host: Survival of Pathogenic Mycobacterial Inside Macrophages", Trends in Microbiology, Mar. 2002, pp. 142-146, vol. 10(3).
Pinto et al., "Enterocyte-like Differentiation and Polarization of the Human Colon Carcinoma Cell Line Caco-2 in Culture", Biol. Cell., 1983, pp. 323-330 vol. 47.
Pizza et al., "Mucosal vaccines: non toxic derivatives of LT and CT as mucosal adjuvants", Vaccine, 2001, pp. 2534-2541, vol. 19(17-19).
Poston et al., "Cobalamins and Cobalamin-Dependent Enzymes in *Candida utilis*", Journal of Bacteriology, Dec. 1979, pp. 1013-1016, vol. 140(3).
Pulvere et al., "Combined immunomodulation (*Propionibacterium avidum* KP-40) and lectin blocking (D-galactose) prevents liver tumor colonization in BALB/c-mice.", Zbl. Bakr., 1994, pp. 491-494, vol. 281(4).
Puuwels et al., "Lactic Acid Bacteria as Antigen Delivery Vehicles for Oral Immunization Purposes", International Journal of Food Microbiology, 1998, pp. 155-167, vol. 41(2).
Quesada-Chanto et al., "Effect of the Oxygen Supply on Pattern of Growth and Corrinoid and Organic Acid Production of *Propionibacterium shermanii*", Appl Microbiol Biotechnol. 1998, pp. 732-736, vol. 49(6).
Quesada-Chanto et al., "Microbial Production of Propionic Acid and Vitamin B12 Using Molasses or Sugar", Appl microbiol Biotechnolog, 1994, pp. 378-383, vol. 41(4).
Quesada-Chanto et al., "Optimization of a *Propionibacterium acidipropionici* Continuous Culture Utilizing Sucrose", Appl. Microbiol Biotechnol, 1994, pp. 16-21, vol. 42(1).
Ravn et al., "Human T Cell Responses Induced by Vaccination with *Mycobacterium bovis bacillus* Calmette-Guerin", The Journal of Immunology, 1997, pp. 1949-1955, vol. 158(4).
Richardson et al., "Application of a Commercial Radioassay Test Kit to the Determination of Vitamin B12 in Food", Analyst, Aug. 1978, pp. 865-868, vol. 103.
Richter et al., "Transgenic Plants as Edible Vaccines", Curr. Top. Microbiol. Immunol., 1999, 159-176, vol. 240.
Riedel et al., "Differentiation of "Classical" *Propionibacterium* Species by Numerical Analysis of Electrophoretic Protein Profiles", System Appl. Microbiol., 1992, pp. 567-572, vol. 15.
Riedel et al., "Identification of Classical *Propionibacterium* Species Using 16S rDNA—Restriction Fragment Length Polymorphisms", System Appl. Microbiol., 1998, pp. 419-428, vol. 21.
Riedel et al., "Justification of the "Classical" *Propionibacterium* Species Concept by Restriction Analysis of the 16S Ribosomal RNA Gnes", Aytem Appl. Microbiol., 1994, pp. 536-542, vol. 17.
Rossi et al., "Genus- and Species-Specific PCR-Based Detection of Dairy *Propionibacteria* in Environmental Samples by Using Primers Targeted to the Genes Encoding 16S rRNA", Applied and Environmental Microbiology, Sep. 1999, pp. 4241-4244, vol. 65(9).
Rossi et al., "Identification and Clustering of dairy *Propionibacteria* by RAPD=PCR and CGE-REA methods", Journal of Applied Microbiology, 1998, pp. 956-964, vol. 85.
Rowland et al., "A Comparison of the Activity of Five Microbial Enzymes in Cecal Content from Rats, Mice and Hamsters and Response to Dietary Pectin", Toxicology and Applied Pharmacology, 1983, pp. 143-148, vol. 69.
Russell-Jones, "Oral Vaccine Delivery", Journal of Controlled Release, 2000, pp. 49-54, vol. 65(1-2).
Salminen et al., "Clinical Applications of Probiotic Bacteria", Int. Dairy Journal, 1998, pp. 563-572, vol. 8(5/6).

Salminen et al., "Demonstration of Safety of Probiotics—A Review", International Journal of Food Microbiology, 1998, pp. 93-106, vol. 44(1-2).
Salminen et al., "Probiotics: How They Should be Defined?". Trends in Food Science & Technology, 1999, pp. 107-110, vol. 10(3).
Sarem et al., "Comparison of the Adherence of Three *Lactobacillus* Strains to Caco-2 and Int-407 Human Intestinal Cell Lines", Letters in Applied Microbiology, 1996, pp. 439-442, vol. 22(6).
Sarkar et al., "Recent Trends in Utilization of *Propionibacterium*—A Review", J. Dairying Foods & Home Sci, 1995, pp. 1-16, vol. 14(1).
Sato et al., "Differential Potentiation of Anti-Mycobacterial Activity and Reactive Nitrogen Intermediate Producing Ability of Murine Peritoneal Macrophages Activated by Interferon-Gamma (IFN-$\gamma$) and Tumour Necrosis Factor-Alpha (TNF-$\alpha$)", Clin Exp. Immunol., 1998, pp. 63-68, vol. 112.
Saunders et al., "Restraining Mycobacteria: Role of granulomas in mycobacterial infections", Immunology and Cell Biology, 2000, pp. 334-341, vol. 78(4).
Schaible et al., "Confrontation between Intracellular Bacteria and the Immune System", Advances in Immunology, 1999, pp. 267-377, vol. 71.
Scheinbach, "Probiotics: Functionality and Commercial Status", Biotechnology Advances, 1998, pp. 581-608, vol. 16(3).
Scott, "Folate and Vitamin B12", Proceedings of the Nutrition Society, 1999, pp. 441-448, vol. 58.
Shaw et al., "Plasma Homocysteine Levels in indigenous Australians", MJA, Jan. 4, 1999, pp. 19-22, vol. 170(1).
Sieling et al., "CD1-Restricted T Cell Recognition of Microbial Lipoglycan Antigens", Science, Jul. 14, 1995, pp. 227-230, vol. 269(5221).
Silva et al., "Cytotoxic T Cells and Mycobacteria", FEMS Microbiology Letters, 2001, pp. 11-18,vol. 197.
Somkuti et al., "Cholesterol Uptake by *Propionibacterium freudenreichii*", Current Microbiology, 1990, pp. 305-309, vol. 20(5).
Stambas et al., "Oxidised Mannan as a Novel Adjuvant Inducing Mucosal IgA Production", Vaccine, 2002, pp. 1068-1078, vol. 20(7-8).
Steffen et al., "Relationship between Cecal Population Levels of Indigenous Bacteria and Translocation to the Mesenteric Lymph Nodes", Infection and Immunity, Mar. 1983, pp. 1252-1259, vol. 39(3).
Stenger et al., "T Cell Mediated Immunity to Mycobacterium tuberculosis", Current Opinions in Microbiology, 1999, pp. 89-93, vol. 2(1).
Sun et al., "Cholera Toxin B Subunit: An Efficient Transmucosal Carrier—Delivery System for Induction of Peripheral Immunological Tolerance", Proc. Natl. Acad. Sci., Nov. 1994, pp. 10795-10799, vol. 91(23).
Sutter, "Anaerobes as Normal Oral Flora", Reviews of Infectious Diseases, Mar.-Apr. 1984, pp. S62-S66, vol. 6(Suppl 1).
Swift et al., "Scanning Electron Microscopy of Rat Intestinal Microvilli", Letters to the Editor, The Lancet, Oct. 26, 1968, p. 915, vol. 2(7574).
Takeda et al., "Mitogenic Activity of Whole Cells and Cell Wall Components of *Lactobacillus acidophilus* Group Lactic acid Bacteria on Murine Spleen and Peyer's Patch Cells", Milchwissenschaft, 1997, pp. 21-25, vol. 52(1).
Tascon et al., "Protection against Mycobacterium tuberculosis Infection by CD8+ T Cells Requires the Production of Gamma Interferon", Infection and Immunity, Feb. 1998, pp. 830-834, vol. 66(2).
Taylor et al., "Effects of Probiotics and Prebiotics on Blood Lipids", British Journal of Nutrition, Suppl. 2, 1998, pp. S225-S230, vol. 80(4).
Toy et al., "Basic and Clinical Overview of the Mucosal Immune System", Seminars in Gastrointestinal Disease, Jan. 1998, pp. 2-11, vol. 7(1).
Tripathy et al., "Fifteen-year Follow-Up of the Indian BCG Prevention Trial", XXVIth IUAT World Conference, 1987, pp. 69-72.
Tsakalidou et al., "The Combined Use of Whole-Cell Protein Extracts for the Identification (SDS-Page) and Enzyme Activity Screening of Lactic Acid Bacteria Isolated from Traditional Greek Dairy Products", System Appl. Microbiol., 1994, pp. 444-458, vol. 17.

Tsuyuguchi, "Regulation of the Human Immune Response in Tuberculosis", Infectious Agents and Disease, 1996, pp. 82-97, vol. 5(2).

Tuomola et al., "Adhesion of Some Probiotic and Dairy *Lactobacillus* Strains to Caco-2 Cell Cultures", International Journal of Food Microbiology, 1998, pp. 45-51, vol. 41(1).

Tuomola et al., "Human Ileostomy Glycoproteins as a Model for Small Intestinal Mucus to Investigate Adhesion of Probiotics", Letters in Applied Microbiology, 1999, pp. 159-163, vol. 28(3).

Van Der Griend et al., "Hyperhomocysteinaemia as a Cardiovascular Risk Factor: an Update", The Netherlands Journal of Medicine, 2000, pp. 119-130, vol. 56(3).

Vogel, F.R., "Improving Vaccine Performance with Adjuvants", Clinical Infectious Diseases, 2000, pp. S266-S270, vol. 30, (Suppl. 3).

Wang et al., "The Protective Effects of High Amylose Maize (Amylomaize) Starch Granules on the Survival of *Bifidobacterium* spp. in the Mouse Intestinal Tract", Journal of Applied Microbiology, 1999, pp. 631-639, vol. 87.

Weldingh et al., "Immunological Evaluation of Novel Mycobacterium tuberculosis Culture Filtrate Porteins", FEMS Immunology and Medical Microbiology, 1999, pp. 159-164, vol. 23(2).

Wilcken et al., "B Vitamins and Homocysteine in Cardiovascular Disease and Aging", Annals of New York Academy of Sciences, 1998, pp. 361-370, vol. 854.

Wynn et al., "The Danger of B12 Deficiency in the Elderly", Nutrition and Health, 1998, pp. 215-226, vol. 12(4).

Ye et al., "Efficient Production of Vitamin B12 from Propionic Acid Bacteria under Periodic Variation of Dissolved Oxygen Concetration", Journal of Fermentation and Bioengineering, 1996, pp. 484-491, vol. 82(5).

Zhou et al., "Acute Oral Toxicity and Bacterial Translocation Studies on Potentially Probiotic Strains of Lactic Acid Bacteria", Food and Chemical Toxicology, 2000, pp. 153-161, vol. 38(2).

Boyd et al., "Comparison of API 50 CH Strips to Whole-Chromosomal DNA Probes for Identification of *Lactobacillus* Species", J Clin Microbiol., Oct. 2005, 5309-5311, vol. 43(10).

McArthur et al., "Genetic diversity of bacteria along a stream continuum", Journal of the North American Benthological Society, 1992, 269-277, vol. 11(3).

Rosenzweig et al., "Microbial Evolution in a Simple Unstructured Environment: Genetic Differentiation in *Escherichia coli*", Genetics, Aug. 1994, 903-917, vol. 137(4).

Harrigan, "A Scheme for the Identification of Gram-positive Bacteria", Laboratory Methods in Food Microbiology, Third Edition, Academic Press, San Diego, California, 1998, Chapter 39, 333-336.

Holt, "Bergey's Manual of Systematic Bacteriology"; Table 15.1; 1986, p. 1263, vol. 2.

Jones et al., "Serology and Chemotaxonomy", Bacterial Classification V, 1989, Bergey's Manual of Systematic Bacterlology. The Williams & Wilkins Co., Baltimore, vol. 4; pp. 979-982.

Stine et al., "Measuring Toxicity and Assessing Risk", Principles of Toxicology, CRC Press, 1996, Chapter 1, pp. 1-10.

\* cited by examiner (A)

(B)

(C)

(D)

SEQUENCE LISTING

```
<160> NUMBER OF SEQ ID NOS: 19

<210> SEQ ID NO 1
<211> LENGTH: 10
<212> TYPE: DNA
<213> ORGANISM: proprionibacterium

<400> SEQUENCE: 1
ggcatgacct                                                            10

<210> SEQ ID NO 2
<211> LENGTH: 10
<212> TYPE: DNA
<213> ORGANISM: proprionibacterium

<400> SEQUENCE: 2
tgggcgtcaa                                                            10

<210> SEQ ID NO 3
<211> LENGTH: 12
<212> TYPE: DNA
<213> ORGANISM: proprionibacterium

<400> SEQUENCE: 3
```

-continued

```
gccgccgccg cc                                           12

<210> SEQ ID NO 4
<211> LENGTH: 12
<212> TYPE: DNA
<213> ORGANISM: : proprionibacterium

<400> SEQUENCE: 4
cgccgccgtc gc                                           12

<210> SEQ ID NO 5
<211> LENGTH: 10
<212> TYPE: DNA
<213> ORGANISM: proprionibacterium

<400> SEQUENCE: 5
acgcaggcac                                              10

<210> SEQ ID NO 6
<211> LENGTH: 16
<212> TYPE: DNA
<213> ORGANISM: proprionibacterium
<220> FEATURE:
<221> NAME/KEY: misc_feature
<222> LOCATION: (1)..(16)
<223> OTHER INFORMATION: m is a or c
      d is a, g or t
      n is a,g,c or t
      w is a or t

<400> SEQUENCE: 6
madgcgtagn cgawgg                                       16

<210> SEQ ID NO 7
<211> LENGTH: 16
<212> TYPE: DNA
<213> ORGANISM: proprionibacterium
<220> FEATURE:
<221> NAME/KEY: misc_feature
<222> LOCATION: (1)..(16)
<223> OTHER INFORMATION: w is a or t
      n is a, g, c or t
      b is c, g or t

<400> SEQUENCE: 7
gtgwcggttt nbggta                                       16

<210> SEQ ID NO 8
<211> LENGTH: 15
<212> TYPE: DNA
<213> ORGANISM: proprionibacterium

<400> SEQUENCE: 8
gggtgaccgg ccaca                                        15

<210> SEQ ID NO 9
<211> LENGTH: 15
<212> TYPE: DNA
<213> ORGANISM: proprionibacterium

<400> SEQUENCE: 9
aaggtgggga tgagc                                        15

<210> SEQ ID NO 10
<211> LENGTH: 15
<212> TYPE: DNA
```

```
<213> ORGANISM: proprionibacterium

<400> SEQUENCE: 10
tcgggtgtta ccgac                                                    15

<210> SEQ ID NO 11
<211> LENGTH: 19
<212> TYPE: DNA
<213> ORGANISM: proprionibacterium
<220> FEATURE:
<221> NAME/KEY: misc_feature
<222> LOCATION: (1)..(19)
<223> OTHER INFORMATION: r is a or g

<400> SEQUENCE: 11
aggaggtgat ccarccgca                                                19

<210> SEQ ID NO 12
<211> LENGTH: 20
<212> TYPE: DNA
<213> ORGANISM: proprionibacterium

<400> SEQUENCE: 12
tgctttcgat acgggttgac                                               20

<210> SEQ ID NO 13
<211> LENGTH: 18
<212> TYPE: DNA
<213> ORGANISM: proprionibacterium
<220> FEATURE:
<221> NAME/KEY: misc_feature
<222> LOCATION: (1)..(18)
<223> OTHER INFORMATION: m is a or c

<400> SEQUENCE: 13
agtttgatcm tggctcag                                                 18

<210> SEQ ID NO 14
<211> LENGTH: 23
<212> TYPE: DNA
<213> ORGANISM: proprionibacterium

<400> SEQUENCE: 14
agtggcgaag gcggttctct gga                                           23

<210> SEQ ID NO 15
<211> LENGTH: 24
<212> TYPE: DNA
<213> ORGANISM: proprionibacterium

<400> SEQUENCE: 15
tggggtcgag ttgcagaccc caat                                          24

<210> SEQ ID NO 16
<211> LENGTH: 24
<212> TYPE: DNA
<213> ORGANISM: proprionibacterium

<400> SEQUENCE: 16
ctttcatcca tgacgaagcg caag                                          24

<210> SEQ ID NO 17
<211> LENGTH: 21
<212> TYPE: DNA
<213> ORGANISM: proprionibacterium
```

-continued

```
<400> SEQUENCE: 17
gacgaagtgc ctatcggggt g                                              21

<210> SEQ ID NO 18
<211> LENGTH: 24
<212> TYPE: DNA
<213> ORGANISM: proprionibacterium

<400> SEQUENCE: 18
gacgaaggca ttcttttagg gtgt                                           24

<210> SEQ ID NO 19
<211> LENGTH: 23
<212> TYPE: DNA
<213> ORGANISM: proprionibacterium

<400> SEQUENCE: 19
ggacaaaagg cctttcgggg ttt                                            23
```

PROBIOTIC PROPIONIBACTERIUM

CROSS-REFERENCE TO RELATED APPLICATIONS

This application is a continuation of International Application PCT/AU2003/000775 filed June 20, which claims priority to Australian Application Nos. PS 3124 filed Jun. 21, 2002, PS 3152 filed Jun. 24, 2002, and 2002952793 filed Nov. 18, 2002.

TECHNICAL FIELD

The present invention relates to probiotic *Propionibacterium* strains and their use in the preparation of probiotic supplements and foods. The invention relates to the provision of Vitamin B12, propionic acid, folacin and bacteriocins by probiotic strains, stimulation of bifidobacteria growth, production of favourable effects on the lipid metabolism and on the immune system of hosts through immunostimulation, immunomodulation or use of a probiotic strain as an adjuvant, reduction of homocysteine and β glucuronidase and the prevention, treatment or amelioration of conditions associated with a need for these activities. The probiotic bacteria of the invention can be used in humans or other animals. In at least some applications, the bacteria can be used dead and parts rather than whole cells may be used. The present invention also relates to the preparation of vaccines for use in protecting patients from infectious diseases, in particular tuberculosis.

BACKGROUND OF THE INVENTION

Probiotics

Probiotics, which are introduced into the gastrointestinal tract, can influence gastrointestinal microflora and play a beneficial role in the host. The term 'probiotic' is derived from the Greek meaning 'for life'. It was first used to describe substances secreted by one microorganism which stimulated the growth of another microorganism (Lilly and Stillwell, 1965). In 1992, Havenaar suggested that probiotics be defined as 'mono- or mixed cultures of live microorganisms which, when applied to animal or man, beneficially affect the host by improving the properties of the indigenous microflora (Havenaar et al., 1992). Havenaar's definition was the first that applied the term probiotics to both humans and animals. In consideration of the current applications and proven effects of probiotics, Salminen et al (1999) proposed a new definition: Probiotics are microbial cell preparations or components of microbial cells that have a beneficial effect on the health and well-being of the host. This definition includes microbial cells (viable or non-viable) and parts of cells as probiotics, but not metabolites such as antibiotics. This definition also indicates the application of probiotics is not restricted to use in foods.

Recently some evidence has indicated that dairy *Propionibacterium* strains can have beneficial effects, including the production of propionic acid, folacin, bacteriocins, and vitamin $B_{12}$; stimulation of bifidobacteria growth, and favourable effects on the lipid metabolism and the immune system of hosts. The use of *Propionibacterium* strains enhances the nutritional and therapeutic qualities of the food, extends the shelf life of the product, inhibits the growth of pathogenic and harmful microflora and contributes better organoleptic properties to the product.

Dairy propionibacteria consist of four species in the genus *Propionibacterium: P. freudenreichii; P. acidopropionici; P. jensenii;* and *P. thoenii.* All four dairy propionibacteria species are found to live in foods, which include any fresh, uncooked food, such as vegetables, fruits, nuts, germinated seeds, beans, dairy products and certain fermented items.

Propionibacteria are widely used as starter cultures in the food industry. *Propionibacterium* species are traditionally used during the manufacture of Swiss or Swiss-type cheeses, producing 'eyes' and the typical sweet flavour of Swiss cheeses. *Propionibacterium* species are also used in vegetable fermentation, as food and feed additives, in infant foods and for the biosynthesis of propionic acid and vitamin $B_{12}$.

Where the probiotic effect depends on a viable organism, a probiotic strain cannot affect its host unless its population reaches a certain minimum level around $10^6$ to $10^8$ cfu/g of intestinal contents. Such probiotic bacteria, which are delivered orally, have to survive the upper gastrointestinal tract, then reach and persist in the lower part of the gut to exert their beneficial effects on the host.

The low pH of the stomach and the antimicrobial action of pepsin are known to provide an effective barrier against entry of bacteria into the intestinal tract. The pH of the stomach ranges from 2.5 to 3.5, but can reach as low as pH1.5, or as high as pH6 or above after food intake. The type of food affects the emptying of the stomach. Normally, food remains in the stomach between two and four hours, however, liquids empty from the stomach within about 20 minutes. Extensive in vitro tests have been used to select gastric transit tolerant, including acid tolerant, lactic acid bacteria (Charteris et al, 1998; Clark et al, 1993; Chou and Weimer, 1999). There has been, however, only limited research into the in vitro acid tolerance of propionibacteria and this was with two *Propionibacterium freudenreichii* strains (Jan et al 2000; Mantere-Alhonen, 1983).

Another barrier probiotic bacteria must survive is the small intestine. The adverse conditions of the small intestine include the presence of bile salts and pancreatin. The transit time for food through the small intestine is generally between one and four hours. Bile salt-resistant lactic acid bacteria can be selected by testing their ability to survive in the presence of bile salt and their growth in selective medium with various levels of bile (Gilliland et al, 1984; Ibrahim and Bezkorovainy, 1993; Clark and Martin, 1994; Chung et al, 1999). A concentration of 0.15-0.3% bile salt has been reported as a suitable concentration to select probiotics for human use. No report has been found concerning the small intestinal transit tolerance of *Propionibacterium* strains.

After surviving passage through the upper gastrointestinal tract, probiotic bacteria need to adhere to the gut epithelium in order to colonize and persist in the gastrointestinal tract. The complexity of the intestinal mucosa and its microflora make it very difficult to study bacterial adhesion in vivo. Living probiotic microorganisms can provide nutritional benefits either during the preparation of fermented probiotic foods or in the digestive tract of hosts. After fermentation, the texture and flavour of raw materials can be significantly improved; the adverse effects of some components in foods can be reduced, such as food intolerance and allergies caused by some oligosaccharides and proteins; levels of amino acids and vitamins can be increased to improve the nutritive value of the food; and sugars and other spoilage promoting components of foods are removed, which leads to longer shelf-life and ensures food safety. Evidence has been presented that the bioavailability of calcium, zinc, iron, manganese, copper and phosphorus is increased in fermented yoghurt compared to in milk. Studies have also demonstrated an increase in riboflavin and niacin in yoghurt, vitamin $B_6$ in cheddar cheese, vitamin $B_{12}$ in cottage cheese and folic acid in a variety of products including yoghurt, cottage cheese, Cheddar cheese and sour cream. The enzymatic hydrolysis of probiotic microorganisms has also been shown to enhance the bioavailability of protein and fat. Bacterial protease can increase the production of free amino acids which can benefit the nutritional status of the host especially if the host has an endogenous protease deficiency.

Consumption of foods containing viable probiotics is reported to produce health benefits which include (1) alleviation of intestinal disorders such as constipation and diarrhoea caused by infection by pathogenic organisms, antibiotics, or chemotherapy; (2) stimulation and modulation of the immune system; (3) anti-tumor effects due to inactivation or inhibition of carcinogenic compounds in the gastrointestinal tract by reduction of intestinal bacterial enzyme activities such as β-glucuronidase, azoreductase, and nitroreductase; (4) reduced production of toxic end products such as ammonia, phenols and other metabolites of protein known to influence liver cirrhosis (5) reduction in serum cholesterol and blood pressure; (6) maintenance of mucosal integrity; (7) alleviation of symptoms of lactose intolerance; (8) prevention of vaginitis.

Non-viable probiotics and cell wall components of some probiotic strains also have beneficial effects on hosts and are less likely to cause safety concerns than intact cells.

*Propionibacterium* strains contain uniquely high concentrations of vitamin $B_{12}$ (Hettinga and Reinbold, 1972a) and their vitamin $B_{12}$ production has been considered the most efficient (Hettinga and Reinbold, 1972b). *Propionibacterium* strains are often used for vitamin $B_{12}$ enrichment of cultured milk products and fermented beverages. Inclusion of *P. freudenreichii* subsp. *shermanii* results in an increase of vitamin $B_{12}$ in Kefir, Streptococci cultured milks, Tvorog cheese, Domiati cheese, and Zabady cheese. Inclusion of *P. freudenreichii* subsp. *shermanii* increases folic acid content in cultured milk products and fermented beverages, including Kefir and Streptococci cultured milks.

Vitamin $B_{12}$ production by propionibacteria has been correlated with cellular yields. The vitamin $B_{12}$ production level is affected by many factors, including the presence of cobalt, inclusion of different media supplements, dissolved oxygen concentration, and the pH of the fermentation broth (Hettinga and Reinbold, 1972b, Quesada-Chanto et al., 1994b, Berry and Bullerman, 1966, Quesada-Chanto et al., 1998).

Vitamin $B_{12}$ is essential for the growth and health of human beings. It is required for the production of red blood cells and myelin surrounding nerves, and acts as a coenzyme in the metabolism of fatty acids, carbohydrates and proteins. Natural synthesis of vitamin $B_{12}$ occurs only in microorganisms. Microbial synthesis of vitamin $B_{12}$ does occur in the human colon, but it is not absorbed. Therefore, human beings appear to be entirely dependent on a dietary intake of vitamin $B_{12}$ to maintain adequate serum levels and body store.

Vitamin $B_{12}$ is a term used in nutritional literature, however, in most biochemical and chemical texts, cobalamin is used rather than vitamin $B_{12}$. The term 'vitamin $B_{12}$' now is used as a generic name for cobalamins which exhibit antipernicious anaemia activity.

Vitamin $B_{12}$ deficiency is reported to be one of the risk factors for heart disease, multiple sclerosis, stroke, breast cancer, Alzheimer's disease, some psychiatric syndromes and accelerated aging (Choi, 1999, Wynn and Wynn, 1998, Gariballa, 2000, Delva, 1997). The prevalence of vitamin $B_{12}$ deficiency varies with the age and general health of the population, the normal serum vitamin $B_{12}$ threshold, and other criteria required for diagnosis.

A more prevalent, mild and preclinical cobalamin deficiency has been recently recognised. Preclinical deficiency is the state in which metabolic evidence of insufficiency exists in a person who has no clinical symptoms, including megaloblastic anaemia (Carmel, 2000).

Vitamin $B_{12}$ deficiency may be caused by either hereditary factors or acquired factors.

Most vitamin $B_{12}$ deficiency is associated with inadequate nutritional intake. Animal products, such as meat, fish, egg, and dairy products contain adequate amounts of vitamin $B_{12}$ for the human body. Vegetarian diets generally have levels of vitamin $B_{12}$ lower than the RDI. People on vegetarian diets and their infants tend to have a low level of vitamin $B_{12}$ and develop vitamin $B_{12}$ deficiency. Studies show that low serum vitamin $B_{12}$ levels are found not only in strict vegetarians but also lactovegetarians and lacto-ovovegetarians. Vitamin $B_{12}$ deficiency is a real hazard in unsupplemented or unfortified vegan and vegetarian diets. Many processed vegetarian foods are fortified with vitamin $B_{12}$, however these foods are not available to some vegetarians because of ethical or economic reasons. Vitamin $B_{12}$ deficiency has been shown to result in retardation of growth and psychomotor development in children. Therefore, particular care should be taken with children on vegetarian diets to ensure adequate vitamin $B_{12}$ intake occurs.

Another cause of vitamin $B_{12}$ deficiency is food-vitamin $B_{12}$ malabsorption.

Laboratory rats have been used to study the effects of vitamin $B_{12}$ deficiency. Vitamin $B_{12}$ deficiency causes growth retardation, energy metabolism depression and an increase in urinary methylmalonic acid (MMA) excretion in rats. Vitamin $B_{12}$ deficiency also affects testicular tissue in rats.

Treatment for vitamin $B_{12}$ deficiency varies according to the cause of the deficiency. The two most frequent treatments for vitamin $B_{12}$ deficiency are parenteral injection and oral therapy.

It has been found that large numbers of patients do not seek medical advice in the early stages of vitamin $B_{12}$ deficiency. Vitamin $B_{12}$ food supplements and common food fortification with vitamin $B_{12}$ could prevent the occurrence of vitamin $B_{12}$ deficiency in some patients, reduce the problems of deficiency and reduce health care costs.

All vaccines have one aim, this being to "prime the immune system to swiftly destroy specific disease-causing agents, or pathogens, before the agents can multiply enough to cause symptoms" (Langridge, 2000).

The world's biggest killer from a single infectious agent is tuberculosis (TB) (WHO, 1992). Tuberculosis is a disease that primarily affects the lungs, and is caused by the bacterium *Mycobacterium tuberculosis*. Currently there are 2 billion people infected with the bacterium (Agger & Andersen, 2001). This equates to one third of the world's population. The majority of these cases are in the developing world where health care is at a minimum. Three million people die annually from the disease that has a fatality rate of 50% if left untreated (Collins & Kaufmann, 2001). The vaccine currently available for TB, the BCG, has varying rates of effectiveness ranging from 0-80% in different populations (Guerin, 1997), and to date has been largely ineffective in preventing the proliferation of this disease. It has been estimated that the development of a new vaccine with only 50% efficacy could prevent 9 million deaths from tuberculosis by the year 2030 (Murray & Salomon, 1998).

*M. tuberculosis* is a highly successful pathogen that has evolved numerous mechanisms to evade the immune response of the host (Flynn, 1999). The human immune response to TB is unique and complicated, involving a strong T helper 1, cell mediated response. The challenges of the bacterium itself, combined with attempting to stimulate the correct aspects of the immune system, has made years of attempts to produce a vaccine significantly better than the BCG, futile.

Tuberculosis, in its active form, causes symptoms such as a persistent cough, chest pain, fever, weight loss, night sweats and in advanced cases bloody sputum (Vaccine Weekly, editorial, 2001a). Tuberculosis is primarily transmitted through the air suspended in tiny droplets of sputum via coughing, sneezing, talking and laughing (Miller & Schieffelbein, 1998). However repeated exposure over a prolonged period of time, in conjunction with the intensity of exposure, is necessary for transmission and establishment of disease in the host (NIAID, 1999; Miller & Schieffelbein, 1998).

With proper antibiotic treatment, there is a 90% cure rate (NIAID, 1999; Collins & Kaufmann, 2001). However there are problems with this method of treatment. Administering treatment requires supervision to ensure compliance, it is relatively expensive, has many side effects and a cure requires more than six months treatment (Broker, 1999). A recent study has shown that resistance has been developed in a multitude of countries to the four main drugs used to treat TB, isoniazid, rifampin, ethambutol and streptomycin (Mustafa, 2002). This means that infection with multi-drug resistant tuberculosis (MDR-TB) strains cannot be effectively treated with any of the available drugs, and the death rate of MDR-TB patients is 40-60% (NIAID, 1999).

Mycobacterium tuberculosis can infect a host but reside dormant inside the body without exhibiting symptoms of active disease. This is known as a latent tuberculosis infection. The danger with latent infections is that they can reactivate at any time, usually when the host is in a weakened state, particularly when co-infected with auto-immune diseases such as HIV/AIDS or in the elderly (NIAID, 1996; Tsuyuguchi, 1996). More than 50% of people with a HIV/TB co-infection will develop active tuberculosis. When the immune system is weakened the bacteria breaks out of the macrophages, where it was residing in a dormant state, and enters the blood stream to cause disease. If left untreated, 50% of those with active disease will die (NIAID, 1996).The majority of tuberculosis cases occur in the world's poorest nations (Kaufmann & Hess, 2000), where health care is at a minimum and malnutrition and HIV are commonplace.

The most popular initiative since BCG to combat tuberculosis, and the ensuing proliferation of resistant stains of TB, is WHO's directly observed therapy short-course (DOTS) (Collins & Kaufmann, 2001). This strategy aims to increase patient compliance to taking the full course of standardised short-course chemotherapy (Gleissberg, 1999). This in turn aims to eliminate the conditions that select out antibiotic resistant strains of M. tuberculosis by ensuring the full course of medication is taken. However this strategy, is likely to be as ineffective as BCG at controlling the problem. Statistics show that the success rate of such therapy is only 62% in certain African countries (Collins and Kaufmann, 2001). Consequently there is a general agreement that TB will not be eradicated from the world through chemotherapeutic regimes alone (Hess & Kaufmann, 1999).

BCG is the most widely used vaccine in the world (Kaufmann and Hess, 2000). To date over 3 billion doses have been administered (Collins, 2000). A controlled, clinical trial beginning in 1968 in India involving 265,000 subjects, showed that participants in the placebo group had marginally better immunity to TB than those that received BCG (Tripathy, 1987). BCG was created at the start of last century and consists of a live attenuated strain of Mycobacterium bovis, the strain of mycobacterium that causes tuberculosis in cattle. This strain is closely related to M. tuberculosis with a greater than 90% DNA homology, hence it was expected that it would prime an excellent immune response to infection with M. tuberculosis (Andersen, 2001). Despite this the BCG vaccine has not been the solution to tuberculosis it was anticipated to be when it was created (Ravn et al, 1997). Recent research has shown that the BCG vaccine actually lacks vital proteins with good antigenic properties that have now been identified as playing a pivotal role in the immune response to TB (Ravn et al, 1997).

It is thought that the lack of certain essential antigens in BCG is due to the occurrence of genetic deletions during the attenuation process (Elhay & Andersen, 1997). BCG was created by attenuating M. bovis through serial passage on bile-containing agar plates (Kaufmann & Hess, 2000). These valuable proteins, now lost, include the intensively researched esat-6, which is strongly recognised in tuberculosis patients (Collins, 2000).

Recent field trials have shown protection levels from BCG to be very low and in some cases undetectable (Andersen, 2001).

Brandt et al (2002) confirmed the long held hypothesis that exposure to certain environmental mycobacteria stimulates an immune response that controls the multiplication of BCG, and hence prevents a full vaccine-induced immune response from developing (Brandt et al, 2002). Although exposure to environmental bacteria does prime the immune system and provides a certain level of protection from other mycobacteria, the protection is not sufficient to significantly reduce the growth of M. tuberculosis in animal models (Brandt et al, 2002).

This study concluded that "BCG, as a live vaccine, is particularly sensitive to the influence of preexisting immune responses to antigens shared between M. avium and BCG" (Brandt et al, 2002), and hence can account, in part for the ineffectiveness of the BCG vaccine. In addition to this BCG is also a hindrance to the detection and early treatment of the disease by producing false positives on the main tool for diagnosis, the PPD skin test (Fatkenheuer et al, 1999).

Despite BCG's clearly evident downfalls and inadequacies, the synthesis of new prototype vaccines has yet to produce immune responses in animal models that are significantly more effective than BCG (Andersen, 1994). The major reason why BCG has continued to be administered around the world is the advantage of the vaccine being safe, easy to produce and cheap, at only a few cents per shot (Orme, 1999).

The above discussion of background art is included to explain the context of the present invention. It is not to be taken as an admission that any of the documents or other material referred to was published, known or part of the common general knowledge in Australia at the priority date of any one of the claims of this specification.

Throughout the description and claims of this specification, the word "comprise" and variations of that word, such as "comprising" and "comprises" are not intended to exclude other additives, steps or integers.

BRIEF SUMMARY OF THE INVENTION

In a first aspect the present invention provides a novel isolated Propionibacterium strain, Propionibacterium jensenii 702. Propionibacterium jensenii 702 was deposited under the provisions of the Budapest Treaty at the Australian Government Analytical Laboratories, 1 Suakin Street Pymble NSW 2073 Australia under accession number NM02/29517 on 12 Jun. 2002.

In a second aspect the invention provides a formulation comprising *Propionibacterium jensenii* 702 together with a culture medium, storage medium excipient, carrier or diluent.

In a third aspect the present invention provides use of *Propionibacterium jensenii* 702 as a probiotic strain. The strain can be used as a probiotic in humans or in other animals. The bacterium can be used alive or dead and parts of the bacterium can be used.

In a fourth aspect the present invention provides a Vitamin $B_{12}$ supplement comprising *Propionibacterium jensenii* 702 together with a delivery agent. It will be understood that delivery agents suitable for use in the supplement include pharmaceutically acceptable delivery agents.

The supplement may be provided in the form of a capsule, tablet or powder (loose or in capsules), granule or paste. The supplement also can be prepared as an oral spray. In another embodiment it is provided in the form of a vitamin $B_{12}$ fortified food product, such as a breakfast cereal, soy milk product, or vegetarian burger patty.

In a fifth aspect the present invention provides a method for preventing, treating or ameliorating the adverse effects of Vitamin $B_{12}$ deficiency in a host which method comprises administering a supplement or food of the invention to the host. The host may be a human or other animal.

In a sixth aspect the invention provides a growth promoter for animal feed comprising *Propionibacterium jensenii* 702 together with a suitable carrier, excipient or diluent.

Feeding animals with propionibacteria can improve their growth, vitamin supply and inhibition of harmful intestinal bacteria without side effects associated with antibiotics or chemotherapeutic growth promoters.

In a seventh aspect the present invention provides a method of improving growth and/or vitamin supply and/or inhibiting harmful intestinal bacteria in a host animal comprising administering an effective dose of the growth promoter of the sixth aspect to the host animal. It will be understood that this aspect of the invention also embraces a method for the manufacture of a growth promoter of the sixth aspect of the invention for use in a method of improving growth and/or vitamin supply and/or inhibiting harmful intestinal bacteria in a host animal comprising administering an effective dose of the growth promoter of the sixth aspect to the host animal.

In an eighth aspect the invention provides a method of preventing food spoilage and/or extending the shelf life of food products comprising preparing the food by including a fermentation step involving use of *Propionibacterium jensenii* 702.

Fermented foods have a long consumption history and often have better quality and function than the original food materials.

Dairy starters, including lactic acid bacteria and propionibacteria, can restrict the growth of spoilage and pathogenic organisms due to their ability to produce inhibitory metabolites in fermented products. Inhibitors include broad-spectrum antagonists, organic acids, diacetyl, and hydrogen peroxide. Some starters also produce bacteriocins or bactericidal proteins active against species that usually are related closely to the producer culture. Propionibacteria can produce propionic acid, propionates, diacetyl and bacteriocins. Propionic acid demonstrates broader inhibition than acetic and lactic acids. Propionic acid and its sodium and calcium salts are effective antimycotics and are added to many baked products to inhibit molds. The propionates also inhibit Gram-negative bacteria but are ineffective against Gram-positive species. Diacetyl has inhibitory effects on yeast, lactic acid bacteria, Gram-positive species and Gram-negative cultures. It has also been reported that *Propionibacterium freudenreichii* subsp. *shermanii* JS has been used with *Lactobacillus rhamnosus* LC 705 in fermented milks and bread to improve the shelf life of the products. The mixed culture was found to inhibit spoilage yeasts, molds and *Bacillus* sp.

In a ninth aspect the present invention provides a method of preventing food spoilage and/or extending the shelf life of food products comprising preparing the food by including a fermentation step involving use of *Propionibacterium jensenii* 702 in mixed culture with another food fermentation microorganism.

In a tenth aspect the invention provides a food prepared using *Propionibacterium jensenii* 702 or parts thereof.

In one embodiment the food is a cultured milk product such as Propioni-*acidophilus* milk.

In an eleventh aspect there is provided a method of preparing a food comprising using *Propionibacterium jensenii* 702 or parts thereof in the preparation.

Probiotic foods include 'fermented' probiotic food and 'non-fermented' probiotic food. 'Fermented' probiotic food contains live probiotic microorganisms which have grown in the food and produced a fermented product. 'Non-fermented' probiotic food contains probiotic microorganisms or their components which have been added to the food without noticeably changing the organoleptic properties of the food. 'Fermented' probiotic foods include probiotic dairy foods, cheese, butter, cream, yoghurt and drinking yoghurt and some frozen foods. The foods may be liquid. The raw materials used in 'fermented' probiotic foods include milk, soy milk, grain, legumes, fruit products and vegetable products.

Probiotic foods may contain one or several strains of microorganisms. The food may be prepared by adding the one or more microorganisms to the already prepared food. Alternatively, the one or more microorganisms may be added to the food during preparation. This may result in growth of the microorganism(s) within the food and resultant effects on the properties of the food. The microorganism(s) may participate in fermentation of raw materials in the preparation. The microorganism(s) may provide partial or complete fermentation of raw materials in the preparation. The microorganisms used in this aspect may only provide fermentative functions or may provide fermentation and probiotic functions.

The food may be prepared using one or more microorganisms and then have further microorganisms added.

Lactic acid bacteria and probiotic cultures for commercial food production, and starter cultures for fermentation can be purchased from international companies such as Christian Hansen Pty Ltd (Bayswater, Australia) and Gist-Brocades Australia Pty Ltd (Moorebank, Australia). Other research organisations such as the CSIRO Starter Culture Collection (Highett, Australia) and the Australian Starter Culture Research Centre (Werribee, Australia), have good lactic acid bacteria and potential probiotic collections but these organisms are only available on a small scale.

In a twelfth aspect the invention provides a method of treating gastrointestinal disease and/or lactose intolerance in a patient comprising administering a food or supplement of the invention to the patient. In one embodiment the patient is an infant. The patient could also be a non-human animal. It will be understood that this aspect of the invention also embraces a method for the manufacture of a food or supplement of the invention for use in a method of treating gastrointestinal disease and/or lactose intolerance in a patient comprising administering a food or supplement of the invention to the patient.

*Propionibacterium* strains are used in infant foods in the treatment of gastrointestinal diseases and lactose intolerance. Propioni-*acidophilus* milk prepared using *Lactobacillus aci-*

*dophilus* and *P. freudenreichii* subsp. *shermanii* was shown to be more efficacious than *acidophilus* milk in the treatment of staphylococcal infection of the intestine of infants. Various cultured milk products have been found to be effective in the treatment of lactose-intolerant infants. The enzyme β-galactosidase, required for lactose hydrolysis, has been found to be present in *Propionibacterium* at higher concentration than those observed in lactic acid bacteria. It has been recommended that propionic acid bacteria be used for the manufacture of cultured milk products to treat lactose intolerant patients.

In a thirteenth aspect the present invention provides a method for enhancing the growth of bifidobacteria in the gut of a host comprising administering *Propionibacterium jensenii* 702 or a food or supplement of the invention to the host. The host may be a human or other animal. It will be understood that this aspect of the invention also embraces a method for the manufacture of a food or supplement of the invention for use in a method for enhancing the growth of bifidobacteria in the gut of a host comprising administering *Propionibacterium jensenii* 702 or a food or supplement of the invention to the host.

*Propionibacterium* has been shown to be able to enhance the growth of bifidobacteria in vitro. A bifidogenic growth stimulator was found to be present in the cell-free filtrate of *Propionibacterium freudenreichii* 7025 culture and in the methanol extract fraction of the cells (Kaneko et al., 1994). This water soluble stimulator is stable to heat and proteolytic enzymes, and is different from vitamin $B_{12}$ and organic acids. This stimulator enhanced the growth of *Bifidobacterium bifidum, B. longum, B. breve* and *B. adolescentis* strains. The stimulation effects on bifidobacteria of *Propionibacterium* was also tested in healthy human subjects (Bougle et al., 1999), and the results confirmed the bifidogenic properties of *Propionibacterium freudenreichii*.

In a fourteenth aspect there is provided a mixed culture of *Propionibacterium jensenii* 702 with one or more other probiotic bacteria.

Mixed cultures containing propionibacteria and other probiotic bacteria result in a number of beneficial effects. Mixed cultures of propionibacteria and lactic acid bacteria are widely used in fermentation. When propionibacteria are added with lactic acid bacteria in vegetable fermentation, there are increases in folacin, vitamin $B_{12}$, propionic and acetic acid contents, inhibition of harmful and pathogenic microorganisms and extension of the shelf-life of the products. Furthermore, mixed cultures of *B. longum* and *P. freudenreichii* yield better antimicrobial activities against *M luteus, Pseudomonas* sp., and *S. aureus* than *B. longum* alone.

In addition proboiic bacteria and formulations thereof of the invention can be combined with other agents such as anti oxidants and other molecules which provide beneficial effect to the probiotic.

In a fifteenth aspect the present invention provides a method for affecting the lipid metabolism of a host comprising administering *Propionibacterium jensenii* 702 or a food or supplement of the invention to the host. The host may be a human or other animal. It will be understood that this aspect of the invention also embraces a method for the manufacture of a food or supplement of the invention for use in a method for affecting the lipid metabolism of a host comprising administering *Propionibacterium jensenii* 702 or a food or supplement of the invention to the host.

Propionibacteria can affect the lipid metabolism of their hosts. Mice fed with a diet containing propionibacteria showed a reduced lipid serum concentration. The hypolipemic effect is believed to be due to lower intestinal absorption or higher lipid catabolism because of the presence of the propionibacteria. In another study, various strains of *Propionibacterium freudenreichii* were tested for cholesterol uptake in brain-heart infusion (BHI) medium supplemented with pleuropneumonia-like organism (PPLO) serum fraction as the cholesterol source. The results indicated that *Propionibacterium freudenreichii* reduced the cholesterol content in the medium by 50% after 10-14 days of incubation at 32° C. Furthermore, 70% of cholesterol removed by propionibacteria from the medium can be recovered by solvent extraction from washed propionibacteria cells. The uptake of cholesterol by the propionibacteria did not require strictly anaerobic conditions and was not affected by the presence of bile acids.

In a sixteenth aspect the present invention provides a method for affecting the immune system of a host and alleviating associated disease conditions which method comprises administering *Propionibacterium jensenii* 702 or a food or supplement of the invention to the host. The immune system of the host can be affected by way of immune stimulation, immune modulation or through *Propionibacterium jensenii* 702 or a food or supplement of the invention functioning as an adjuvant. Also *Propionibacterium jensenii* 702 or a food or supplement of the invention can provide alleviation of allergy. Further, dead *Propionibacterium jensenii* 702 or parts thereof can be used for affecting the immune system of a host. The host can be a human or other animal. It will be understood that this aspect of the invention also embraces a method for the manufacture of a food or supplement of the invention for use in a method for affecting the immune system of a host which method comprises administering *Propionibacterium jensenii* 702 or a food or supplement of the invention to the host.

*Propionibacterium* can affect the immune system of the host. The injection of *Propionibacterium avidum* KP-40 into mice decreased the colonization of a lymphosarcoma in liver tissue (Pulverer et al., 1994). *Propionibacterium freudenreichii* subsp. *shermanii* JS has been found to affect the proliferative activity of B and T lymphocytes. An increase in the phagocytic activity of peritoneal macrophages and in carbon-clearance activity was also observed in mice fed with *P. acidopropionici*. Dead *propionibacterium* have been use as immune stimulants in horses.

In a seventeenth aspect the invention provides a method for protecting a probiotic microorganism during passage through the gastrointestinal tract of a host which method comprises administering the probiotic in the presence of a food including a soy or cereal based product. The host may be a human or other animal. In one embodiment the soy based product is soy milk. In another embodiment the cereal based product is a cereal beverage.

In an eighteenth aspect the invention provides a method for treating, preventing or ameliorating the adverse effects of high homocysteine in a host which method comprises administering a food or supplement of the invention to the host. The host may be a human or other animal. It will be understood that this aspect of the invention also embraces a method for the manufacture of a food or supplement of the invention for use in a method for treating, preventing or ameliorating the adverse effects of high homocysteine in a host which method comprises administering a food or supplement of the invention to the host.

In a nineteenth aspect the invention provides a method for treating, preventing or ameliorating the adverse effects of β-glucuronidase in a host which method comprises administering a food or supplement of the invention to the host. The host may be a human or other animal. It will be understood that this aspect of the invention also embraces a method for the manufacture of a food or supplement of the invention for use in a method for treating, preventing or ameliorating the adverse effects of β-glucuronidase in a host which method comprises administering a food or supplement of the invention to the host.

Steroids and some carcinogenic compounds are metabolised in the liver and conjugated with glucuronic acid before secretion via bile into the small intestine. Bacterial β-glucuronidase can hydrolyse the glucuronide releasing the apparently harmful compounds (Gadelle et al., 1985, Fujisawa and, Mori, 1996, Nanno et al., 1986). Strains of *Propionibacterium* isolated from human faeces have been found to be β-glucuronidase positive in vitro (Nanno et al., 1986). Interestingly, in an in vivo study, the glucuronidase activity in the faeces of mice was reported to be the same or even reduced after the mice were fed with dairy propionibacteria strains, including strains of *P.freudenreichii* and *P.acidipropionici* (Perez-Chaia et al., 1999). It has been suggested that the *Propionibacterium* strains have different glucuronidase activity depending upon it growing in an in vitro or an in vivo environment.

In a twentieth aspect the invention provides a method for reducing the risk of cardiovascular disease in a host which method comprises administering a food or supplement of the invention to the host. The host may be a human or other animal. It will be understood that this aspect of the invention also embraces a method for the manufacture of a food or supplement of the invention for use in a method for reducing the risk of cardiovascular disease in a host which method comprises administering a food or supplement of the invention to the host.

Probiotic *Propionibacteria* sp. may produce beneficial effects on serum cholesterol. Somkuti and Johnson (1990) demonstrated in vitro that *P. freudenreichii* could uptake cholesterol from a growth medium. There have been a number of in vivo studies on the cholesterol lowering effects of probiotics and fermented milks. Controversy exists due to the results being varied and the experimental design often having faults (Taylor and Williams, 1998). Cardiovascular disease (CVD) is one of the world's major killers, being responsible for at least one third of deaths annually (WHO, 2001). High cholesterol is one of the major risk factors for CVD. Recently it has also been realised that high homocysteine levels can also increase the risk of CVD (Ozkan et al., 2002; van der Griend et al., 2000). There is an inverse relationship between Vitamin $B_{12}$ levels and homocysteine. *P. jensenii* 702 can produce high levels of vitamin $B_{12}$. Therefore the beneficial effects of *P. jensenii* 702 could extend beyond improving vitamin $B_{12}$ levels in the host, to reducing the risk of CVD by lowering homocysteine levels, and exerting a positive effect on serum lipids.

In a twenty first aspect the present invention provides a method for preventing, treating or ameliorating the adverse effects of an immune imbalance in a host which method comprises administering *P. jensenii* 702, a supplement or food of the invention to the host. The host may be a human or other animal. It will be understood that this aspect of the invention also embraces a method for the manufacture of a food or supplement of the invention for use in a method for preventing, treating or ameliorating the adverse effects of an immune imbalance in a host which method comprises administering a supplement or food of the invention to the host.

In a twenty second aspect the present invention provides a method for modulating the immune response in a host which method comprises administering *P. jensenii* 702, a supplement or food of the invention to the host. The host may be a human or other animal. It will be understood that this aspect of the invention also embraces a method for the manufacture of a food or supplement of the invention for use in a method for enhancing the immune response in a host which method comprises administering a supplement or food of the invention to the host.

The immune modulation may comprise immune stimulation in which *P. jensenii* 702, the supplement or food functions as an adjuvant to a particular antigen or antigens in a vaccine. Alternatively *P. jensenii* 702, the supplement or food may act as a general immune stimulant providing overall stimulation to the recipient's immune system.

In a twenty third aspect the present invention provides a mucosal vaccine for tuberculosis comprising an antigen comprising at least one cellular or secreted protein of *Mycobacterium tuberculosis* or at least one immunologically active part thereof together with a mucosal adjuvant.

Typically the vaccine is an oral vaccine. The vaccine may alternatively be administered via another mucosal surface. An example is nasal administration. It will be understood that the adjuvant chosen is suited to the route of administration; for instance for an oral vaccine an effective oral adjuvant is used.

In one embodiment the oral adjuvant is a bacterial vector. In a preferred embodiment the oral adjuvant is *P. jensenii* 702, or part thereof.

The antigen is typically selected from the group consisting of whole *M. tuberculosis* cells, disrupted *M. tuberculosis* cells or parts thereof, and soluble *M. tuberculosis* proteins which are either secreted or cellular or a combination of secreted and cellular soluble proteins, collected from actively multiplying *M tuberculosis* cultures. The antigen can be provided as a short term culture filtrate. The antigen can be a combination of whole cell sonicate and short term culture filtrate. Antigen preparations comprising soluble proteins can be fractionated into different size ranges. For example, an initial size separation into fractions of <20 kDa, 20-30 kDa, 30-35 kDa, 35-65 kDa, and >65 kDa can be employed to determine the fraction or fractions which provide a suitable response. These size fractions can be further refined. Combinations of selected fractions of secreted and cellular proteins can be utilized with the proportion of each fraction optimised to produce the desired immune response.

In one embodiment the antigen comprises an effective amount of a combination of secreted and cellular soluble proteins present at an effective ratio.

The vaccine is administered at an effective dose as determined in accordance with routine practice in this field. An effective dose is sufficient to produce immunity but not large enough to induce tolerance.

The number and timing of administrations is also determined in accordance with routine practice in this field.

The vaccine may be formulated in accordance with standard procedures for the preparation of mucosal vaccines. The vaccine may, for instance, be formulated as a liquid, tablet, powder, as part of a food or in an aerosol.

The vaccine may provide a systemic or a mucosal immune response or both in the host to *Mycobacterium tuberculosis.*

In a twenty fourth aspect the present invention provides a method for producing an immune response in a patient to *Mycobacterium tuberculosis* which method comprises delivering a vaccine of the twenty third aspect to a patient via a mucosal surface.

In a twenty fifth aspect the present invention provides a method for vaccinating a patient against *Mycobacterium tuberculosis* which method comprises delivering a vaccine of the twenty third aspect to a patient via a mucosal surface.

In a twenty sixth aspect the present invention provides a method for protecting a patient against *Mycobacterium tuber-*

*culosis* infection which method comprises delivering a vaccine of the twenty third aspect to a patient via a mucosal surface.

In a twenty seventh aspect the present invention provides a method for protecting a patient against *Mycobacterium tuberculosis* reactivation which method comprises delivering a vaccine of the twenty third aspect to a patient via a mucosal surface.

In a twenty eighth aspect the present invention provides a method for protecting a patient against tuberculosis which method comprises delivering a vaccine of the twenty third aspect to a patient via a mucosal surface.

In a twenty ninth aspect the present invention provides the use of an antigen comprising at least one cellular or secreted protein of *Mycobacterium tuberculosis* or at least one immunologically active part thereof in the manufacture of a vaccine for use in a method for producing an immune response in a patient to *Mycobacterium tuberculosis* which method comprises delivering a vaccine of the twenty third aspect to a patient via a mucosal surface.

In a thirtieth aspect the present invention provides the use of an antigen comprising at least one cellular or secreted protein of *Mycobacterium tuberculosis* or at least one immunologically active part thereof in the manufacture of a vaccine for use in a method for vaccinating a patient against *Mycobacterium tuberculosis* which method comprises delivering a vaccine of the twenty third aspect to a patient via a mucosal surface.

In a thirty first aspect the present invention provides the use of an antigen comprising at least one cellular or secreted protein of *Mycobacterium tuberculosis* or at least one immunologically active part thereof in the manufacture of a vaccine for use in a method for protecting a patient against *Mycobacterium tuberculosis* infection which method comprises delivering a vaccine of the twenty third aspect to a patient via a mucosal surface.

In a thirty second aspect the present invention provides the use of an antigen comprising at least one cellular or secreted protein of *Mycobacterium tuberculosis* or at least one immunologically active part thereof in the manufacture of a vaccine for use in a method for protecting a patient against *Mycobacterium tuberculosis* reactivation which method comprises delivering a vaccine of the twenty third aspect to a patient via a mucosal surface.

In a thirty third aspect the present invention provides the use of an antigen comprising at least one cellular or secreted protein of *Mycobacterium tuberculosis* or at least one immunologically active part thereof in the manufacture of a vaccine for use in a method for protecting a patient against tuberculosis which method comprises delivering a vaccine of the twenty third aspect to a patient via a mucosal surface.

Typically the mucosal surface is the mouth, nose or gut.

The vaccine may provide a systemic or a mucosal immune response or both in the patient to *Mycobacterium tuberculosis*. The immune response may prevent TB disease from occurring and/or it may prevent initial infection with TB from occurring.

The vaccine of the invention may be used as an initial vaccination, or to prime the immune response after an initial vaccination.

In a thirty fourth aspect of the present invention there is provided a method for preparing a vaccine of the invention comprising combining an antigen comprising at least one cellular or secreted protein of *Mycobacterium tuberculosis* or at least one immunologically active part thereof, a mucosal adjuvant and a suitable carrier wherein the antigen is selected to provide an immune response against *Mycobacterium tuberculosis*.

In a thirty fifth aspect there is provided an isolated *Mycobacterium tuberculosis* antigen comprising at least one cellular or secreted protein of *Mycobacterium tuberculosis* or at least one immunologically active part thereof.

The antigen is typically selected from the group consisting of soluble *M. tuberculosis* proteins which are either secreted or cellular or a combination of secreted and cellular soluble proteins, collected from actively multiplying *M. tuberculosis* cultures. The antigen can be provided as a short term culture filtrate. Antigen preparations comprising soluble proteins can be fractionated into different size ranges. For example, an initial size separation of <20 kDa, 20-30 kDa, 30-35 kDa, 35-65 kDa and >65 kDa can be employed to determine the fraction or fractions which provide a suitable response. These size fractions can be further refined. Combinations of selected fractions of secreted and cellular proteins can be utilized with the proportion of each fraction optimised to produce the desired immune response.

In one embodiment the antigen comprises an effective amount of a combination of secreted and cellular soluble proteins present at an effective ratio.

It will be understood that this invention can also be applied with respect to tuberculosis in animals other than humans. The *Mycobacterium* species which provides the antigen(s) for the vaccine is one which produces TB in the relevant host or one which can provide effective protection against the *Mycobacterium* species which causes TB in the relevant host.

The invention therefore also provides a method for producing an immune response in an animal host to a *Mycobacterium* species which is capable of causing tuberculosis in the host which method comprises delivering a vaccine of the invention to the animal host via a mucosal surface wherein the vaccine comprises an antigen derived from a *Mycobacterium* species which produces TB in the relevant host or one which can provide effective protection against the *Mycobacterium* species which causes TB in the relevant host.

The invention further provides a method for vaccinating an animal host against a *Mycobacterium* species which is capable of causing tuberculosis in the host which method comprises delivering a vaccine of the invention to the animal host via a mucosal surface wherein the vaccine comprises an antigen derived from a *Mycobacterium* species which produces TB in the relevant host or one which can provide effective protection against the *Mycobacterium* species which causes TB in the relevant host.

The present invention provides a method for protecting an animal host against a *Mycobacterium* species which is capable of causing tuberculosis in the host which method comprises delivering a vaccine of the invention to the animal host via a mucosal surface wherein the vaccine comprises an antigen derived from a *Mycobacterium* species which produces TB in the relevant host or one which can provide effective protection against the *Mycobacterium* species which causes TB in the relevant host.

The present invention also provides a method for protecting an animal host against tuberculosis reactivation which method comprises delivering a vaccine of the invention to the animal host via a mucosal surface wherein the vaccine comprises an antigen derived from a *Mycobacterium* species which produces TB in the relevant host or one which can provide effective protection against the *Mycobacterium* species which causes TB in the relevant host.

The present invention provides a method for protecting an animal host against a *Mycobacterium* species which is capable of causing tuberculosis in the host which method comprises delivering a vaccine of the invention to the animal host via a mucosal surface wherein the vaccine comprises an antigen derived from a *Mycobacterium* species which produces TB in the relevant host or one which can provide effective protection against the *Mycobacterium* species which causes TB in the relevant host.

The invention also provides the use of an antigen comprising at least one cellular or secreted protein of a *Mycobacterium* species or at least one immunologically active part thereof in the manufacture of a vaccine for use in a method of the invention.

The present invention provides a method for preparing a vaccine of the invention comprising combining an antigen comprising at least one cellular or secreted protein of a *Mycobacterium* species or at least one immunologically active part thereof, a mucosal adjuvant and a suitable carrier wherein the antigen is selected to provide an immune response against a *Mycobacterium* species.

The invention further provides an isolated *Mycobacterium* antigen comprising at least one cellular or secreted protein of a *Mycobacterium* species or at least one immunologically active part thereof.

The antigen is typically selected from the group consisting of soluble proteins which are either secreted or cellular or a combination of secreted and cellular soluble proteins, collected from actively multiplying cultures. The antigen can be provided as a short term culture filtrate. Antigen preparations comprising soluble proteins can be fractionated into different size ranges. For example, an initial size separation of <20 kDa, 20-30 kDa, 30-35 kDa, 35-65 kDa and >65 kDa can be employed to determine the fraction or fractions which provide a suitable response. These size fractions can be further refined. Combinations of selected fractions of secreted and cellular proteins can be utilized with the proportion of each fraction optimised to produce the desired immune response.

The WHO and NIAID have outlined various features that an ideal vaccine for TB should possess. These characteristics include: the vaccine should be safe; have demonstrated protection in animal models; protect against disease, but also infection; be protective after a single or, if necessary a small number of doses, preferably not requiring injection; be long-lasting and confer immunological memory; not interfere with the tuberculin skin test for diagnosis of disease; be inexpensive to produce; be heat stable and have a long shelf life; not interfere with protection engendered by existing vaccines; and be capable of integrating into existing vaccine programs (NIAID, 2000). However it is acknowledged that a vaccine that does not meet all of these requirements can still be considered a useful vaccine.

The present inventor(s) produced oral vaccines for tuberculosis for trial in C57 mice to determine the immunological response of the mice to the vaccines in investigating the underlying hypothesis that the mucosal administration of the soluble proteins of *Mycobacterium tuberculosis* can provide immunity to tuberculosis infection.

This research consisted of three distinct stages, these being the production and analysis of the vaccines, the vaccination trial in test animals and measurement of immunological parameters indicative of the immune response obtained. This research aimed to optimise technical procedures in testing the immune response and then to test the immune response at these optimum levels. In addition to this, the efficacy of two different oral adjuvants, Cholera toxin and *P. jensenii* 702, was tested to see which best stimulated a mucosal and systemic immune response. The immune responses were tested through T cell proliferations, cytokine analysis and presence of the secretory antibodies IgA and total IgG.

Currently there is a partial understanding of the complex immune response to TB. The immune response to TB is predominantly cell-mediated not humoral (Ehlers, 1999). This means that the main immune cells involved in the immune response are T-cells. It is thought that B cells or antibodies are irrelevant or play a very minor role in the control of mycobacterial growth (Ehlers, 1999; Lowrie, Silva & Tascon, 1997).

The immune response to TB can be categorized into three interrelated phases: the first being the initiation and development of specific cellular immunity; secondly the expression of protective immunity in the lungs; and thirdly the maintenance of this protective immunity (Saunders & Cooper, 2000). It is a breakdown of this protective immunity stage that leads to reactivation of latent TB infections.

Once inhaled, *M. tuberculosis* bacilli are internalised by alveolar macrophages and set up infection foci in the lung tissue (Silva et al, 2001). Through bacterial growth these foci expand and recruitment of macrophages and lymphocytes builds the granuloma that defines this disease (Silva et al, 2001). While they inhibit metastasis of live bacteria throughout the lung, the resistance of the infected alveolar macrophages to lysis offers bacteria a safe haven to evade the host's defense mechanisms (Stenger & Modlin, 1999).

Granulomas play a role in maintenance immunity. The maintenance phase of protective immunity requires a strong, prolonged memory T-cell response to maintain the integrity of the granuloma and hence control bacterial replication (Saunders & Cooper, 2000). Granulomas are not only crucial in controlling bacterial growth, but also assist in the management of TB by containing the toxic environment necessary to control mycobacteria, so that it does not damage delicate alveolar tissue.

Macrophages play a variety of important roles in TB infection, ranging from antigen processing and presentation to effector cell functions (Silva et al, 2001). There is evidence to suggest that appropriately activated macrophages have the ability to destroy live *M. tuberculosis*, however this is not generally sufficient to provide and sustain sterilising immunity (Sato, Akaki & Tomioka, 1998), and thus the bacteria can live chronically in the host (Bermudez & Sangari, 2001). Macrophages are typically activated in response to mycobacterial infections in two main ways.

Firstly, macrophages can be directly stimulated by the actual *mycobacterium* in the early phase of infection, or indirectly by cytokines in the later phase of infection (Tsuyuguchi, 1996).

The major effector functions of T-cells in the immune response to *M. tuberculosis* are cytokine secretion, cytotoxic effector function and cell-contact-dependent helper functions (Boom, 1999). The aim of these diverse effector functions is to assist in containing mycobacterial growth and to stimulate memory immunity. Primarily, $CD4^+$, $CD8^+$ and $\gamma\delta$ T-cells, in addition to some non-classical lymphocytes such as double negative (DN) $\alpha\beta$ T-cells, have been shown to react to mycobacterial antigens and also proliferate in an infected lung (Feng, Bean & Hooi, 1999).

The majority of knowledge on the immune response to TB has been gleaned from animal models (Elhay & Andersen, 1997). A wide array of animal models indicate the essential protective role of $CD4^+$ T-cells in TB immunity and that it is the single, most important T-cell subset in the immune response to TB (Kaufmann & Andersen, 1998). The protective $CD4^+$ T-cell response to active TB is a Th1 response, and produces a typical Th1 cytokine profile to fight infection (Silva et al, 2001; Havlir et al, 1991). This includes secretion of IFN-γ, IL-12, IL-2 and TNF-α (Barnes et al, 1993).

CD4$^+$ T-cells have also been identified as having cytotoxic activity. The mycobactericidal activity of CD4$^+$ Cytotoxic T-cells (CTLs) is contact dependent using both the Fas-Fas ligand and granule exocytosis pathways of cytotoxicity, to kill intracellular mycobacteria (Stenger & Modlin, 1999). The action of CD4$^+$ T-cells is however subsidised by the action of CD8$^+$ T-cells, to provide a comprehensive immune response.

Evidence suggests CD8$^+$ T-cells play an equally important role to that of CD4$^+$ T-cells in eliciting an effective long term immune response to tuberculosis. In particular it has been found that CD8$^+$ T-cell responses primed via mucosal immunisation provide longer immunity compared with systemic immunisation (Feng & Britton, 2000). CD8$^+$ T-cells are also an important source of cytokines, especially IFN-γ (Elhay & Andersen, 1997).

CD8$^+$ T-cells are effective through mechanisms of cytokine production and direct cytolytic activity (Stenger & Modlin, 1999). CD8$^+$ T-cells have been found to have only a minor effect in protection against acute infection, however CD8$^+$ T-cells have been found to be "a major mediator of protection against reactivation of latent disease" in mouse models (Andersen, 2001).

Although both CD4$^+$ and CD8$^+$ T-cells can produce IFN-γ, animals studies have revealed that neither T-cell subset can adequately compensate for the other in protection against TB (Caruso et al, 1999; Tascon et al, 1998).

γδ T Cells also produce IFN-γ. It is thought that γδ T Cells are more efficient producers of IFN-γ and are also competent cytotoxic effector cells (Boom, 1999). Along with CD4$^+$ T-cells, γδ T Cells also produce TNF-α, and in conjunction they enhance TNF-α production by *M. tuberculosis* infected monocytes (Boom, 1999).

Although CD4$^+$ T-cells still remain the most dominant and critical T-cell subset, γδ T-cells play an important complementary role, which is primarily expressed around maturing granulomas. The main difference between CD4$^+$ and γδ T-cells lies in the ability of the two subsets to identify different antigens that are presented in an alternate manner by *M. tuberculosis* infected macrophages. In particular γδ T-cells have a distinct responsiveness to non-peptidic molecules (Balaji & Boom, 1999).

DN αβ T-cells are a minor subset that responds to mycobacterial glycolipids in the context of CD1 molecules. CD1 molecules present antigens independent of the MHC pathways (Stenger & Modlin, 1999; Sieling et al, 1995). Glycolipids from the mycobacterial cell wall that have been found to be recognised by DN αβ T-cells, include mycolic acids and lipoarabinomannans (LAM) (Sieling et al, 1995). Together with γδ T-cells, DN αβ T-cells, provide further mechanisms by which the immune system could be primed to mycobacterial infection.

TNF is crucial to antimycobacterial immunity (Schaible, Collins & Kaufmann, 1999). It is an important cytokine, playing a major part in the modulation of chemokine responses. This is important as chemokines are critical mediators of leucocyte trafficking and activation and hence are vital in granuloma formation. (Saunders and Cooper, 2000).

Dendritic cells produce the cytokine IL-12, which has been implicated as a key element of protective immunity to TB. IL-12 functions to activate naïve Natural Killer (NK) and T-cells in addition to directing CD4$^+$ T-cells to secrete IFN-γ (Cooper, Roberts & Rhoades, 1995). Through these mechanisms, IL-12 serves as a bridge between innate resistance and adaptive immunity against intracellular bacteria such as TB (Demangel & Britton, 2000).

The primary entrance point of pathogens into the body is via the nose and mouth. Consequently the first line of defense they encounter is the mucosal membranes that line the respiratory and gastrointestinal tracts (GIT) (Langridge, 2000). These membranes constitute one of the largest pathogen-deterring surfaces in the body (Langridge, 2000), since the intestines form one of the largest immunological organs in the human body (Pouwels et al, 1998). Each day, 60% of the antibodies produced in the body are secreted into the GIT (Pouwels et al, 1998). Immunologically, oral vaccines provide the benefit of stimulating the mucosal immune system (Richter & Kipp., 1999)

Oral vaccines are an example of mucosal vaccines that are easy to administer, inexpensive, and results in increased patient compliance due to the non-invasive method of administration of the vaccine (Russell-Jones, 2000; Richter & Kipp., 1999). Oral administration also offers convenience and efficiency when administering to large numbers of people, particularly in less industrialized countries (Pouwels et al, 1998). There is also the possibility that oral vaccination could yield "herd immunity", where the immunity is spread among member of a community, after the immunisation of a small portion of the population (Pouwels et al, 1998).

The limitations of oral vaccination are often focused on and hence this important mechanism of eliciting a mucosal immune response is often disregarded.

Parenterally administered vaccines are effective in stimulating systemic immunity, however this does not include mucosal surfaces, which are important in TB immunity (Russell-Jones, 2000). Oral administration has the ability to stimulate both local mucosal and systemic immune responses, resulting in the more efficient elimination of foreign pathogens (Pouwels et al, 1998). In particular the Mucosal Associated Lymphoid Tissue (MALT) can be considered a system separate from the systemic lymphoid system, because the cells of the MALT recirculate mainly within the mucosal system (Erickson & Hubbard, 2000). This means that cells created in the MALT are disseminated specifically to mucosal surfaces throughout the body, and herein lies the value of orally administering antigens to induce protective immunity.

Studies have also shown that virus-specific CD8$^+$ T-cell responses are generated more effectively by mucosal rather than systemic immunisation (Feng & Britton, 2000). Since it has been established that CD8$^+$ T-cells are critical to the immune response to TB, oral administration of the vaccine should provide access to this aspect of the immune system.

The mucosal immune system is constantly active, striving to differentiate between all of the different antigens it comes into contact with daily, including food, environmental commensals, live pathogens, binding molecules, toxins and inflammatory agents without immune dysfunction (Kenney et al, 2002). Evidence suggests that the mucosal immune system is a "functional system integrated by cell and molecule exchange among all mucosal surfaces throughout the body" (Famularo et al, 1997). This means that an immune response established in the GALT by an oral vaccine, will confer mucosal immunity in the lungs and respiratory tract where *micobacterium* infections occur, and hence a more efficient immune response will be mounted.

The gastrointestinal tract features specialised lymphoid tissue known as the Gut-Associated Lymphoid Tissue (GALT). The lymphoid aggregates in the GALT feature specialised epithelial cells known as M (Membranous) cells. M cells line the wall of the small intestine (Langridge, 2000) and play a role in the uptake of antigens that enter the small intestine (Toy & Mayer, 1996). M cells take up materials from the gut lumen and transport them to a subepithelial area. Particulates commonly processed by M cells includes, bacteria, viruses, protozoa and soluble proteins (Famularo et al, 1997), such as those commonly found in subunit vaccines.

M cells are of great importance in relation to vaccines as they have the potential to direct vaccine vectors to the mucosal lymphoid compartments (Famularo et al, 1997). M cells are designed to facilitate the binding and transporting of particulate antigens, and have a surface specialized for endocytosis, rich in the antigen presenting cells (APC's), macrophages, dendritic cells and lymphocytes (Famularo et al, 1997). From here the antigens are processed by APC's and presented in conjunction with a MHC class II to lymphocytes which in turn triggers the impending immune response (Famularo et al, 1997).

The mucosal immune system has evolved down-regulatory mechanisms to avoid local and peripheral overreaction (hypersensitivity) towards innocuous substances bombarding the mucosal surfaces (Brandtzaeg, 1998). The result of this evolutionary development is known as Oral Tolerance.

The term "Oral Tolerance" refers to "the antigen specific suppression of an immune response following administration of oral antigen" (Marth & Strober, 1997). This down-regulatory phenomenon induced via the gut involves more than one immune mechanism (Brandtzaeg, 1998). Both cellular and humoral immune responses are suppressed by oral tolerance, and this cessation of immune response is often associated with the generation of cytokine producing suppressor T-cells. In relation to cellular immunity, which is particularly relevant to vaccines, it has been found that oral tolerance can suppress cell mediated immunity (CMI) in the form of proliferation and cytokine production by T-cells, as well as inhibiting Delayed Type Hypersensitivity (DTH) (Marth & Strober, 1997). While suppressing the DTH reaction to orally administered antigens may be viable, suppression of the entire CMI is detrimental to incurring an immune response to an oral antigen.

Brandtzaeg (1996) identified a number of variables that can effect the induction of oral tolerance. These include genetics, age, antigen dose, timing of antigen administration, antigenic structure, epithelial barrier integrity and the degree of concurrent local immune activation (Brandtzaeg, 1996). Consequently the dose of antigen delivered is relevant to the success of an oral vaccine in relation to preventing oral tolerance.

Cholera toxin (CT) is amongst one of the strongest known mucosal adjuvants when co-administered mucosally with antigens (Del Giudice, Podda & Rapuoli, 2002). The use of CT has been limited due to its high toxicity, however through site-directed mutagenesis, a non-toxic B subunit of CT has been created, which retains its mucosal adjuvant properties but lacks its toxic activity (Del Giudice, Podda & Rapuoli, 2002), thus making it safe for use in humans.

Cholera Toxin Subunit B adjuvant works by binding to a molecule on M cells that ushers foreign materials into those cells, hence enhancing antigen presentation and stimulation of an immune response to those antigens (Langridge, 2000). Studies involving CTB have shown that recombinantly produced CTB which is inherently devoid of all toxicity, present in regular CT, still serves as a powerful carrier-enhancing agent for induction of antigen specific immune responses (Sun, Holmgren & Czerkinsky, 1994)

It is thought that probiotics may have an adjuvant effect by stimulating the Gut Associated Lymphoid Tissue (GALT) (Fang et al, 2000) and hence improve the mucosal immune response. Fang et al (2000) defines probiotics as "microbial cell preparations or components of microbial cells which have a beneficial effect on the host". Previous research has shown that lactic acid producing probiotic bacteria can boost immune responses in test animals by promoting secretory IgA, enhancing phagocytosis and altering the balance between a Th1 and Th2 response and its associated cytokine production (Fang et al, 2000).

In a further aspect the present invention provides a method for increasing infectious disease resistance in a host which method comprises administering a supplement or food of the invention to the host. The host may be a human or other animal. It will be understood that this aspect of the invention also embraces a method for the manufacture of a food or supplement of the invention for use in a method for increasing infectious disease resistance in a host which method comprises administering a supplement or food of the invention to the host.

Features of Probiotics

A probiotic which needs to be viable to exert its probiotic effect should possess at least the following four characteristics:

it should be capable of being prepared as a viable product on an industrial scale, it should remain stable and viable for long periods under storage and field conditions, it should have the ability to survive (not necessarily grow) in the intestine, it must produce a beneficial effect in the host animal.

All microorganisms can be divided into three groups in terms of their relative safety: non-pathogenic, opportunistic pathogens and pathogenic. The first step in the selection of microbial strains for probiotic use is that it must be representative of microorganisms that are 'Generally Recognized As Safe' (GRAS) microorganisms (Havenaar et al., 1992). In the dairy industry, the currently used probiotic bacteria include lactic acid bacteria (LAB), bifidobacteria and yeasts. The use of *Lactobacillus* in foods has a long history and most strains are considered GRAS microorganisms. This also true for dairy propionibacteria.

Safety is an important requirement for probiotics. There are increasing demands to extend the range of foods containing probiotic organisms from dairy foods to infant formulae, baby foods, fruit juice-based products, cereal-based products and pharmaceuticals. New and more specific strains of probiotic bacteria are being selected. However, these novel probiotic organisms may not share the safety of traditional strains. Their safety should be carefully assessed before their use in food.

Three approaches can be used to assess the safety of a probiotic strain: studies on the intrinsic properties of the strain; studies on the pharmacokinetics of the strain; and studies searching for interactions between the strain and the host. Models and methods recommended to test the safety of probiotic bacteria include (1) determination of the intrinsic properties of bacteria and strains selected for probiotic use, for example, adhesion factors, antibiotic resistance, plasmid transfer, enzyme profile; (2) assessment of the effects of the metabolic products of the bacteria; (3) assessment of the acute and sub acute toxicity of ingestion of extremely large amounts of the bacteria; (4) estimation of the in vitro infective properties of probiotic bacteria using cell lines and human intestinal mucus degradation; (5) assessment of infectivity in animal models, for example, immunocompromised animals or lethally irradiated animals; (6) determination of the efficacy of ingested probiotic bacteria as measured by dose-response (minimum and maximum dose required, consequent health effects), assessment of the effect of massive probiotic doses on the composition of human intestinal microflora; (7) assessment of the side-effects in human volunteer studies and in clinical studies of various disease-specific states; (8) epidemiological surveillance of people ingesting large amounts of newly introduced probiotic bacteria for infections; (9) extra attention to genetically modified strains and strains derived from animals.

Assessment of a novel probiotic can be performed by in vitro methods, animal models and human subjects. In vitro studies provide indirect measure of the potential for a test organism to invade intestinal cells and to damage the intestinal mucus. Most strains of lactic acid bacteria have shown no invasive properties towards a human gut epithelial cell line, Caco-2. There is no report on the potential for propionibacteria to invade intestinal cells and to damage the intestinal mucus and no toxicity data is available relating to the ingestion of large quantities of dairy propionibacteria.

An important factor modifying toxicity is microbial metabolism in the gut. Profound toxicological and carcinogenic consequences may result from changes in microbial enzyme activity in animal gut. It is generally known that colonic microflora can generate mutagens, carcinogens and tumour promoters from dietary and endogenously produced precursors. The bacterial enzymes involved in these harmful processes include azoreductase, nitroreductase, nitrate reductase, β-glucuronidase and β-glycosidase. Some probiotic strains of *Lactobacillus* and *Bifidobacterium* sp. have been shown to reduce β-glucuronidase and β-glycosidase activities in the lower gut of rats.

Six isolated *Propionibacterium* spp. strains from human faeces have been found to have β-glucuronidase activity (Nanno et al., 1986), whereas two strains of *P. freudenreichii* and three strains of *P. acidipropionici* in another study have been shown to lower the β-glucuronidase activity in mice, but had no inducing effects on the activities of azoreductase, nitroreductase, nitrate reductase, and β-glycosidase of the intestinal microflora (Perez-Chaia et al., 1999).

During the development of probiotics, it is very important to investigate the viability of the microorganisms during processing and storage (Havenaar et al., 1992). The processing and storage methods for a probiotic are determined by its application and the administration methods.

High correlation has been found between the results of in vitro and in vivo studies of gastrointestinal tract transit tolerance of probiotics (Havenaar et al., 1992). Therefore, selection of probiotic strains with gastrointestinal tract tolerance can be based on in vitro experiments (Havenaar et al., 1992). Several in vitro methods have been developed to select gastrointestinal transit tolerant probiotic strains. The most widely used methods include the use of HCl-acidified distilled water, broth and buffers (Chou and Weimer, 1999, Chung et al., 1999, Clark et al., 1993, Clark and Martin, 1994, Wang et al., 1999).

Another in vitro method, which simulates the human upper gastrointestinal transit conditions, was developed by Charteris et al (Charteris et al., 1998). The simulated gastric juice (pH2.0) contained pepsin (0.3% w/v) and sodium chloride (0.5% w/v) while the simulated small intestinal juice(pH8.0) contained pancreatin (0.1% w/v) and sodium chloride (0.5% w/v).

Selection of bile-resistant bacteria can be made by culturing on selective agar medium with various levels of bile (Gilliland et al., 1984, Ibrahim and Bezkorovainy, 1993, Clark and Martin, 1994, Chung et al., 1999). Because Oxgall (Oxoid) is readily available and is used extensively in selective media for human enteric pathogens, its use has been adopted widely to select bile-tolerant probiotic strains (Clark and Martin, 1994).

The ability to survive and colonize the intestine can be both species and strain-dependent (Wang et al., 1999).

Adhesion to intestinal surfaces is regarded as the first step for colonization and immune stimulation for probiotics (Havenaar et al., 1992). Since it is very difficult to study bacterial adhesion in vivo, selection of strains with the capacity to adhere to gastrointestinal cells is based on in vitro tests (Tuomola et al., 1999, Sarem et al., 1996, Lehto and Salminen, 1997, Crociani et al., 1995, Mayra-Makinen et al., 1983). One of the models used is the human intestinal Caco-2 epithelial cell line. The Caco-2 cell line was originally isolated from a human colon adenocarcinoma (Pinto et al., 1983). This cell line spontaneously differentiates under standard in vitro culture conditions and the differentiated cells express characteristics of mature enterocytes (Pinto et al., 1983).

In vitro methods are suitable for assessment of some of the probiotic bacteria selection criteria. Nevertheless, regardless of the results of in vitro tests, it is still difficult to predict the actual conditions in vivo (Havenaar et al., 1992). The adherence and colonization in vivo is affected by different animal species, the specificity of microorganism species and strains, and the different food or feed consumed (Havenaar et al., 1992). Adherence in vitro is no guarantee for adherence in vivo and subsequent colonization but is usually predictive of in vivo efficacy.

The results reported here provide evidence that *Propionibacterium jensenii* 702 will adhere and colonise in vivo. Confirmation is provided by in vivo rat studies. Animal models using Balb/c mice have been used to determine the survival through gastrointestinal tract of strains of *Bifidobacterium* spp, which have shown resistance to acid and bile in in vitro tests (Wang et al., 1999). In this study, the mice were oro-gastrically fed with a strain of *Bifidobacterium*, and the viable cell numbers of this strain in faeces were determined. The recovery rate of the strains of *Bifidobacterium* spp. in faeces was found to be only 4.3% (Wang et al., 1999).

The survival and colonisation of some *Propionibacterium* strains in the gastrointestinal tract has been examined through in vitro tests, animal studies and human trials (Perez-Chaia et al., 1995, Mantere-Alhonen, 1983, Bougle et al., 1999). A strain of *P. freudenreichii* has been reported to be able to survive during in vitro gastric digestion at pH4.8 (Mantere-Alhonen, 1983), while in in vivo tests, strain *P. acidipropionici* CRL 1198 has shown the ability to survive in the gut of BALB/c male albino mice (Perez-Chaia et al., 1995). In a human trial, it was also found that part of the ingested propionibacteria were able to survive the digestive transit (Bougle et al., 1999). In the present study, the gastrointestinal resistance of selected *Propionibacterium* strains has been tested under both in vitro and in vivo conditions.

A *Propionibacterium* strain, *P. freudenreichii* ssp. *shermanii* JS, has been shown to be able to adhere to human gut epithelial Caco-2 cell line in vitro (Lehto and Salminen, 1997). The adhesion rate was 12.2% of the number of added bacteria. The results also show that the adhesion of *P. freudenreichii* ssp. *shermanii* JS was significantly reduced by previously adhered *Lactobacillus rhamnosus* LC-705. This may indicate that bacteria may compete for adhesion sites (Lehto and Salminen, 1997). In the present study, the adhesive abilities of selected *Propionibacterium* strains have been tested using a subclone of the Caco-2 cell line, c2bbe1.

In in vivo tests, strain *P. acidipropionici* CRL 1198 has shown the ability to establish in the gut of BALB/c male albino mice (Perez-Chaia et al., 1995). The numbers of fed *P.* acidopropionici CRL 1198 remain stable in the mouse gut contents and mouse gut walls one week after the cessation of the diet. In contrast, in a human trial, propionibacteria were found to be able to adhere but unable to colonise the digestive tract (Bougle et al., 1999). The numbers of fecal propionibacteria returned to the level observed prior to the supplementation within a few days of stopping the supplement.

Because *Propinibacterium* strains utilize lactate, they can be isolated, from food and environmental samples, using Yeast Extract Lactate medium (YELA), which contains sodium lactate, casein peptone, yeast extract and agar (Harrigan, 1998a, Fessler et al., 1998, Britz-and Riedel, 1994, Cummins and Johnson, 1986).

Primary identification of isolated strains to the genus *Propionibacterium* is based on microscopic examination for morphological and staining characteristics, cultural characteristics and simple biochemical tests. *Propionibacterium* is separated from related bacterial species by positive Gram stain, negative acid fast stain, no endospore formation, positive catalase, positive lactate fermentation, and irregular shaped rods (Harrigan, 1998b).

Conventional methods of identifying *Propionibacterium* strains to species level include carbohydrate fermentation tests, nitrate reduction test, β-hemolysis test and morphological analysis of cells and colonies. Different selected biochemical characteristics of *Propionibacterium* species are shown in Table 1 (Cummins and Johnson, 1986, Holt et al., 1997).

The protein profile method is based on the principle that closely related organisms should have similar or identical kinds of cellular proteins (Jones and Krieg, 1986). A strain is considered to belong to a particular species when there is more than 70% identity of the protein profile with the type strain (Fessler et al., 1999). Whole cells, cellular membrane fractions and water-soluble protein fractions are separated by polyacrylamide gel electrophoresis (PAGE) and stained gels are used to distinguish related from unrelated organisms (Jones and Krieg, 1986). Sodium dodecyl sulfate-PAGE (SDS-PAGE) of soluble proteins has been used to distinguish different species of *Propionibacterium*. It has been reported that the SDS-PAGE profile of cell free soluble protein can differentiate the four species of dairy propionibacteria (Fessler et al., 1999, Baer, 1987, Riedel and Britz, 1992). These results also show the correlation between a SDS-PAGE protein profile identification method and a genetic method (Fessler et al., 1999).

There are several genetic analysis methods applied to the identification of dairy *Propionibacterium* species, including DNA fingerprinting by pulsed-field gel electrophoresis and various PCR methods (Gautier et al., 1996, Meile et al., 1999, Fessler et al., 1998, Riedel et al., 1998). The details of PCR methods and primers used in *Propionibacterium* identification are summarised respectively in Table 2 and Table 3 (Meile et al., 1999, Fessler et al., 1999, Rossi et al., 1998, Fessler et al., 1998, Riedel et al., 1998, Riedel et al., 1994, Rossi et al., 1999)

TABLE 1

Characteristics differentiating the species of *Propionibacterium*[a]

| Characteristics | P. acidipropionici | P. acne | P. avidum | P. freudenreichii | P. granulosum | P. jensenii | P. lymphophilum | P. thoenii |
|---|---|---|---|---|---|---|---|---|
| Hydrolysis of: | | | | | | | | |
| Esculin | + | − | + | + | − | + | − | + |
| Gelatin | − | + | + | − | d | − | d | − |
| Acid produced from: | | | | | | | | |
| Maltose | + | − | + | − | + | + | + | + |
| Sucrose | + | − | + | − | + | + | d | + |
| L-Arabinose | + | − | d | + | − | − | − | − |
| Cellobiose | + | − | − | − | − | d | − | − |
| Glycerol | + | d | + | + | + | + | − | + |
| Starch | + | − | − | − | − | − | d+ | + |
| Color of pigment | White | White To gray | White to cream | May be tan or pink | White to gray | White to pink | White | Orange to red–brown |
| β - Hemolysis | − | d | (+) | − | (−) | − | − | + |
| Nitrate reduction | + | d+ | − | − | − | − | d− | − |

[a] Symbols:
+, 90% or more of strains are positive;
(+), 80-89% of strains are positive;
d+, 40-90% of strains are positive;
d, 21-79% of strains are positive;
d−, 10-40% of strains are positive;
(−), 11-20% of strains are positive;
−, 90% or more of strains are negative.

Conventional methods are mostly based on phenotypic characteristics, however, species differentiation is not always reproducible due to variation in specific phenotypic characteristics (Cummins and Johnson, 1986, Britz and Riedel, 1994). Therefore, alternative classification techniques, such as protein profile studies and genetic analysis, are used to identify the genus and species more accurately, more sensitively and more rapidly (Jones and Krieg, 1986, Jones, 1986).

TABLE 2

PCR Methods used to identify *Propionibacterium*

| Method | Primer name | Identification specificity | Target | Endo-nucleases |
|---|---|---|---|---|
| RAPD-PCR | OPL-01 | Strains within P. species | Genome DNA | N/A |

TABLE 2-continued

PCR Methods used to identify *Propionibacterium*

| Method | Primer name | Identification specificity | Target | Endo-nucleases |
|---|---|---|---|---|
| | OPL-02 | Strains within *P.* species | Genome DNA | |
| | SK-2 | Strains within *P.* species | Genome DNA | |
| | DF4 | Strains within *P.* species | Genome DNA | |
| | OPL-05 | Four dairy *P.* species | Genome DNA | |
| PCR & RFLP | A-B | Four dairy *P.* species | 23s rRNA | MspI |
| | 16sP1-16sP4 | Four dairy *P.* species | 16s rDNA | AluI, HaeIII |
| | 16sP3-16sP4 | Four dairy *P.* species | 16s rDNA | HpaII |
| MPCR | gd1-bak11w | Genus *Propionibacterium* | 16s rDNA | N/A |
| | gd1-bak4 | Genus *Propionibacterium* | 16s rDNA | |
| Specific PCR | PB1-PB2 | Dairy *P.* & *P. acne* | 16s rDNA | |
| | PF-PB2 | *P. freudenreichii* | | |
| | PJ-PB2 | *P. jensenii* | | |
| | PA-PB2 | *P. acidipropionici* | | |
| | PT3-PB2 | *P. thoenii* & *P. acne* | | |

TABLE 3

Primers used in identifying *Propionibacterium*

| Primer name (SEQ ID No) | Primer sequence |
|---|---|
| OPL-01 (SEQ ID No: 1) | 5'-GGCATGACCT-3' |
| OPL-02 (SEQ ID No: 2) | 5'-TGGGCGTCAA-3' |
| SK-2 (SEQ ID No: 3) | 5'-GCCGCCGCCGCC-3' |
| DF4 (SEQ ID No: 4) | 5'-CGCCGCCGTCGC-3' |
| OPL-05 (SEQ ID No: 5) | 5'-ACGCAGGCAC-3' |
| A (SEQ ID No: 6) | 5'-MADGCGTAGNCGAWGG-3' |
| B (SEQ ID No: 7) | 5'-GTGWCGGTTTNBGGTA-3' |
| 16sP1 (SEQ ID No: 8) | 5'-GGGTGACCGGCCACA-3' |
| 16sP3 (SEQ ID No: 9) | 5'-AAGGTGGGGATGAGC-3' |
| 16sP4 (SEQ ID No: 10) | 5'-TCGGGTGTTACCGAC-3' |
| Bak4 (SEQ ID No: 11) | 5'-AGGAGGTGATCCARCCGCA-3' |
| Gd1 (SEQ ID No: 12) | 5'-TGCTTTCGAT ACGGGTTGAC-3' |
| Bak11w (SEQ ID No: 13) | 5'-AGTTTGATCMTGGCTCAG-3' |
| PB1 (SEQ ID No: 14) | 5'-AGTGGCGAAGGCGGTTCTCTGGA-3' |
| PB2 (SEQ ID No: 15) | 5'-TGGGGTCGAGTTGCAGACCCCAAT-3' |
| PF (SEQ ID No: 16) | 5'-CTTTCATCCATGACGAAGCGCAAG-3' |
| PJ (SEQ ID No: 17) | 5'-GACGAAGTGCCTATCGGGGTG-3' |
| PA (SEQ ID No: 18) | 5'-GACGAAGGCATTCTTTTAGGGTGT-3' |
| PT3 (SEQ ID No: 19) | 5'-GGACAAAAGGCCTTTCGGGGTTT-3' |

B = C, G, T; D = A, G, T; M = A, C; N = A, G, C, T; R = A, G; W = A, T

Different PCR methods have different capabilities. A multiplex-PCR (MPCR) using two sets of primers, namely, gd1-bak11w and gd1-bak4, can differentiate *Propionibacterium* from related genera but can not differentiate species of *Propionibacterium* (Meile et al., 1999). RAPD-PCR method using primer OPL-05 can differentiate four dairy *Propionibacterium*, while other RAPD-PCR methods using primers OPL-01, OPL-02, SK2, DF-4 give better results in dividing different strains into different groups within single species (Fessler et al., 1999, Rossi et al., 1998). The use of both RFLP and PCR (primer A and B) targeting 23s rDNA and restriction endonuclease MspI can differentiate dairy *Propionibacterium* species from related species (Fessler et al., 1998). The four dairy *Propionibacterium* species can be separated using other combinations of PCR and restriction fragment length polymorphisms (RFLP) which target 16s rDNA. These methods use primer sets 16sP1-16sP4, 16sP3-16sP4 in combination with the endonucleases AluI, HaeI, HpaII (Riedel et al., 1998, Riedel et al., 1994). Recently, a rapid, genus-specific and species-specific PCR targeting the genes encoding 16s rRNA was developed to detect the dairy Propionibacteria in environmental samples (Rossi et al., 1999). In this method, the primers PB1-PB2, PF-PB2, PJ-PB2, PA-PB2, and PT3-PB2 were designed specifically for dairy propionibacteria and *P. acne*; *P. freudenreichii*, *P. jensenii*; *P. acidipropionici*; and *P. thoenii* respectively.

The human mouth and intestine provide suitable habitats for numerous bacterial genera. Propionibacteria are found as normal oral flora (Sutter, 1984) and have also been found in the human colon (Allison et al., 1989, Macfarlane et al., 1986). Propionibacteria are observed to be present from $10^{4.3}$ cfU/g to $10^{12}$ cfu/g in faeces (Finegold et al., 1983, Macfarlane, 1986).

| ABBREVIATIONS | |
|---|---|
| α | Alpha |
| AIDS | Auto-Immune Deficiency Syndrome |
| APC | Antigen Presenting Cell |
| β | Beta |
| BCG | *M. bovis* Bacille Calmette-Guerin |

-continued

ABBREVIATIONS

| | |
|---|---|
| CD | Cluster of Differentiation |
| CD1 | Cluster of Differentiation one |
| $CD4^+$ T-cells | Cluster of Differentiation four positive T cells |
| $CD8^+$ T-cells | Cluster of Differentiation eight positive T cells |
| CFU | Colony Forming Units |
| Con A | Concanavalin A |
| CPM | Counts Per Minute |
| CT | Cholera Toxin |
| CTB | Cholera Toxin subunit B |
| CTL | Cytotoxic T Lymphocytes |
| δ | Delta |
| Da | Dalton |
| DN αβ T cells | Double negative alpha beta T cells |
| DNA | Deoxyribose nucleic acid |
| DOTS | Directly Observed Therapy Short Course |
| DTH | Delayed-type hypersensitivity |
| ELISA | Enzyme-Linked Immunosorbent assay |
| et al. | and others |
| γ | Gamma |
| g | gram |
| GALT | Gut-Associated Lymphoid Tissue |
| HIV | Human Immunodeficiency Virus |
| IFN | Interferon |
| Ig | Immunoglobulin |
| IL | Interleukin |
| kDa | Kilodalton |
| L | Liter |
| LAM | Lipoarabinomannans |
| LJ | Lowenstein-Jensen (medium) |
| M. | Mycobacterium |
| M | Molar |
| mA | Milli Ampere |
| MALT | Mucosal Associated Lymphoid Tissue |
| MDR-TB | Multi-drug resistant tuberculosis |
| mg | milligram |
| MHC | Major Histocompatibility Complex |
| Min | minute |
| ml | milliliter |
| mM | Millimolar |
| MSM | Modified Sauton's Medium |
| MWCO | Molecular Weight Cut-Off |
| NIAID | National Institute of Allergy and Infectious Diseases |
| NK | Natural Killer |
| nm | nanometer |
| PBS | Phosphate Buffered Saline |
| pg | picagram |
| PMSF | Phenyl Methyl Sulfonyl Fluoride |
| RPMI | Roswell Park Memorial Institute (medium) |
| SA-HRP | *Streptavidin* Horse-Radish Peroxidase |
| SDS-PAGE | Sodium Dodecyl Sulfate Polyacrylamide Gel Electrophoresis |
| sec | seconds |
| SLA | Sodium Lactate Agar |
| SLB | Sodium Lactate Broth |
| STCF | Short Term Culture Filtrate |
| Th | T helper cells |
| TAP1 | Transporter Associated with Antigen Processing 1 |
| TB | Tuberculosis |
| TCR | T cell receptor |
| TNF | Tumour Necrosis Factor |
| TNF-α | alpha- tumour necrosis factor |
| μCi | microCurie |
| μg | microgram |
| μl | microliter |
| UV | ultra violet (light) |
| V | Volts |
| WHO | World Health Organisation |
| WTB | Whole Tuberculosis cells (sonicated) |

DETAILED DESCRIPTION OF THE INVENTION

Analysis of Vitamin $B_{12}$

Figure 1:
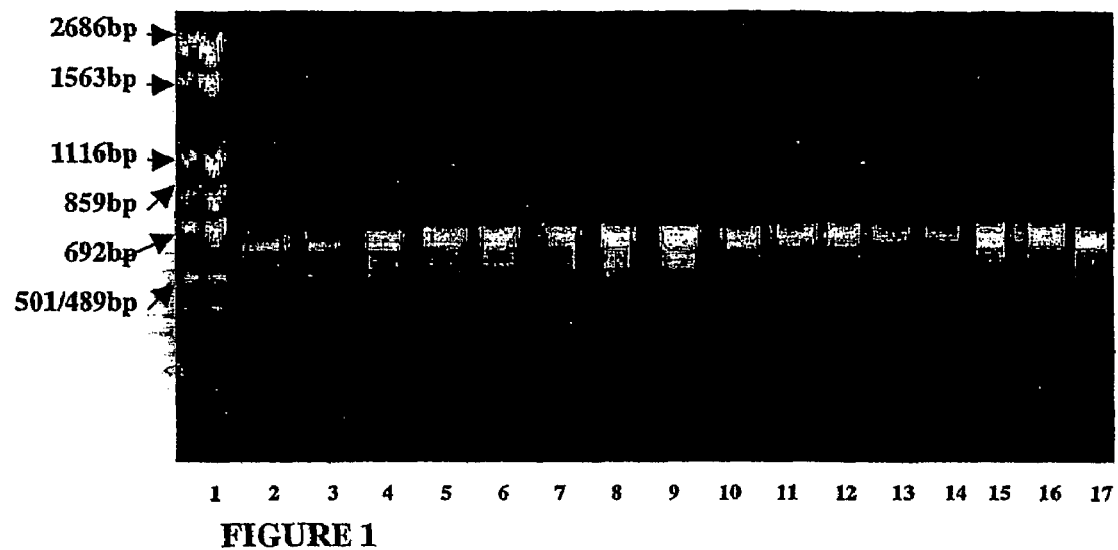
FIG. 1 shows genus-specific amplification with primer set PB1-PB2. Lane 1: PCR DNA Marker (FN-1, Biotech), Lane 2, 12, 13: 702, Lane 3: 801, Lane 4: 901, Lane 5: 1001, Lane 6: *P.freudenreichii* CSCC 2200, Lane 7: *P.freudenreichii* CSCC 2201; Lane 8: *P.freudenreichii* CSCC 2207, Lane 9: *P.acidopropionici* ATCC 25562, Lane 10, 201a1 Lane 11: *P.jensenii* NCFB572, Lane 14, 201b, Lane 15: *P.thoenii* ACM 365, Lane 16: *P.freudenreichii* CSCC 2207, Lane 17: *P.acidopropionici* ATCC 25562

Several analytic methods, including spectrophotometry, microbiological assay, protein-binding assay, radioassay and high performance liquid chromatography (HPLC), are available to determine the levels of vitamin $B_{12}$ in different samples. No IU for vitamin $B_{12}$ activity has been defined, and the assay results are expressed in milligrams, micrograms or nanograms of pure crystalline cyanocobalamin (Ball, 1998).

Extraction procedures are generally required for the determination of total vitamin $B_{12}$ content (Ball, 1998). Vitamin $B_{12}$ occurs intracellularly in the living tissues of animals and most biosynthetic microorganisms or is bound to some proteins in food. The extraction procedure liberates protein-bound cobalamins and converts the different forms to a single and stable form, cyanocobalamin or sulphitocobalamin, by reaction with cyanide or metabisulphite respectively (Ball, 1998).

Several extraction methods have been used to extract vitamin $B_{12}$ from food or microorganism cell samples. In the AOAC [Association of Official Analytical Chemists prior to 1990 but now AOAC International] official method, samples in the extracting solution, which contains 1.3% sodium hydrogen phosphate, 1.2% citric acid.$H_2O$, and 1.0 g sodium metabisulfite, are autoclaved 10 min at 121-123° C. (AOAC, 1995). Vitamin $B_{12}$ in P. acidopropionici cells has been extracted by autoclaving the samples at 121° C. 10 min in a 0.1M phosphate buffer solution (pH6), containing 0.1% KCN or 0.01% KCN (Quesada-Chanto et al., 1994b, Quesada-Chanto et al., 1994a, Quesada-Chanto et al., 1998). Another procedure, which has been described for extracting vitamin $B_{12}$ from food samples, includes homogenising the food sample with 0.1 M sodium acetate-acetic acid buffer (pH4.5), containing 1 mM potassium cyanide, by sonication; and then autoclaving the mixture for 10 min at 121° C. (Muhammad et al., 1993c). Boiling at 100° C. for 20 min has also been used for the extraction of vitamin $B_{12}$ from Propionibacterium freudenreichii cells in a 0.1M phosphate buffer solution (pH5.5), containing 0.01% potassium cyanide (KCN) (Ye et al., 1996). Since autoclaving may result in better extraction than heating by boiling water as the boiling water may not completely extract all of the bound vitamin (Casey et al., 1982), the method of autoclaving the samples at 121° C. for 10 min in 0.05M phosphate buffer solution (pH5.5), containing 0.01% KCN has been used to extract vitamin $B_{12}$ from Propionibacterium cells in this study.

Radioassay

Radioassay was first used to determine the vitamin $B_{12}$ content of serum in the clinical environment (Lau et al., 1965). Now radioassay techniques have been developed to determine vitamin $B_{12}$ levels in food (Casey et al., 1982, Richardson et al., 1978).

Radioassay is based on the competitive binding capacity of radioactive vitamin $B_{12}$ and the vitamin $B_{12}$ in samples for binding protein. Cyanocobalamin is recommended as the calibration standard for the competitive binding radioassay (Muhammad et al., 1993b, Muhammad et al., 1993a). A preparation procedure, which converts different vitamin $B_{12}$ forms (except methylcobalamin) into dicyanocobalamin, is suggested to provide accurate results (Muhammad et al., 1993a). This is because the binding affinity for hog intrinsic factor by hydroxocobalamin, adenosylcobalamin and sulphitocobalamin has been found to be statistically different from that of cyanocobalamin, but the relative binding affinity of dicyanocobalamin or methylcobalamin does not differ significantly from that of cyanocobalamin (Muhammad et al., 1993a).

There are several commercial radioassay kits available for vitamin $B_{12}$ determination (Richardson et al., 1978), including Pharmacia $B_{12}$ Test 50 Radioassay (Poston and Hemmings, 1979), and Bio-Rad $B_{12}$/Folate (used in this study). The Bio-Rad commercial radioassay kit utilizes [$^{57}Co$] cyanocobalamin as the tracer, hog intrinsic factor as the binding protein and cyanocobalamin as the calibration standard. The testing range of this commercial kit is from 50 pg/ml to 2000 pg/ml.

EXAMPLE 1

Isolation and Identification of Dairy Propionibacteria Strains from Raw Milk, Cheese and Human Small Intestine Biopsy Samples The purpose of this study was to isolate strains of dairy propionibacteria species from raw milk, cheese products and human small intestine biopsy samples, and further identify the isolated strains into species. For this purpose, different identification methods, including traditional identification methods, API 50 CH carbohydrate fermentation profiles, PCR identification methods and whole cell water-soluble protein analysis by SDS-PAGE, were used.

Materials and Methods

Reference Strains

Reference strains used throughout this study are listed in Table 4.

TABLE 4

Details of reference strains used

| STRAIN | SPECIES | SUPPLIER |
|---|---|---|
| CSCC 2200 | Propionibacterium freudenreichii | Australian Starter Culture Research Centre, Australia |
| CSCC2201 | P. freudenreichii | CSIRO Melbourne, Australia |
| CSCC2206 | P. freudenreichii | CSIRO Melbourne, Australia |
| CSCC2207 | P. freudenreichii | CSIRO Melbourne, Australia |
| CSCC2216 | P. freudenreichii | CSIRO Melbourne, Australia |
| ACM365 | P. thoenii | Australian Collection of |

TABLE 4-continued

Details of reference strains used

| STRAIN | SPECIES | SUPPLIER |
| --- | --- | --- |
| | | Microorganisms, University of Queensland, Australia |
| ATCC25562 | P. acidopropionici | American Type Culture Collection, the United States |
| 341 | P. acidopropionici | Microbiology Department, University of Melbourne, Australia |
| NCFB571 | P. jensenii | Dr. Franca Rossi, University of Verona, Italy |
| NCFB572 | P. jensenii | Dr. Franca Rossi, University of Verona, Italy |
| MJLA1 | Lactobacillus acidophilus | Gist Brocades, Australia |

Strain Recovery

Strains were recovered in liquid medium, Sodium Lactate Broth (SLB) for *Propionibacterium*, de Man, Rogosa and Sharp medium (MRS, Oxoid) for *Lactobacillus* at 30° C. anaerobically, and then streaked onto agar plates, Sodium Lactate Agar (SLA) for *Propionibacterium*, and MRS agar (Oxoid) for *Lactobacillus* to establish purity. Pure colonies were Gram stained, and catalase tested. All strains were examined microscopically for correct cell morphology.

Strain Preservation

*Propionibacterium* strains were harvested from SLA plates and resuspended in Sodium Lactate Glycerol Broth, which is SLB with 20% glycerol (Sigma). 1 mL of the bacterial suspension was dispensed into a 2 mL Corning Cryogenic vial (Corning Glass Works), frozen in dry ice, and stored at −70° C.

*L. acidophilus* MJLA1 was harvested from MRS plates and resuspended in MRS broth containing 20% glycerol. 1 mL of the bacterial suspension was dispensed into a 2 mL Corning Cryogenic vial (Corning Glass Works), frozen in dry ice, and stored at −70° C.

Isolation of Dairy Propionibacteria Strains

Ethics Approval

Ethics approvals for studies of human biopsy samples, were obtained from both the Ethics Committee of the University of Newcastle of Australia, and the Ethics Committee of the Sydney Adventist Hospital, Sydney, NSW, Australia. The ethics certificate number is H6700499.

Human Biopsy Sample, Milk and Cheese Sample Collection

Human gut biopsy samples were collected at the Sydney Adventist Hospital, Sydney, NSW, Australia, stored in 2 mL Corning Cryogenic vials, containing 1 mL Maximum Recovery Diluent (MRD, Oxoid), and delivered to the laboratory at ambient temperature.

Raw milk samples were obtained from a dairy farm at Cooranbong, NSW, Australia.

Cheese samples, including Parmesan cheese (Bonlac), Swiss cheese (Dairy Good), Best Quality Gouda (New Zealand), Grana Papano cheese (Bengodi) and Jarlsberg cheese (Norway), were purchased from Woolworths supermarket in Gosford, NSW, Australia.

Procedures for Isolation of Dairy Propionibacteria Strains 1 in 5 dilutions of cheese samples were prepared by mixing 10 g of each cheese sample with 40 mL of MRD in a stomacher bag, and then stomaching for 1 min in a stomacher (Calworth).

Corning Cryogenic vials containing human biopsy samples were vortex mixed at maximum setting for 10s using a vortex mixer (Ratex).

A loop of each cheese suspension, human biopsy suspension, and each raw milk sample was streaked onto duplicate Yeast Extract Lactate Agar (YELA) plates, and incubated anaerobically at 30° C. for 10 days. After 10 days incubation, different single colonies on YELA plates were picked and streaked onto SLA plates, and incubated anaerobically at 30° C. for 7 days. Then pure single colonies were streaked onto SLA slopes, and stored at 4° C. for up to 3 month for identification.

Traditional Identification Method

Species Identification Scheme

A quick traditional identification scheme was designed for the identification of isolated strains:

| | | |
| --- | --- | --- |
| 1 | Gram positive, catalase positive, non spore-forming, irregular shaped short rods | 2 *Propionibacterium* genus |
| 2 | Gelatin hydrolysis positive | cutaneous propionibacteria |
| | Gelatin hydrolysis negative | 3 dairy propionibacteria |
| 3 | Fermentation of maltose and sucrose positive | 4 |
| | Fermentation of maltose and sucrose negative | P. freudenreichii |
| 4 | β hemolysis positive | P. thoenii |
| | β hemolysis negative | 5 |
| 5 | Reduction of nitrate positive | P. acidopropionici |
| | Reduction of nitrate negative | P. jensenii |

This scheme was formulated from the information contained in 'A scheme for the identification of Gram-positive bacteria' (Harrigan, 1998b) and the differentiation characteristics of dairy propionibacteria in Bergey's Systematic Bacteriology (Cummins and Johnson, 1986). The identification is based on phenotypic characteristics, including morphological properties and biochemical properties (catalase test, gelatin hydrolysis, maltose and sucrose fermentation, β-hemolysis, and reduction of nitrate).

Gram-stain

A single colony of each strain was selected from an SLA plate. A smear of bacteria was prepared on a clean, grease-free slide. After the smear was air dried and heat fixed, it was flooded with Crystal violet stain (Micro Diagnostics) for 30 seconds, rinsed with tap water and blot dried; the smear then was flooded with Gram Iodine stain (Micro Diagnostics) for 30 seconds, rinsed with tap water and blot dried; the smear then was decolourised with 95% ethanol (Micro Diagnostics) for 5-15 seconds, and counterstained with safranine stain (Micro Diagnostics) for 30 seconds. The slides were rinsed with tap water and the stain deposits were carefully removed from the back of the slide with filter paper. The slide was blot dried and examined under a light microscope at 1 000× magnification.

Catalase Test

3% Hydrogen peroxide (Chem-Supply) was freshly prepared daily and stored at 4° C. until use. A single colony of each isolated strain was picked from the SLA plate and emulsified with the 3% hydrogen peroxide on a clean grease-free slide using a wooden tooth pick. Production of gas bubbles indicated the presence of catalase in the tested culture.

Gelatin Hydrolysis

Nutrient broth (NB) (Oxoid) containing 12% gelatin (Oxoid) was prepared in 10×130 mm test tubes with screw caps. A single colony of each isolated strain on an SLA plate was inoculated into the medium with a straight stabbing wire, and incubated anaerobically at 30° C. for 30 days. The tubes containing cultures were removed from the incubator and placed in a 4° C. fridge for 4 h or until the medium in the negative control tube set. Liquefaction of medium indicated a positive gelatin hydrolysis reaction.

β-Haemolysis Reaction

A single colony of each isolated strain on an SLA plate was streaked onto a sheep blood agar plate (HAPS), and incubated anaerobically at 30° C. for 7 days. The plates were then checked for signs of hemolysis. An uninoculated sheep blood agar plate was used as negative control to prevent false positive results, since sheep blood agar can be naturally hemolyzed during storage or incubation.

Carbohydrate Fermentation

The carbohydrate fermentation medium consists of Sodium Lactate Base (SL) containing 1% each of maltose or sucrose. Aliquots of 10 mL of each carbohydrate medium were prepared in 20 mL bottles (Oxoid) with screw caps, and inoculated with one single colony of each isolated strain grown on sheep blood agar anaerobically at 30° C. for 5 days. Each strain was tested in duplicate. The inoculated bottles were incubated anaerobically at 30° C. for 7 days. Turbidity or precipitation of the broth indicated a positive growth. Yellow colorization of the broth or pH of the broth below 5.7 indicated positive fermentation.

Dairy Propionibacteria Genus and Species Specific PCR

Preparation of Genomic DNA

Purification of genomic DNA of 6 isolated strains and reference *Propionibacterium* strains was based on the method described by Rossi (1998), and as outlined briefly below:

Strains were grown anaerobically in SLB broth for 48-72 hr. 1 mL of each strain was transferred to a 1.5 mL eppendorf tube (Sarstedt), and centrifuged at 2 500×g (Beckman) for 5 min. The supernatant was decanted. The cell pellet was then resuspended with 900 μL of TE buffer. Lysozyme (100 μL) (Sigma, 100 mg/mL) was added to the cell suspension and mixed by inverting the tubes 30 times. The mixture then was incubated in a 37° C. water bath for 2 hours. After incubation, the treated cells were collected by centrifugation (2500×g, 5 min). The supernatant was removed and each of the pellets was resuspended in TE buffer (370 μL), and 20% (w/v) sodium dodecyl sulfate (10 μL, SDS), then mixed by inverting the tube 10 times. DNase-free RNAase (20 μL) (Sigma, 2 mg/mL) was added to the suspension and mixed by inverting the tube 20 times and incubated in a 37° C. water bath for 30 min. Proteinase K (8 μL) (Sigma, 1 mg/mL) was added and mixed by inverting the tubes 20 times, and incubated in a 37° C. water bath for 1 hour. Sodium perchloride (3M, 215 μL) (Sigma) was added and mixed by inverting the tubes 30 times. The aqueous phase was extracted with an equal volume of phenol:chloroform:iso-amylalcohol (Sigma), followed by chloroform (Ajax): iso-amylalcohol (Ajax) (24:1), centrifuging (3500×g, 5 min) in between, and transferring to a new Eppendorf tube after each extraction. The DNA was precipitated with an equal amount of isopropanol (Unilab) by gently mixing the tubes 50 times. The DNA was pelleted by centrifugation (3500×g, 1 min). The DNA pellet was then washed with cold 70% (vol/vol) ethanol (Rhone-Poulenc), air dried for 30 min, and resuspended in 100 μL of PCR-grade water (Biotech) at 4° C. overnight. The DNA solution was mixed gently for 10 s by a vortex mixer (Ratex), and stored at 20° C.

Determination of DNA Concentration

DNA concentration was determined as described by Towner (1999).

Briefly, 5 μL of DNA solution was added to an eppendorf tube containing 995 μL distilled water, and mixed gently by a vortex mixer (Ratex). The absorbance of the DNA solution was measured at 260 nm and 280 nm. The ratio of $OD_{260}/OD_{280}$ indicated the purity of the DNA sample. Samples with a ratio above 1.7 were accepted. The concentration of DNA (ng/μL) is equivalent to $10^4 * OD_{260}$.

Dairy Propionibacteria Genus Specific and Species Specific Primers

Primers were constructed by Genes Works, Perth, WA, Australia, according to the description by Rossi (1999), as in Table 5. Primer pairs are PB1-PB2, PF-PB2, PJ-PB2, PA-PB2, and PT3-PB2.

TABLE 5

Primer sequence

| Primer name | Primer sequence |
|---|---|
| PB1 (SEQ ID No. 14) | 5'-AGTGGCGAAGGCGGTTCTCTGGA-3' |
| PB2 (SEQ ID No. 15) | 5'-TGGGGTCGAGTTGCAGACCCCAAT-3' |
| PF (SEQ ID No. 16) | 5-CTTTCATCCATGACGAAGCGCAAG-3' |
| PJ (SEQ ID No. 17) | 5'-GACGAAGTGCCTATCGGGGTG-3' |
| PA (SEQ ID No. 18) | 5'-GACGAAGGCATTCTTTTYAGGGTGT-3' |
| PT3 (SEQ ID No. 19) | 5'-GGACAAAAGGCCTTTCGGGGTTT-3' |

PCR Amplification Procedure

PCR was performed in a reaction volume of 20 μL containing 1× reaction buffer (Biotech), 1.5 mM $MgCl_2$ (Biotech), 100 μM of each dATP, dCTP, dTTP, and dGTP (Biotech), 0.5 μM each primer, 1 UI of Taq DNA polymerase, and 1 μL of diluted target DNA solution (around 20 ng DNA). PCR was performed in a thermal cycler (Corbett Research). After an initial denaturation at 94° C. for 4 min, the PCR conditions used consisted of 40 cycles of denaturation at 94° C. for 30 s, annealing for 15 s at different temperatures for each different upstream primer (at 68° C. for PA and PJ, at 69° C. for PF, and at 70° C. for PT3 and PB1), and extension at 72° C. for 1 min. After the final cycle, the temperature was maintained at 72° C. for 5 min to complete extension.

Analysis of Dairy Propionibacteria Genus Specific PCR Products

The PCR mixtures were analysed for amplification products by mixing 5 μL of the mixture with 1 μL of 6× sample buffer (Biotech) and observing after agarose gel electrophoresis at 100 volts for 20 min using a 1.5% agarose gel containing 0.5 μg/mL ethidium bromide (Bio-Rad) in 0.5× TAE buffer (Sigma). Following electrophoresis the agarose gel was examined and photographed using Gel-Doc Computer software (Bio-Rad).

RAPD-PCR Using Primer OPL-05 for Identification of Dairy Propionibacteria

Genomic DNA preparations and DNA concentration determination were performed as previously described.

Primer OPL-05

Primer OPL-05 (5'-ACGCAGGCAC-3') was constructed by Genes Works, Perth, WA, Australia.

RAPD-PCR Amplification Procedure

PCR was performed in a reaction volume of 25 μL containing 1× reaction buffer (Biotech), 1.5 mM $MgCl_2$ (Biotech), 100 μM of each dATP, dCTP, dTTP, and dGTP (Biotech), 1 μM primer OPL-05, 2.5 UI of Taq DNA polymerase, and 5 μL of diluted target DNA solution (around 25 ng DNA). RAPD-PCR reaction was performed in a thermal cycler (Corbett Research). After an initial denaturation at 94° C. for 4 min, the PCR conditions used consisted of 45 cycles of denaturation at 94° C. for 1 min, annealing at 35° C. for 1 min, and extension at 72° C. for 2 min. After the final cycle, the temperature was maintained at 72° C. for 5 min to complete extension.

Analysis of RAPD-PCR Products

The PCR mixtures were analysed for amplification products by mixing 5 μL of the mixture with 1 μL of 6× sample buffer (Biotech) and observing after agarose gel electrophoresis at 80 volts for 40 min using a 1.5% agarose gel containing 0.5 μg/mL ethidium bromide (Bio-Rad) in 0.5× TBE buffer (Sigma). Following electrophoresis the agarose gel was examined and photographed using a Gel-Doc (Bio-Rad).

SDS-PAGE of Whole Cell Water-soluble Protein

Preparation of Whole Cell Water-soluble Proteins

Whole cell soluble proteins extraction was based on the method described by Fessler (1999). In brief, each strain was grown anaerobically in 10 mL of SLB for 48 hours at 30° C. Cells were centrifuged (3500×g, 10 min) and the pellets were washed in 1 mL 0.9% NaCl twice. The pellets were then resuspended in 200 μL of TES buffer. Approximately 0.5 g of glass beads (0.25 mm-0.5 mm, Australian Scientific) were added to the suspension and the suspension was vortexed at maximum speed five times at 1 min intervals. The suspensions were chilled on ice for at least 1 min between vortexing. The suspensions were centrifuged (600×g, 10 min) and the supernatants, containing whole cell soluble proteins, were collected for analysis by SDS-PAGE.

Determination of Protein Concentration

The protein concentration of each sample was determined using the Bio-Rad Protein Assay, Microtiter Plate Protocols. A standard curve was constructed using bovine serum albumen (Bio-Rad) concentrations of 0.073, 0.137, 0.247, and 0.336 mg/mL protein. Each standard and sample (10 μL) was placed in triplicate in a 96 well microtitre plate. Protein samples were diluted if required, so the reading fell within the boundaries of the standard curve. Bio-Rad dye reagent (100 μL) was added to each well and mixed gently. Reaction was allowed between 5 min to 1 hour. The absorbance of each well was read and the protein concentration of the tested sample was automatically calculated using a Bio-Rad Microplate Reader (Model 550).

SDS-PAGE Electrophoresis

SDS-PAGE electrophoresis conditions were a modification of those described by Baer (1987). Briefly, vertical 12% acrylamide gels of 0.75 mm thickness were prepared using the Bio-Rad Protean II xi Cell cooled vertical slab apparatus. Each gel was prepared by slowly pipetting the 12% acrylamide separation gel mix along the edge of the glass plates, leaving 4 cm at the top for the stacking gel. Sterile water was layered over the top and the acrylamide gel was allowed to set for 40-45 min at room temperature. The water layer was carefully drained and 4-4.5 mL of 4% acrylamide stacking gel was added to the top of the separating gel, leaving 0.5 cm at the top. A 15-well comb was then inserted into the stacking gel. The gels were left to solidify for 30-35 minutes at room temperature. Samples were diluted with Sample Buffer to a final protein concentration of 10-15 μg/μL, and heated to 94° C. for 3 min. Samples (30 μL) were added to each well. Double gels were run fully immersed in 1× Running Buffer at a constant current of 30 mA at room temperature for 5 hr.

Coomassie Blue Staining SDS-PAGE Gel

The gels were carefully removed from the glass plate, immersed in 1× Coomassie Blue stain (Bio-Rad) and incubated at room temperature for 30 min with constant shaking on a rotating incubator (10 rpm).

The gels were then destained by immersion in Destaining Solution for 90 min at room temperature with constant shaking and replacement of destaining solution a few times until the gel background was clear.

Analysis of SDS-PAGE Gels

The gels were photographed and band profiles analysed using GelDoc computer software (Bio-Rad).

Storage of SDS-PAGE Gels

Gels were stored by drying in cellophane. Briefly, gels were washed with deionised water three times and immersed in gel-dry solution (Bio-Rad) for 30 minutes with constant shaking, then dried in cellophane by the Bio-Rad GelAir Drying System.

API CH 50 Carbohydrate Profile Using SL

The *Propionibacterium* strains were assessed for carbohydrate profile using API CH 50 strips. The preparation and analysis of isolates were conducted according to the manufacturer's instructions. SL broth was adopted as the growth medium.

Briefly, each strain was grown on sheep blood agar anaerobically at 30° C. for 5 days. The inoculum of each strain was prepared using SL broth according to the manufacturer's instructions. API CH50 kits were inoculated and mineral oil was added to each tube of the API CH50 kit to provide anaerobic conditions. The kits were incubated at 30° C. aerobically for 4 days. The tests were read after 24 hr, 48 hr, 72 hr, and 96 hr of incubation. A positive test corresponded to acidification revealed by the bromocresol purple indicator, which was contained in SL, changing to yellow. For the Esculin test, a change from purple to black indicated a positive reaction.

Results

Isolated strains were identified to dairy propionibacteria species by the method summarised below:

Identification of isolated *Propionibacterium* strains

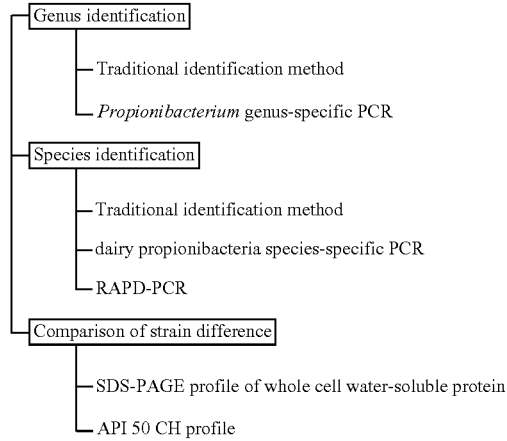

Presence of Dairy Propionibacteria Strains

Six dairy propionibacteria strains were isolated of which four were from milk and two were from the Swiss-cheese sample (Table 6). These six isolates were Gram positive, catalase positive, non-spore forming, irregular short rods. These six isolates did not hydrolyse gelatin and can therefore be included in dairy propionibacteria species.

No dairy propionibacteria strains were isolated from Parmesan cheese, Best Quality Gouda cheese, Grana Papano cheese and Jarlsberg cheese samples (results not shown). No dairy propionibacteria strains were isolated from 87 human gut biopsy samples (results not shown).

TABLE 6

Labels and origin of isolated strains

| Isolates strains | Source |
| --- | --- |
| 201a1 | Swiss-cheese |
| 201b | Swiss-cheese |
| 702 | Milk sample 1 |
| 801 | Milk sample 2 |
| 901 | Milk sample 3 |
| 1001 | Milk sample 4 |

Genus Identification Using *Propionibacterium* Genus-specific PCR Method

FIG. 1 shows the agarose gel electrophoretic profiles of PCR products obtained for six isolated and six reference strains using *Propionibacterium* genus-specific primers PB1-PB2. Identification of isolated strains was performed by visual comparison of the electrophoretic profiles of PCR products of isolated strains with that of reference strains of dairy propionibacteria species. Only one PCR product was produced for all the tested strains. Primer pair PB1-PB2 has been proven to be specific for dairy propionibacteria and *P. acnes* (Rossi, 1999). *P. acnes* belongs to cutaneous propionibacteria (Cummins and Johnson, 1986). Therefore, the six isolates can be identified as strains of genus *Propionibacterium*, but not necessarily as strains of dairy propionibacteria, using genus specific PCR with primer sets PB1-PB2.

Species Identification of Isolated Strains Using Traditional Methods

The morphological and tested biochemical characteristics of the isolated *Propionibacterium* strains are listed in Table 7. For the purpose of comparison, the morphological and tested biochemical characteristics of some reference strains are also listed in Table 7. All the reference strains, except for *P. freudenreichii* CSCC2206, gave expected results based on published data (Cummins and Johnson, 1986). Isolated strains were identified to species by the quick traditional identification scheme. *P. freudenreichii* CSCC2206 did not give expected results for maltose and sucrose fermentation of *P. freudenreichii* species (Cummins and Johnson, 1986).

Most of the strains of dairy propionibacteria will be catalase positive (Cummins and Johnson, 1986). Strain *P. acidopropionici* ATCC25562 showed negative for catalase tests, but this is not a false negative because only 40-90% of strains of *P. acidopropionici* have been reported to be positive for catalase (Cummins and Johnson, 1986).

There is variation in nitrate reduction amongst the *P. freudenreichii* strains. This indicates strain differences between the 9 identified *P. freudenreichii* strains. This variation is supported by the published data on nitrate reduction by *P. freudenreichii* strains (Cummins and Johnson, 1986), that is, that 11-89% of the strains will reduce nitrate.

TABLE 7

A summary of the different characteristics of tested strains

| Tests | 201a1 | 201b | 801 | 901 | 1001 | P. freudenreichii CSCC2207 | P. freudenreichii CSCC2200 |
| --- | --- | --- | --- | --- | --- | --- | --- |
| Pigmentation | cream | cream | cream | cream | cream | cream | cream |
| Catalase | + | + | + | + | + | + | + |
| Gelatin hydrolysis | − | − | − | − | − | − | − |
| Maltose | − | − | − | − | − | − | − |
| Sucrose | − | − | − | − | − | − | − |
| β-haemolysis | − | − | − | − | − | − | − |
| Nitrate reduction | − | − | + | + | + | + | − |
| Species | P. freudenreichiichii | P. freudenreichii | P. freudenreichii | P. freudenreichii | P. freudenreichii | P. freudenreichii | P. freudenreichii |

| Tests | P. freudenreichii CSCC2201 | P. freudenreichii CSCC2216 | P. freudenreichii CSCC2206 | 702 | P. jensenii NCFB572 | P. acidopropionici ATCC25562 | P. thoenii ACM 365 |
| --- | --- | --- | --- | --- | --- | --- | --- |
| Pigmentation | cream | cream | cream | cream | Cream | Cream | Red |
| Catalase | + | + | + | + | + | − | + |
| Gelatin hydrolysis | − | − | − | − | − | − | − |
| Maltose | − | − | + | + | + | + | + |
| Sucrose | − | − | + | + | + | + | + |
| β-haemolysis | − | − | − | − | − | − | + |

TABLE 7-continued

A summary of the different characteristics of tested strains

| Nitrate reduction | – | – | – | – | – | + | – |
|---|---|---|---|---|---|---|---|
| Species | P. freudenreichii | P. freudenreichii | ??? | P. jensenii | P. jensenii | P. acidopropionici | P. thoenii |

Symbols:
+, positive reaction or pH below 5.7;
–, negative reaction or pH above 5.7.

Species Identification of Isolated Strains Using *Propionibacterium* Species-specific PCR Identification of isolated strains was performed by visual comparison of the electrophoretic profiles of species-specific PCR products of isolated strains with those of reference strains. PCR products were detected from the PCR reaction using primer sets PF-PB2, PJ-PB2, and PT3-PB2 (FIG. 2, FIG. 3, FIG. 4); however, no PCR products were found from the PCR reaction using primer set PA-PB2 (results not shown).

Figure 2:
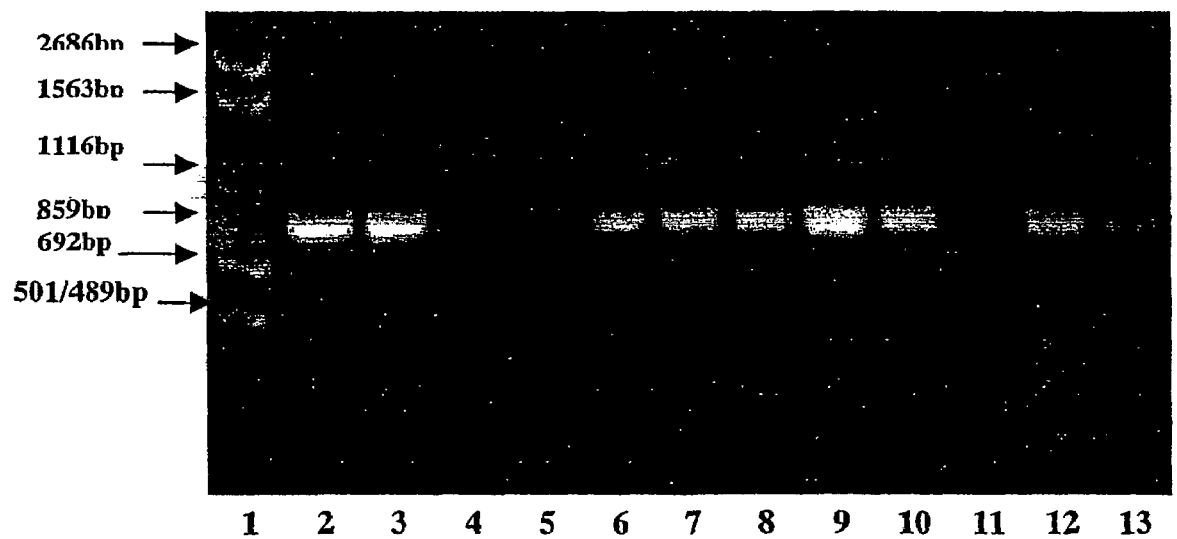
FIG. 2 shows species-specific amplification with primer set PF-PB2. Lane 1: PCR DNA Marker (FN-1, Biotech), Lane 2: 201a1, Lane 3: 201b, Lane 4: 702, Lane 5: 801, Lane 6: 901, Lane 7,8: 1001, Lane 9: *P.freudenreichii* CSCC 2200; Lane 10: *P.freudenreichii* CSCC 2201, Lane 11: *P.freudenreichii* CSCC 2206, Lane 12: *P.freudenreichii* CSCC 2207, Lane 13: *P.freudenreichii* CSCC 2216

FIG. 2 shows the electrophoretic profiles of PCR products produced by primer set PF-PB2. Only one PCR product of the same size was produced for strains 201a1, 201b, 801, 901, 1001, P. freudenreichii CSCC2200, P. freudenreichhi CSCC2201, P. freudenreichii CSCC2207, and P. freudenreichii CSCC2216. However, strain 702 and P. freudenreichii CSCC2206 produced no PCR product. Primer set PF-PB2 has been found to be specific for P. freudenreichii (Rossi et al, 1999). Therefore, strains 201a1, 201b, 801, 901 and 1001 were identified as strains of P. freudenreichii but not strain 702 and P. freudenreichii CSCC2206. This result correlates with the results using traditional identification methods (Table 7). In addition, this may suggest that the identification status of P. freudenreichii CSCC2206 is in doubt. It may not belong to P. freudenreichii.

Figure 3:
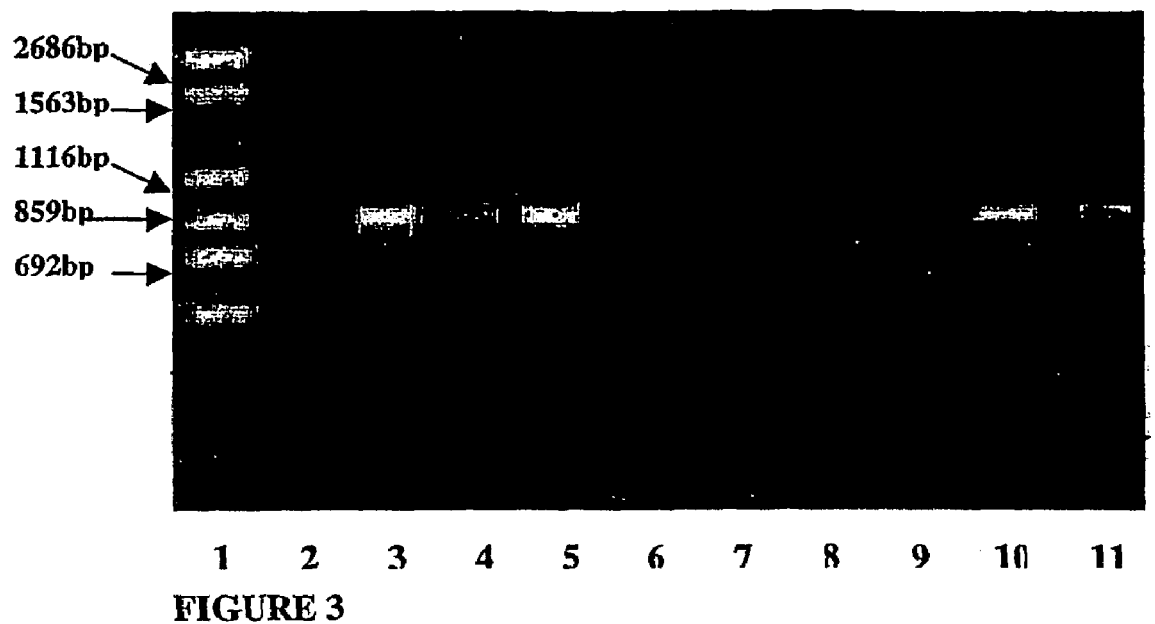
FIG. 3 shows species-specific amplification with primer set PJ-PB2 Lane 1: PCR DNA Marker (FN-1, Biotech), Lane 2: Negative control, Lane 3-5: 702; Lane 6: *P.acidopropionici* ATCC 25562, Lane 7,8: *P.freudenreichii* CSCC 2206, Lane 9: *P.freudenreichii* CSCC 2207; Lane 10: *P.jensenii* NCFB571; Lane 11: *P.jensenii* NCFB572

FIG. 3 shows the agarose gel eletrophoretic profiles of strain 702 and reference strains, which were obtained with primer pair PJ-PB2. Only one PCR product of the same size was produced by strains 702, P. jensenii NCFB571 and NCFB572. No PCR products were produced by strains P. freudeireichii CSCC2206, CSCC2207, or P. acidopropionici ATCC25562. Primer pair PJ-PB2 has been found to be specific to P. jensenii (Rossi et al, 1999). Therefore, strain 702 was identified as a strain of P. jensenii.

Figure 4:
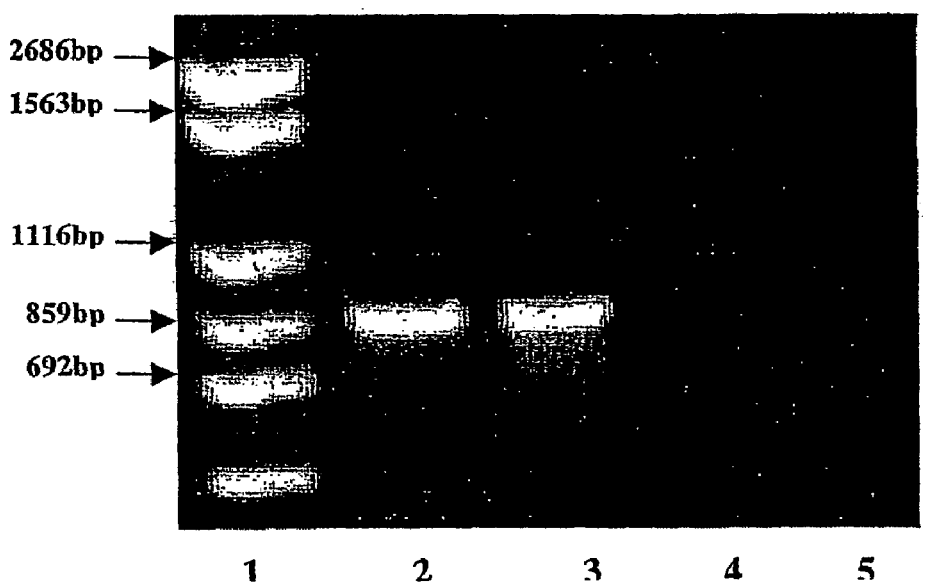
FIG. 4 shows species-specific amplification with primer set PT3-PB2 Lane 1: PCR DNA Marker (FN-1, Biotech), Lane 2,3: *P.thoenii* ACM 365, Lane 4,5: 702

FIG. 4 shows the agarose gel electrophoresis profiles of strain 702 and P. thoenii ACM365, which were obtained with primer pairs PT3-PB2. P. thoenii ACM365 produced one PCR product of the same size. No PCR products were produced by strain 702. Primer pair PT3-PB2 has been found to be specific to P. thoenii (Rossi et al, 1999). Therefore, strain 702 was not a strain of P. thoenii.

Species Identification of Isolated Strains Using RAPD-PCR

Figure 5:
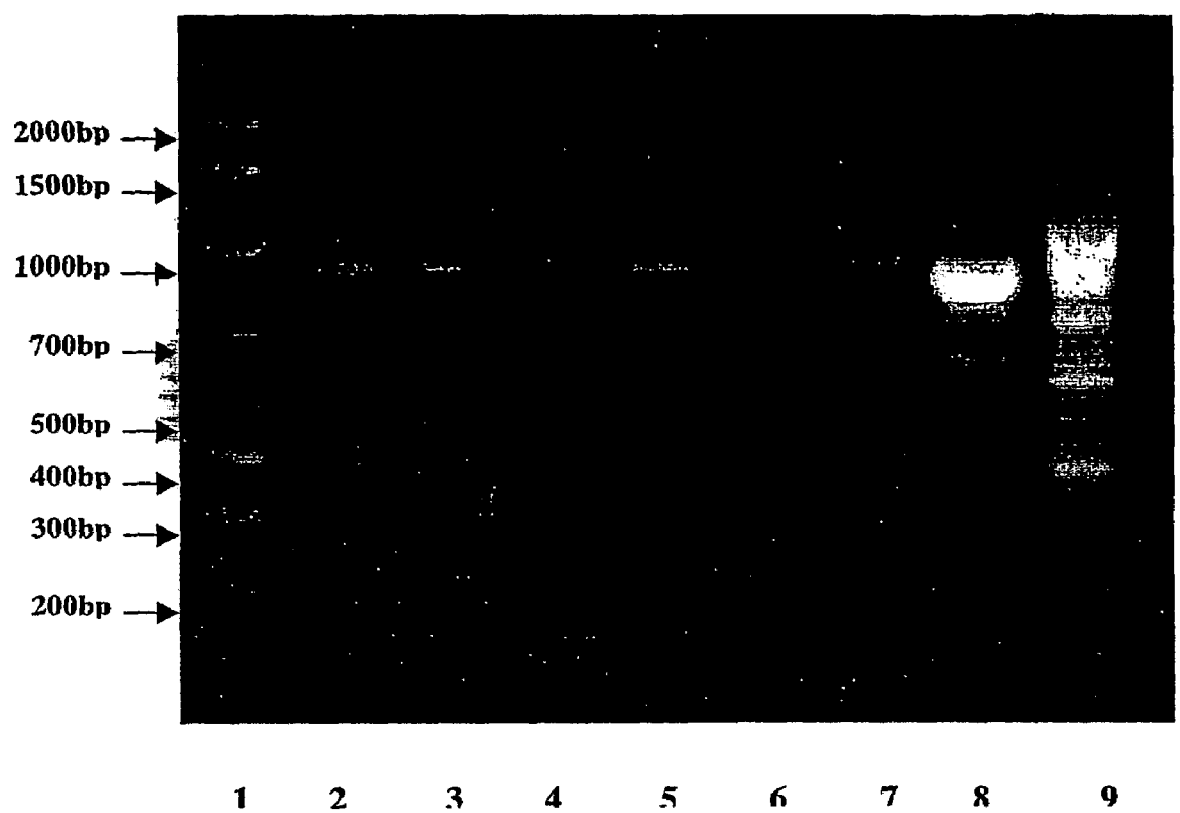
FIG. 5 shows electrophoretic profiles obtained for tested strains of *Propionibacterium* spp. by RAPD-PCR with primer OPL-05. Lane 1: PCR DNA Marker (Bio-Rad AmpliSize™ Molecular Ruler, 50-2000 bp ladder); Lane 2: 1001; Lane 3: 901; Lane 4: 801; Lane 5: 201b; Lane 6: *P. freudenreichii* CSCC 2206; Lane 7: 201a1; Lane 8: *P. acidopropionicii* ATCC 25562; Lane 9: *P. acidopropionicii* 341

FIG. 5 shows the agarose gel electrophoresis profiles obtained by RAPD-PCR with OPL-05. Identification of six isolated strains was performed by visual comparison of their electrophoretic profiles with those of reference strains. Strain 201a1, 201b, 801, 901, 1001, and P.freudenreichii CSCC2206 produced only one PCR product of the same size; while strains P. acidopropionici ATCC25562 and 341 had patterns of multiple PCR products with some common bands. Strain 702, P. jensenii NCFB572 and strain P. freudenreichii CSCC2207 did not produce any products when tested under the same amplification program using OPL-05 (results not shown). Therefore, strain 201a1, 201b, 801, 901 and 1001 can be identified as strains of P. freudenreichii, while strain 702 could not be identified using this RAPD-PCR method.

SDS-PAGE Profile of Whole Cell Water-soluble Proteins of Isolated Strains

Whole cell water-soluble proteins of six isolated strains and reference strains were analysed by SDS-PAGE. The electrophoretic profile of each isolated strain was compared with those of reference strains. SDS-PAGE band patterns of different strains were compared by the presence or the absence of typical bands but not their intensity, since intensity of the bands may vary for different batches of protein samples for the same bacteria (Baer, 1987).

Figure 6:
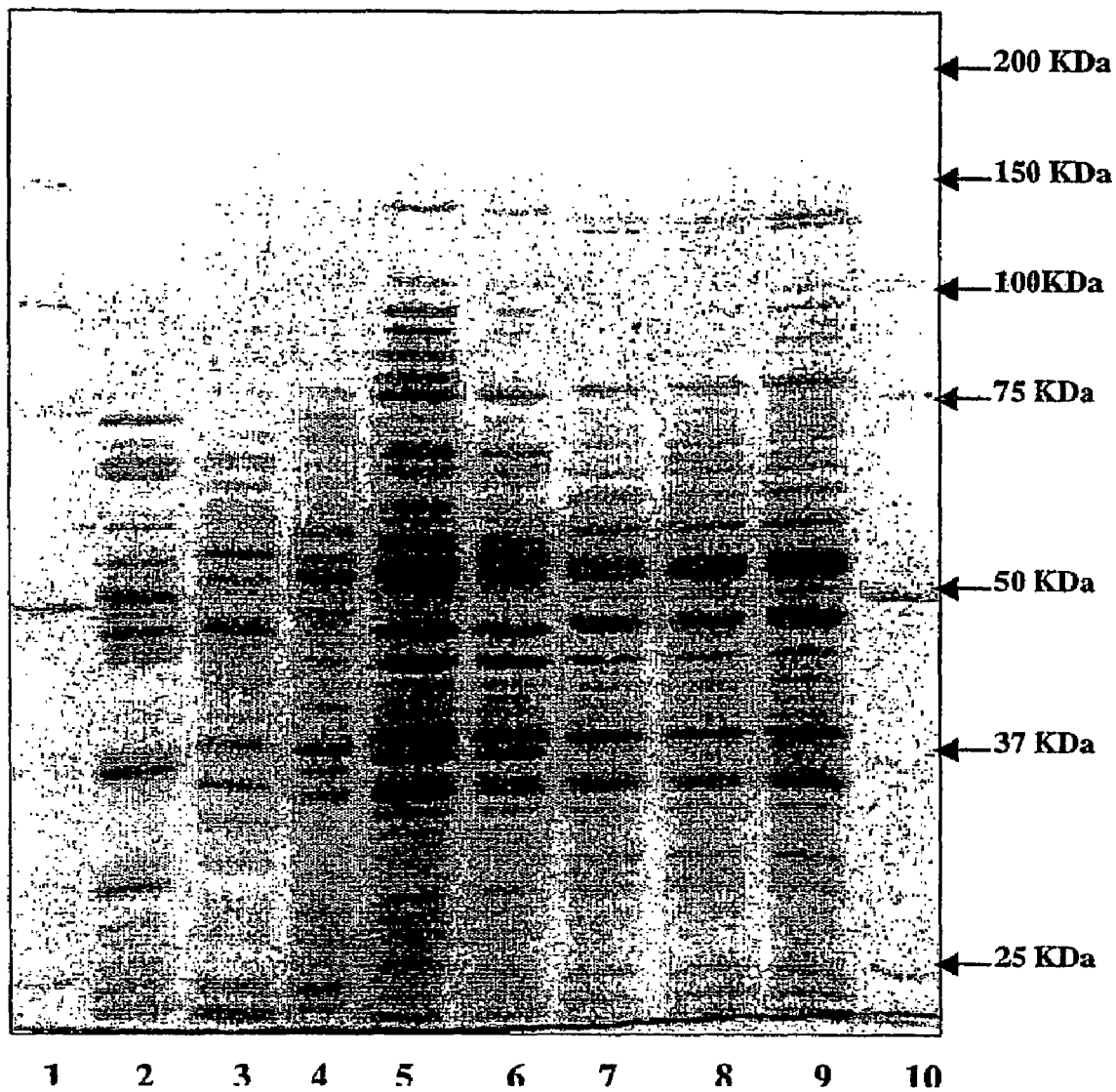
FIG. 6 shows SDS-PAGE analysis of whole cell-water-soluble proteins of an isolated strain 702 and reference strains. Lane 1,10: SDS-PAGE Protein Marker (Bio-Rad Precision Protein Standard, Broad Range, Unstained), Lane 2: *Lactobacillus acidophilus* (MJLA1), Lane 3: *P.freudenreichii* CSCC 2207, Lane 4: *P.acidopropionici* ATCC 25562, Lane 5 and 6: *P.thoenii* ACM 365, Lane 7 to 9: Strain 702
Figure 7:
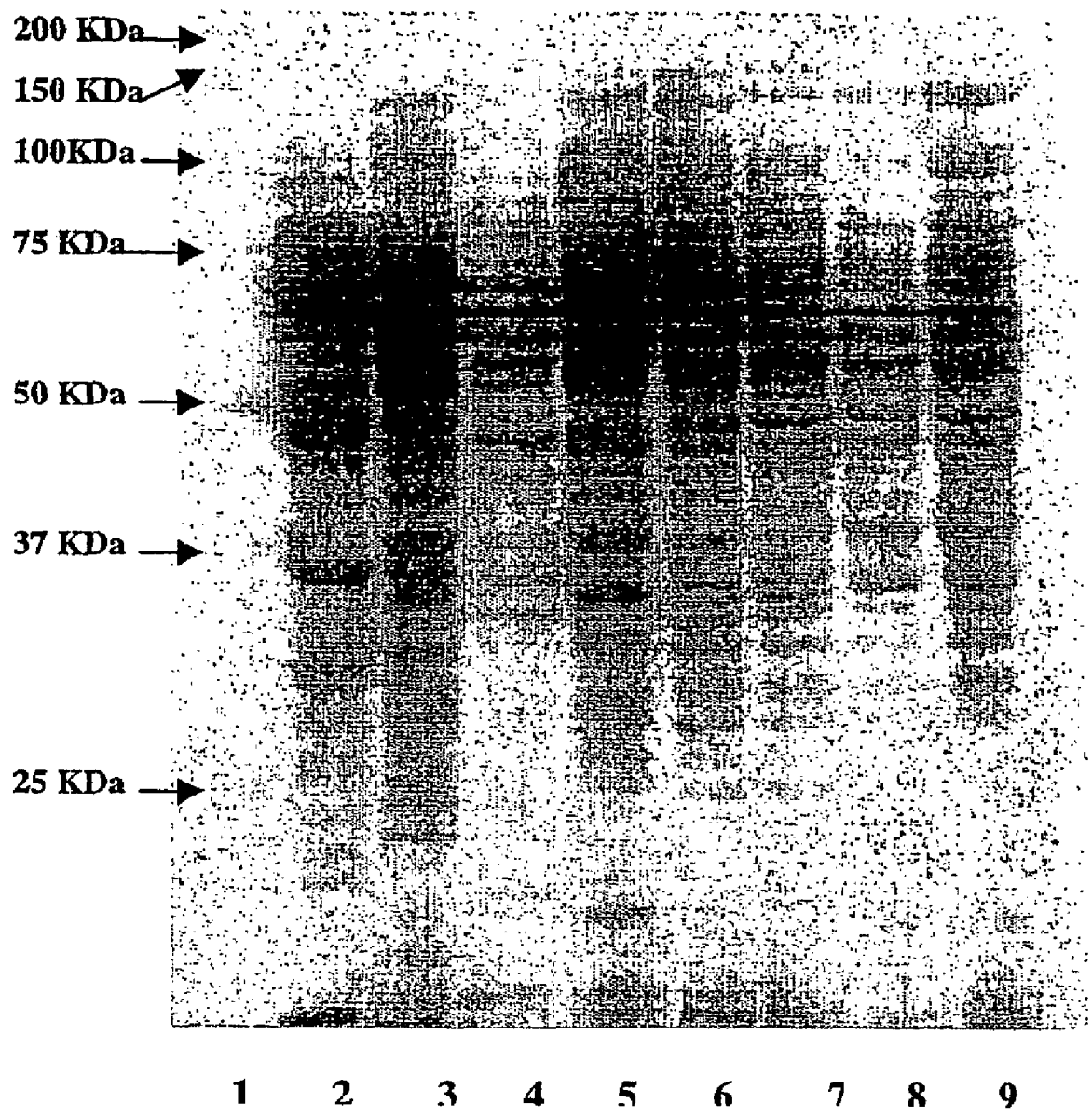
FIG. 7 shows SDS-PAGE analysis of whole cell water-soluble proteins of an isolated strain 702 and reference strains. Lane 1: SDS-PAGE Protein Marker (Bio-Rad Precision Protein Standard, Broad Range, Unstained), Lane 2: *Lactobacillus acidophilus* MJLA1, Lane 3: *P.freudenreichii* CSCC 2207, Lane 4: *P.acidopropionici* ATCC 25562, Lane 5: *P.thoenii* ACM 365, Lane 6, 7: *P.jensenii* NCFB 572, Lane 8-9: 702

FIG. 6 and FIG. 7 show the SDS-PAGE band patterns of one isolate, strain 702, and reference strains of four species of dairy propionibacteria. The SDS-PAGE band patterns of replicate samples of strain 702, P.jensenii NCFB572, and P. thoenii ACM365 were identical. This indicates the high reproducibility of the SDS-PAGE identification method. The band pattern of strain 702 was almost identical to that of P.jensenii NCFB572, but different from that of P. thoenii ACM365, P. freudenreichii CSCC2207, P.acidopropionici ATCC25562 and L. acidophilus MJLA1. Therefore, strain 702 was closely related to P.jensenii NCFB572.

Figure 8:
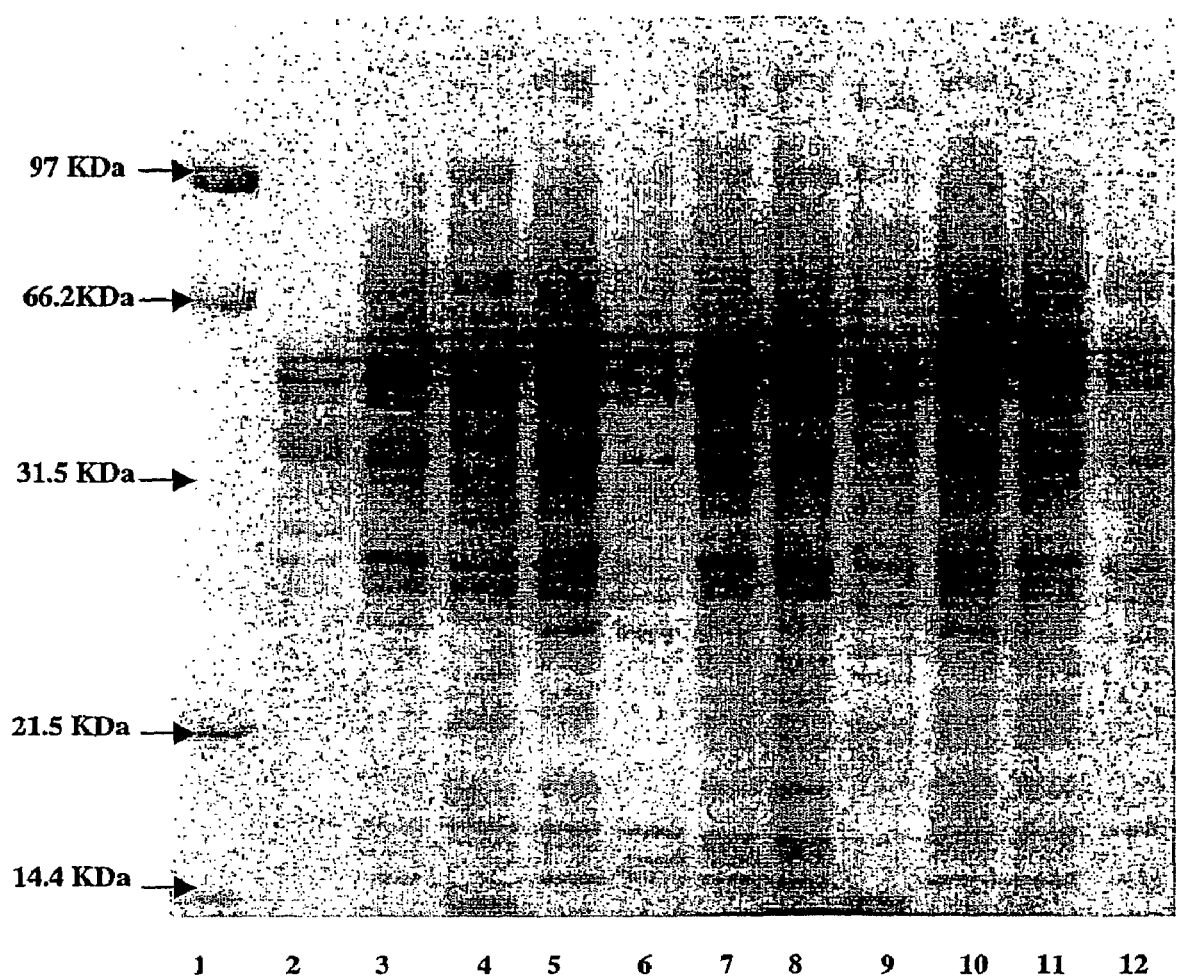
FIG. 8 shows SDS-PAGE analysis of whole cell water-soluble proteins of six isolated strains and five *Propionibacterium* reference strains. Lane 1; SDS-PAGE Protein Marker (Bio-Rad SDS-PAGE Molecular Standards, low range); Lane 2: *P. freundenreichii* CSCC2200; Lane 3: *P. freundenreichii* CSCC2201; Lane 4: *P. freundenreichii* CSCC2206; Lane 5: *P. freudenreichii* CSCC2207; Lane 6: *P.freundenreichii* CSCC2216; Lane 7 strain 201a1; Lane 8: strain 201b; Lane 9: strain 702; Lane 10; strain 801; Lane 11: strain 901; Lane 12: strain 1001

FIG. 8 shows SDS-PAGE band patterns of six isolated strains and five reference strains of P. freudenreichii. Isolated strain 702 had different patterns from those of the five strains of P. freudenreichii, while isolated strains 201a1, 201b, 801, 901 and 1001 had partly similar band patterns to those of five reference strains of P. freudenreichii.

The relatedness of isolated strains to five reference strains of P. freudenreichii is further revealed in Table 8 by homology analysis of SDS-PAGE protein banding patterns using Dice Coeffient (Quality One software package, Bio-Rad). The homology percentile indicates genetic relatedness, calculated using the number of shared genetic markers or bands. The higher percentiles, the more closely related the strains. The matching percentages of strain 201a1, 201b, 801, 901 and 1001, with P. freudenreichii CSCC2207, were higher than with any of the other four P. freudenreichii reference strains. Strain 702 had a low matching percentage with the five reference P. freudenreichii strains. Strains 201a1, 201b, 801, 901 and 1001 were considered closely related to P. freudenreichii CSCC2207, while strain 702 was not closely related to any of the five P. freudenreichii reference strains.

TABLE 8

Correlation matrix: homology from SDS-PAGE of whole cell soluble proteins of *Propionibacterium* strains

| Percent homology* | 201a1 | 201b | 702 | 801 | 901 | 1001 | P. freudenreichii CSCC2200 | P. freudenreichii CSCC2201 | P. freudenreichii CSCC2206 | P. freudenreichii CSCC2207 | P. freudenreichii CSCC2216 |
|---|---|---|---|---|---|---|---|---|---|---|---|
| P. freudenreichii CSCC2216 | 57.8 | 60.7 | 57.1 | 62.8 | 64.8 | 65.9 | 41.0 | 67.1 | 48.3 | 69.3 | 100.0 |
| P. freudenreichii CSCC2207 | 73.1 | 69.6 | 57.7 | 73.2 | 73.6 | 73.9 | 46.7 | 82.8 | 51.5 | 100.0 | |
| P. freudenreichii CSCC2206 | 49.5 | 51.5 | 59.3 | 54.5 | 49.0 | 46.5 | 46.7 | 45.3 | 100.0 | | |
| P. freudenreichii CSCC2201 | 66.9 | 67.7 | 51.3 | 69.9 | 70.2 | 74.5 | 52.7 | 100.0 | | | |
| P. freudenreichii CSCC2200 | 48.3 | 46.4 | 32.7 | 56.5 | 56.4 | 36.6 | 100.0 | | | | |
| 1001 | 61.4 | 64.5 | 66.9 | 61.6 | 63.7 | 100.0 | | | | | |
| 901 | 77.2 | 78.2 | 47.1 | 91.0 | 100.0 | | | | | | |
| 801 | 74.6 | 75.5 | 44.2 | 100.0 | | | | | | | |
| 702 | 51.8 | 50.4 | 100.0 | | | | | | | | |
| 201b | 86.8 | 100.0 | | | | | | | | | |
| 201a1 | 100.0 | | | | | | | | | | |

*homology derived using the Dice Coefficient, Quality One Software (Bio-Rad)

TABLE 9

API 50 CH results of tested strains

| Carbohydrate | Strain 702 | P. jensenii NCFB 572 | P. jensenii NCFB 571 | P. cidopropionici ATCC 25562 | P. thoenii ACM 365 | P. freudenreichii CSCC2207 |
|---|---|---|---|---|---|---|
| Negative control | − | − | − | − | − | − |
| Glycerol | + | + | + | + | + | + |
| Erythritol | + | + | + | + | + | + |
| D-Arabinose | − | − | − | + | − | − |
| L-Arabinose | − | − | − | + | − | + |
| Ribose | + | + | + | + | + | + |
| D-Xylose | − | − | − | − | − | − |
| L-Xylose | − | − | − | − | − | − |
| Adonitol | + | + | + | + | + | + |
| β Methyl-xylose | − | − | − | − | − | − |
| Galactose | + | + | + | + | + | + |
| D-Glucose | + | + | + | + | + | + |
| D-Fructose | + | + | + | + | + | + |
| D-Mannose | + | + | + | + | + | + |
| L-Sorbose | − | − | − | − | − | − |
| Rhamnose | − | − | − | + | − | − |
| Dulcitol | − | − | − | − | − | − |
| Inositol | + | + | + | + | − | + |
| Mannitol | + | + | + | + | − | − |
| Sorbitol | − | − | − | + | + | − |
| α Methyl-D-mannoside | − | − | − | − | + | − |
| α Methyl-D-glucoside | − | − | − | + | + | − |
| N Acetyl glucosamine | − | − | − | + | + | − |
| Amygdaline | − | − | − | − | − | − |
| Arbutine | − | − | − | + | + | + |
| Esculine | + | + | + | + | + | − |
| Salicine | + | + | − | + | + | − |
| Cellobiose | − | − | − | + | − | − |
| Maltose | + | + | + | + | + | − |
| Lactose | + | − | + | + | + | + |
| Melibiose | + | + | + | + | − | + |
| Saccharose | + | + | + | + | + | − |
| Trehalose | + | + | + | + | + | − |
| Inuline | − | − | − | − | − | − |
| Melezitose | − | + | − | + | + | + |
| D-Raffinose | − | + | + | − | − | − |
| Amidon | − | − | − | + | + | + |
| Glycogene | − | − | − | − | − | − |
| Xylitol | + | + | − | + | + | + |
| β Genitobiose | + | + | − | − | + | + |
| D-Turanose | + | + | + | + | + | + |
| D-Lyxose | − | − | − | − | − | − |
| D-Tagatose | − | − | − | − | − | − |
| D-Fucose | − | − | − | − | − | − |

TABLE 9-continued

API 50 CH results of tested strains

| Carbohydrate | Strain 702 | P. jensenii NCFB 572 | P. jensenii NCFB 571 | P. cidopropionici ATCC 25562 | P. thoenii ACM 365 | P. freudenreichii CSCC2207 |
|---|---|---|---|---|---|---|
| L-Fucose | − | − | − | − | − | − |
| D-Arabitol | + | + | + | + | + | + |
| L-Arabitol | + | + | + | + | + | + |
| Gluconate | + | + | + | + | + | + |
| 2 ceto-gluconate | − | − | − | − | − | − |
| 5 ceto-gluconate | − | − | − | − | − | − |

API 50 CH Profile of Dairy Propionibacteria Strains

API 50 CH strips were used to look at the difference of strain P. jensenii 702 from the reference strains of P. jensenii, P. jensenii NCFB 571 and NCFB572. As reaction control, reference strains of the other three dairy propionibacteria species, P. freudenreichii CSCC2207, P. acidopropionici ATCC25562, and P. thoenii ACM365, were also tested using API 50 CH strips. Table 9 presents the 49 carbohydrate fermentation patterns of those six strains using API 50 CH strips.

The API 50 CH profiles of all tested strains (Table 9) were compared to available published carbohydrate profiles of each species (Cummins and Johnson, 1986). The API 50 CH profiles of strain P. freudenreichii CSCC2207, P. acidopropionici ATCC25562, P. jensenji NCFB572 and P. thoenii ACM365 correlated with published data; while P. jensenii NCFB 571 had one different reaction, namely, the inability to ferment salicine, which has been reported positive for 90-100% strains of P. jensenii (Cummins and Johnson, 1986). Isolated strain 702 had similar carbohydrate profiles to those reported for P. jensenii (Cummins and Johnson, 1986), except for its inability to ferment D-Raffinose, which has been reported positive for 90-100% strains of P. jensenii (Cummins and Johnson, 1986).

Discussion and Conclusions

Six dairy propionibacteria strains were isolated using YELA and were identified to species by traditional methods, Propionibacterium genus-specific PCR, Propionibacterium species-specific PCR, RAPD-PCR, and SDS-PAGE analysis of whole cell water-soluble protein. The relatedness of isolated strains to selected reference strains was also illustrated by SDS-PAGE analysis of whole cell water-soluble proteins. In addition, the different carbohydrate profiles for five reference and one isolate strain (702) were compared using API 50 CH carbohydrate fermentation profile.

The six dairy propionibacteria strains were found in Swiss cheese and raw milk samples but not in samples of Parmesan cheese, Best Quality Gouda cheese, Grana Papano cheese and Jarlsberg cheese. However, other studies have reported that Propionibacterium have been isolated from Grana, Parmesan and Pasta Filata cheese samples as well as raw milk samples (Rossi et al, 1998; Fessler et al, 1999). These results confirm the known habitats of Propionibacterium, which primarily are dairy products, human skin and silage (Jones and Collins, 1986; Grant and Salminen, 1998).

No dairy propionibacteria strains were isolated from the 87 biopsy samples in this study. The collection of biopsy samples was from patients at the Sydney Adventist Hospital. This hospital has been established by the Sydney Seventh Day Adventist Church, which is well recognised for promoting vegetarianism. As a consequence, these biopsy samples may have been collected from a predominantly vegetarian population, who would have had little exposure to dairy products containing dairy propionibacteria. The results of biopsy samples may indicate that differential vitamin $B_{12}$ levels in certain vegetarians may be more a consequence of exposure to certain food microorganisms rather than dietary intake.

The six isolated strains were identified to dairy propionibacteria species by traditional identification methods, based on morphological and biochemical characteristics. Only four characteristics were adopted in this study to differentiate four species of dairy propionibacteria, including fermentation of sucrose and maltose; reduction of nitrate; β-hemolysis, and pigment colour. The isomer of diaminopimelic acid (DAP) in the cell wall, which has been recommended as one of the differentiation characteristics for the four dairy propionibacteria species, was not tested in this study.

The species status of isolated strains, which were identified by traditional methods, was confirmed by Propionibacterium genus-specific and species-specific PCR profiles. All reference strains of Propionibacterium and six isolated strains had the expected PCR product, which confirms the findings of Rossi, et al. (1999). Tested Propionibacterium strains produced PCR products (FIG. 3, FIG. 4) as described by Rossi, et al. (1999), using primer sets PJ-PB2, and PT3-PB2. Four out of five reference strains of P. freudenreichii produced the same PCR products as described by Rossi, et al. (1999) using primer set PF-PB2 (FIG. 2); however, P. freudenreichii CSCC2206 did not produce any PCR product (FIG. 2). There was also no PCR product detected for both P. acidopropionici ATCC25562 and P. acidopropionici 341 (data not shown) when using PA-PB2, which is specific for P. acidopropionici (Rossi, 1999). P. freudenreichii CSCC2206, P. acidopropionici ATCC25562 and P. acidopropionici 341, have not been used in the study by Rossi, et al. (1999). This discrepancy may be due to the different preparation of genomic DNA or difference between laboratory conditions.

Like species-specific PCR, the RAPD-PCR analysis using primer OPL-05 demonstrates that this technique shows clear similarity between strains of P. freudenreichii and the difference between strains of P. freudenreichii and P. acidopropionici. This is correlated with the results of Rossi (1998). There was no PCR product produced by P. freudenreichii CSCC2207, strain 702 and P. jensenii NCFB572. This may indicate the limitation of RAPD-PCR, which may not be applied to all strains of Propionibacterium.

SDS-PAGE protein analysis is a quick technique for species and strain differentiation of Propionibacterium strains (Baer, 1987; Fessler et al, 1999). The almost identical SDS-PAGE profiles of replicate samples of strain 702 (FIG. 6, FIG. 7), replicate samples of P.thoenii ACM365 (FIG. 6) and replicate samples of P. jensenii NCFB572 (FIG. 7) indicates the high reproducibility of SDS-PAGE analysis of bacterial soluble protein. The reproducibility of SDS-PAGE analysis of bacterial soluble protein has been reported to be 92-98%

(Costas et al, 1990; Costas, 1990), and 93-97% (Tsakalidou et al, 1994) for the identification of the species.

A 70% homology of SDS-PAGE profile cut off has been recommended for species differentiation (Fessler et al, 1999). This separates the five reference strains of *P. freudenreichii* used here into four species, with only *P. freudenreichii* CSCC2201 and CSCC2207 having greater than 70% homology (82.8%) (Table 8). If 201a1 and 801 are to be considered the same species as *P. freudenreichii* CSCC2207, they should be the same species as *P. freudenreichii* CSCC2201. Therefore, further studies may be needed to screen more reference strains and to identify their common bands for species differentiation rather than just comparing homology of patterns of all the bands.

The clearly different API profiles for different species of dairy propionibacteria can be used to separate species (Table 9). The variation of the API 50 CH profile with three strains of *P. jensenii* is also a useful tool to show strain differences, which is essential for the selection of certain strains as probiotics.

EXAMPLE 2

Dairy Propionibacteria Simulated Upper Gastrointestinal Transit Tolerance and Adhesion to C2BBE1 Cells In Vitro This study aimed to assess in vitro upper gastrointestinal tract transit tolerance and adhesion to human epithelial cells of some dairy propionibacteria strains, which are able to synthesize vitamin $B_{12}$. For this purpose, the following were examined, (1) the viability of dairy propionibacteria strains in simulated gastric transit conditions (pH2, pH3 and pH4 gastric juices); (2) the influence of vegetarian food on the pH2 gastric transit tolerance of dairy propionibacteria strains; (3) the viability of dairy propionibacteria strains in simulated small intestinal transit conditions; (4) the growth of dairy propionibacteria strains in SLB containing 0.3% bile salt; and (5) the adhesion of dairy propionibacteria strains to cell line C2BBe1, a clone of the Caco-2 cell line.

Materials and Methods

Bacterial Strains

Thirteen dairy propionibacteria strains were screened for their in vitro gastrointestinal transit tolerance and adhesion to cell line C2BBe1. These strains were selected based on their vitamin $B_{12}$ synthesis in Fermentation Medium (FM). The sources and vitamin $B_{12}$ production levels of these strains are presented in Table 10.

*Lactobacillus acidophilus* MJLA1 and *Bifidobacterium lactis* BDBB2 were provided and described as Caco-2 cell adhesion positive and negative respectively by Gist Brocades, Australia. They were used as positive and negative controls respectively in the C2BBe1 adhesion assay.

The Recovery and Preservation of Bacterial Strains

The recovery and preservation of *Propionibacterium* strains and *L. acidophilus* MJLA1 was performed as described in Example 1. *B. lactis* BDBB2 was recovered in Reinforced Clostridial Medium (RCM, Oxoid), and then streaked onto Reinforced Clostridial Agar (RCA, Oxoid) to establish purity. It was Gram stained, catalase tested, and examined microscopically for correct cell morphology.

Determination of Vitamin $B_{12}$ Production by Dairy Propionibacteria in Fermentation Medium (FM)

The determination of vitamin $B_{12}$ production by dairy propionibacteria strains in FM was adapted from the method of Quesada-Chanto, et al. 1998.

Briefly, strains of dairy propionibacteria were grown in SLB for 48 hr anaerobically. The 48 hr culture (20 µL) of each strain was inoculated into FM broth (20 mL) and incubated at 37° C. for 4 days. Bacteria cells in FM (10 mL) were then collected by centrifugation (3 500×g, 15 min) in a 10 mL sterile centrifuge tube. Bacteria pellets were then washed in 0.9% NaCl (10 mL) twice. The bacteria pellets were then resuspended in 0.1M pH 5.5 phosphate buffer (8 mL), and 1% KCN (0.1 mL) (Chem supply) was added. The bacterial suspension was then autoclaved at 121° C. for 10 min. After cooling to room temperature, the suspension was centrifuged at 3 500×g for 20 min. The supernatant was collected, and stored at 4° C. prior to vitamin $B_{12}$ testing. Vitamin $B_{12}$ levels were determined by Quantaphase $B_{12}$/Folate assay (Bio-Rad) at the Sydney Adventist Hospital, Sydney, NSW, Australia.

Human Gut Epithelial Cell Line C2Bbe1

Cell culture C2BBe1 was kindly provided by Dr. Matthias Ernst of the Ludwig Institute in Melbourne, Australia. C2BBe1 is a clone of cell culture Caco-2, which is a human colon epithelial cell line.

Subculturing of C2BBe1 Cells

C2BBe1 cells were cultured in 25 $cm^3$ tissue culture flasks containing 10 mL of Supplemented RPMI 1640 at 37° C., 95% air/5% $CO_2$ for 7 days or until confluent. Cells were fed with fresh Supplemented RPMI 1640 every second day.

Preservation of C2BBe1 Cells

The C2BBe1 cells were grown in a 25 $cm^3$ tissue culture flask until confluent. The growth medium was then and a solution of 0.25% trypsin, 0.2% EDTA (1 mL) (Sigma) was added to the culture flask to rinse the cells. An additional 1.5 mL of 0.25% trypsin, 0.2% EDTA solution was then added and the flask was allowed to stand at 37° C., 95% air/5% $CO_2$ for 10 min or until the cells detached. The detached C2BBe1 cells were resuspended in 10 mL of RPMI 1640 broth (Trace Biosciences) with 5% DMSO (Sigma) using Pasteur pipettes. Aliquots of 1 mL of cell suspension were dispensed into in 2 mL Corning Cryogenic vials, and stored at −70° C.

Simulated Upper Gastrointestinal Transit Tests

The gastric transit tolerance and small intestinal transit tolerance in vitro tests were based on the methods described by Charteris (1998).

Preparation of Bacteria Suspension

All 13 dairy propionibacteria strains were grown anaerobically in SLB broth at 30° C. for 48 hours. Aliquots (1 mL) were transferred to 1.5 mL eppendorf tubes, and bacterial cells were collected by centrifugation (2500×g, 5 min) and washed three times with 1 mL PBS buffer (pH7.0), centrifuging (2500×g, 5 min) between each wash. Bacterial cells were then resuspended in 1 mL PBS buffer (pH7.0). Dilutions of bacterial suspensions were made to acquire a concentration of approximately $10^8$ cfu/mL, and were stored at 37° C. prior to use.

Simulated Gastric Transit Tolerance Test

The simulated gastric transit tolerance test was performed in a reaction volume of 1.5 mL containing 300 µL of 0.5% NaCl or food in liquid form, 200 µL of bacterial suspension, and 1 mL of simulated gastric juice. The test mixture was vortexed at a maximum setting for 10 sec and then incubated at 37° C. in an air forced incubator for 180 min. At 1 min, 60 min, 90 min, 180 min incubation time, an aliquot (0.1 mL) was taken from each test mixture and viable cell counts were determined by the pour plate method.

Small Intestinal Transit Tolerance Test

The simulated small intestinal transit tolerance test was performed in a reaction volume of 1.5 mL containing 300 μL of 0.5% NaCl or food in liquid form, 200 μL of bacterial suspension, and 1 mL of simulated small intestinal juices with or without 0.3% bile salt. Test mixtures were vortexed at a maximum setting for 10 sec, and then incubated at 37° C. in an air forced incubator for 240 min. At 1 min, and 240 min incubation time, an aliquot (0.1 mL) was taken from each test mixture and viable cell counts were determined by the pour plate method.

Determination of Viable Cell Counts Using the Pour Plate Method

Viable cell counts were estimated using the pour plate method. Briefly, serial dilutions of 0.1 mL aliquots from the test mixture were made with MRD broth. Aliquots (1 mL) of selected dilutions were transferred to each of two sterile Petri dishes. SLA agar (15 mL), which was stored in a 50° C. water bath, was then poured into each plate. The medium and the inoculum were mixed by five to-and-fro movements, followed by five circular clockwise movements, followed by five to-and-fro movements at right angles to the first set, followed by five circular anti-clockwise movements. The Petri dishes were left to stand at room temperature until the medium had set. As soon as the medium had set, the Petri dishes were inverted, and incubated anaerobically at 30° C. After 6 days incubation, colonies were counted using a colony counter (Stuart Scientific).

Growth of Dairy Propionibacteria Strains in the Presence of Bile Salts

The method was extrapolated from the published methods developed for selecting bile tolerant *Lactobacillus* and *Bifidobacterium* strains (Gilliland et al, 1984; Chou and Weimer, 1999; Ibrahim and Bezkorovainy, 1993). Bile salts (Oxoid) were chosen in this study because it is a standardised bile extract and is extensively used as a selective inhibitory agent in bacteriological culture media to allow only bile-tolerant organisms to grow.

*Propionibacterium* strains were screened for their ability to grow in SLB broth containing 0.3% bile salts (Oxoid) at 37° C. Aliquots (100 μL) of 48 hr cultures of *Propionibacterium* strains were inoculated in 10 mL of SLB with or without 0.3% bile salt in triplicate, and incubated anaerobically at 37° C. for 5 days. The extent of growth was determined by measuring the optical density at 650 nm at 10 intervals during the five day incubation period. Growth curves ($A_{650}$ versus time) of each strain were generated using Microsoft Excel software.

Adhesion to Human Gut Epithelial Cell Line C2BBe1

Preparation of Bacteria Suspension

Strains were grown anaerobically in liquid broth, SLB for *Propionibacterium*, MRS for *L. acidophilus* MJLA1, and RCM for *B. lactis* BDBB2, at 30° C. for 48 hours. Aliquots (1 mL) were transferred to 1.5 mL eppendorf tubes, and bacterial cells were collected by centrifugation (2500×g, 5 min) and washed three times with 1 mL PBS buffer (pH7.0), centrifuging (2500×g, 5 min) between each wash. Bacterial cells were then resuspended in PBS buffer (pH7.0) to acquire a concentration of approximately $10^9$ cfu/mL, stored at 37° C. for maximum 1 hr prior to the adhesion test.

Preparation of C2BBe1 Monolayers

C2BBe1 stock culture (1 mL) was thawed in a 37° C. water bath and mixed with Supplemented RPMI 1640 medium (7.5 mL) in a 25 cm$^3$ tissue culture flask. C2BBe1 cells were incubated at 37° C. in 5% $CO_2$/95% air atmosphere until confluent. Fresh Supplemented RPMI 1640 medium was fed to cells when the medium turned yellowish red during incubation. After the cells were confluent, Supplemented RPMI 1640 medium was removed, and 0.25% trypsin, 0.2% EDTA solution (1.5 mL) was added to the flask, and incubated at 37° C. in 5% $CO_2$/95% air atmosphere for 10 min or until the cells detached. The detached cells were resuspended in 30 mL Supplemented RPMI 1640 medium using sterile Pasteur pipettes. Aliquots (1 mL) of cell suspension were dispensed into each well of a tissue culture plate (24 well, Becton Dickinson) containing sterile coverslips (13 mm, Sarstedt). The plates were then incubated at 37° C., in 5% $CO_2$/95% air atmosphere until there was confluent growth on the coverslips (around 7-8 days). Fresh Supplemented RPMI 1640 medium was fed to the cells when the medium turned yellowish red during incubation.

In Vitro Adhesion Assay

The in vitro adhesion assay for bacterial strains to C2BBe1 cells was based on the in vitro assays for adhesion to Caco-2 cells (Tuomola and Salminen, 1998; Sarem et al, 1996).

The monolayers of C2BBe1 on coverslips in the 24 wells of the microtitre plate were washed with 1 mL of RPMI 1640 (Trace Biosciences), and supplemented with 950 μL of fresh RPMI 1640. The plate was incubated at 37° C., in 5% $CO_2$/95% air. Aliquots (50 μL) of each bacterial suspension were added in duplicate to each well of the microtitre plate. The cultures were incubated at 37° C., in 5% $CO_2$/95% air atmosphere for 2 hours. The monolayers were then washed four times with 1 mL prewarmed (37° C.) PBS buffer (pH 7.0) using Pasteur pipettes, and fixed with 500 μL of fixation buffer at room temperature overnight, ready for scanning electron microscopy.

Scanning Electron Microscopy

The tissue monolayers in the wells of the microtitre plates were washed three times with 1 mL of 0.1 M Cacodylate buffer. The monolayers were then dehydrated in 1 mL of graded series of ethanol (30%, 50%, 70%, 90%, and 100%), each for 10 minutes. The monolayers were stored in 1 mL of 100% ethanol during transportation to the Electron Microscopy Unit, University of Newcastle, NSW, Australia. The monolayers were then dried by a critical point drier and stored in a desiccator in the Electron Microscopy Unit.

The dried monolayers were observed by scanning electron microscopy by Mr. David Phelan of the Electron Microscopy Unit, University of Newcastle.

Results

Production of Vitamin B12

The vitamin B12 production is shown in Table 10. All strains of *Propionibacterium* produced vitamin B12 ranging from 0.61 ng/mL to 20.29 ng/mL.

TABLE 10

Vitamin $B_{12}$ production of dairy *propionibacteria* strains in Fermentation Medium

| Strain | Species | Source | Vitamin $B_{12}$ (ng/ml) |
|---|---|---|---|
| CSCC2200 | P. freudenreichii | Australian Starter Culture Research Centre | 10.92 ± 0.58* |
| CSCC2201 | P. freudenreichii | CSIRO Melbourne, Australia | 4.04 ± 0.70 |
| CSCC2206 | P. freudenreichii | CSIRO Melbourne, Australia | 0.73 ± 0.28 |

TABLE 10-continued

Vitamin $B_{12}$ production of dairy *propionibacteria* strains in Fermentation Medium

| Strain | Species | Source | Vitamin $B_{12}$ (ng/ml) |
|---|---|---|---|
| CSCC2207 | P. freudenreichii | CSIRO Melbourne, Australia | 5.99 ± 0.34 |
| CSCC2216 | P. freudenreichii | CSIRO Melbourne, Australia | 11.59 ± 0.83 |
| 201a1 | P. freudenreichii | This study | 1.60 ± 0.09 |
| 201b | P. freudenreichii | This study | 2.97 ± 0.25 |
| 801 | P. freudenreichii | This study | 2.09 ± 0.43 |
| 901 | P. freudenreichii | This study | 15.69 ± 1.02 |
| 1001 | P. freudenreichii | This study | 20.29 ± 0.78 |
| 702 | P. jensenii | This study | 12.84 ± 0.65 |
| 341 | P. acidopropionici | University of Melbourne, Australia | 0.61 ± 0.19 |
| ATCC25562 | P. acidopropionici | American Type Culture Collection | 0.91 ± 0.23 |

*Results shown are mean (S.D.), n = 2.

Effect of Simulated Gastric Juices (pH2, pH3, pH4) on the Viability of Dairy Propionibacteria Strains The effect of simulated gastric juices (pH2, pH3, and pH4) on viability of 13 dairy propionibacteria strains is presented in Table 11. The average final pH of the simulated transit mixture was 2.33, 3.80, and 5.97 for pH2, pH3, and pH4 gastric juices.

Each strain showed higher viability in pH3 or pH4 simulated gastric juice than pH2 simulated gastric juice (Table 11).

When the simulated gastric juice was at pH2, all the strains showed progressive reduction in viability during the 180 min simulated gastric transit. After incubation with simulated gastric juice (pH2) for only 1 min, strains P.freudenreichii CSCC2206, P. acidopropionici 341 and P. acidopropionici ATCC25562 had 2 to 3-log reduction in viability (Table 11). After 60 min incubation, viability of most of the strains decreased substantially, except for P.freudenreichii 801, and P.freudenreichii 901 with only 1-log decrease in viability. After 90 min to 180 min incubation with simulated gastric juice (pH2), all the strains showed significant reduction (P<0.05) in viability at different levels (Table 11), especially P. freudenreichii CSCC2200, P.freudenreichii CSCC2206 and P.freudenreichii CSCC2216, which completely lost viability after 180 min simulated gastric transit (Table 11). This indicates all the strains are sensitive to simulated gastric juice at pH2.

When the simulated gastric juice was at pH3, ten out of 13 tested strains retained similar viability during simulated gastric tract transit for up to 180 min (Table 11). Three strains, P.freudenreichii CSCC2206, P. acidopropionici 341 and ATCC25562 CSCC2206 showed only 1-log cycle reduction in viability after 180 min simulated gastric tract transit (Table 11). This indicates that the majority of the tested strains were tolerant to simulated gastric juice at pH3 and may survive gastric passage.

When the simulated gastric juice was at pH4, all of the tested strains retained the same level of viability during 180 min simulated gastric tract transit (Table 11). This indicates that the cells of 13 tested dairy propionibacteria strains may survive gastric passage, when gastric juice is at pH4.

TABLE 11

Effect of simulated gastric juices (pH 2, pH 3, pH 4) on the viability of dairy *propionibacteria* strains

| Strains | Simulated gastric juices | Viable Count (log cfu/ml) during simulated gastric transit tolerance | | | | |
|---|---|---|---|---|---|---|
| | | 0 min | 1 min | 60 min | 90 min | 180 min |
| P. freudenreichii CSCC2200 | pH 2[a] | 8.46(0.42) | 8.19(0.02) | 4.16(0.08)** | 0.84(0.09)*** | <1 |
| | pH 3[b] | 8.46(0.42) | 8.25(0.24) | 8.32(0.05) | 8.28(0.20) | 8.28(0.28) |
| | pH 4[c] | 8.46(0.42) | 8.26(0.17) | 8.38(0.18) | 8.35(0.21) | 8.38(0.18) |
| P. freudenreichii CSCC2201 | pH 2 | 8.60(0.43) | 8.80(0.09) | 3.98(0.13)* | 3.72(0.21)* | 2.00(0.09)** |
| | pH 3 | 8.60(0.43) | 8.86(0.09) | 8.88(0.00) | 8.90(0.01) | 8.87(0.03) |
| | pH 4 | 8.60(0.43) | 8.70(0.04) | 8.89(0.02) | 8.84(0.03) | 8.83(0.04) |
| P. freudenreichii CSCC2206 | pH 2 | 7.65(0.08) | 4.67(0.00)*** | 2.72(0.00)*** | <1 | <1 |
| | pH 3 | 7.65(0.08) | 7.75(0.00) | 6.84(0.34)* | 6.84(0.34)* | 6.75(0.21)* |
| | pH 4 | 7.65(0.08) | 7.63(0.14) | 7.80(0.02) | 7.89(0.03) | 7.86(0.09) |
| P. freudenreichii CSCC2207 | pH 2 | 8.63(0.09) | 8.77(0.05) | 4.85(0.05)** | 2.87(0.21)** | 1.36(0.03)*** |
| | pH 3 | 8.63(0.09) | 8.94(0.10) | 8.92(0.07) | 8.89(0.05) | 8.88(0.00) |
| | pH 4 | 8.63(0.09) | 8.87(0.02) | 8.83(0.00) | 8.91(0.09) | 8.84(0.05) |
| P. freudenreichii CSCC2216 | pH 2 | 8.61(0.03) | 8.49(0.02) | 2.00(0.00)*** | 0.69(0.12)*** | <1 |
| | pH 3 | 8.61(0.03) | 8.72(0.11) | 8.65(0.03) | 8.67(0.05) | 8.66(0.13) |
| | pH 4 | 8.61(0.03) | 8.64(0.03) | 8.63(0.05) | 8.72(0.03) | 8.65(0.04) |
| P. freudenreichii 201a1 | pH 2 | 8.43(0.03) | 8.36(0.04) | 5.04(0.12)*** | 3.93(0.04)*** | 3.47(0.18)*** |
| | pH 3 | 8.43(0.03) | 8.29(0.01) | 8.30(0.05) | 7.82(0.64) | 8.27(0.01) |
| | pH 4 | 8.43(0.03) | 8.30(0.04) | 8.25(0.03) | 8.43(0.15) | 8.46(0.12) |
| P. freudenreichii 201b | pH 2[a] | 8.46(0.07) | 8.26(0.12) | 5.58(0.17)*** | 5.18(0.07)*** | 4.89(0.00)*** |
| | pH 3[b] | 8.46(0.07) | 8.29(0.08) | 8.34(0.03) | 8.36(0.01) | 8.43(0.22) |
| | pH 4[c] | 8.46(0.07) | 8.17(0.13) | 8.44(0.05) | 8.36(0.00) | 8.38(0.00) |
| P. jensenii 702 | pH 2 | 8.21(0.12) | 8.29(0.20) | 5.96(0.00)*** | 4.03(0.05)*** | 2.61(0.01)*** |
| | pH 3 | 8.56(0.05) | 8.60(0.04) | 8.50(0.02) | 8.44(0.03) | 8.50(0.03) |
| | pH 4 | 8.56(0.05) | 8.62(0.04) | 8.83(0.12) | 8.26(0.29) | 8.50(0.22) |
| P. freudenreichii 801 | pH 2 | 8.78(0.11) | 8.54(0.00) | 7.83(0.00)*** | 5.89(0.15)*** | 3.49(0.16)*** |
| | pH 3 | 8.78(0.11) | 8.83(0.02) | 8.83(0.04) | 8.82(0.06) | 8.94(0.03) |
| | pH 4 | 8.78(0.11) | 8.77(0.04) | 8.87(0.11) | 8.91(0.03) | 8.91(0.05) |
| P. freudenreichii 901 | pH 2 | 8.71(0.06) | 8.78(0.14) | 7.58(0.15)** | 6.75(0.00)*** | 3.89(0.22)*** |
| | pH 3 | 8.76(0.01) | 8.83(0.03) | 8.78(0.03) | 8.85(0.01). | 8.94(0.03) |
| | pH 4 | 8.76(0.01) | 8.77(0.04) | 8.96(0.01) | 8.87(0.02) | 8.94(0.01) |

TABLE 11-continued

Effect of simulated gastric juices (pH 2, pH 3, pH 4) on the viability of dairy *propionibacteria* strains

| Strains | Simulated gastric juices | Viable Count (log cfu/ml) during simulated gastric transit tolerance | | | | |
|---|---|---|---|---|---|---|
| | | 0 min | 1 min | 60 min | 90 min | 180 min |
| *P. freudenreichii* 1001 | pH 2 | 8.60(0.00) | 8.46(0.00) | 7.25(0.09)*** | 4.67(0.09)*** | 3.13(0.25)*** |
| | pH 3 | 8.60(0.00) | 8.64(0.02) | 8.61(0.00) | 8.49(0.00) | 8.69(0.00) |
| | pH 4 | 8.60(0.00) | 8.61(0.00) | 8.76(0.00) | 8.72(0.00) | 8.76(0.00) |
| *P. acidopropionici* 341 | pH 2 | 8.25(0.03) | 6.00(0.00)** | 4.90(0.17)*** | 4.64(0.23)*** | 2.95(0.00)*** |
| | pH 3 | 8.25(0.03) | 8.20(0.00) | 7.96(0.08)* | 8.01(0.01)** | 7.54(0.34)*** |
| | pH 4 | 8.25(0.03) | 8.13(0.02) | 8.23(0.07) | 8.29(0.10) | 8.18(0.10) |
| *P. acidopropionici* ATCC25562 | pH 2 | 9.09(0.00) | 6.50(0.28)** | 5.54(0.08)*** | 5.40(0.16)*** | 4.90(0.00)*** |
| | pH 3 | 9.09(0.00) | 9.05(0.00) | 8.96(0.00)* | 8.45(0.02)*** | 8.03(0.01)*** |
| | pH 4 | 9.09(0.00) | 9.08(0.00) | 9.24(0.00) | 9.16(0.00) | 9.20(0.00) |

Results are shown as mean (S.D.), n = 2.
Compare the values of different incubation time with 0 min, use Anova, single factor statistics
*P value < 0.05,
**P value < 0.01,
***P value < 0.001,
a,b,c, mixture pH was 2.34, 3.80, 5.97 respectively Effects of Food Addition on Viability of Dairy Propionibacteria Strains During Simulated Gastric Tract Transit Tolerance (pH2 Gastric Juice)

Since tested dairy propionibacteria strains were sensitive to pH2 simulated gastric juice (Table 11) the effect of two kinds of vegetarian food, So-good soymilk (Sanitarium) and Up & Go cereal breakfast (Sanitarium), were tested for their effects on the viability of dairy propionibacteria strains during 180 min simulated gastric transit tolerance with pH2 gastric juice. The average final pH of the simulated transit mixture was 2.33, 5.23, and 5.34 for control, So-Good soymilk, and Up & Go cereal breakfast groups.

In general, addition of So-good soymilk and Up & Go cereal breakfast improved the viability of each strain significantly (P<0.05) when simulated gastric juice was at pH2 (Table 12).

All the 13 tested dairy propionibacteria strains showed 3.5 to 8-log reduction in viability during the 180 min simulated gastric tract transit with pH2 simulated gastric juice without any food addition (Table 12).

In the presence of So-good soymilk, twelve out of 13 tested dairy propionibacteria strains exhibited complete tolerance to simulated gastric transit with pH2 gastric juice with no loss of viability after the 180 min simulated gastric transit (Table 12). Only strain *P. freudenreichii* CSCC2200 showed 0.3-log reduction in viability (Table 12). Interestingly, strain *P. freudenreichii* CSCC2206 showed a slight reduction in its viability after 1 min of simulated gastric transit but recovered to the same level of viability as that at 0 min at the end of 180 min gastric transit.

In the presence of Up & Go cereal breakfast, eleven out of 13 tested dairy propionibacteria strains maintained the same viability through the 180 min simulated gastric transit with pH2 gastric juice (Table 12). The other two strains, *P. freudenreichii* CSCC2200 and strain *P. jensenii* 702 showed only 0.3-log reduction in viability. However, they still had viability of about 8-log value compared to 2.6-log and <1-log for strain *P. jensenii* 702 and *P. freudenreichii* CSCC2200 respectively without the addition of Up & Go after 180 min simulated gastric tract transit with pH2 gastric juice. These results indicate that all 13 tested dairy propionibacteria strains may survive passage through the human stomach, even when the gastric juice is at pH2, if tested strains are ingested with So-Good soymilk or Up & Go cereal beverages.

TABLE 12

Effect of food addition on the viability of *Propionibacterium* strains during gastric transit (pH2)

| Strains | Conditions | Viable Count (log cfu/ml) during simulated gastric transit tolerance | | |
|---|---|---|---|---|
| | | 0 min | 1 min | 180 min |
| *P. freudenreichii* CSCC2200 | control[a] | 8.46 (0.42) | 8.19 (0.02) | <1 |
| | So-good[b] | 8.83 (0.00) | 8.48 (0.12)* | 8.51 (0.00)* |
| | Up & Go[c] | 8.83 (0.00) | 8.46 (0.09)* | 8.53 (0.01) |
| *P. freudenreichii* CSCC2201 | control | 8.60 (0.43) | 8.80 (0.09) | 2.00 (0.00)** |
| | So-good | 8.70 (0.00) | 8.76 (0.01) | 8.91 (0.05) |
| | Up & Go | 8.70 (0.00) | 8.76 (0.00) | 8.91 (0.02) |
| *P. freudenreichii* CSCC2206 | control | 7.65 (0.08) | 4.67 (0.00)*** | <1 |
| | So-good | 7.69 (0.00) | 7.45 (0.00)*** | 7.81 (0.04) |
| | Up & Go | 7.69 (0.00) | 7.60 (0.07) | 7.84 (0.04) |
| *P. freudenreichii* CSCC2207 | control | 8.63 (0.09) | 8.77 (0.05) | 1.36 (0.03)*** |
| | So-good | 8.70 (0.00) | 8.87 (0.02) | 8.81 (0.09) |
| | Up & Go | 8.70 (0.00) | 8.80 (0.10) | 8.89 (0.00) |

TABLE 12-continued

Effect of food addition on the viability of *Propionibacterium* strains during gastric transit (pH2)

| Strains | Conditions | Viable Count (log cfu/ml) during simulated gastric transit tolerance | | |
|---|---|---|---|---|
| | | 0 min | 1 min | 180 min |
| *P. freudenreichii* CSCC2216 | control | 8.61 (0.03) | 8.49 (0.02) | <1 |
| | So-good | 8.64 (0.00) | 8.74 (0.11) | 8.75 (0.10) |
| | Up & Go | 8.64 (0.00) | 8.54 (0.11) | 8.73 (0.18) |
| *P. freudenreichii* 201a1 | control | 8.43 (0.03) | 8.36 (0.04) | 3.47 (0.18)*** |
| | So-good | 8.43 (0.03) | 8.34 (0.06) | 8.40 (0.05) |
| | Up & Go | 8.43 (0.03) | 8.31 (0.05) | 8.39 (0.01) |
| *P. freudenreichii* 201b | control[a] | 8.46 (0.07) | 8.26 (0.12) | 4.89 (0.00)*** |
| | So-good[b] | 8.46 (0.07) | 8.43 (0.16) | 8.32 (0.00) |
| | Up & Go[c] | 8.46 (0.07) | 8.32 (0.15) | 8.37 (0.01) |
| *P. jensenii* 702 | control | 8.21 (0.12) | 8.29 (0.20) | 2.61 (0.01)*** |
| | So-good | 8.21 (0.12) | 8.22 (0.14) | 8.30 (0.18) |
| | Up & Go | 8.21 (0.12) | 8.23 (0.07) | 7.95 (0.07)* |
| *P. freudenreichii* 801 | control | 8.78 (0.11) | 8.54 (0.00) | 3.49 (0.16)*** |
| | So-good | 8.78 (0.11) | 8.56 (0.00) | 8.64 (0.00) |
| | Up & Go | 8.78 (0.11) | 8.52 (0.00) | 8.35 (0.14) |
| *P. freudenreichii* 901 | control | 8.71 (0.06) | 8.78 (0.14) | 3.89 (0.22)*** |
| | So-good | 8.71 (0.06) | 8.73 (0.00) | 8.81 (0.00) |
| | Up & Go | 8.71 (0.06) | 8.68 (0.00) | 8.79 (0.00) |
| *P. freudenreichii* 1001 | control | 8.60 (0.00) | 8.46 (0.00) | 3.13 (0.25)*** |
| | So-good | 8.60 (0.00) | 8.60 (0.00) | 8.66 (0.00) |
| | Up & Go | 8.60 (0.00) | 8.60 (0.00) | 8.72 (0.00) |
| *P. acidopropionici* 341 | control | 8.25 (0.03) | 6.00 (0.00)*** | 2.95 (0.00)*** |
| | So-good | 8.25 (0.03) | 8.08 (0.06) | 8.33 (0.01) |
| | Up & Go | 8.25 (0.03) | 8.09 (0.06) | 8.38 (0.10) |
| *P. acidopropionici* ATCC25562 | control | 9.09 (0.00) | 6.50 (0.28)*** | 4.90 (0.00)*** |
| | So-good | 9.09 (0.00) | 9.06 (0.00) | 9.28 (0.00) |
| | Up & Go | 9.09 (0.00) | 9.17 (0.00) | 9.24 (0.00) |

Results are shown as mean (S.D.), n = 2.
Compare the values of different incubation time with 0 min, use Anova, single factor statistics
*P value < 0.05,
**P value < 0.01,
***P value < 0.001,
[a],[b],[c], mixture pH was 2.34, 5.23, 5.35 respectively Simulated Small Intestinal Transit Tolerance of Dairy Propionibacteria Strains The effect of simulated small intestinal transit on the viability of 13 dairy propionibacteria strains is presented in Table 13.

All tested strains retained the same viability during 240 min simulated small intestinal transit in the absence of bile salt (Table 13). In contrast, in the presence of 0.3% bile salts, eleven of 13 tested dairy propionibacteria strains maintained the same viability during 240 min simulated small intestinal transit; the other two strains, *P. freudenreichii* CSCC2207 and *P. acidopropionci* 341, showed slight reduction in viable counts, of 0.2-log and 0.97-log respectively (Table 13).

TABLE 13

Effect of simulated small intestinal transit on viability of dairy propionibacteria strains

| | Viable count (log cfu/mL) during simulated small intestinal transit tolerance | | | | | |
|---|---|---|---|---|---|---|
| | Absence of bile salts | | | In the presence of 0.3% bile salts | | |
| Strains | 0 min | 1 min | 240 min | 0 min | 1 min | 240 min |
| CSCC2200 | 8.17 (0.04) | 8.24 (0.01) | 8.29 (0.03) | 8.42 (0.02) | 8.54 (0.04) | 8.46 (0.03) |
| CSCC2201 | 8.80 (0.01) | 8.82 (0.01) | 8.86 (0.10) | 8.75 (0.01) | 8.75 (0.12) | 8.76 (0.01) |
| CSCC2206 | 7.53 (0.21) | 7.84 (0.04) | 7.78 (0.12) | 7.87 (0.02) | 8.00 (0.06) | 7.85 (0.06) |
| CSCC2207 | 8.87 (0.04) | 8.81 (0.03) | 8.81 (0.04) | 8.70 (0.01) | 8.71 (0.08) | 8.49 (0.01)** |
| CSCC2216 | 8.62 (0.04) | 8.67 (0.12) | 8.54 (0.03) | 8.58 (0.01) | 8.74 (0.02) | 8.61 (0.01) |
| 201a1 | 8.59 (0.04) | 8.43 (0.01) | 8.46 (0.05) | 7.56 (0.03) | 7.54 (0.10) | 7.61 (0.05) |
| 201b | 8.20 (0.10) | 8.23 (0.07) | 8.45 (0.06) | 7.55 (0.01) | 7.61 (0.13) | 7.70 (0.05) |
| 702 | 8.56 (0.05) | 8.64 (0.02) | 8.50 (0.06) | 8.64 (0.06) | 8.98 (0.03) | 8.66 (0.26) |
| 801 | 8.78 (0.11) | 8.63 (0.04) | 8.86 (0.02) | 7.75 (0.14) | 7.70 (0.08) | 7.72 (0.06) |
| 901 | 8.76 (0.01) | 8.83 (0.02) | 8.85 (0.03) | 7.58 (0.05) | 7.66 (0.01) | 7.73 (0.10) |
| 1001 | 8.68 (0.03) | 8.82 (0.03) | 8.83 (0.02) | 7.72 (0.03) | 7.65 (0.04) | 7.68 (0.07) |

TABLE 13-continued

Effect of simulated small intestinal transit on viability of dairy propionibacteria strains Viable count (log cfu/mL) during simulated small intestinal transit tolerance

| Strains | Absence of bile salts | | | In the presence of 0.3% bile salts | | |
|---|---|---|---|---|---|---|
| | 0 min | 1 min | 240 min | 0 min | 1 min | 240 min |
| 341 | 8.08 (0.07) | 8.15 (0.04) | 8.31 (0.16) | 7.75 (0.09) | 6.54 (0.09)** | 6.78 (0.25)* |
| ATCC25562 | 7.97 (0.09) | 8.14 (0.13) | 8.61 (0.14) | 7.71 (0.01) | 7.7 (0.14) | 7.83 (0.05) |

Results are shown as mean (S.D.), n = 2.
Compare the values of different incubation time with 0 min, use Anova, single factor statistics
*P value < 0.05,
**P value < 0.01,
***P value < 0.001.

Growth of Dairy Propionibacteria Strains in SLB with 0.3% Bile Salt

The growth of the 13 dairy propionibacteria strains in this experiment was evidenced by the increase in optical density ($A_{650}$) of the growth broth. The higher the optical density of the broth, the more bacterial cells in the broth. The total viable cell counts of dairy propionibacteria strains were found to be around $10^8$ cfu/mL when the value of $A_{650}$ was 0.5 (Table 14). Probiotic bacteria cannot affect their environment unless the population reaches a certain minimum level around $10^6$ to $10^8$ cfu/g of intestinal contents (Charteris et al, 1998). Therefore, $A_{650}$=0.5 was considered as the threshold for effective growth of dairy propionibacteria strains in this experiment.

TABLE 14

Total viable cell counts of dairy *propionibacteria* strains at $A_{650}$ of 0.5.

| Strains | Total viable cell counts (cfu/mL) |
|---|---|
| P. freudenreichii CSCC2200 | 5.11 * $10^8$ |
| P. freudenreichii CSCC2201 | 8.31 * $10^8$ |
| P. freudenreichii CSCC2206 | 3.41 * $10^8$ |
| P. freudenreichii CSCC2207 | 5.91 * $10^8$ |
| P. freudenreichii CSCC2216 | 7.51 * $10^8$ |
| P. freudenreichii 201a1 | 7.11 * $10^8$ |
| P. freudenreichii 201b | 7.78 * $10^8$ |
| P. jensenii 702 | 3.32 * $10^8$ |
| P. freudenreichii 801 | 9.94 * $10^8$ |
| P. freudenreichii 901 | 9.92 * $10^8$ |
| P. freudenreichii 1001 | 5.96 * $10^8$ |
| P. acidopropionici 341 | 2.67 * $10^8$ |
| P. acidopropionici ATCC25562 | 3.39 * $10^8$ |

Figure 9:
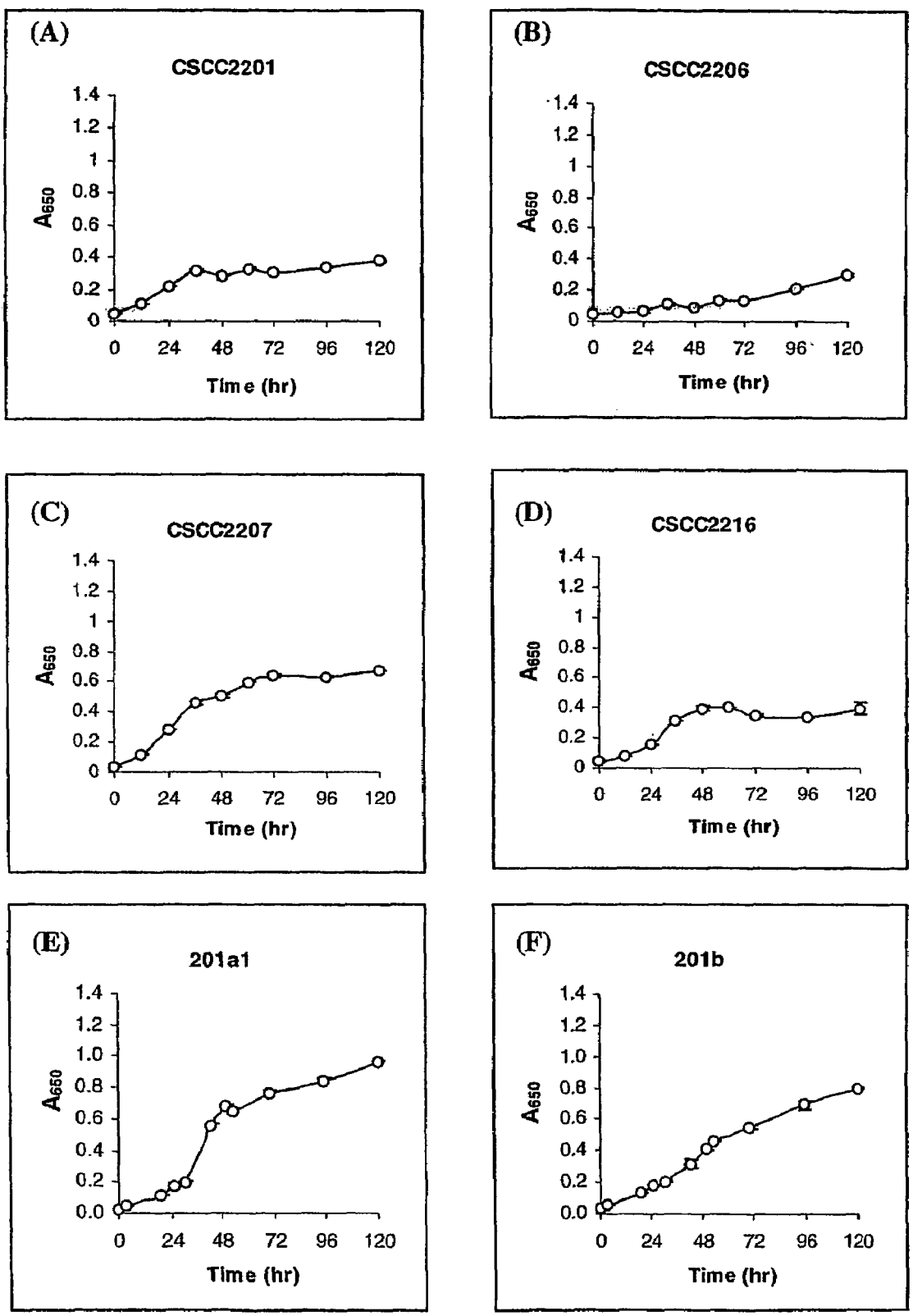
FIG. 9 shows growth curves of dairy propionibacteria strains in SLB with 0.3% bile salt at 37° C. anaerobically. (A) *P. freudenreichii* CSCC2201; (B) *P. freudenreichii* CSCC2206; (C) *P. freudenreichii* CSCC2207; (D) *P. freudenreichii* CSCC2216; (E) *P. freudenreichii* 201a1; (F) *P. freudenreichii* 201b; (G) *P. jensenii* 702 (H) *P. freudenreichii* 801, (I) *P. freudenreichii* 901; (J) *P. freudenreichii* 1001; (K) *P. acidopropionici* ATCC25562; (L) *P. acidopropionici* 341; (M) *P. freudenreichii* CSCC2200.
Figure 9:
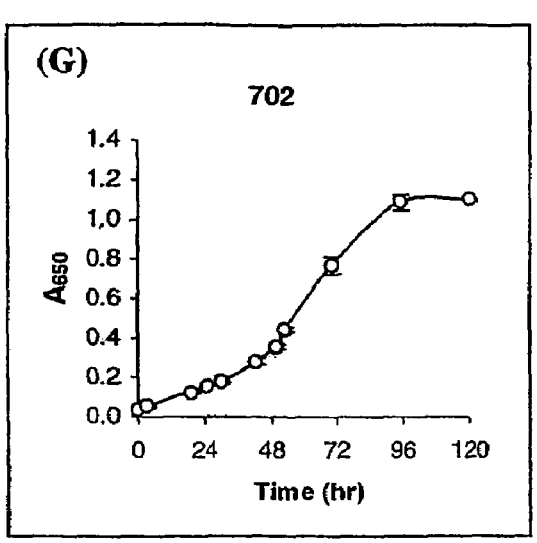
Figure 9:
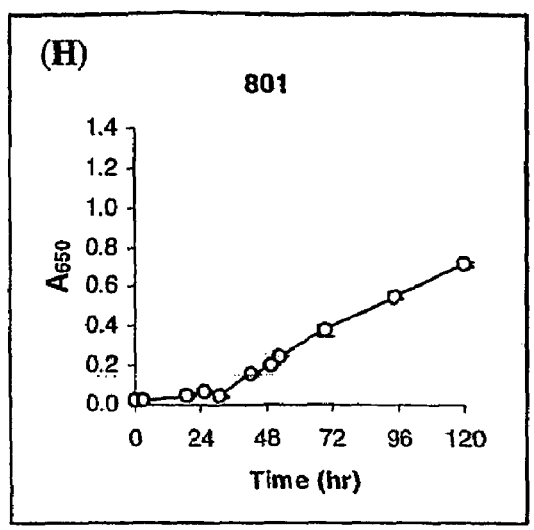
Figure 9:
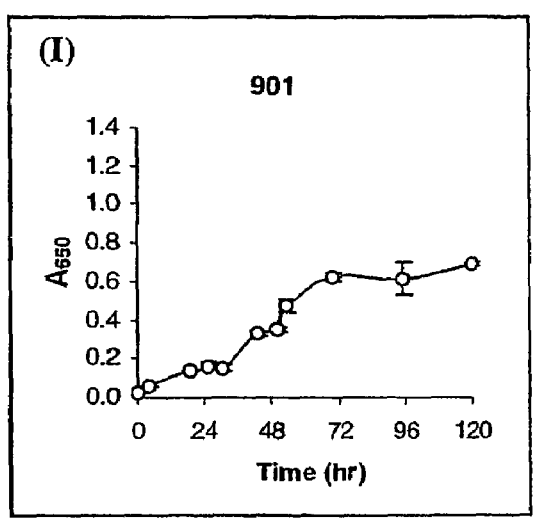
Figure 9:
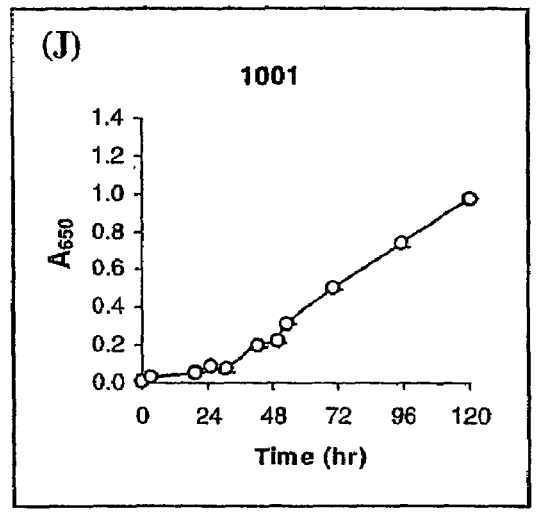
Figure 9:
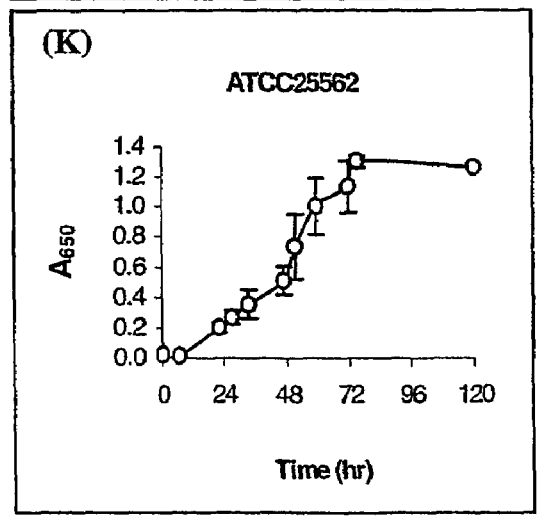
Figure 9:
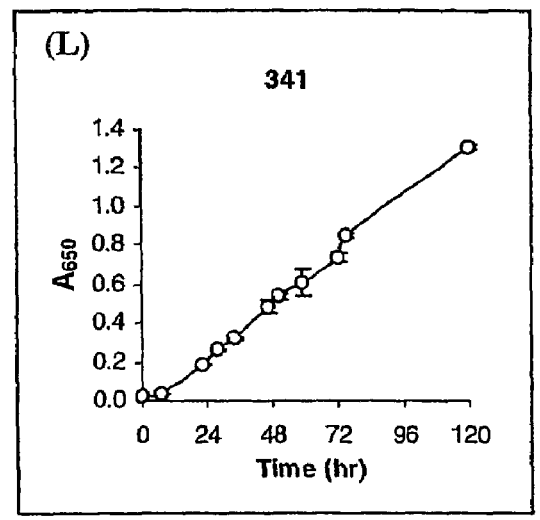
Figure 9:
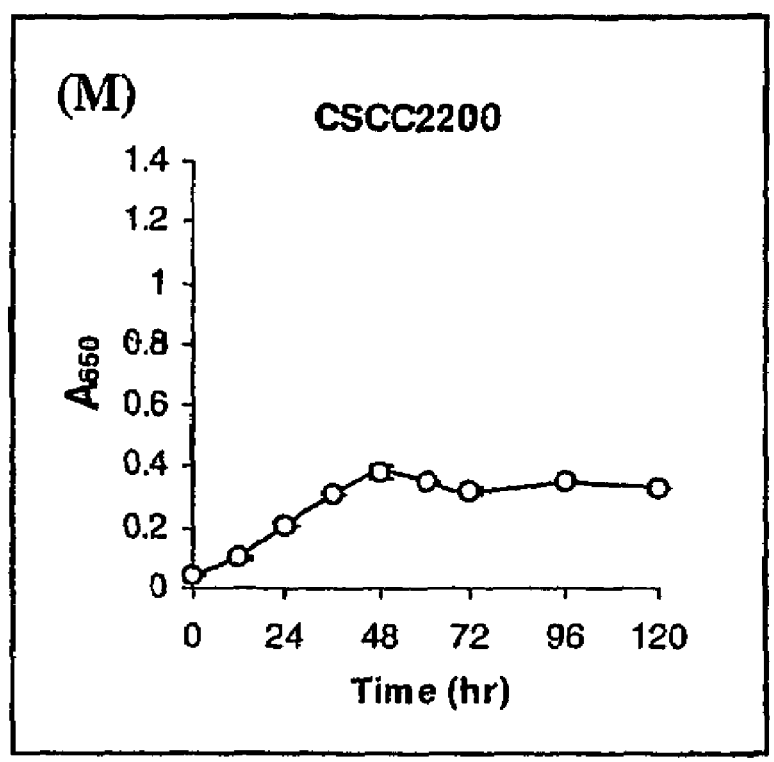

FIG. 9 and Table 15 show the growth characteristics of 13 dairy propionibacteria strains, including six isolated strains, 5 strains of *P. freudenreichii* and 2 strains of *P. acidopropionici*, in SLB with 0.3% bile salts incubated anaerobically at 37° C.

Nine out of 13 tested dairy propionibacteria strains reached their maximum growth ($A_{650}$) during a 5-day incubation period (FIG. 9A, C, D, E, F, G, I, K, M). The other four strains, including *P. freudenreichii* CSCC2206, *P. freudenreichii* 801, *P. freudenreichii* 1001, and *P. acidopropionici* 341 (FIG. 9B, H, J, L), did not reach their maximum growth ($A_{650}$) during the 5-day incubation period. This was particularly evident for *P. freudenreichii* CSCC2206, which only demonstrated active growth after day 5 (FIG. 9B).

Nine out of the thirteen tested strains had an $A_{650}$ higher than the threshold value of 0.5. In particular, *P. jensenii* 702, *P. acidopropionici* ATCC25562 and *P. acidopropionici* 341 obtained $A_{650}$ above 1.0 during the 5-day incubation (Table 15). In contrast, the other four strains, *P. freudenreichii* CSCC2206, CSCC2200, CSCC2201, and CSCC2216 did not pass the growth threshold ($A_{650}$=0.5) (Table 15).

None of the tested strains reached $A_{650}$=0.5 within 24 hr incubation (Table 15). However, four strains had $A_{650}$ higher than 0.5 after 48 hr incubation, including *P. acidopropionici* ATCC25562, *P. acidopropionici* 341, *P. freudenreichii* 201a1, and *P. freudenreichii* CSCC2207 (Table 15).

TABLE 15

Comparison of bile tolerance of *Propionibacterium* strains

| Strains | Absorbance at 650 nm | | |
|---|---|---|---|
| | 24 h | 48 h | Maximum |
| P. acidopropionici 341 | 0.186 (0.003) | 0.537 (0.022) | 1.310 (0.010) |
| P. acidopropionici ATCC25562 | 0.201 (0.054) | 0.737 (0.304) | 1.302 (0.054) |
| P. jensenii 702 | 0.155 (0.002) | 0.355 (0.020) | 1.096 (0.013) |
| P. freudenreichii 1001 | 0.090 (0.010) | 0.224 (0.013) | 0.972 (0.003) |
| P. freudenreichii 201a1 | 0.175 (0.021) | 0.680 (0.019) | 0.965 (0.010) |
| P. freudenreichii 901 | 0.162 (0.026) | 0.353 (0.018) | 0.853 (0.042) |
| P. freudenreichii 201b | 0.185 (0.004) | 0.413 (0.017) | 0.800 (0.010) |
| P. freudenreichii 801 | 0.064 (0.002) | 0.202 (0.007) | 0.720 (0.016) |
| P. freudenreichii CSCC2207 | 0.281 (0.003) | 0.501 0.013) | 0.673 (0.001) |
| P. freudenreichii CSCC2216 | 0.160 (0.003) | 0.395 (0.021) | 0.398 (0.000) |
| P. freudenreichii CSCC2200 | 0.212 (0.001) | 0.386 (0.028) | 0.386 (0.028) |
| P. freudenreichii CSCC2201 | 0.216 (0.004) | 0.287 (0.005) | 0.375 (0.011) |
| P. freudenreichii CSCC2206 | 0.070 (0.016) | 0.094 (0.005) | 0.301 (0.013) |

Results shown as mean (S.D.), n = 3

Adhesion to Cell Line C2BBe1

Figure 10:
FIG. 10 shows scanning electron micrographs of adhesive bacterial strains to human epithelial cell line C2BBel. (A) *L. acidophilus* MJLA1; (B) *B. lactis* BDBB2; (C, D) *P. jensenii* 702.
Figure 10:
Figure 10:
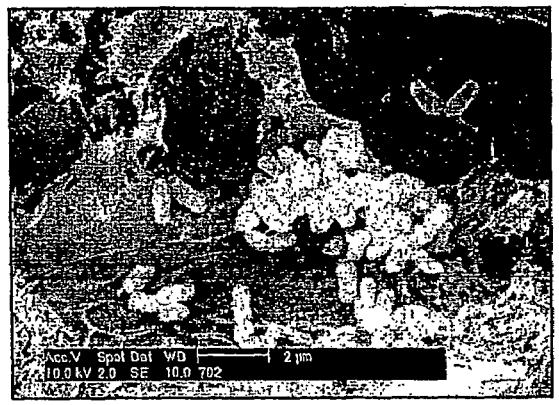
Figure 10:

13 *Propionibacterium* strains, including 6 isolated strains, *P. freudenreichii* CSCC2200, CSCC2201, CSCC2206, CSCC2207, and CSCC2216, *P. acidopropionicii* ATCC25562 and *P. acidopropionicii* 341, were tested for their adhesion to cell line C2BBe1. The positive control, *Lactobacillus acidophilus* MJLA1, and the negative control, *Bifidobacterium lactis* BDBB2, reacted as expected for adhesive ability (FIG. 10A, B). Only one strain of *Propionibacterium, P. jensenii* 702 was found to be adhesive to C2BBe1 (FIG. 10C, D). The other 12 tested strains were not found to be adhesive to C2BBe1 (pictures not shown).

Discussion

Probiotic microorganisms introduced orally are required at least to survive in the upper gastrointestinal tract, that is, stomach and small intestine. In vitro acid-resistance, bile resistance, gastric juice tolerance, and intestinal juice tolerance have been related to the in vivo gastrointestinal tolerance characteristics of microorganisms (Havenaar et al, 1992; Conway et al, 1987; Charteris et al, 1998; Chou and Weimer, 1999). However, there is no standard screening method for testing the upper gastrointestinal tract transit tolerance of microorganisms.

In this study, thirteen dairy propionibacteria strains were screened in vitro for their upper gastrointestinal tract transit tolerance, including (1) the effect of different pH of simulated gastric juices (pH2, pH3, and pH4) on the viability of dairy propionibacteria strains; (2) the effects of two kinds of vegetarian food, So-Good soymilk and Up & Go cereal breakfast on the 180 min gastric transit (with pH2 simulated gastric juice) tolerance of dairy propionibacteria strains; (3) the viability of dairy propionibacteria strains in simulated small intestinal juice with or without 0.3% bile salt; (4) the growth of dairy propionibacteria strains in SLB containing 0.3% bile salt anaerobically at 37° C.

Acid tolerance refers to the ability of microorganisms to survive in low pH conditions. There are no agreed rules for the screening of acid tolerance. A range of pH values, pH1-pH5, have been used in vitro to screen the acid tolerance of *Lactobacillus, Bifidobacterium* and dairy propionibacteria strains (Mantere-Alhonen, 1983; Charteris et al, 1998; Clark et al, 1993; Conway et al, 1987; Chou and Weimer, 1999; Chung et al, 1999). The inhibitory effect of low pH on the survival of microorganisms was not only observed in this study, but also several other studies (Hood and Zottola, 1988; Clark et al, 1993; Chung et al, 1999; Jan et al, 2000). In this study, all 13 tested dairy propionibacteria strains showed highly decreased viability at pH2 in simulated gastric juice over the three-hour incubation [Table 11]. This was especially evident for *P. freudenreichii* CSCC2200, *P. freudenreichii* CSCC2206 and *P. freudenreichii* CSCC2216, with no viable cells detected after the three hour incubation period. At pH3, ten strains of dairy propionibacteria maintained constant viability after the three-hour incubation; in contrast, viable cell numbers of *P. freudenreichii* CSCC2206, *P. acidopropionici* ATCC25562 and *P. acidopropionici* 341 fell significantly. At pH4, cell numbers of all tested strains remained constant after three-hour incubation. Hood and Zottola (1988) reported a rapid decline to zero in numbers of *L. acidophilus* BG2F04 at pH2 in MRS broth, potassium chloride buffer, and potassium phthalate buffer after 45 min from an initial cell number of $10^7$ to $10^8$ cfu/mL. At pH 3, cell numbers of *L. acidophilus* BG2F04 remained relatively constant over two hours in MRS broth and potassium chloride buffer, however, numbers rapidly declined to zero after 30 min in potassium phthalate buffer. At pH4, cell numbers of *L. acidophilus* BG2F04 remained the same after two hours in MRS broth, potassium chloride buffer, and potassium phthalate buffer. Clark, et al. (1993) examined the response of four *Bifidobacterium* strains to pH levels of 1, 2 and 3 using 37% HCl solutions. At pH1, the numbers of *Bifidobacterium* strains declined rapidly, especially *B. bifidum* which declined to zero after one hour. At pH2, there was no decrease in the numbers of *B. infantis, B. adolescentis*, and *B. longum*; in contrast, the number of *B. bifidum* decreased to 10% of its original number after one hour and no viable cells were detected after two hours. At pH3, almost all cells of the four strains of *Bifidobacterium* survived during the three hours incubation. Jan, et al. (2000) tested the survival of propionibacteria in acidified cheese with pH levels of 2, 2.5, 3 and 4. No significant loss of viability was observed at pH3 or 4 after one-hour incubation. In contrast, rapid decrease of bacterial viable numbers was detected in cheeses acidified to a final pH of 2.5 or pH2.

The results of this current study [Table 11], as well as those of other investigators (Hood and Zottola, 1988; Clark et al, 1993; Chung et al, 1999; Jan et al, 2000) demonstrate that a key factor influencing the survival of microorganism during gastric transit is the pH. The results also indicate that some strains have stronger acid-tolerance than other strains.

The survival of microorganisms through gastric transit is not only pH-dependant, but also affected by the presence of food and food ingredients (Conway et al, 1987; Charteris et al, 1998; Wang et al, 1999). Conway, et al. (1987) reported that addition of 10% skim milk significantly enhanced the survival of *Lactobacillus* strains in gastric juice. Charteris, et al found that the viability of *Lactobacillus* and *Bifidobacterium* strains was improved by the addition of milk proteins (sodium caseinate and whey protein). In this study, the viability of 13 tested dairy propionibacteria strains was highly improved during pH2 simulated gastric transit by the addition of So-Good soymilk and Up & Go cereal breakfast. There was a pH increase in the gastric transit mixture with the addition of So-Good soymilk and Up & Go cereal breakfast (Table 12). The improvement in viability may therefore be partly due to the pH increase of simulated gastric juice caused by the food addition. However, there may be some other physical protection mechanism. The enhancement of viability of microorganisms through gastric transit indicates that low acid tolerant strains may not need to be excluded from probiotic application as long as they can be delivered to the intestine in high numbers through use of food or another suitable delivery system, such as in a buffered menstrum or in an encapsulated system.

Small intestinal transit tolerance (including bile tolerance) is essential for probiotic strains to colonise the small intestine. All thirteen tested strains showed no reduction of viability after four hour simulated small intestinal transit without bile (Table 13). Even in the presence of bile, almost all the tested strains showed the same viability after a four hour incubation, except for *P. freudenreichii* CSCC2207 and *P. acidopropionici* 341, which had only 0.2-log and 0.97-log reduction in viability respectively (Table 13). This indicates that the 13 tested dairy propionibacteria strains were able to survive during small intestinal transit.

In microbiological terms bile tolerance means not only surviving but also multiplying in the presence of bile. All 13 tested dairy propionibacteria strains were able to grow in SLB with 0.3% bile salts (FIG. 9). However, different strains yielded different maximum growth ($A_{650}$) during a 5-day incubation (Table 15). It is not surprising that two strains of *P. acidopropionci* yielded higher $A_{650}$ than the strains of *P. jensenii* and *P. freudenreichii* (Table 15), since strains of *P. acidopropionici* have been found to be able to grow the best amongst dairy propionibacteria strains in the presence of 20% bile (Cummins and Johnson, 1986). Noticeably, *P. jensenii* 702 also yielded high growth ($A_{650}$) in SLB with 0.3% bile. The threshold level of $A_{650}=0.5$ may exclude four dairy propionibacteria strains, *P. freudenreichii* CSCC2200, *P. freudenreichii* CSCC2201, *P. freudenreichii* CSCC2206, and *P. freudenreichii* CSCC2216 as potential probiotic candidates.

In order for a probiotic strain to be effective, the capacity to adhere to gastrointestinal tract is essential. The selection of adhesive strains can be based on the adhesion to gastrointestinal cells in vitro. Cell line C2BBe1 was first used to study the adhesion of bacteria. The adhesion results of reference strain *L. acidophilus* MJLA1 and *B. lactis* BDBB2 indicate that C2BBe1 is suitable for screening bacterial adhesion. In this study, only one among thirteen dairy propionibacteria strains, *P. jensenii* 702, was found to be adhesive to C2BBe1.

Conclusions

This research screened 13 dairy propionibacteria strains by standard in vitro methods for use as potential probiotics. Comparison of their gastrointestinal tolerance and adhesion, resulted in only one strain, *P. jensenii* 702, being found to be a suitable candidate for further in vivo study.

This research has demonstrated the relatively high gastric tolerance of three species of dairy propionibacteria. In addition, it was shown that the presence of food clearly enhances the survival of dairy propionibacteria strains during gastric transit and therefore suggest that acid-tolerance may not necessarily be the essential selection criterion for potential probiotic bacteria.

EXAMPLE 3

Survival, Safety and Probiotic Effects of Orally Administered Viable *Propionibacterium Jensenii* 702 on Male Wistar Rats A novel probiotic strain not only needs to be assessed for its the safety but also the efficacy of its proposed use before its corporation into food products. The aim of this study was to evaluate the safety and potential probiotic effects of *P. jensenii* 702 using a male Wistar rat model. For this purpose, the following were examined, (1) acute oral toxicity; (2) translocation of bacterial cells to liver, mesenteric lymph nodes and spleen tissues; (3) faecal aerobic and anaerobic bacteria; (4) faecal β-glucuronidase levels; (5) testicular histological changes of rats; (6) adherence of *P. jensenii* 702 to the small intestine; (7) intestinal content counts of *P. jensenii* 702; (8) vitamin $B_{12}$ and homocysteine levels in serum; and (9) total cholesterol and triglycerides.

Materials and Methods

Ethics Approval

The ethics approval, for this study involving the use of animals, was obtained from the Ethics Committee of the University of Newcastle, NSW, Australia. The ethics certificate number is 7180902.

Preparation of Bacterial Suspension for Rat Feeding

*P. jensenii* 702, which was isolated from raw milk (Example 1), was used in this study. The recovery and preservation of *P. jensenii* 702 was performed as previously described in Example 1.

The bacterial suspension for feeding was prepared as follows. Strain *P. jensenii* 702 was grown anaerobically in 20 McCartney bottles, each containing 20 mL of SLB broth, at 30° C. for 3 days. The cultures were then transferred to two sterile 250 mL centrifuge tubes. The bacterial cells were collected by centrifugation (3500×g, 5 min). The supernatants were discarded and the cell pellets were washed twice in 60 mL of 0.85% NaCl (Sigma), with centrifugation (3500×g, 5 min) between each wash. Bacteria cells were then resuspended in 30 mL of 0.85% NaCl and aliquots (3.5 mL) of the bacteria suspension were dispensed into 5 mL sterile tube and stored at 4° C. for up to 7 days. The viable cell counts of bacterial suspensions were tested using the pour plate method. Using this method, it was found that viable cell counts of the bacterial suspensions were around $10^{10}$ cfu/mL (raw data not shown).

Animals and Feeding Procedures

The animal model was modified from that described by Kawata, et al. (1997), and used male Wistar weanling rats. A previous experiment (data not shown) using the Kawata diet resulted in severely malnourished rats that required euthanasia prior to the experiment being completed. Unlike the method described by Kawata, et al. (1997), the rats in this study were born to normal, healthy mothers, and were given access to normal rat chow until weaning; and a commercially prepared and pelleted diet, Vitamin $B_{12}$ Deficient Diet Modified (ICN), was adopted to feed all rats for the treatment period in this study.

On arrival at the animal holding facility, the weanling rats were randomly divided into three groups, namely, a Deficiency group (VD), a Bacteria group (B), and a Control group (VC), each group containing seven rats. Each group were housed in three cages, with two or three rats in one cage. For the first week, rats were given a diet of 50% of normal rat chow and 50% of Vitamin $B_{12}$ Deficient Diet Modified. After the first week all rats were fed solely on the Vitamin $B_{12}$ Deficient Diet Modified and were maintained on this diet for the duration of the study. Excess sterile water was provided for drinking, and from the second week the groups were given a 1% supplement of, 1 μg/mL of cyanocobalamin (Sigma) (vitamin $B_{12}$) in 0.85% NaCl (Control group), 0.85% NaCl (Deficiency group), or ~$10^{10}$ cfu/mL of *P. jensenii* 702 in 0.85% NaCl (Bacteria group), in their water supply. The water in the water bottles was changed and fresh supplements for each group were added every day.

Monitoring of the Rats

Throughout the experiment, the feed and water intakes, the animals' activities, behaviours, and general health status were monitored every day. As water and feed was provided ad libitum, no measure of individual intake could be calculated, however, total food and water intake per cage was measured and an average intake per rat was determined. The individual weight of the rats was monitored once a week.

Bacterial Viable Counts of the Rat Faeces

Once a month, the rats were placed into single cages overnight with paper towel as bedding, and the 24 hr faeces of each rat were collected for bacteria counts and glucuronidase test. The faecal bacterial viable counts method was based on the method of Wang et al. (Wang et al., 1999).

Preparation of Serial Dilutions of Rat Faeces

Faeces from each rat were collected in 20 mL of 0.05 M sodium phosphate buffer and stored at 4° C. for up to 24 hr before testing. The faecal suspensions were prepared by stirring using a spatula and then vortexed at a maximum setting for 10 seconds by a vortex mixer. When the faecal suspensions were too dense to mix, extra 5 to 10 mL of 0.05 M sodium phosphate buffer was added to help mixing. The 1 in 10 dilution was then prepared by transferring 1 mL of the faecal suspension to 9 mL of half strength of Wilkins-Chalgren Anaerobe Broth (WCAB) (Oxoid) by 1 mL syringe. Further serial dilutions were made using 9 mL of half strength of WCAB.

Viable Cell Counts of Bacteria in Rat Faeces

Bacterial viable cell counts of rat faeces were determined by the spread plate method. Briefly, 100 μL of the selected dilutions, which were prepared as described above, were transferred onto Nutrient Agar (NA) (Oxoid), Wilkins-Chalgren Anaerobe Agar (WCAA) (Oxoid), and SLA plates. The inoculum (100 μL) was spreaded gently and evenly onto each plate with a bent spreader. The plates were left to stand on the bench at room temperature for 15 min or until the inoculum on each plate had been completely absorbed. Plates were inverted, then NA plates were incubated at 37° C. for 48 hr, WCAA plates were incubated at 37° C. anaerobically for 5 days, and SLA plates were incubated at 30° C. anaerobically for 5 days. Colonies on NA and WCAA were counted for total aerobe viable cell counts and total anaerobe viable cell counts respectively. SLA plates were examined and typical colonies of dairy propionibacteria were counted for dairy propionibacteria counts.

β-Glucuronidase Test

β-Glucuronidase activity was assayed according to the method described by Nanno (1986). Serial dilutions of faeces were prepared as previously described. Selected faecal dilutions (0.1 mL) or bacterial suspension (0.1 mL) were added to a 5 mL tube, which contained 0.9 mL of a reaction mixture. The tubes were incubated at 37° C. for 2 hr. Glycine-NaOH-NaCl buffer (0.23M, pH10.4, 2.5 mL) was then added to each tube to stop the reaction. The reaction solution was then centrifuged at 3500×g for 30 min and the absorbance of the supernatant was measured at 400 nm using a spectrophotometer (Pharmacia Biotech).

Standard solutions were made with ρ-nitrophenol (Sigma). A standard curve was constructed using concentrations of 0.1, 0.2, 0.5, 1 and 10 mM of ρ-nitrophenol. One million unit (1 MU) was defined as the activity required to release 1 mmol of ρ-nitrophenol in 1 hr.

Serum Vitamin $B_{12}$ and Homocysteine Levels in Rat Blood

A blood sample from each rat was collected from saphenous vein at the beginning of treatment (Month 0), at the end of Month 1 and Month 2. At the end of Month 3, blood was collected under anaesthetic by cardiac puncture and rats were euthanased, using carbon dioxide, without recovering. Blood samples were stored on ice for maximum of two hours and sera were separated from packed cells by centrifugation (450×g, 10 min, 4° C.). Serum samples were transferred into eppendorf tubes and stored at −70° C. before testing. Packed cells were also kept and stored at −70° C.

The serum vitamin $B_{12}$ levels were determined by a Quantaphase $B_{12}$/Folate assay (Bio-Rad) at the Pathology Unit, at the Sydney Adventist Hospital, Sydney, NSW, Australia.

The serum homocysteine levels of Month 0, Month 1, and Month 2 samples were determined by Abbott IMx, and the serum homocysteine levels of Month 3 samples were determined by DPC Immulite 2000 at the Pathology Unit, at the Sydney Adventist Hospital.

Translocation Tests of Feeding Bacterial Strain P. jensenii 702

The study of translocation of feeding P. jensenii 702 was designed based on the methods of Zhou, et al. (2000). The details of the method follow.

At the end of the experiment, the rats were euthanased and autopsied. Before excising tissue samples, the surface of viscera was swabbed with a sterile bacteriological swab (IDEXX-Veterinary Pathology Services). The swabs were then streaked onto Brain Heart Infusion agar (BHA) (Oxoid) plates and SLA plates to test the microbial sterility of viscera surface. The BHA plates were incubated at 37° C. aerobically for 3 days to check any microbial growth on the plates. The SLA plates were then incubated anaerobically at 30° C. for 6 days to check any microbial growth and the presence of typical colonies of dairy propionibacteria.

Following swabbing, the size and appearance of visceral organs were examined microscopically. Then the mesenteric lymph nodes (MLN), spleen and a sample of liver tissues were excised aseptically. The tissue samples were collected into a set of pre-weighed 5 mL containers, each containing 2 mL of Brain Heart Infusion Broth (BHI) and reweighed. The spleen weight index (SWI) was then determined as the actual spleen weight (mg) divided by the last measure of live body weight (g). Then the whole MLN, spleen and a portion of liver were cut into small pieces aseptically. The tissue suspensions and samples of blood from cardiac puncture were plated separately on SLA and BHA plates (0.1 mL on each plate). The BHA plates were incubated at 37° C. aerobically for 3 days to check for any microbial growth. The SLA plates were then incubated anaerobically at 30° C. for 6 days to check any microbial growth and the presence of typical colonies of dairy propionibacteria.

Dairy Propionibacteria Counts in Small Intestine Section

During the autopsy of the rat body, a section of ileum with contents (10 cm) was excised aseptically and collected into a pre-weighted 30 mL container containing 5 mL of BHI broth and stored on ice until processing.

Within 24 hr of collection, the section of ileum was cut open longitudinally and separated from its content. The tissue of ileum section was then placed into another 30 mL container and washed twice with 5 mL of PBS buffer (pH7.0). A small piece (approximately 1 cm) was removed and pinned to the wax of a dissection tray for scanning Electron Microscopy. The remainder of the ileum section tissue was then weighed and cut into small pieces in 2 mL PBS buffer (pH7.0). The small intestine tissue suspension was vortexed vigorously for 1 min. Serial dilutions of contents and tissue suspension of ileum section were made using 9 mL of MRD (Oxoid). Selected dilutions were plated out on SLA plates (0.1 mL for each plate). The SLA plates were then incubated at 30° C. for 6 days to check the presence of typical colonies of dairy propionibacteria.

Scanning Electron Microscopy (SEM) of Samples of Small Intestine Tissue

Scanning electron microscopy (SEM) of samples of small intestine tissue The sample preparation for SEM was based on the methods of Brooker and Fuller (1975), and Swift and Marsh (1968). Briefly, the pieces of ileum section tissues previously pinned on the wax dissection tray were fixed by immersion in 10% Formal saline (IDEXX-Veterinary Pathology Services) at room temperature for 2 hr. After fixation, the tissues were washed three times with PBS buffer (pH7.0). The tissues were then dehydrated using a graded series of ethanol (30%, 50%, 70%, 90%, and 100%), each for 10 min. The tissues were then removed to a 24-well microplate and stored in 1 mL of 100% ethanol during transportation to the Electron Microscopy Unit, University of Newcastle, NSW, Australia, where the tissues were further processed and examined by Mr. Dave Phelan using Scanning Electron Microscopy.

Study of Testicular Morphology

The testes of the rats were immediately removed after death, weighed and stored in 10% Formal Saline (IDEXX-Veterinary Pathology Services) with a single longitudinal incision. The relative testes weight was determined as the ratio of testes weight (g) to 100 g of last measure of live body weight. The histopathology of the testes was examined by IDEXX-Veterinary Pathology Services, Brisbane, Australia.

Statistical Analysis

Data obtained for different rat groups were statistically analysed using either a two-tailed student's t-test or a one way-ANOVA (Microsoft, Excel software). Statistical data in texts and tables were presented mean±standard deviation (SD). The data in figures were presented as mean and error bars were presented as standard error of mean (SEM). P values of <0.05 were taken as significant unless otherwise indicated.

Results

General Health Status

Throughout the experiment rats appeared healthy, inquisitive and active. No illness or death occurred. In the last month of the experiment the activity of the Deficiency group appeared reduced, and they became more irritable on handling. No observable difference in the animal's hair lustre was noticed between the groups.

Feed Intake and Live Weight Gain

Figure 11:
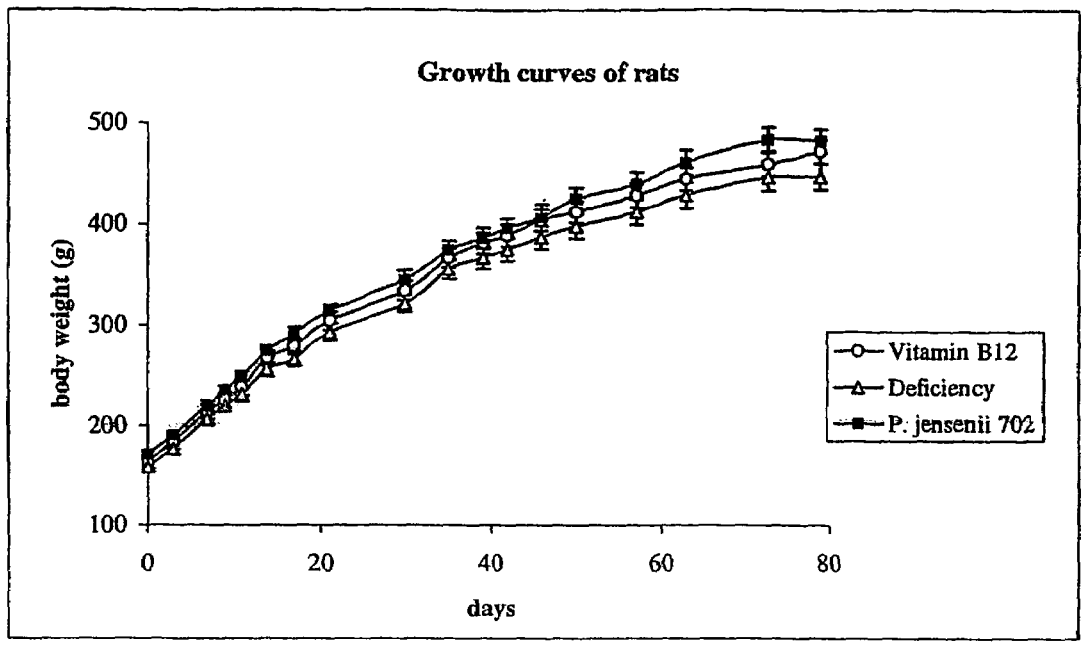
FIG. 11 shows the growth curve of the rat groups fed ad libitum (n=7)

There was no significant difference (p>0.05) in the body weight gain among three tested groups (Table 16, FIG. 11). The daily feed intake of the Bacteria group was significantly higher than that of the Control group and the Deficiency group. This indicates that feeding with *P. jensenii* 702 may have stimulated the appetite of rats of the Bacteria group.

TABLE 16

Compare body weight, body gain (g) and feed intake (g) of different group of male Wistar rats during 81 days treatment

| Rat groups | Initial body weight (g) | Last body weight (g) | Daily Body weight gain (g) | Daily feed intake (g) |
|---|---|---|---|---|
| Control | 162.9 ± 15.1 [a] | 471.9 ± 30.8 [b] | 4.4 ± 0.3 [c] | 22.2 ± 0.1 [d] |
| Deficiency | 158.4 ± 13.8 [a] | 446.9 ± 33.4 [b] | 4.1 ± 0.3 [c] | 21.6 ± 0.6 [d] |
| Bacteria | 170.7 ± 9.4 [a] | 482.0 ± 30.4 [b] | 4.4 ± 0.3 [c] | 22.9 ± 0.1 [e] |

Values are means ± SD (n = 7); values within a given column with the same superscripts are not significantly different (p > 0.05, Student's t-test, two tailed)

Water Intake and Bacteria Dose for the Bacteria Group

Figure 12:
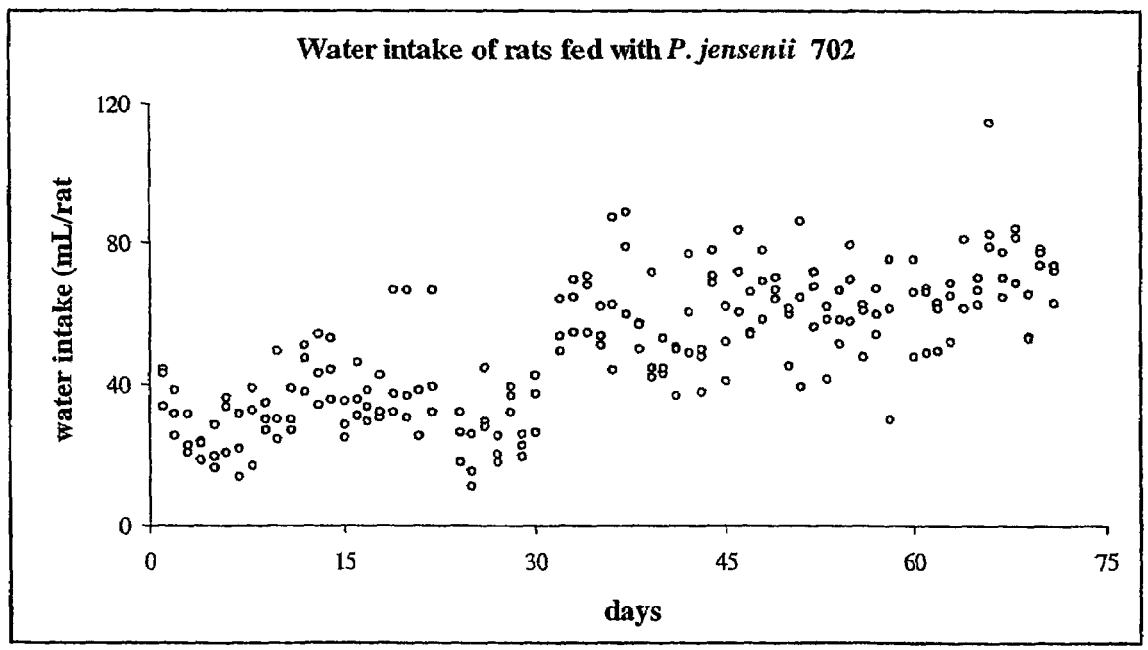
FIG. 12 shows the water intake by rats of P. jensenji 702 group.

The water intake by each cage of rats of the Bacteria group was measured daily, and the average water intake per rat was calculated. FIG. 12 presents the average daily water intake (mL/rat) for each cage of the Bacteria group, which was given *P. jensenii* 702 suspension.

The concentration of *P. jensenji* 702 given in the water was measured by the pour plate method as previously described, and the average log value of *P. jensenii* 702 provided in the rat drinking water per day was calculated as 8.79±0.36 (n=12) (raw data not shown). From this data the average bacteria intake per day was calculated (Table 17). No allowance has been given to the proportional increase in water intake as the rats grew.

TABLE 17

Average daily water and *P. jensenii* 702 intakes by male Wistar rats of the Bacteria group, n = 7

| Intake | Average | Maximum | Minimum |
|---|---|---|---|
| Water (mL/rat/day) | 49.8 | 115 | 11 |
| *P. jensenii* 702 (log cfu/rat/day) | 10.61 | 10.97 | 9.95 |

Translocation of *P. jensenii* 702 Cells

There was no bacterial growth from swabs taken from the visceral surfaces of the rats of the three experimental groups, which indicates that the visceral surface was not contaminated with bacteria.

No bacteraemia was detected in any of the three experimental groups. There was no growth of *P. jensenii* 702 in any cultures of blood, spleen, mesenteric lymph nodes and liver samples. This indicates that there is no translocation of *P. jensenii* 702 to blood and tissues, which suggests that the intake of *P. jensenii* 702 will not result in any invasion to the tissue cells of the host.

Examination of Visceral Organs

Macroscopic examination did not reveal any obvious differences in the size and appearance of visceral organs between each group. No hepatomegaly or splenomegaly occurred.

The spleen weight and spleen weight index of the rats are shown in Table 18. There is no significant difference in the spleen weight between the Control group, the Deficiency Group and the Bacteria group (p>0.05). The spleen weight index of the Bacteria group is significantly lower than that of the Deficiency group (p<0.05), however, the spleen weight index of the Bacteria group or that of the Deficiency group is not significantly different from that of the Control group (p>0.05). The difference of the spleen weight index between the Bacteria group and the Deficiency group may be due to the difference of the body weight, although not significant.

TABLE 18

Spleen weight (g) Spleen weight index (mg/g) of different groups of male Wistar rats fed with vitamin $B_{12}$ deficient diet for 3 month

| Rat groups | Spleen weight (g) | Spleen weight index (mg/g) |
|---|---|---|
| Control | 1.28 ± 0.07 [a] | 2.73 ± 0.22 [b, c] |
| Deficiency | 1.22 ± 0.05 [a] | 2.74 ± 0.12 [b] |
| Bacteria | 1.21 ± 0.08 [a] | 2.52 ± 0.23 [c] |

Values are means ± SD (n = 7); values within a given column with the same letter superscripts are not significantly different (p > 0.05, Student's t-test, two tailed)

Faecal Bacteria Viable Counts

Total Faecal Aerobe Counts

The levels of total aerobes in the faeces of the three experimental groups of male Wistar rat faeces during the 81 days treatment period are shown in Table 19.

Within each experimental group, the total faecal aerobe counts of Day 36, Day 64, and Day 81 were compared to that of Day 0 (Table 19). The total faecal aerobes of the Bacteria group at Day 36 and Day 64 were significantly higher than Day 0 (p<0.05), however, by Day 81 the total faecal aerobe counts of the Bacteria group reduced to the same level of Day 0 (p>0.05) (Table 19). The same pattern was also observed in the Control group and the Deficiency group (Table 19). The result indicates that intake of *P. jensenii* 702 did not affect the faecal aerobic population.

At each testing time, the faecal aerobe counts of different experimental groups were compared (Table 19). At Day 36, the total faecal aerobic counts of the Deficiency group and the Bacteria group were significantly lower than that of the Control group (p<0.05). However, by Day 64 and Day 81, the faecal aerobic counts of the Control group, the Deficiency group and the Bacteria group were not significantly different (P>0.05).

TABLE 19

Total faecal aerobe counts (log cfu/g)
in male Wistar rats during treatment

| Groups | Day 0 | Day 36 | Day 64 | Day 81 |
|---|---|---|---|---|
| Control | 7.63 ± 0.30 [a] | *8.90 ± 0.22 [b] | *8.39 ± 0.51 [d] | 8.19 ± 0.62 [e] |
| Deficiency | 7.80 ± 0.29 [a] | *8.48 ± 0.43 [c] | *8.48 ± 0.37 [d] | 8.40 ± 0.67 [e] |
| Bacteria | 7.61 ± 0.13 [a] | *8.50 ± 0.13 [c] | *8.41 ± 0.24 [d] | 7.85 ± 0.22 [e] |

Values are means ± SD (n = 7).
Values of Day 36, Day 64, and Day 81 were compared with that of Day 0 within each group,
*p < 0.05, (Student's t-test, two tailed).
Values of different groups at each testing time were compared with each other; values within a given column with the same letter superscripts are not significantly different (p > 0.05, Student's t-test, two tailed).

Total Faecal Anaerobe Counts

The levels of total anaerobe counts in male Wistar rat faeces during the 81 days feeding period are shown in Table 20.

Within each group, the faecal anaerobe counts at Day 36, Day 64, and Day 81 were compared to that of Day 0 (Table 20). The total faecal anaerobes in the Control group and the Deficiency group at Day 36, Day 64 and Day 81 were not significantly different from that of Day 0 (p>0.05) (Table 20). In contrast, the total faecal anaerobes of the Bacteria group at Day 36 and Day 64 were not significantly different from that of Day 0 (p>0.05) (Table 20); but the total faecal anaerobes of the Bacteria group at Day 81 was significantly lower than that of Day 0 (p<0.05). The reduction in the total faecal anaerobe counts of the Bacteria groups suggests that feeding with *P. jensenii* 702 may have an effect on the faecal anaerobic microflora.

At each testing time, the faecal anaerobes counts of different groups were compared (Table 20). There was no significant difference of faecal anaerobic counts between the Control group, the Deficiency group and the Bacteria group during the 81 days feeding period (p>0.05).

TABLE 20

Total faecal anaerobe counts (log cfu/g)
in male Wistar rats during treatment

| Groups | Day 0 | Day 36 | Day 64 | Day 81 |
|---|---|---|---|---|
| Control | 9.22 ± 0.18 [a] | 9.46 ± 0.41 [b] | 9.43 ± 0.36 [c] | 9.25 ± 0.39 [d] |
| Deficiency | 9.36 ± 0.29 [a] | 9.04 ± 0.39 [b] | 9.30 ± 0.26 [c] | 8.94 ± 0.30 [d] |
| Bacteria | 9.66 ± 0.19 [a] | 9.30 ± 0.25 [b] | 9.31 ± 0.33 [c] | *9.15 ± 0.24 [d] |

Values are means ± SD (n = 7).
Values of Day 36, Day 64, and Day 81 were compared with that of Day 0 within each group,
*p < 0.05 (Student's t-test, two tailed).

Values of different groups at each testing time were compared with each other; values within a given column with the same letter superscripts are not significantly different (p>0.05, Student's t-test, two tailed).

Faecal Dairy Propionibacteria Counts of the Bacteria Group

Figure 13:
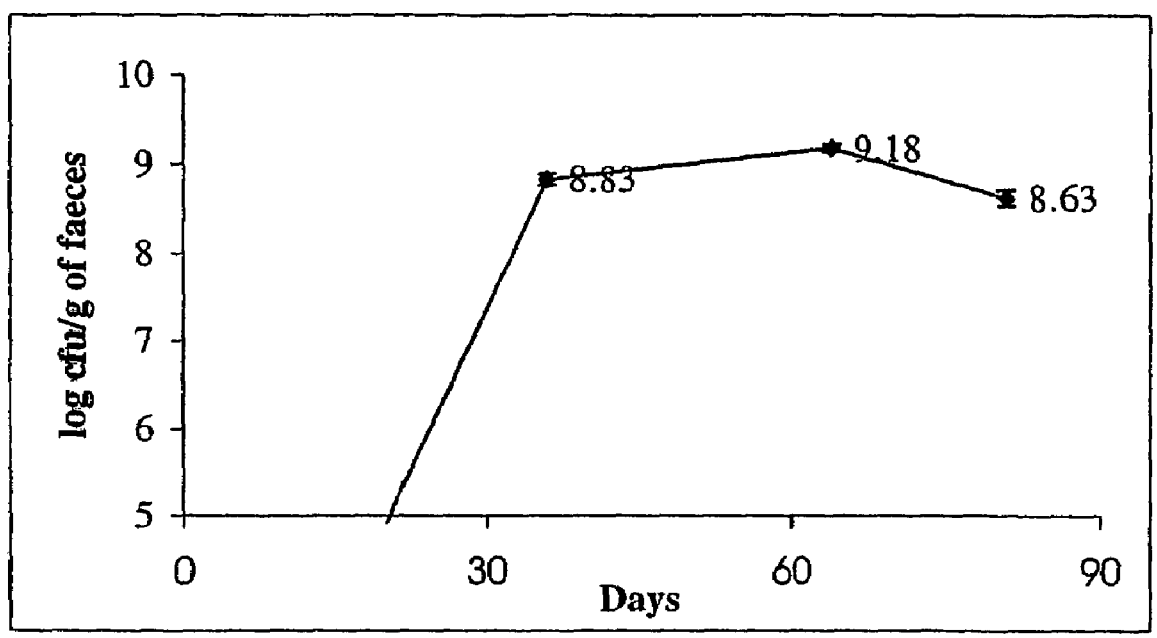
FIG. 13 shows the enumeration of dairy propionibacteria in faeces of rats fed with P. jensenii 702, n=7.

No dairy propionibacteria were detected in the rats of the Bacteria group prior to providing *P. jensenii* 702 in their drinking water (FIG. 13). At the second test time (after 36 days feeding with *P. jensenii* 702), the dairy propionibacteria level in the faeces of the Bacteria group increased to 8-log value and remained at the level of 8-log to 9-log value until the end of the experiment (FIG. 13). No dairy propionibacteria were detected in the faeces of the Control group and the Deficiency group during the 81 days treatment period.

Faecal β-Glucuronidase Activities

The β-glucuronidase acivity of *P. jensenii* 702 suspension ($10^{10}$ cfu/mL) was below the testing limit (IU).

The average faecal β-glucuronidase activities of different experimental groups of male Wistar rats during 81 days of treatment period are shown in Table 21. There was variation of β-glucuronidase activities among the rats within each group at each testing time.

Within each group, the average faecal β-glucuronidase activity of Day 36, Day 64, and Day 81 were compared to that of Day 0 (Table 21). The average faecal β-glucuronidase activity of the Control group at Day 36 and Day 64 remained the same level as that of Day 0, but increased significantly at Day 81 (p<0.05). The average faecal β-glucuronidase activity of the Deficiency group remained at the same level during the whole 81 days feeding period (p>0.05). In contrast, the average faecal β-glucuronidase activity of the Bacteria group at Day 36 was significantly higher than that at Day 0, then decreased at Day 64 and remained at the same level as that at Day 0 until the end of 81 days of treatment period (p>0.05).

At each testing time, the average faecal β-glucuronidase activities of different groups were compared (Table 21). There was no significant difference of average faecal β-glucuronidase activities between the Control group, the Deficiency group and the Bacteria group at Day 0, Day 36 and Day 64. In contrast, at Day 81, the average faecal β-glucuronidase activities of the Bacteria group and the Deficiency group were significantly lower than that of the Control group (p<0.05) (Table 21).

TABLE 21

Faecal β-glucuronidase activities (MU/g) of male Wistar rats during treatment

| Groups | Day 0 | Day 36 | Day 64 | Day 81 |
|---|---|---|---|---|
| Control | 8.33 ± 4.04 [a] | 12.26 ± 3.42 [b] | 11.00 ± 3.69 [c] | *13.25 ± 1.73 [d] |
| Deficiency | 11.34 ± 5.30 [a] | 18.16 ± 6.86 [b] | 13.07 ± 1.97 [c] | 9.33 ± 1.65 [e] |
| Bacteria | 7.51 ± 2.98 [a] | *14.62 ± 4.13 [b] | 13.41 ± 5.59 [c] | 7.61 ± 1.81 [f] |

Values are means ± SD (n = 7).
Values of Day 36, Day 64, and Day 81 were compared with that of Day 0 within each group,
*p < 0.05 (student's t-test, two tailed).

Values of different groups at each testing time were compared with each other; values within a given column with the same letter superscripts are not significantly different (p>0.05, Student's t-test, two tailed).

Dairy Propionibacteria in Small Intestine

Dairy propionibacteria was isolated from the contents and tissues of the ileum sections of the rats from the Bacteria group. The viable counts of dairy propionibacteria from these samples was quite low ($10^1$ to $10^2$ cfu/g), however, as only 10 cm of the small intestine was sampled, this does not reflect the total intestinal number. No dairy propionibacteria was isolated from the contents and tissues of ileum sections of the rats from the Deficiency group and the Control group.

Figure 14:
FIG. 14 shows a scanning electron micrograph of the inner surface of a male Wistar rat small intestine fed P. jensenii 702 for a period of 81 days.
Figure 16:
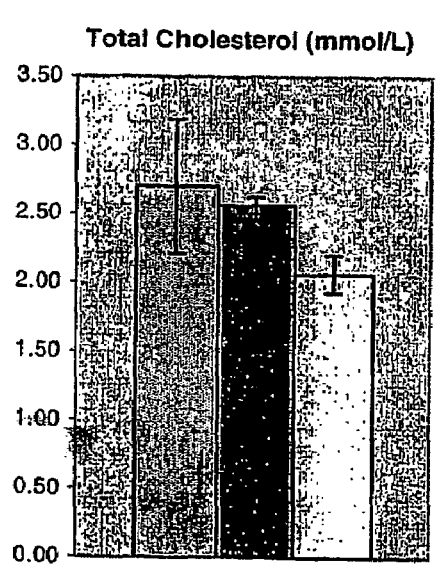
FIG. 16 shows the comparison of the average total cholesterol and triglycerides in the three Wistar rat groups at the completion of the three month feeding trial, each group containing 7 rats.
Figure 16:
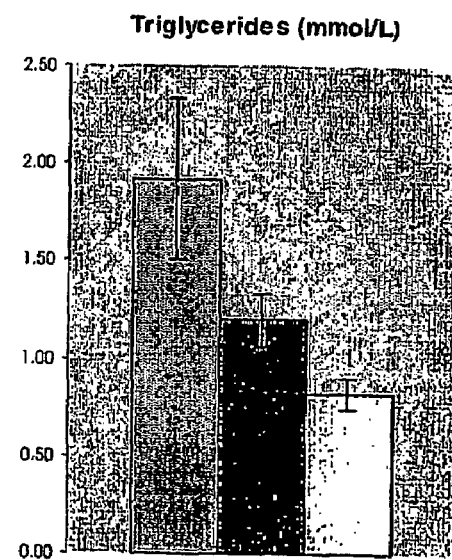

Observation of Scanning Electron Microscope micrographs of the small intestine tissue samples were difficult to interpret as there were no monoclonal antibodies available to specifically stain for *P. jensenii* 702. No structures that resembled bacteria in the samples of small intestine tissue were observed for the Deficiency group and the Control group. In the case of the Bacteria group, short rod shaped structures of the expected shape and size were present (FIG. 14). These rod shaped structures were not observed for the other two groups.

Serum Vitamin $B_{12}$ and Homocysteine Levels

Serum Vitamin B12 Levels

The mean serum vitamin B12 levels (pmol/L) for the three experimental groups of Male Wistar rats during the three-month feeding period are presented in Table 22.

The serum vitamin $B_{12}$ levels for the Control group increased significantly after one month feeding (p<0.05) and remained at a relatively constant level for the remainder of the experiment (Table 22). There was no significant difference in the serum vitamin $B_{12}$ levels from Month 1 to Month 3 for the Control group (p>0.05) (Table 22). The results may indicate that the rats of the Control group absorbed vitamin $B_{12}$ from the drinking water to build up serum vitamin $B_{12}$ during the first month, and then reached their upper absorption limit for this vitamin after one-month treatment.

The serum vitamin $B_{12}$ levels of the Deficiency group decreased significantly from 444.4 pmol/L to 131.3 pmol/L after one month (p<0.05), and remained at the significant lower level till the end of 3-month feeding period (p<0.05) (Table 22). This indicates the Vitamin $B_{12}$ Deficient Diet resulted in the depletion of serum vitamin $B_{12}$ in rats.

The serum vitamin $B_{12}$ levels of the Bacteria group decreased significantly after the first month feeding period (p<0.05) (Table 22). After two-months feeding period, the serum vitamin $B_{12}$ levels of the Bacteria group increased significantly compared to that of Month 1 (p<0.05), and was at the same level as that at Month 0 (p>0.05). The serum vitamin $B_{12}$ level of the Bacteria group at Month 3 was significantly lower than that at Month 0 (Table 22), but significantly higher than that at Month 1, and not significantly different from that at Month 2 (p<0.05).

TABLE 22

Comparison of serum vitamin $B_{12}$ levels (pmol/L) of male Wistar rats during feeding period

| Groups | Month 0 | Month 1 | Month 2 | Month 3 |
|---|---|---|---|---|
| Control | 464.9 ± 50.4 [a] | *914.6 ± 200.8 [b] | *1096.2 ± 365.7 [d] | *949.2 ± 375.0 [g] |
| Deficiency | 444.3 ± 28.2 [a] | *131.3 ± 54.4 [c] | *135.7 ± 50.8 [e] | *105.5 ± 34.1 [h] |
| Bacteria | 387.2 ± 62.3 [a] | *119.9 ± 67.9 [c] | 241.6 ± 101.5 [f] | *216.0 ± 72.8 [i] |

Values are means ± SD (n = 7).
Values of Month 1, Month 2, and Month 3 were compared with that of Month 0 within each group,
*p < 0.05 (student's t-test, two tailed).
Values of different groups at each testing time were compared with each other; values within a given column with the same superscripts are not significantly different (p > 0.05, Student's t-test, two tailed)

The serum vitamin $B_{12}$ levels of different group were compared at each testing time (Table 22). At the beginning of the feeding period, there was no significant difference in the serum vitamin $B_{12}$ levels between the Control group, the Deficiency group, and the Bacteria group (p>0.05). After the $1^{st}$ month, the serum vitamin $B_{12}$ levels of the Deficiency group and the Bacteria group were significantly lower than that of the Control group (p<0.05). This is attributed to the vitamin $B_{12}$ depletion effect of the Vitamin $B_{12}$ Deficient Diet Modified. The fact that the serum vitamin B12 level increased in the Control group indicates that the pharmaceutical form of vitamin $B_{12}$ in the drinking water provided adequate dietary source of the vitamin $B_{12}$. After two months until the end of the experiment, the serum vitamin $B_{12}$ level of the Bacteria group was significantly higher than that of the Deficiency group. This confirms that *P. jensenii* 702 cells provided vitamin $B_{12}$ to the rats of the Bacteria group. The fact that the Bacteria group had significantly lower serum vitamin $B_{12}$ than that of the Control group at the end of the study is not of concern, and will be addressed in the subsequent discussion.

Serum Homocysteine Levels

The mean serum homocysteine levels (μmol/L) for the three experimental groups of male Wistar rats during the three-month feeding period are presented in Table 23.

The mean serum homocysteine levels of the Control group remained at the same level during the 3 months feeding period (p>0.05) (Table 23). The serum homocysteine level of the Deficiency group increased significantly after the $1^{st}$ month (p<0.05) and remained at a significantly higher level than that of Month 0 until the end of 3 months feeding period (p<0.05). The serum homocysteine level of the Bacteria group initially increased significantly after the $1^{st}$ month (p<0.05); but then decreased significantly at Month 2 and Month 3 (p<0.05). The serum homocysteine level of the Bacteria group at Month 3 was not significantly different from the original value of Month 0 (p>0.05).

The serum homocysteine levels of the different groups, at each testing time, were compared (Table 23). At the beginning of the feeding period, there was no significant difference in the serum homocysteine levels between the Control group, the Deficiency group, and the Bacteria group (p>0.05). At Month 1, the serum homocysteine level of the Deficiency group and the Bacteria group were significantly higher than that of the Control group. At Month 2 and Month 3, the serum homocysteine level of the Deficiency group still significantly higher than that of the Control group (p<0.05). In contrast, the serum homocysteine level of the Bacteria group decreased at Month 2, and was not significantly different from that of the Deficiency group or the Control group; at Month 3, the serum homocysteine level of the Bacteria group decreased further to a significantly lower level than that of the Deficiency group (p<0.05), and still at the same level as that of the Control group (p>0.05). The gradual decrease in serum homocysteine level of the Bacteria group indicates that feeding with *P. jensenii* 702 reduces the serum homocysteine. As serum homocysteine levels reflect the store of vitamin B12 in an animal, it is likely that the low levels of homocysteine reached by the Control group are the low ends of homocysteine values found in a rat.

TABLE 23

Comparison of serum homocysteine levels (μmol/L) of different groups of male Wistar rats during 3 months feeding period

| Groups | Month 0 | Month 1 | Month 2 | Month 3 |
|---|---|---|---|---|
| Control | 18.1 ± 2.4 [a] | 15.4 ± 3.4 [b] | 16.8 ± 2.6 [d] | 16.4 ± 2.0 [f] |
| Deficiency | 15.4 ± 1.5 [a] | *24.8 ± 4.7 [c] | *23.1 ± 5.3 [e] | *26.4 ± 7.4 [g] |
| Bacteria | 13.3 ± 1.9 [a] | *24.1 ± 5.9 [c] | *18.9 ± 2.2 [d, e] | 16.7 ± 2.6 [f] |

Values are means ± SD (n = 7).
Values of Month 1, Month 2, and Month 3 were compared with that of Month 0 within each group,
*p < 0.05 (student's t-test, two tailed).
Values of different groups at each testing time were compared with each other; values within a given column with the same superscripts are not significantly different (p > 0.05, Student's t-test, two tailed)

TABLE 24

Testes weight (g) and relative testes weight (g/100 g body weight) of male Wistar rats fed with vitamin $B_{12}$ deficient diets

| Rat groups | Testes weight (g) | Relative testes weight (g/100 g body weight) |
|---|---|---|
| Control | 3.19 ± 0.21 [a] | 0.67 ± 0.03 [b] |
| Deficiency | 3.50 ± 0.35 [a] | 0.79 ± 0.08 [c] |
| Bacteria | 3.47 ± 0.25 [a] | 0.72 ± 0.05 [c] |

Values are means ± SD (n = 7);
Values within a given column with the same superscripts are not significantly different (p > 0.05, Student's t-test, two tailed)

Cholesterol and Triglycerides

The mean serum lipid concentrations for the Control, Deficiency and Bacteria Group are shown in Table 25. The mean serum cholesterol concentration of the experimental groups were compared at month 3. The Bacteria group had lower cholesterol levels than the Control group, but not significantly (p>0.05). The Bacteria group, however, were found to have significantly lower total cholesterol concentration than the Deficiency group (p<0.05). No significant difference was observed for lipoproteins between the three experimental groups.

The serum triglyceride concentrations of the experimental groups were compared at the end of the experiment (Table 25). The Bacteria group had significantly lower triglycerides than both the Control and Deficient groups (p<0.05). The rats in the Deficient group had significantly lower concentration of triglycerides than the Control group (p<0.05), but significantly higher than the rats in the Bacteria group (p<0.05)

TABLE 25

Serum lipid parameters (mmol/l) of the three experimental groups of male Wistar rats at the end of three-month feeding treatment

| Experimental Groups | Total Cholesterol (mmol/l) | HDL (mmol/l) | LDL (mmol/l) | Triglycerides (mmol/l) |
|---|---|---|---|---|
| Control | 2.70 ± 0.49 [a, b] | 0.76 ± 0.15 [c] | 1.08 ± 0.14 [d] | 1.92 ± 0.42 [e] |
| Deficiency | 2.56 ± 0.06 [b] | 0.69 ± 0.02 [c] | 1.33 ± 0.14 [d] | 1.19 ± 0.14 [f] |
| Bacteria | 2.06 ± 0.14 [a] | 0.51 ± 0.04 [c] | 1.18 ± 0.08 [d] | 0.82 ± 0.08 [g] |

HDL = High-density lipoprotein;
LDL = low density lipoprotein. The LDL was calculated by the equation of Friedewalds et al. (1972).
Values are means ± standard deviation (n = 7)
Values within a given column with the same superscripts are not significantly different (p > 0.05, one way - ANOVA)

Testes Weight and Morphology

There was no significant difference in the wet weight of testes between the Control group, the Deficiency group, and the Bacteria group (Table 24). However, the relative testes weight (g/100 g of body weight) of the Control group was significantly lower than that of the Deficiency group and the Bacteria group (Table 24). One possible reason for this result is that one rat in the Control group was noted to have smaller testes (data not shown), which apparently sometimes occurs in healthy Wistar rats (Dr. Mary Bate, Animal Ethics Officer, University of Newcastle, personal communication). This probably skewed the results.

According to the report from the IDEXX-Veterinary Pathology Services, Brisbane, Australia (not shown), the testicular morphology of all tested three groups was also normal.

Discussion

Safety is the most important criterion for selection of new probiotic strains, and it is unfortunate that there are no general guidelines or specific policies for safety assessment. In this study, recommended safety testing was undertaken, including measurement of acute oral toxicity, bacterial translocation to blood and organ tissues, and the production of harmful enzymes.

Acute oral toxicity has been advocated as a fundamental test for assessing safety (Donohue et al., 1998; Stine and Brown, 1996). Acute oral toxicity has been applied previously in the safety assessment of lactic acid bacteria (Zhou et al., 2000). In these assessments, appetite, activity, and live weight gain have been regarded as general and sensitive indicators for the health status of animals.

On average, the rats of the Bacteria group consumed a very high number of viable bacteria per day ($10^{10}$ cfu/rat/day) (Table 17). All rats in this group were healthy, as indicated by their activity, feed intake, daily weight gain, growth curves, and general appearance, and no adverse effect of *P. jensenii* 702 was observed. The average dose of *P. jensenii* 702 ($10^{10}$ cfu/day) used in this study for rat weight ranging from 150 g to 500 g would correspond to an average dose of *P. jensenii* 702 ($10^{12}$ cfu/day) for a 70 kg human. The general suggested level of probiotic bacteria in food is $10^6$ cfu/mL (or cfu/g). Therefore, this study suggests that consumption of *P. jensenii* 702 at general probiotic food level would unlikely result in adverse effect to humans.

In addition to acute oral toxicity, bacterial translocation is another highly recommended indicator for probiotic safety assessment (Marteau et al., 1997; Zhou et al., 2000). Bacterial translocation is a measure of infectivity. In this study, no translocation of *P. jensenii* 702 from the gut to tissues including spleen, liver, mesenteric lymph nodes and blood was observed.

From the evidence above it is apparent that *P. jensenii* 702 is not pathogenic in rats. This result was expected as dairy propionibacteria strains have been consumed by people over long periods of time without any adverse consequences. The limitation of this study is that it was performed on healthy rats, and therefore does not provide data on the effect of consumption of large quantities of dairy propionibacteria by an immunosuppressed population. Further a single animal model always has limitations as the physiology between species is different.

Another safety concern for probiotic bacteria is the production of potentially harmful enzymes, one of which is β-glucuronidase. Bacterial β-glucuronidase can hydrolyze glucuronide in the diet and release steroids and certain carcinogenic compounds. The β-glucuronidase activity for strain *P. jensenii* 702 in vitro was below the testing limit (1 U) using the method described previously. In this study, the faecal β-glucuronidase activities of the three experimental groups of male Wistar rats were difficult to interpret due to the large variation between rats within the same group. The faecal β-glucuronidase activity of the Bacteria group, however, at Day 81 (Table 21) was significantly lower than that of the Control group. It is important to note that the level of faecal β-glucuronidase in the Deficiency group at Day 81 was also significantly lower than that of the Control group. This may indicate that vitamin $B_{12}$ in the diet alters the type of microbiota in the gut.

The reduction of the faecal β-glucuronidase has also been found in a dairy propionibacteria strain, *P. acidipropionici* CRL 1198 (Perez-Chaia et al., 1999). It has been suggested that the anaerobes and coliform bacteria are the major contributor to the faecal β-glucuronidase activity; and the lower activity of faecal β-glucuronidase results from the change of faecal population and their metabolic activities after the inclusion of *P. acidipropionici* CRL 1198 (Perez-Chaia et al., 1999).

Viable bacteria counts demonstrated that there was no significant difference of total aerobe and total anaerobe counts between the Control group, the Deficiency group, and the Bacteria group at each time interval (Table 19, Table 20). But the total faecal anaerobes of the Bacteria group at Day 81 were significantly lower than that at Day 0 (Table 20). This suggests the lower faecal β-glucuronidase in the Bacteria group may also due to the decrease of intestinal anaerobes or their β-glucuronidase activity, which may result from the inclusion of *P. jensenii* 702 in the intestinal flora. Further, as the dairy propionibacteria counts reached $10^8$ cfu/g faeces after only 36 days of feeding, without any subsequent significant decrease in anaerobic counts, but with relative increase in faecal β-glucuronidase levels, it could be speculated that the influence of the *P. jensenii* 702 on the gut anaerobes does not occur until there is sufficient time for it to adhere and colonise the small intestine. The colonisation of the *P. jensenii* 702 may be competitive to the other anaerobic bacteria, or the *P. jensenii* 702 may secrete inhibitory compounds during its growth phase. This would explain why just the transit of the *P. jensenii* 702 through the gastrointestinal tract exerts no obvious effect on the rats of the Bacteria group during the first month of the feeding period. As the presence of β-glucuronidase in the gastrointestinal tract increases the risk of colon cancer, it is possible that *P. jensenii* 702 may also act as an anti-cancer agent. To confirm this, a more detailed study would be necessary.

Effective probiotic bacteria must be capable of maintaining their viability in the gastrointestinal tract, despite the numerous adverse factors that may affect them, including acids and enzymes in the stomach, bile salts and enzymes in the intestine and antagonistic bacterial interactions in the gut.

In Example 2, strain *P. jensenii* 702 has been shown to be resistant to acid and enzyme conditions in the stomach and small intestine in vitro. In this study, *P. jensenii* 702 proved to be resistant to the in vivo conditions of rat gastrointestinal tract. Dairy propionibacteria were not detected in the faeces of the Bacteria group before the rats were fed with *P. jensenii* 702 and were not isolated from the Deficiency group or the Control group. The constant presence of dairy propionibacteria in the rat faeces of the Bacteria group confirms the in vitro results demonstrating that *P. jensenii* 702 is tolerant to the conditions of the gastrointestinal tract in vivo.

Dairy propionibacteria were also isolated from the small intestine of the male Wistar rats, albeit in relatively small numbers. This probably reflects the small section of intestine sampled rather than giving a true indication of bacteria number.

The in vivo adhesion of *P. jensenii* 702 to the small intestine was determined by sectioning the small intestine tissue and examining the tissue samples using scanning electron microscopy. Without monoclonal antibodies it is not possible to be certain that the bacteria-shaped structures observed by scanning electron microscopy adhering to the small intestine samples of the Bacteria group were in fact *P. jensenii* 702 (FIG. 14). However, these structures resembled those observed in in vitro experiments (FIG. 10C, D) and were not seem in either the Deficiency group or the Control groups. It is likely, these were *P. jensenii* 702, and demonstrate in vivo adherence to gut epithelium of rats.

A bacterial strain that is safe, and survives the gastrointestinal tract still must exert a positive effect on the host to be considered as a probiotic strain. In this study the probiotic property that was selected was vitamin $B_{12}$ production.

It has been found that vitamin $B_{12}$ deficient rats show growth retardation, which is caused by a decrease in food intake (Kawata et al., 1995). In this study, we also found that daily food intake of the Deficiency group was significantly lower than that of the Bacteria group (Table 16). The Control group, however, also had a significantly lower feed intake compared to the Bacteria group (Table 16). There was no significant difference between the food intake of the Control group and that of the Deficiency group (Table 16), which suggests that food intake may not reflect vitamin B12 status indicated by the Kawata et al. study (Kawata et al., 1995). The reason the Bacteria group had a higher daily food intake can not be explained by this experiment, and further more detailed studies would be required to determine what the actual mechanism of this appetite stimulation was.

The daily body weight gain of the Deficiency group was lower than that of the Bacteria group, however, not significant (p>0.05) (Table 16). There are two possible reasons for this. Although the feed intake for both the Control group (p>0.05) and the Bacteria groups (p<0.05) were higher than that of the Deficient group (Table 16), these two groups also demonstrated a higher physical activity. Further as the rats used in this study were at an age of rapid growth, it is likely that this rapid growth period clouded the weight gain, particularly when considering deficiency was not instantaneous, and occurred over a period of one month. It is anticipated that a difference in body weight gain would have been observed had the experiment been extended.

In this study, serum vitamin $B_{12}$ was measured as one of the indication of vitamin $B_{12}$ deficiency. The time zero measurement of vitamin $B_{12}$ levels in all groups was statistically the same, and probably reflects the average normal vitamin $B_{12}$ level in a healthy rat. After the $1^{st}$ month of feeding with a vitamin $B_{12}$ deficient diet, the Deficiency and the Bacteria groups both had a significantly lower serum vitamin $B_{12}$ level than that of the Control group (Table 22). At Month 2, the vitamin $B_{12}$ level of the Bacteria group was significantly higher than that of the Deficiency group (p<0.05), and remained statistically higher until the end of the experiment (p<0.05). This suggests that feeding with $P.$ $jensenii$ 702 cells has supplemented the diet of the Bacteria group with Vitamin $B_{12}$. The reason for the initial drop in vitamin $B_{12}$ in the Bacteria group at Month 1 is explained by the fact that the probiotic bacteria require time to colonise the intestine before exerting any beneficial effects to the host. Once $P.$ $jensenii$ 702 established in the gut and then became an active contributor to the dietary vitamin B12 source, the serum vitamin $B_{12}$ levels of the Bacteria group begin to increase (Table 22). This was discussed previously in respect to the total anaerobic count and β-glucuronidase activity, and the results of the vitamin $B_{12}$ levels correlates with this discussion point. It is impossible to speculate how much higher the vitamin $B_{12}$ levels of the Bacteria group would go if the study had of been continued. Clearly a maximum population of $P.$ $jensenii$ 702 would eventually be established in the small intestine, which would reflect the number of binding sites, available nutrients, and other ecological criteria. It would be when colonisation is at this level that a constant vitamin $B_{12}$ level could be reached. It is evident however, that after two months, the vitamin $B_{12}$ level in the Bacteria group had returned to the same level as its original level (Table 22).

At Month 3, a drop in the serum vitamin $B_{12}$ levels was observed in the Bacteria group. Although the serum vitamin $B_{12}$ levels at Month 3 was not significantly different to that at Month 2, it was significantly different to the initial level at Month 0. This does not detract from $P.$ $jensenii$ 702 as a source of vitamin $B_{12}$. The Bacteria group still had twice the level of serum vitamin $B_{12}$ (216.0 pmol/L than that of the Deficiency group (105.3 pmol/L). It is likely that the serum vitamin $B_{12}$ level of the Bacteria group at Month 3 was still within the normal range of serum vitamin $B_{12}$ levels for male Wistar rats, reflected by the normal homocysteine levels of the Bacteria group at Month 3 (Table 23). The variations among serum vitamin $B_{12}$ level within each experimental group (Table 22) suggests that a larger population (n>7) group may be required for a more accurate study.

The large difference between the vitamin $B_{12}$ levels in the Control group and the Bacteria group was not unexpected. An excess amount of vitamin $B_{12}$ was provided in the drinking water of the Control group, and the level reached is probably the upper adsorption limit for this vitamin. This is reflected by the fact that the vitamin $B_{12}$ level increased rapidly after one month and remained relatively constant for the remainder of the experiment (Table 22).

Figure 15:
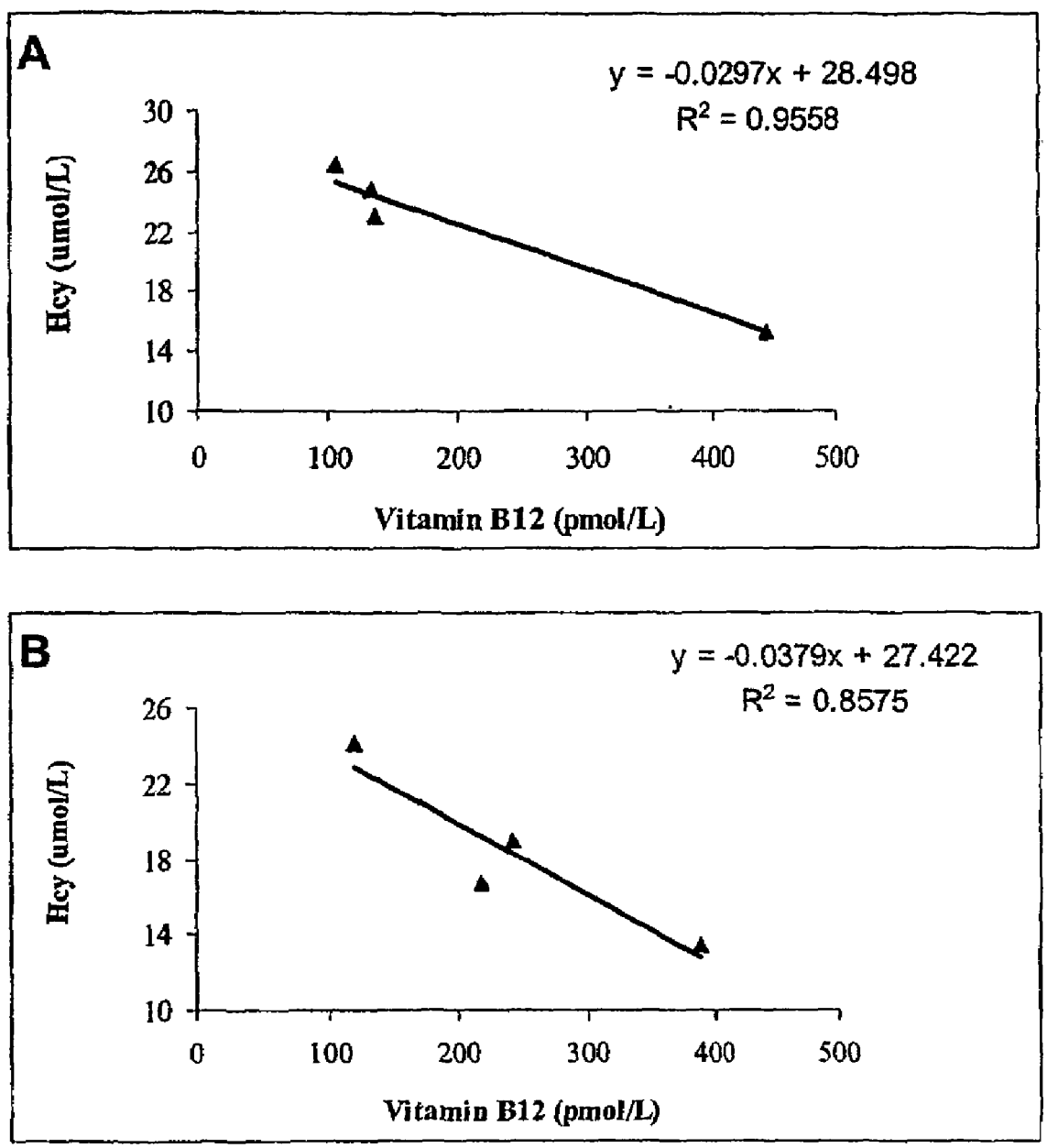
FIG. 15 shows the inverse relationship between serum vitamin $B_{12}$ levels and homocysteine levels of male Wistar rats during three-month feeding treatment. A: Deficiency group; B: Bacteria group, each group contained 7 rats.

Vitamin $B_{12}$ deficiency has been found to cause hyperhomocysteinaemia in humans (Bjorkergren and Svardsudd, 2001). Serum/plasma homocysteine levels show an inverse association with serum/plasma vitamin $B_{12}$ levels (Mann et al., 1999). In this study, this inverse relationship was clearly observed between serum vitamin $B_{12}$ and serum homocysteine levels of the rats from the Deficiency group and the Bacteria group (FIG. 15). The decreased serum vitamin $B_{12}$ levels were correlated with the increase of serum homocysteine levels in the Deficiency group (FIG. 15). This confirms that vitamin $B_{12}$ deficiency result in the increase of homocysteine, and the measurement of serum homocysteine is a complementary diagnosis tool for vitamin $B_{12}$ deficiency (Bjorkegren and Svardsudd, 2001).

High levels of homocysteine are now recognised as a risk factor for cardiovascular disease (Shaw et al., 1999; Wilcken and Wilcken, 1998). At Month 0, there were no statistical differences between the homocysteine levels between the three rat groups (Table 23), but thereafter the change in homocysteine levels (Table 23) inversely reflecyed the vitamin $B_{12}$ levels (FIG. 15). Intake of $P.$ $jensenii$ 702 lowered the serum homocysteine levels of the Bacteria group (FIG. 15), and at the end of the two and three months, there was no significant difference in the homocysteine levels of the Bacteria group and the Control group (p>0.05) (Table 23). This result suggests that the vitamin $B_{12}$ level in the Bacteria group at the completion of the study was within the normal rat range. The application of $P.$ $jensenii$ 702 as probiotic bacteria can therefore be extended to reduce the risk of cardiovascular disease.

In the study by Kawata et al (1997), one measure of vitamin $B_{12}$ deficiency was an abnormality of the testes. In this study, no abnormality of testes due to diet was indicated. It was not possible to compare the vitamin $B_{12}$ levels between the two studies, as Kawata et al (1997) measured testicular tissue not serum levels, and these are not comparable. Furthermore, the rat model used in this study was a modification of the Kawata et al. (1997) model, in that unlike the Kawata et al (1997) model, the rats in this study were born to healthy mothers and not made deficient until after weaning. The diet used also was different. In a previous experiment, the Kawata et al (1997) diet was tested, and the rats became malnourished, suffered stunted growth and were euthanated prior to the completion of the study (data not shown). The diet lacked more than just vitamin $B_{12}$, and therefore for this study a commercial pelleted preparation, Vitamin $B_{12}$ Deficient Diet Modified (ICN) was used.

The association between cardiovascular disease and cholesterol is well established. A number of studies have identified the possibility of using probiotics to lower cholesterol, and with dietary management being the preferred method of treatment, the potential market for a cholesterol lowering probiotic is substantial. The Wistar rat model used in this study was primarily selected as a vitamin $B_{12}$ deficient model, and hence not optimum for a cholesterol study. Regardless of this, a shift in cholesterol was observed between the groups, with a significantly lower cholesterol identified for the Bacteria group compared to the Deficiency group (Table 25).

Previous studies suggest that probiotics can only alter cholesterol in subjects with already high serum cholesterol levels (de Rossa and Katan, 2000). In this experiment the rats were not feed with a high cholesterol diet. Furthermore, as one of the mechanisms of cholesterol reduction by probiotics is the deconjugation of bile, any measurable effects of this mechanism could not be determined in this study due to the rats lack of a gall bladder. For these reasons, we anticipate a more significant response when this bacteria is trailed in a more suitable model.

After the three-month feeding period, the Bacteria group had significantly lower triglycerides than both the Vitamin $B_{12}$ supplementation and the Deficiency groups (Table 25). High triglycerides are identified as a risk factor in cardiovascular disease due to their influence on cholesterol metabolism. The ability of P. jenenii 702 to lower triglycerides is likely to be related to its influence on fatty acid metabolism, and has likewise been demonstrated with other intestinal and probiotic bacteria (Kankaanpaa et al., 2002).

Conclusion

As a new probiotic P. jensenii 702 appears to have remarkable potential. It clearly exerts a positive effect on vitamin $B_{12}$ and homocysteine, and its applications in this area extends beyond purely diet supplementation, to an effective treatment in patients with gastric atropy, R-factor disorders and other physiological causes of vitamin $B_{12}$ deficiency. Due to the potential of intrinsic factor independent mass pharmaceutical uptake of vitamin $B_{12}$ to occur in the small intestine (Herbert 1988), P. jensenii 702 may offer a cheaper alternative to treatment of those patients with pernicious anaemia. In addition, the fact that P. jensenii 702 may have a positive effect on serum cholesterol and triglycerides gives it an added advantage over food fortification as has been used extensively in the vegetarian food industry. Finally as a naturally occurring bacterial strain, P. jensenii 702 is likely to have high consumer acceptability, which is important, in particular for those who maintain a strict dietary program.

EXAMPLE 4

The Use of the Probiotic Bacterium P. Jensenii 702 as an Immune Stimulant, Immune Modulator and Adjuvant There are many reports on the role of probiotics on immune function, however these studies are primarily on *Lactobacilli* sp. and *Bifidobacteria* sp. The type of immune response includes enhancement of phagocytosis (Fooks et al., 1999), stimulation of immunoglobulin (Ig)-A production (Fooks et al., 1999), stimulation of the cell-mediated immune response (Kaur et al., 2002), enhancement of immune response to oral vaccines (Salminen et al., 1998b), immunomodulation (Kitazawa et al., 1992), and mitogenic B lymphocyte stimulation (Takeda et al., 1997). Inactivated *Propionibacterium acnes* is know to act as a non-specific immunostimulant (Julia et al., 1998). There are no reports of dairy *propionibacterium* being used to enhance immune function.

The aim of this Example is to demonstrate that *Propionibacterium jensensii* 702 acts to: (1) enhance humoral immune response; (2) enhances and modulates cell-mediated response; and (3) enhances response to vaccines (acts as an adjuvant). In this example live P. jensenii 702 will be used, however one can extrapolate that inactivated, killed or selected part or parts of P. jensenii 702 will also produce an equivalent response.

Furthermore this example provides evidence of the ability to produce an oral vaccine for tuberculosis. No previous studies have been able to do this due to the fact that no oral adjuvant currently approved for human use can stimulate an immune response as demonstrated in this example.

Materials and Methods

Stimulation and Modulation of Humoral Immune Response

In Example 3 above, P. jensenii 702 was fed to Wistar male rats for a period of three months. At the conclusion of this study blood was collected. In this example some of the blood collected will be used to measure total IgA, IgG and IgE, using a standard Enzyme Linked Immunosorbent Assay (ELISA). The expected outcome is that the group fed the bacteria will have a higher IgA and IgG and a lower IgE than the other two groups.

Stimulation, Modulation and Enhancement of Immune Response to Vaccine (Humoral and Cell-mediated)

Vaccine

In this example a non-living bacterial vaccine will be given orally. It can be extrapolated that the results would be equivalent if the vaccine was (a) living or attenuated, (b) the whole organism or part or parts of the organism, (c) viral, bacterial or fungal and (d) given orally, parenterally or subcutaneously. The vaccine in this example will be given as two types: (i) soluble protein extracted from the whole bacteria combined with soluble protein excreted from the bacteria during growth and (ii) soluble protein excreted from the bacteria during growth.

Further, this example uses *M. tuberculosis* as the antigen demonstrating the first evidence of a successful oral vaccine for tuberculosis. Application of the principle demonstrated can be extrapolated for animal tuberculosis and other oral vaccines.

Finally from the immune response produced in this example, it is possible to extrapolate that *P. jensenii* 702 can act as an immune modulator, that is it would have efficacy in either (a) living or attenuated form, or (b) as the whole organism or part or parts of the organism, to modify the immune response correcting an allergy-type immune system.

General Equipment

All work involving live *M. tuberculosis* organisms was carried out in a Class II Biological Safety cabinet (Gelman Sciences). Reagents used in the following experiments were obtained either ready-made from the respective suppliers or formulated as listed above. Unless otherwise indicated all pipetting was performed using Gilson automatic pipettes and Bonnet Equipment pipette tips.

Growth of Live *M. Tuberculosis*

Lowenstein Jensen Slopes

Only one *Mycobacterium* strain was used in this research, *Mycobacterium tuberculosis* H37Rv strain (ATCC 27294), and it was grown and maintained on Lowenstein Jensen (LJ) slopes (Micro Diagnostics). LJ slopes were maintained throughout the duration of this research for stock culture purposes. The inoculated LJ slopes were incubated at 37° C. in air for up to three weeks, and then were subcultured onto fresh slopes to ensure continued growth and survival of the bacteria.

Modified Sauton's Medium

Modified Sauton's Medium (MSM) was used for supporting the rapid growth of *M. tuberculosis* in this experiment. A culture was set up on the Modified Sauton's Medium by firstly transferring, via a loop, *M. tuberculosis* from the LJ slope to a 0.45 μm cellulose ester membrane (Advantec MFS). Using sterile forceps the membrane disc was floated on the surface of the liquid Modified Sauton's Medium. The culture vessel was then incubated (Thermoline) at 37° C. in air for 2 weeks. After this time had expired, the bacteria was separated from the membrane using a teaspoon ladle and transferred to a fresh Modified Sauton's Medium.

Subcultures were made every 4-7 days depending on the extent of bacterial growth.

From the growth on the MSM a two-fold collection of protein occurred. Firstly there was the harvesting of whole *M. tuberculosis* cells from the surface of the medium and secondly there was the sterile filtration of the excreted proteins, known as Short-Term Culture Filtrate (STCF). These two sources were further processed to produce the protein used for the vaccine.

Antigen Production

Collection of Whole *Mycobacterium tuberculosis* Cells

After 4 days of growth the cells were collected from the MSM. The cells were scooped from the surface of the medium and collected into a 10 ml sterile centrifuge tube (Sarstedt). The cells were spun at 4000 rpm for 15 minutes for a total of 3 times to wash the cells. Between each session the supernatant was pipetted off using a 3 ml disposable pipette and sterile distilled water was added up to 10 ml. The water was pipetted off and the cells were frozen at −80° C. until required in the next stage of the experiment.

Short-Term Culture Filtrate (STCF) (Based on Methods Described by Andersen et al. 1991)

Short-term culture filtrate (STCF) consisted of the Modified Sauton's Medium containing excreted proteins from 4 days of logarithmic *M. tuberculosis* growth. The Modified Sauton's Medium with whole cells removed was sterile filtered using a 60 ml syringe and a Ministart (0.22 μm) sterile filter head into a sealed vessel and frozen at −80° C. until required for use.

Concentration of STCF Protein

Two Step Ultrafiltration of STCF

This process aimed to remove the STCF via filtering straight from the MSM growth medium. Specifically, it involved using a 10 kDa molecular weight cut off regenerated cellulose ultrafiltration membrane (Millipore) to filter the STCF and medium. The liquid from the waste line of the ultrafiltration unit was collected in a sterile 70 ml pot (Sarstedt). After the sample had filtered through until there was approximately 2 ml left, ultrafiltration was paused and this concentrated solution was removed and placed in a sterile 5 ml tube (Sarstedt). This contained all proteins larger than 10 kDa and was refrigerated while the next step of ultrafiltration was performed. The next stage involved replacing the 10 kDa filter (Millipore) with a 3 kDa molecular weight cut off and refiltering the initial filtrate from the waste line, which contains proteins less than 10 kDa. Once this sample had reduced to 2 ml, the remaining sample from the refrigerator was added. Fluid from the waste line was discarded during this filtration stage. Once the total volume of the final sample had reduced to less than 2 ml it was removed and placed in a cryogenic tube and stored at −80° C. Once a considerable volume of STCF had been collected it was washed to remove any residual MSM. This involved defrosting the sample and ultrafiltering it through a 3 kDa filter and running 20 ml of sterile distilled water through. This wash step was repeated 3 times.

Sonication of Whole *M. tuberculosis* Cells

Cells that were removed from the top of the Modified Sauton's Medium were washed prior to sonication in sterile PBS at 4000 rpm for 15 minutes, and the supernatant was removed. All sonication performed in this research utilized a Branson Digital Sonifier 250 with a Microtip Tapered ⅛" horn.

For each round of sonication, 6 ml of packed cells were placed in a 10 ml round bottomed test tube (Crown Scientific), along with 6 ml of glass beads and 7.5 ml of PBS. This test tube was fixed in position with the sonicator tip inside it by a clamp attached to a retort stand. The sonicator itself was mounted on a retort stand with two clamps securing it at a 45° angle, to accommodate it within the Class II Biological Safety Cabinet. Also included inside the test tube, alongside the tip of the sonicator was a temperature probe that monitored the temperature of the sample. The temperature limit was set to 20° C., and when this temperature was reached the sonicator would pause until the temperature had lowered. To further control the temperature of the sample a beaker filled with ice and 50 ml of 100% ethanol was fixed with another clamp and attached to the first retort stand, so as to envelop the bottom of the test tube containing the sample. This aimed to further minimise the heat damage to vital proteins due to the heat created by the sonication process. The sonication was performed at an amplitude of 35% for 20 minutes with a temperature limit of 20° C. as mentioned previously.

Following sonication the sample was transferred from the test tube to an ultracentrifuge tube, via a transfer pipette leaving the glass beads behind. The sample was centrifuged (Beckman, J2-MC centrifuge) 14000 rpm for 30 minutes at 4° C. to remove any insoluble proteins. The sample was then sterile filtered using a 0.22 μm Sartorius Ministart filter into a sterile container and stored at −80° C. until required. The protein concentration of the sample was determined by performing a protein assay.

Protein Assay to Determine Protein Concentration of Vaccine

To determine the amount of protein in milligrams per millilitre that a sample may contain, a Bio-Rad protein Assay kit was used. The linear range for this assay is between 0.05 mg/ml and 0.5 mg/ml, consequently samples were tested in the neat form and prepared in the dilutions of 1:5, 1:10 and 1:20. Then 10 μl of blank (distilled water), standard or sample was pipetted into the assigned wells of a 96 well Nunc microtitre plate. Then 100 μl of diluted dye reagent was added to each well and the plate was left to incubate at room temperature for a minimum of 5 minutes and a maximum of 1 hour.

A Bio-Rad Microplate Reader (Model 550) was used to read the plates at 595 nm wavelength. Raw data was automatically processed through the Bio-Rad Microplate Manager computer program (Version 5.0.1), producing a standard curve and calculating the protein concentration of the samples.

Production of Probiotic Adjuvant, *P. jensenii* 702

The strain of probiotic used as an adjuvant in this experiment is *Propionibacterium jensenii* 702. It is referred to as '*P. jensenii* 702' or 'probiotic' in this example.

Preparation of *P. jensenii* 702 for Drinking Water

The *Propionibacterium* was resuscitated from frozen culture by placing 100 μl in 20 ml of Sodium Lactate Broth (SLB) and grown anaerobically at 30° C. for 3 days. After the three days, 100 μl was transferred into 20 new bottles each containing 20 ml of SLB. These were also grown anaerobically at 30° C. for 3 days. The bacterial cells were then collected by combining all of the culture bottles, except one and putting them into 2 sterile 250 ml centrifuge bottles (Nalgene). The one extra bottle was kept aside for use in preparing the adjuvant for the vaccine. These were centrifuged at 10,000 rpm for 7 minutes at 4° C. and the supernatant was discarded. The cells were washed a further 2 times in 60 mL of sterile 0.85% NaCl (Sigma). After the final wash the cells were resuspended in 30 ml of sterile 0.85% NaCl (Sigma) and aliquoted in 0.5 ml lots in 5 ml sterile containers (Sarstedt) and stored at 4° C. until required for use in drinking water. This produced bacteria at a concentration of $10^8$ cfu when added to the drinking water. Each week a fresh lot of bacteria was produced for use in the drinking water to ensure its viability.

Preparation of *P. jensenii* 702 for Use as Adjuvant in Vaccine 10 mL from the remaining 20 ml bottle of *P. jensenii* 702 growth in SLB was centrifuged separately at 5000 rpm for 10 minutes. The supernatant was removed and it was washed two times in sterile 0.85% NaCl (Sigma) at 5000 RPM for 10 minutes. After the final wash, the supernatant was removed and the pellet of cells was resuspended in 200 µl of sterile 0.85% NaCl (Sigma) in a sterile container. This was prepared the day prior to vaccination and stored at 4° C. until used. The concentration of bacteria was approximately $10^9$ cfu.

Immunisation

Ethics Approval

Ethics approval was gained from The University of Newcastle Animal Ethics Committee. Consequently, this research was carried out under the ethics approval number of 712 0902.

Handling of Test Animals

The animals used for this experiment were between 8-12 week old female C57 mice. The mice were separated into 5 groups, with 8 mice in each group, according to the vaccine that they were to be administered. Within each group the mice were further split into two more groups to accommodate 4 mice per cage with a total of 10 cages housing the total of 40 mice used in this experiment. All mice were checked daily and provided with fresh drinking water and feed. The 3 groups of mice that were given *P. jensenii* 702 in their vaccine were also given the probiotic in their drinking water. The 0.5 ml aliquots of $10^8$ bacteria that were prepared earlier were added to 50 ml of drinking water. Fresh bacteria were added each day. After arrival at the animal holding facilities, the mice were allowed a week of rest to adjust to their new surroundings.

Oral Vaccine Administration

The vaccine was administered orally by a 21-gavage lavage needle. Each mouse was anaesthetised by inhalation (CIG TM41 Anaesthetic Apparatus, Nova Medical Vaporiser) in an anaesthetic chamber, using Halothane BP (1 ml/ml, Laser Animal Health) at a rate of 5 L/min and 4 L/min oxygen prior to having the needle inserted into the mouse's stomach. A total of 100 µl of vaccine (Table 26) was administered to each animal. The vaccines were made up in PBS. The animals were vaccinated a total of three times, with a 7 day period elapsing between each vaccination.

TABLE 26

Five vaccines tested in this study and their contents

| Vaccine Number | Antigen/ Adjuvant | Contents Concentration | Administered to Cages |
|---|---|---|---|
| 1 | STCF | 200 µg/100 µl | 5-6 |
|   | P | 50 µl $10^8$ cfu/100 µl |  |
| 2 | STCF | 100 µg/100 µl | 7-8 |
|   | WTB | 100 µg/100 µl |  |
|   | P | 50 µl $10^8$ cfu/100 µl |  |
| 3 | P | 100 µl $10^8$ cfu/100 µl | 9-10 |
| 4 | STCF | 200 µg/100 µl | 1-2 |
|   | CT | 10 µl |  |
| 5 | STCF | 100 µg/100 µl | 3-4 |
|   | WTB | 100 µg/100 µl |  |
|   | CT | 10 µl |  |

STCF = Short Term Culture Filtrate;
WTB = Sonicated Whole Tuberculosis;
P = *P. jensenii* 702,
CT = Cholera Toxin (Sigma, 1 mg/ml in PBS)

Blood Samples

Blood was taken on two occasions. On the same day prior to the first vaccination and on the last day of the animal study, blood was taken from the saphenous vein of each mouse. The blood was then pumped into 1.5 ml eppendorf tubes and centrifuged at 5000 rpm for 8 minutes. The serum was then transferred to a new eppendorf tube and stored at −80° C. until required for immunoglobulin testing.

Faeces Collection

Two lots of faeces had to be collected for analysis in two separate tests. Both faecal samples were collected at the same time, on day 0 (first day of vaccination) and day 25 (final day of experiment). The two tests were to test for the antibody IgA and the other sample was to be used for testing for viable *P. jensenii* 702 cells.

Preparation of Faecal Pellets for IgA Analysis

The faecal pellets were collected from each mouse and placed into an eppendorf tube containing 0.5 ml of Protease Inhibitor. The samples were then vortexed for 15 minutes at room temperature. Once the pellets had dissolved, the samples were centrifuged (Eppendorf Centrifuge 5415C) at full speed for 15 minutes at 4° C. Then 400 µl of the supernatant from each sample was transferred to a new eppendorf tube containing 100 µl of glycerol (Sigma) and then 10 µl of PMSF solution was added. The tubes were vortexed again briefly and then stored at −80° C. until required for IgA testing.

Faecal Plate Counts

The faeces were also tested for viable *Propionibacterium jensenii* 702. This was performed to see if the bacteria survived the gastrointestinal tract. The faeces samples collected for this test were contained from each animal and placed in 2 ml of faeces buffer. Dilutions of $10^{-4}$, $10^{-5}$, and $10^{-6}$ Diluted Wilkins Chalgren Anaerobe Broth (WCAB) (Oxoid). The samples were vortexed and 1 ml was placed into the dilute WCAB and the serial dilutions were made, vortexing the samples between each dilution. Then 100 µl of each dilution were put onto plates containing Sodium Lactate Agar (SLA). The plates were spread with a glass rod, left to dry and then inverted and incubated anaerobically at 30° C. for 6 days.

Removal of Tissue Samples

The mice were euthanased by firstly anaesthetising with Halothane and then submersion in a tank containing excess carbon dioxide. The abdomen area was then sterilised with 70% ethanol. The abdomen was cut open with sterile dissection scissors and the spleen, Peyer's patches and mesenteric lymph nodes were placed in 40 ml of cold sterile PBS and kept on crushed ice. Organs from each vaccine group were pooled to ensure an adequate number of cells.

Preparation of Lymphocyte Proliferations and Cultures

A sterile environment was set up in a Clemco Laminar flow hood by subjecting the cabinet to UV light overnight prior to use. Anything that entered the hood was sprayed with 70% alcohol to retain the sterile environment.

Sieve Method for Preparing Cell Suspensions from Tissue Samples

Single cell suspensions were created by macerating the tissue through a sterile sieve using the flat end of a sterile 20 ml syringe plunger. The cells were washed through the sieve with sterile PBS and tissue debris, fat and connective tissue remained on the sieve surface. The cell suspension was collected in a 50 ml centrifuge tube (FALCON, Becton Dickinson).

Isolation of Lymphocytes

Spleen Cells

The cell suspension in PBS was placed on ice for several minutes. Large pieces of debris were removed and then suspension was centrifuged (Heraeus Megafuge 1.0R) at 1200 rpm for 10 minutes at 4° C. The supernatant was removed and then the spleen cell pellet was resuspended in 5 ml of Red Blood Cell Lysis Buffer and placed on ice for 5 minutes. Then 5 ml of RPMI complete medium was added and centrifuged for a further 10 minutes at 1200 rpm at 4° C. The spleen cell pellet was washed 3 times with 10 ml RPMI complete medium and finally resuspended in 10 ml of RPMI complete medium and stored on ice until required.

Peyer's Patches and Mesenteric Lymph Nodes

The cell suspension in PBS was centrifuged (Heraeus Megafuge 1.0R) at 1200 rpm for 10 minutes at 4° C. The supernatant was discarded and the pellet was washed a further 3 times with 10 ml RPMI complete medium, and finally resuspended in 10 ml RPMI complete medium and stored on ice until required.

Cell Counts of Spleen, Mesenteric Lymph Nodes and Peyer's Patches

Cell counts were made by using trypan blue dye exclusion. The spleen cells were diluted 1 in 5 with trypan blue (Sigma), and the Peyer's patches and Mesenteric lymph nodes were diluted 1 in 2. The cell count was obtained using a counting chamber (WEBER) and an Olympus inverted microscope. The number of cells per ml was then calculated.

Lymphocyte Proliferations

The lymphocyte proliferations were set up in Nunclon Surface tissue culture plates. A total of eighteen plates were set up. Six plates were needed to accommodate the several different proliferation combinations for each day of harvest. The plates were set up in a manner, as to test for the optimum antigen concentration, the best stimulating antigen, WTB, STCF, or a combination of WTB/STCF and the best vaccine. The optimum day for T-cell proliferation was determined by setting the plates up in replicate and harvesting the plates on day 3, 4 and 5, to determine which gave the highest T-cell proliferations.

100 µl of each respective antigen was added to the plates. The antigens were incorporated at different concentrations in RPMI complete medium. The final antigen concentrations tested were 2.5, 5 and 10 µg/ml of each STCF, WTB or the combination WTB/STCF. Four wells were designated as blank control wells and were filled with 100 µl of RPMI complete medium.

100 µl of the cell suspensions were added to the plates at a concentration of $2 \times 10^6$ cells/ml: Tissue samples were run in quadruplicate where possible, however in some cases where low cell counts were obtained, particularly in the case of Peyer's patches, it was only possible to test some samples in duplicate or singlicate. The plates were incubated at 5% carbon dioxide ($CO_2$) at 37° C. for 3-5 days.

Concanavalin A Control Plate

A plate was set up containing 100 µl of Lectin Concanavalin A (Con A) (Boehringer Mannheim). The Con A was made up to 2.5 µg/ml. To the wells of the plate, 100 µl of tissue cells were added at concentrations of $2 \times 10^6$ cells/ml in RPMI complete medium. The plate was then incubated for 48 hours in 5% $CO_2$ at 37° C.

Lymphocyte Cultures for Cytokine Analysis

Spleen lymphocyte cultures were set up for use in testing for the presence of the cytokines, Interleukin 2 (IL-2), Interleukin 4 (IL-4) and Interferon Gamma (IFN-γ). The cultures were set up in duplicate in Multiwell tissue culture plates (Falcon, Becton Dickinson) using spleen cell tissue. Then 0.5 ml of $2 \times 10^6$ lymphocyte cells/ml in RPMI complete medium were added to each well. Different concentrations of the stimulating antigens, WTB, STCF and WTB/STCF were made up in RPMI complete medium in the following concentrations 2.5 µg, 5 µg and 10 µg. 0.5 ml of each of these antigens were added to the plate. The cultures were incubated for 72 hours in 5% carbon dioxide at 37° C. The supernatants from each well were then collected and stored at −80° C. until required for testing.

Harvesting of T-Cell Proliferations

On day 3 of the proliferation the first set of 6 plates were removed from the incubator and in a sterile bio-safety cabinet, 10 µl of [methyl-$^3$H] thymidine tracer (Amersham) diluted in complete RPMI was added to each well (0.5 µCi/well). The plates were incubated for a further 6 hours before harvesting and reading. This process was repeated on the next two consecutive days for the day 4 and 5 sets of plates.

After the 6 hour incubation, the lymphocytes were harvested on a Packard Filtermate 196 onto glass fibre filters (Packard) and dried in a 60° C. incubator. Once dry, each filter was placed on a plastic film on a hotplate and a sheet of Meltilex A scintillator wax (Wallac) was placed on top and melted through the filter. Once the filter cooled and the wax hardened, the filter was trimmed and placed in a sample bag (Wallac) and sealed on a Wallac 1295-012 Heat Sealer. The trimmed and sealed sample bag was placed in a cassette and read on a Liquid Scintillation and Luminescence Counter (TRILUX 1450 MicroBeta).

ELISA Assays

ELISA Testing for IL-2, IL-4 and IFN-γ

Pharmingen OptEIA Kits were used in cytokine testing. The ELISAs and required buffers and reagents were prepared according to manufacturer's instructions.

NUNC Immunosorbent multi-well plates were coated with 100 µl of dilute capture antibody (Pharmingen), sealed and incubated overnight at 4° C. The wells were then washed 5 times with wash buffer. The plates were then blocked with Assay Diluent (Pharmingen) and incubated at room temperature for 1 hour. Following that the plates were washed 5 times with wash buffer. Then 100 µl of standard or sample was added to each well and incubated for 2 hours at room temperature. The plates were once again washed 5 times with wash buffer, and then 100 µl of Working Detector (Pharmingen) was added to each well, and the plate was incubated for a further hour at room temperature.

The plates were then washed 10 times with 30 second soaks. 100 µl of TMB substrate solution (Pharmingen) was added to each well, and was incubated at room temperature for 30 minutes in the dark. After this time had elapsed, 50 µl of stop solution was added to each well. The resulting plates were immediately read on a Bio-Rad Microplate Reader (Model 550) at an absorbance of 450 nm and 570 nm. The 570 nm reading gave the background reading that could be subtracted from the 450 nm readings to give the final absorbance. The microplate reader adjusted results automatically, according to the standards run in each plate and gave final cytokine concentrations in picograms/ml (pg/ml).

ELISA Testing of Serum and Faecal Samples for IgG and IgA

The appropriate wells of NUNC Immunosorbent multiwell plates were coated with 100 µl of 25 µg/ml of antigen, STCF or combination STCF/WTB diluted in Bicarbonate Buffer. The plates were incubated overnight at 4° C. The plates were then washed twice with wash buffer. The plates were then blocked with 5% heat inactivated Foetal calf Serum (FCS) and incubated for 1 hour at 37° C. The samples were diluted. The serum was titrated 10 fold from 1 in 10 to 1 in 10000. Doubling dilutions were performed on the faeces from 1 in 10 to 1 in 80. Control serum was diluted 1 in 100 and added to each plate as a control. Two wells were also designated as blank wells, to act as a control for the presence of background staining. When the appropriate wells were filled with sample the plates were incubated for 1 hour at 37° C. The plates were then washed 3 times with wash buffer.

Then 100 µl of labeled anti-mouse IgG Biotinylated (1.0 mg/ml) was tested for serum samples or anti mouse IgA biotinylated (0.5 mg/ml) (Southern Biotechnology Associates) for faeces samples was added to each plate. They were then returned to the incubator for 2 hours at 37° C. After this time elapsed, the plates were washed 3 times with wash buffer and then 100 µl of Streptavidin Horse Radish Peroxidase (SA-HRP) was added to each plate. The plates were incubated for a further 1 hour at 37° C.

Then 100 µl of the colour reagent TMB substrate solution (Pharmingen) was added to each well and the reaction was checked after 5 minutes for a change in colour. After 5 to 7 minutes, 50 µl of stop solution was added to each well. The plates were then read at 450 nm on a Bio-Rad Microplate Reader (Model 550).

Statistical Analysis

Statistical analysis of the results were performed using Microsoft Excel 2000. Student t-test, two-tailed, assuming equal variance was used. A 'p' value of less than 0.05 was considered indicative of statistical significance between sets of data. Mean, standard deviation and all graphs were also generated in Microsoft Excel 2000.

Results

Vaccine Preparation

Vaccine production for this study involved producing and concentrating sufficient quantities of STCF and sonicated WTB Vaccine Administration Animal Model: Mouse Monitoring Mice were monitored daily by examination of their general appearance and behaviour. The mice were weighed prior to every procedure. Following any procedure mice were monitored regularly for one to two hours.

TABLE 27

Average weight of mice over study period of 25 days

| Vaccine | Average Weight on Days (g) | | | |
| --- | --- | --- | --- | --- |
|  | 0 | 7 | 14 | 25 |
| 1 | 18.6 ± 0.9 | 19.4 ± 0.8 | 18.4 ± 2.0 | 18.5 ± 1.3 |
| 2 | 18.6 ± 0.9 | 19.3 ± 0.8 | 19.1 ± 0.8 | 18.6 ± 1.3 |
| 3 | 18.2 ± 0.9 | 19.0 ± 1.0 | 19.2 ± 0.9 | 19.1 ± 0.6 |
| 4 | 18.0 ± 1.5 | 18.8 ± 1.1 | 19.3 ± 1.1 | 18.1 ± 0.8 |
| 5 | 18.0 ± 0.7$^{ab}$ | 18.7 ± 0.6$^{c}$ | 19.4 ± 0.6$^{ac}$ | 19.0 ± 0.7$^{b}$ |

Values are mean ± SD (n = 6-8). The same alphabetical prefix on values within a row indicates significant statistical difference (p < 0.05, student's t-test, two-tailed) between the weights on the indicated days.

The weight of mice in the study group remained relatively constant across the study period (Table 27). No statistical difference was observed in the weights between the mice groups on each weighing day. A statistically significant difference (p<0.05) was identified between the weights of the mice in vaccine group 5 over the four week period. However this is not of any significance to the vaccine trial, nor did it affect results in other areas either.

In the last week of the vaccine trial, several of the test animals became sick and either died, or were euthanased. An autopsy on the deceased animals revealed that pneumonia caused by a presumptive mycoplasma infection was the cause of death. The source of the infection was not identified. The deaths were spread out over the vaccine groups, with one death in vaccine group 2, and two deaths in both vaccine groups 4 and 5. The overall loss of five of the forty mice did not affect the statistical validity of mice numbers in each group. Interestingly only one death occurred within the vaccine groups receiving P. jensenii 702, suggesting a possible protective effect of the probiotic bacteria, on the animals' overall health and immune system functioning.

Change in the Gut Microbiology of Mice During the Study Period

Anaerobic and Probiotic Counts were Performed on the Mice Faeces.

Recovery of P. jensenii 702 from Mice Faeces

Plate counts were performed on faecal samples from the test animals, to ensure that P. jensenii 702 both survived and colonised the gastrointestinal tract of the mice, and that the mice that were not receiving the probiotic were not cross contaminated or naturally contain P. jensenii 702 within their gastrointestinal tract.

TABLE 28

Viable counts of P. jensenii 702 in the faeces of mice during the study period

| Faecal Sample Vaccine Group | Plate Count (cfu) | | |
| --- | --- | --- | --- |
|  | Day 0 | Day 7 | Day 25 |
| 1 | 0 | 1.25 × 10$^6$ ± 5.0 × 10$^5$ | 1.60 × 10$^6$ ± 5.47 × 10$^5$ |
| 2 | 0 | 1.60 × 10$^6$ ± 8.9 × 10$^5$ | 1.24 × 10$^6$ ± 9.52 × 10$^5$ |
| 3 | 0 | 0 | 3.50 × 10$^6$ ± 2.59 × 10$^6$ |
| 4 | 0 | 0 | 0 |
| 5 | 0 | 0 | 0 |

Values are mean ± SD (n = 6-8)

Faeces samples were collected on day 0 (prior to *P. jensenii* 702 administration), day 7 and day 25 (Table 28). No *P. jensenii* 702 were found in the faeces of any mouse prior to administration of the bacteria. By day 7 the probiotic was present in faecal samples of mice in vaccine group 1 and 2, and by day 25, all vaccine groups receiving *P. jensenii* 702 (1, 2 and 3) had high counts of the probiotic bacteria. No *P. jensenii* 702 was isolated from any mouse not receiving the bacteria.

Anaerobic Plate Counts of Mice Faeces

Total anaerobe plate counts were performed to detect if the presence of the probiotic caused any reduction in anaerobes in the gastrointestinal tract (Table 29). This was used as a measure of colonization of *P. jensenii* 702 in the gastrointestinal tract.

TABLE 29

Anaerobic plate counts on mice faeces during the 25 day study

| Faecal Sample Vaccine Group | Plate Count (cfu) | | |
|---|---|---|---|
| | Day 0 ($\times 10^7$) | Day 7 ($\times 10^7$) | Day 25 ($\times 10^7$) |
| 1 | 3.98 ± 3.56 | $^1$4.78 ± 1.15 | 5.79 ± 2.41 |
| 2 | 6.14 ± 3.84 | $^1$8.68 ± 4.99 | 8.33 ± 9.61 |
| 3 | 6.25 ± 5.74 | 5.78 ± 3.93 | 12.08 ± 8.15 |
| 4 | 7.13 ± 10.5 | 4.64 ± 1.94 | 7.18 ± 3.11 |
| 5 | 10.2 ± 5.59$^{ab}$ | $^1$3.04 ± 1.47$^a$ | 3.42 ± 1.96$^b$ |

Values are mean ± SD (n = 6-8).
The same alphabetical prefix across rows indicates a significant difference between anaerobic plate counts over the three sampling occasions of day 0, day 7 and day 25. The same numerical prefix down a column indicates significant difference ($p < 0.05$) between vaccine groups on a given day There was no significant difference in faecal anaerobe counts within vaccines groups 1, 2, 3 and 4 over the three sampling occasions (Table 29). Vaccine group 5 had a significant reduction in plate count between day 0 and days 7 and 25 (Table 29). On day 0 and 25 there was no statistical difference between faecal anaerobic counts between vaccine groups. At day 7 there was a statistical difference ($p<0.05$) between vaccine groups 1, 2, and 5.

T-cell Proliferations

Concanavalin A

The Concanavalin A (Con A) control plate was used as a general indicator of T-cell reactivity and proliferative ability to the mitogen Con A. Table 30 displays the proliferations in counts per minute (CPM) for the three lymphocyte sources, for each vaccine group. Higher proliferations were seen from all tissues to vaccine 1 and 3, however statistical significance was not tested on these results, as they were a general indicator of proliferation only and do not specifically indicate the effectiveness of one vaccine over another.

TABLE 30

Concanavalin A T-cell Proliferations

| | T-cell proliferation for Tissues (CPM) | | |
|---|---|---|---|
| Vaccine | Spleen | Peyer's Patches | Mesenteric Lymph Nodes |
| 1 | 1326 ± 72 | 5230 ± 664 | 82577 ± 3242 |
| 2 | 517 ± 203 | 434 ± 260 | 367 ± 196 |
| 3 | 1315 ± 112 | 3058 ± 294 | 67324 ± 949 |
| 4 | 649 ± 301 | 140 ± 16 | 24 ± 15 |
| 5 | 2697 ± 529 | 94 ± 53 | 478 ± 0 |

Values are mean ± SD (N = 6-8) in counts per minute (CPM)

T-Cell Proliferation to Administered Vaccine

For each vaccine, T-cell proliferation was measured using the variables: antigen concentration, type of stimulating antigen, time of incubation, and type of tissue used for lymphocyte collection.

Table 31 indicates the average T-cell proliferation results for Day 3. Data for day 4 and 5 is not shown. Day 3 was selected as the optimum day for T-cell proliferations based upon higher T-cell proliferations overall, but also because it had the greatest amount of statistically higher proliferations. Where the T-cell response was significantly higher for Day 3 compared to days 4 and 5, this is indicated on Table 31.

TABLE 31

Day 3 T-cell Proliferation Results

| Vaccine | Incubation Time (days) | Tissue | Stimulating Antigen | Antigen Concentration (µg) | Average Proliferation |
|---|---|---|---|---|---|
| 1 | 3 | Spleen | STCF | 10 | 22211 ± 3645 |
| | 3 | | | 5 | 46183 ± 10494 $^a$ |
| | 3* | | | 2.5 | 35216 ± 4243 $^a$ |
| 1 | 3 | Peyer's Patches | STCF | 10 | — |
| | 3 | | | 5 | 2788 ± 2724 |
| | 3 | | | 2.5 | 1852 ± 1565 |
| 1 | 3 | Mesenteric Lymph Nodes | STCF | 10 | 43747 ± 8516 $^{ab}$ |
| | 3 | | | 5 | 6342 ± 10534 $^a$ |
| | 3# | | | 2.5 | 3044 ± 3631 $^b$ |
| 2 | 3 | Spleen | STCF | 10 | 16971 ± 2061 $^{ab}$ |
| | 3 | | | 5 | 26770 ± 6074 $^a$ |
| | 3* | | | 2.5 | 27557 ± 5034 $^b$ |
| 2 | 3 | Peyer's Patches | STCF | 10 | — |
| | 3 | | | 5 | 1203 ± 574 |
| | 3# | | | 2.5 | 1324 ± 98 |
| 2 | 3 | Mesenteric Lymph Nodes | STCF | 10 | 10836 ± 9228 |
| | 3 | | | 5 | 12262 ± 10266 |
| | 3 | | | 2.5 | 389 ± 88 |

TABLE 31-continued

Day 3 T-cell Proliferation Results

| Vaccine | Incubation Time (days) | Tissue | Stimulating Antigen | Antigen Concentration (µg) | Average Proliferation |
|---|---|---|---|---|---|
| 2 | 3 | Spleen | WTB | 10 | 34607 ± 9597 |
|  | 3 |  |  | 5 | 40528 ± 4270 |
|  | 3* |  |  | 2.5 | 32887 ± 4012 |
| 2 | 3 | Peyer's Patches | WTB | 10 | — |
|  | 3 |  |  | 5 | 588 ± 129 |
|  | 3 |  |  | 2.5 | 324 ± 61 |
| 2 | 3 | Mesenteric Lymph Nodes | WTB | 10 | 1039 ± 140 |
|  | 3 |  |  | 5 | 970 ± 102 |
|  | 3* |  |  | 2.5 | 979 ± 98 |
| 2 | 3 | Spleen | STCF/WTB | 10 | 20560 ± 1847 |
|  | 3 |  |  | 5 | 22790 ± 3553 |
|  | 3# |  |  | 2.5 | 35319 ± 14319 |
| 2 | 3 | Peyer's Patches | STCF/WTB | 10 | — |
|  | 3 |  |  | 5 | 1106 ± 362 |
|  | 3 |  |  | 2.5 | 1014 ± 211 |
| 2 | 3 | Mesenteric Lymph Nodes | STCF/WTB | 10 | 1057 ± 538 |
|  | 3 |  |  | 5 | 7272 ± 11698 |
|  | 3* |  |  | 2.5 | 382 ± 65 |
| 3 | 3 | Spleen | STCF | 10 | 22307 ± 7309 |
|  | 3 |  |  | 5 | 19423 ± 1105 |
|  | 3* |  |  | 2.5 | 19544 ± 4182 |
| 3 | 3 | Payer's Patches | STCF | 10 | 25884 ± 9838 |
|  | 3 |  |  | 5 | 10248 ± 17341 |
|  | 3 |  |  | 2.5 | 9533 ± 9814 |
| 3 | 3 | Mesenteric Lymph Nodes | STCF | 10 | — |
|  | 3 |  |  | 5 | — |
|  | 3 |  |  | 2.5 | 6039 ± 4746 |
| 3 | 3 | Spleen | WTB | 10 | 10006 ± 1301 [a] |
|  | 3 |  |  | 5 | 24159 ± 3743 [a] |
|  | 3* |  |  | 2.5 | 34319 ± 2801 [a] |
| 3 | 3 | Peyer's Patches | WTB | 10 | 573 ± 210 [ab] |
|  | 3 |  |  | 5 | 1224 ± 228 [a] |
|  | 3 |  |  | 2.5 | 929 ± 194 [b] |
| 3 | 3 | Mesenteric Lymph Nodes | WTB | 10 | — |
|  | 3 |  |  | 5 | — |
|  | 3 |  |  | 2.5 | 4075 ± 4754 |
| 3 | 3 | Spleen | STCF/WTB | 10 | 16661 ± 4818 |
|  | 3 |  |  | 5 | 17678 ± 4433 |
|  | 3# |  |  | 2.5 | 23106 ± 7980 |
| 3 | 3 | Peyer's Patches | STCF/WTB | 10 | — |
|  | 3 |  |  | 5 | 3528 ± 1671 |
|  | 3# |  |  | 2.5 | 8210 ± 3860 |
| 3 | 3 | Mesenteric Lymph Nodes | STCF/WTB | 10 | — |
|  | 3 |  |  | 5 | 358 ± 36 |
|  | 3 |  |  | 2.5 | 425 ± 98 |
| 4 | 3 | Spleen | STCF | 10 | 19068 ± 5021 [a] |
|  | 3 |  |  | 5 | 12702 ± 5101 |
|  | 3* |  |  | 2.5 | 7853 ± 1894 [a] |
| 4 | 3 | Peyer's Patches | STCF | 10 | — |
|  | 3 |  |  | 5 | — |
|  | 3# |  |  | 2.5 | 10810 + 2561 |
| 4 | 3 | Mesenteric Lymph Nodes | STCF | 10 | 469 + 28 |
|  | 3 |  |  | 5 | 430 ± 106 |
|  | 3 |  |  | 2.5 | 509 ± 94 |
| 5 | 3 | Spleen | STCF | 10 | 22309 ± 731 |
|  | 3 |  |  | 5 | 27230 ± 6176 |
|  | 3* |  |  | 2.5 | 23619 ± 3499 |
| 5 | 3 | Peyer's Patches | STCF | 10 | — |
|  | 3 |  |  | 5 | — |
|  | 3 |  |  | 2.5 | 37729 ± 4626 |
| 5 | 3 | Mesenteric Lymph Nodes | STCF | 10 | 625 ± 71 |
|  | 3 |  |  | 5 | 833 ± 972 |
|  | 3 |  |  | 2.5 | 337 ± 86 |
| 5 | 3 | Spleen | WTB | 10 | 20966 ± 5345 [a] |
|  | 3 |  |  | 5 | 37563 ± 3961 [a] |
|  | 3* |  |  | 2.5 | 48587 ± 7123 [a] |
| 5 | 3 | Peyer's Patches | WTB | 10 | — |
|  | 3 |  |  | 5 | — |
|  | 3# |  |  | 2.5 | 9870 ± 1390 |
| 5 | 3 | Mesenteric Lymph Nodes | WTB | 10 | 416 ± 100 |
|  | 3 |  |  | 5 | 520 ± 58 |
|  | 3 |  |  | 2.5 | 393 ± 125 |

TABLE 31-continued

Day 3 T-cell Proliferation Results

| Vaccine | Incubation Time (days) | Tissue | Stimulating Antigen | Antigen Concentration (μg) | Average Proliferation |
|---|---|---|---|---|---|
| 5 | 3 | Spleen | STCF/WTB | 10 | 25899 ± 6288 |
|   | 3 |   |   | 5 | 29397 ± 23319 |
|   | 3* |   |   | 2.5 | 45135 ± 10877 |
| 5 | 3 | Peyer's Patches | STCF/WTB | 10 | — |
|   | 3 |   |   | 5 | 30994 ± 8780 |
|   | 3# |   |   | 2.5 | 55576 ± 7169 |
| 5 | 3 | Mesenteric Lymph Nodes | STCF/WTB | 10 | 5716 ± 10298 |
|   | 3 |   |   | 5 | 461 ± 81 |
|   | 3 |   |   | 2.5 | 207 ± 88 |

Values are mean ± SD (n = 6-8) in counts per minute (CPM).
Alphabetical prefix denotes significant differences (p < 0.05, student's t-test, two-tailed) between proliferation levels at different antigen concentrations within each vaccine group and respective stimulating antigen.
*denotes a significant difference(p < 0.05, student's t-test, two-tailed) in proliferation between days 4 and 5
denotes when day 3 was not significantly different to days 4 or 5, however it did display the lowest variance, and hence was chosen on this basis
— indicates there was insufficient cells to perform proliferations on Summary of T-cell Proliferations Using 2.5 μg Antigen on Day 3

Three different antigen combinations were tested against each tissue lymphocyte source. In each case the stimulating antigen was only tested where it was a component of the original vaccine. On Day 3 the optimum concentration of stimulating antigen was 2.5 μg/ml based upon it producing overall, the highest proliferation readings (Table 31). This concentration was selected for the remaining analysis.

T-cell Proliferations on Day 3 with 2.5 μg of STCF as Stimulating Antigen

Table 32 shows the average proliferation results from day 3 against 2.5 μg of STCF for all vaccines tested in this study.

TABLE 32

Average Proliferation for each tissue with 2.5 μg of STCF

Average Proliferation for Tissue (CPM)

| Vaccine | Spleen | Peyer's Patches | Mesenteric Lymph Nodes |
|---|---|---|---|
| 1 | 35216 ± 4243[a] | 1852 ± 1565[c] | 3044 ± 3631[e] |
| 2 | 27557 ± 5034[ab] | 1324 ± 98[c] | 389 ± 88[e] |
| 3 | 19544 ± 4182 | 9533 ± 9814[cd] | 6039 ± 4746[e] |
| 4 | 7853 ± 1894 | 10810 ± 2561[d] | 509 ± 94[e] |
| 5 | 23619 ± 3499[b] | 37729 ± 4626 | 337 ± 86[e] |

Values are mean ± SD (n = 6-8) in counts per minute (CPM)

The same alphabetical prefix within a column indicates no significance between the marked vaccine groups for a given lymphocyte source (p>0.05, student's t-test, two-tailed). Within the column, the remainder of the unmarked values, in addition to the values that do not share a similar letter indicator, are significantly different (p<0.05 to p<0.001, student's t-test, two-tailed)

Significance was only tested for across the vaccine groups within each tissue group. The lymphocyte proliferation results using the different tissue reflects the type of immune response and is not being used to determine the best vaccine. This will be covered further in the discussion. Proliferation results for the spleen show that vaccine 1, 2 and 5 had counts significantly higher than vaccine 3, the control. Vaccine 1 had the highest count for the spleen. In the Peyer's patches however vaccine 5 had the highest proliferation to 2.5 μg of STCF protein and was the only reading significantly higher than the control. There was no statistical significance between any of the vaccine groups for proliferation counts for the mesenteric lymph nodes.

T-cell Proliferations on Day 3 with 2.5 μg of WTB as Stimulating Antigen

Table 33 shows the average proliferation values for each T-cell source when stimulated with 2.5 μg of the WTB antigen.

TABLE 33

Average Proliferation for each tissue with 2.5 μg of WTB

Average Proliferation for Tissue (CPM)

| Vaccine | Spleen | Peyer's Patches | Mesenteric Lymph Nodes |
|---|---|---|---|
| 2 | 32887 ± 3475[a] | 324 ± 50 | 979 ± 80[b] |
| 3 | 34319 + 2426[a] | 929 ± 168 | 4075 ± 3882[b] |
| 5 | 48587 ± 6169 | 9870 ± 983 | 393 ± 108[b] |

Values are mean ± SD (n = 6-8)
The same alphabetical prefix within a column indicates no significance between the marked vaccine groups (p > 0.05, student's t-test, two-tailed) for each tissue lymphocyte source. The remainder of the unmarked values, in addition to the values that do not share a similar letter indicator, are significantly different (p < 0.05 to p < 0.001, student's t-test, two-tailed)

Separate testing of the antigens STCF and WTB, was performed in an attempt to distinguish if one component was responsible for higher proliferations than the other. From Table 33 vaccine 5 once again displayed significantly higher proliferations than the control and vaccine 2, for both the spleen and Peyer's patches. The mesenteric lymph nodes had the highest scintillation count with the control.

T-cell Proliferations on Day 3 with 2.5 μg of STCF-WTB as Stimulating Antigen

Table 34 shows the average proliferation values for each T-cell source when stimulated with 2.5 μg of the STCF-WTB combination antigen.

TABLE 34

Average Proliferation for each tissue with 2.5 µg of STCF-WTB

| | Average Proliferation for Tissue (CPM) | | |
|---|---|---|---|
| Vaccine | Spleen | Peyer's Patches | Mesenteric Lymph Nodes |
| 2 | 35319 ± 14139[ab] | 1014 ± 211 | 382 ± 65[c] |
| 3 | 23106 ± 7980[a] | 8210 ± 3860 | 425 ± 98[c] |
| 5 | 45135 ± 10877[b] | 55576 ± 7169 | 207 ± 88 |

Values are mean ± SD (n = 6-8)
The same alphabetical prefix within a column indicates no significance between the marked vaccine groups (p > 0.05, student's t-test, two-tailed) for each tissue lymphocyte source. The remainder of the unmarked values, in addition to the values that do not share a similar letter indicator, are significantly different (p < 0.05 to p < 0.001, student's t-test, two-tailed).

Using STCF-WTB as the stimulating antigen, and lymphocytes from the spleen cells, vaccine 5 was significantly different to the control, exhibiting a very high proliferation of 45,135 cpm. Vaccine 2 was also relatively high reading however it was not significantly different to the control. The Peyer's patches lymphocytes again showed a significantly higher proliferation (55,516 cpm) for vaccine 5 compared to the control. The scintillation counts for the mesenteric lymph nodes were all low, and likely to be background rather than true readings.

Cytokine Analysis Using Lymphocyte Culture Supernatant

Cytokines are used to determine the type of immune response. Three cytokines were measured; IL-2, IL-4 and IFN-γ. Only lymphocytes from spleen cells were cultured for cytokine production. As optimal proliferation was determined to be with a stimulating antigen concentration of 2.5 ug/ml, the results of the cytokines at 5 ug/ml and 10 ug/ml are not shown.

Interleukin 2 Levels

Figure 17:
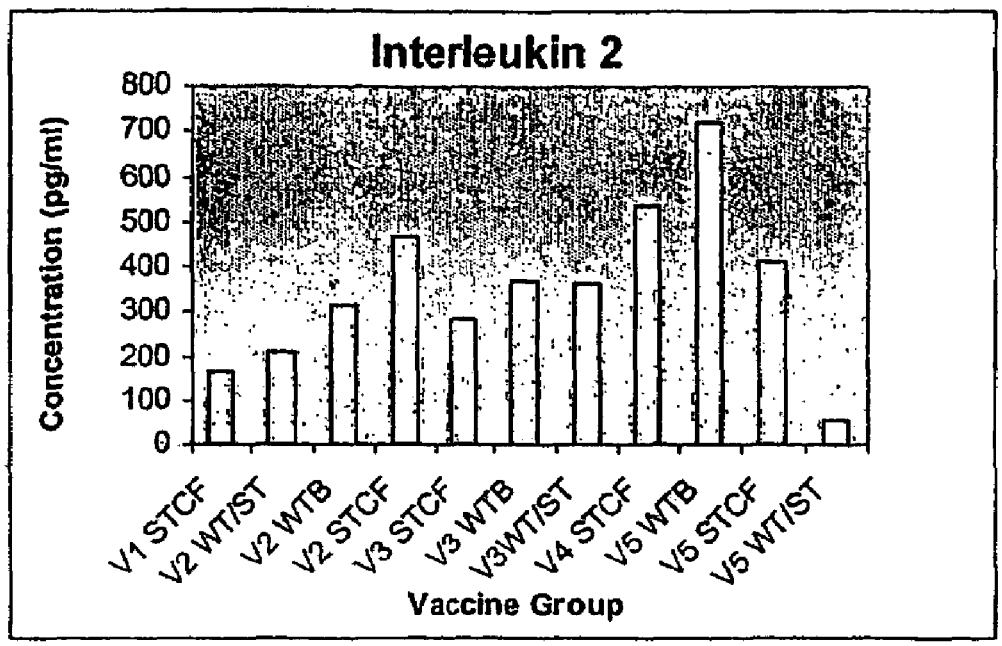
FIG. 17 shows interleukin 2 levels in serum samples from mice

IL-2 is a general indicator of T-cell response. Cell supernatant was collected at day 3, which is not optimal for IL-2, however the results clearly indicate that all vaccines stimulated an IL-2 response (FIG. 17).

IFN-γ and IL-4 as a Measure of the Type of T-cell Response

Comparison of IFN-γ and IL-4 (FIG. 18) gives an indication of the type of T-cell response, that is, whether a Th1 or Th2 response is occurring.

In all cases except V1 (STCF) the IFN-γ response was significantly higher than the IL-4, indicating a Th1 response. The results of Vaccine 1 (STCF) however are still significant. Vaccine 1 (STCF) produced an average IL-4 level of 7.58 pg/ml. Large difference between the duplicate in IFN-γ readings (160.5 pg/ml and 743.0 pg/ml) caused a large error, negating any measure of significance. It is evident however that even if the larger value is excluded, the IFN-γ result is clearly much higher than the IL-4 result.

Measurement of Immuonoglobulin Levels in Mice

ELISAs were performed to measure immunoglobulin. IgG and IgA were measured and compared. Table 35 shows the average absorbances of ELISA readings at a wavelength of 450 nm. For IgG serum was tested at a 1:100 dilution, while IgA faecal supernatant was measured at a 1:10 dilution. Each vaccine group was tested for antibody against the antigen that each contained. The P. jensenii 702 control group was tested against both antigens, STCF and combination STCF-WTB, as it contained neither and was necessary for its role as a control.

TABLE 35

Average Absorbance Values of each Immunoglobulin for vaccine groups

| | | Vaccine | | | | | |
|---|---|---|---|---|---|---|---|
| Immunoglobulin | Day | 1 | 2 | 3 STCF | 3 STCF/WTB | 4 | 5 |
| Total | 0 | 0.18 ± 0.05* | 0.26 ± 0.07* | 0.18 ± 0.06 | 0.28 ± 0.07* | 0.16 ± 0.05 | 0.17 ± 0.05* |
| IgG | 25 | 0.41 ± 0.17* | 0.43 ± 0.12* | 0.22 ± 0.08 | 0.41 ± 0.08* | 0.48 ± 0.54 | 0.61 ± 0.38* |
| IgA | 0 | 0.58 ± 0.03 | 0.31 ± 0.03 | 0.51 ± 0.04 | 0.31 ± 0.03 | 0.58 ± 0.06* | 0.32 ± 0.03* |
| | 25 | 0.55 ± 0.06 | 0.27 ± 0.07 | 0.55 ± 0.08 | 0.34 ± 0.05 | 0.46 ± 0.11* | 0.26 ± 0.06* |

Values are mean plus standard deviation (n = 6-8) in Absorbance (nm), measured at 450 nm (Bio-Rad Microplate Reader (Model 550)
*denotes a significant difference between immunoglobulin levels (p < 0.05, student's t-test, two-tailed) within each vaccine group, between days 0 and 25.

The total IgG levels increased for each vaccine from day 0 to day 25, but significant increases were seen only in Vaccine 1, 2, 3 (STCF/WTB) and 5.

There was no significant difference in the IgA levels for Vaccine 1, 2 and 3. Vaccine 4 and 5 showed a significant reduction in IgA. Preparation of the faeces may have had a detrimental effect on preservation of the IgA, and will be addressed further in the Discussion.

Discussion

The efficacy of four oral vaccines against M. tuberculosis was tested. In addition to finding the most immune stimulating components of each vaccine, the effectiveness of adjuvant containing the probiotic bacteria P. jensenii 702 was tested against the commonly used mucosal adjuvant, Cholera Toxin, for its ability stimulate an immune response to the given antigens. It is clear from the results that the vaccines effectively induced an immune response in vitro.

The importance of a strong Th1 T-cell response to TB immunity is recognised (Kaufmann & Andersen, 1998). The intracellular nature of M. tuberculosis makes the role of T-cells vital in the immune response to this bacterium. Consequently in vitro T-cell proliferations provide a good indicator for the success of a potential vaccine. An optimal adjuvant for a TB vaccine should favour the development of a cell-mediated immune response and preferentially stimulate a strong IFN-γ response (Agger & Andersen, 2001). The demonstrated efficacy of *P. jensenii* 702 as an adjuvant is noteworthy, particularly in light of the fact that currently, none of the adjuvants generally approved for human vaccination promote the development of the type 1 immune responses that are crucial for the establishment of protective immunity to *M. tuberculosis* (Medina & Guzman, 2000).

Since it is notoriously difficult to generate an adequate immune response against soluble peptides and proteins, immunisation with an appropriate adjuvant is essential (Mahairas et al, 1995). Consequently the results obtained across all tests for the different vaccines, containing the two tested adjuvants, provide valuable information and insight into the effectiveness of the adjuvants.

Data was collected in this study to determine the optimum antigen concentration and day of T-cell proliferation (Table 31). It is important to determine the optimum antigen concentration for T-cell proliferation. This is due to the fact that if the antigen is present in too higher concentrations it may exert a toxic effect on the lymphocytes, too low a concentration may be insufficient to stimulate any response at all. Three antigen concentrations were tested in this research, 2.5 µg, 5 µg and 10 µg/ml. From statistical analysis it was found that Day 3 with a stimulating antigen concentration of 2.5 µg/ml gave the highest T-cell proliferations in most situations (Table 31).

The three tissue samples that were chosen to perform T-cell proliferations, were selected for their ability to represent the different aspects of the immune response. Spleen T-cell proliferations are indicative of a systemic immune response, whereas the Peyer's patches were tested for evidence of a mucosal immune response (Bouvet, Decroix & Pamonsinlapatham, 2002). Mesenteric lymph nodes, which are also a part of the mucosal associated lymphoid tissue (MALT), were tested (Roitt & Delves, 1997). However since the Peyer's patches have first contact with an antigen, and play a role in stimulating antigen-sensitised lymphocytes, they were chosen as the primary indicator of a mucosal immune response. These stimulated lymphocytes from the Peyer's patches enter the lymph and drain through the mesenteric lymph nodes (Roitt & Delves, 1997). Consequently the mesenteric lymph nodes were used as a secondary indicator of a mucosal immune response, in the instance that an insufficient quantity of Peyer's patches was obtained. Since the Peyer's patches gave a sufficient indication of T-cell proliferations, the mesenteric lymph nodes will not be further discussed.

In general the systemic immune response was better than the mucosal, shown by higher proliferation of spleen cells, compared to that of the Peyer's patches and mesenteric lymph nodes. The preferred aim of orally administering the vaccines is to induce a mucosal immune response. It has long been hypothesised that immunisation via one mucosal surface will lead to enhanced immunity at other mucosal surfaces (Famularo, 1997). Doherty (et al, 2002) found that orally administering a booster vaccine, produced high levels of protection in the lungs of previously primed animals, displaying the ability to confer immunity across mucosal surfaces. Induction of an immune response at the mucosal surface is of major interest because of its ability to modulate colonisation by commensals, as well as increase defenses against penetration of pathogens through the epithelium, reducing their concentration to a harmless level (Bouvet, Decroix & Pamonsinlapatham, 2002). The ability to prevent establishment of *M. tuberculosis* in the body would be an extremely beneficial achievement.

Results from immunoglobulin testing further reinforce that a strong systemic immune response was obtained, shown through an increase in Total IgG levels in serum (Table 35).

Low IgA levels were observed (Table 35). Secretory IgA is the predominant form of antibody that mediates specific immunological defense at mucosal surfaces, and has been found to have a role in limiting respiratory infections (Gleeson et al, 1999). The low IgA response to vaccines 1 and 2 containing the adjuvant *P. jensenii* 702, could be due to the need for a longer exposure time to the bacteria to obtain the desired mucosal immune response. Bouvet et al (2002) found that the extent of the immune response is associated with the degree of colonisation of the vaccine microorganism. Subsequently this suggests that allowing sufficient time for the colonisation of *P. jensenii* 702 would further improve its activity as a vaccine vector.

From the faecal plate counts for *P. jensenii* 702 (Table 28) it can be seen that at least 7 days were required to obtain viable *P. jensenii* 702 counts from the mice faeces, however at the same time there was not a corresponding reduction in total anaerobes (Table 29). In previous research by Huang (2002) in male Wistar rats it took one month for *P. jensenii* 702 to colonise, and it was not until a competitive colonisation of *P. jensenii* 702 occurred that a reduction of anaerobes was evident. Further measures in this study, such as beneficial production of Vitamin B12 and reduction of serum cholesterol levels, also revealed that it took a month for the bacteria to establish, before it could exert any beneficial effect on the host (Huang, 2002). For *P. jensenii* 702 to work as an efficient adjuvant in producing a mucosal response, exposure time may be critical. It is also likely that this colonisation period is species specific.

Results from Peyer's patches indicate that the vaccine can stimulate a mucosal immune response when cholera toxin is the adjuvant (Tables 32-34). Therefore there is no doubt that the vaccine itself is effective as an oral vaccine in stimulating a mucosal and systemic immune response. This is an important finding since oral vaccination to facilitate effective mucosal and systemic immunity has to date been largely ineffective (Russell-Jones, 2000; Doherty et al, 2002).

It is worthwhile noting that the proliferation results varied depending on the type of stimulating antigen. Vaccine 2 and 5 contained equal amounts of STCF and WTB. When stimulated by STCF alone (Table 32), the proliferation results for spleens were much lower than when stimulated with the combination of STCF-WTB (Table 34). When stimulated by WTB (Table 33), vaccine 2 had a lower result than with the combination (Table 34), but vaccine 5 had a higher result. In the case of vaccine 5, there was a significant increase in proliferation when the stimulating antigen was either STCF-WTB or WTB, when compared to STCF alone. The fact that the same significant differences were not observed for vaccine 2 indicates that the mitogenic effect of WTB is more pronounced when Cholera toxin is used as the adjuvant. Significant difference between vaccine 2 and 5 was only observed when the stimulating antigen was WTB, which could also be attributed to this mitogenic effect. For protective immunity, a specific immune response is desired, not a mitogenic response. Therefore, although the vaccine containing STCF and WTB proteins is effective in inducing an immune response, for protective immunity, *P. jensenii* 702 may be the better adjuvant.

A T-cell proliferation response was observed for the control, vaccine 3, which contained only *P.jensenii* 702. This may have been due to shared immunogenic proteins with *M. tuberculosis*, and is discussed further below. Regardless of this, proliferation results significantly higher than the control were found with vaccine 1, 2 and 5, using STCF as the stimulating antigen in spleen cells (Table 32). When spleen lymphocytes were stimulated with WTB (Table 33) or the combination of WTB/STCF (Table 34), vaccine 5 was significantly higher than the control. There was no significant difference between vaccine 1 and vaccine 5 when stimulated by any of the antigen combinations (Tables 32-34). Therefore both vaccine 1 and vaccine 5 demonstrate a significant systemic T-cell response. In consideration of the proposed mitogenic effect of the WTB, it is concluded that vaccine 1 was the better vaccine.

There was however, no significant difference in proliferation response between vaccine 1 and vaccine 2, indicating that when the adjuvant is the same, this data cannot identify what protein composition produces the better vaccine. Previous data on parenteral vaccines demonstrated that secreted *M. tuberculosis* proteins are more important than whole cell protein in inducing an immune response (Weldingh and Anderson, 1999). This study suggests that soluble cellular proteins of the *M. tuberculosis* may in fact play a role in this response. It hypothesized that the percentage of these proteins in the vaccine may be a critical factor in it efficacy.

Furthermore, vaccine 1 produced significantly higher proliferations than vaccine 4. As these two vaccines contained the same proteins, this indicates that the adjuvant is a critical indicator for vaccine success. Vaccine 4 failed to induce T-cell responses higher than the control, vaccine 3 (Table 32). This demonstrates that *P. jensenii* 702 is an effective oral adjuvant. Few vaccines administered via the mucosal route have actually been able to stimulate effective cell-meditated immune responses (Doherty et al, 2002), so the significant spleen cell proliferations, indicative of systemic immunity, obtained in this study are unique and important.

In the case of the Peyer's patches, only vaccine 5 when stimulated with all 3 combinations of antigen, STCF, WTB and STCF-WTB (Tables 32-34), showed a significant difference to the *P. jensenii* 702 control. As Peyer's patches are a measure of mucosal immunity, this indicates that the proposed vaccine will induce a significant mucosal immune response. It is probable that the reason that vaccine 5 produced this response, and vaccine 2, which contained the same protein components, did not, is because cholera toxin acts more immediately as an adjuvant than *P. jensenii* 702. Cholera toxin however cannot be used in humans due to its toxic nature, and although non-toxic subunits of cholera toxin are available, they are still yet to be permitted for use in humans (Pizza et al, 2001). *P. jensenii* 702 is a safe food-based bacteria. Studies by Yang (2002) suggest that increasing the colonisation period of *P. jensenii* 702 would likely enhance the adjuvant effect, such that it demonstrates similar or better activity than cholera toxin, with the advantage that it is suitable for use in humans.

Testing for cytokines is extremely important to this study, as cytokines are a key indicator of the type of immune response (Kaufmann & Andersen, 1998). The type of immune response induced by a vaccine is crucial to TB immunity, as the incorrect immune response (Th2) has been found to be ineffective in controlling TB and actually elicits a disease exacerbating effect (Linblad et al, 1997). Th1 responses are characterised by secretion of IL-2 and IFN-γ (Kaufmann & Andersen, 1998), and efficient protection from TB requires the induction of a potent Th1 response with high levels of IFN-γ (Agger & Andersen, 2001). Th1 cytokine production is inhibited by IL-4, and the generation of a Th2 response is favoured by production of IL-4 and inhibited by IFN-γ (Marth & Strober, 1997). IL-2 is precursor to a Th1 response inducing proliferation of activated T and B cells (Roitt & Delves, 2001)

Cytokines were measured on day 3, which for IFN-γ and IL-4 (FIG. 18) is suited to their optimum presence, while for IL-2 (FIG. 17), this time represents a decline phase because it is an early responding cytokine, found in high amounts in response to TB as soon as 24 hours after infection (Kaufmann & Andersen, 1998). Extended presence of IL-2, found in this study, indicates that a more prolonged immune response has been incurred, which is desirable for a vaccine. Any IL-2 response is significant. Clearly the strongest response came from vaccine 5 stimulated with WTB (FIG. 17), once again suggesting there is some interaction of WTB with the lymphocytes.

Figure 18:
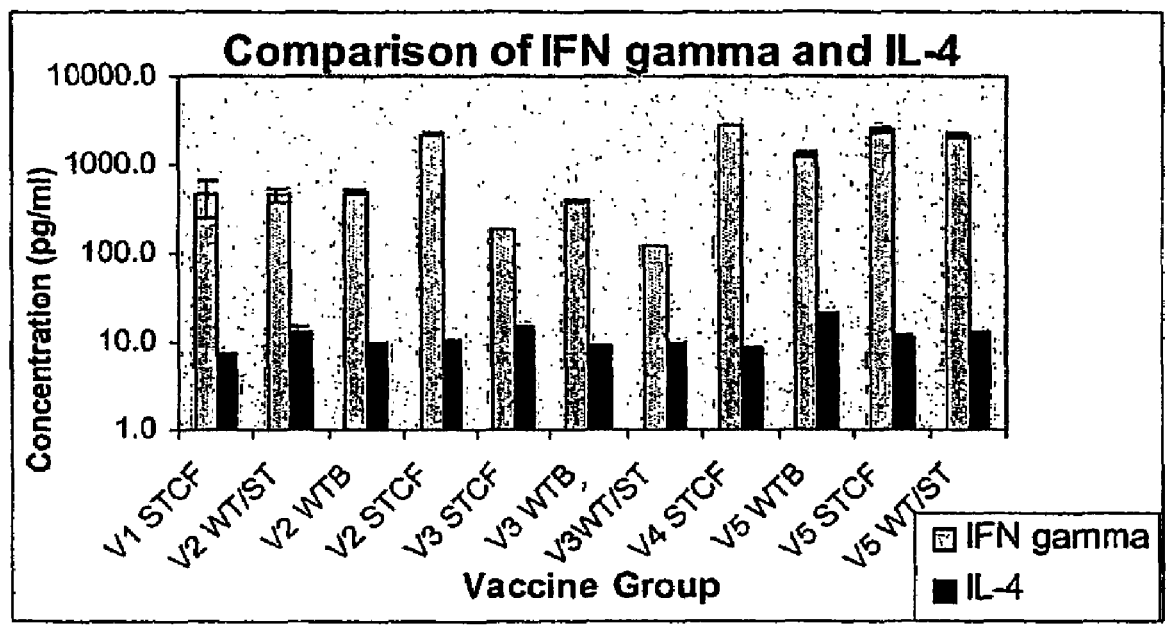
FIG. 18 shows a comparison of IFN gamma and IL-4 levels between vaccine groups. Values are mean. Error bars depict standard deviation.

A comparison of IFN-γ and IL-4 results was used to determine the Th1 or Th2 nature of the T-cell response (Marth & Strober, 1997). Current knowledge indicates that an optimal adjuvant for a tuberculosis vaccine should skew the response in a Type 1 direction (Elhay & Andersen, 1997). All results across all vaccine groups showed that IFN-γ was significantly higher than IL-4 levels (FIG. 18). Previous studies have shown that oral vaccines typically induce a Th2 response (Doherty et al, 2002) and this is why oral vaccines are often overlooked as a method of vaccine administration. This study is unique, as it is the first to demonstrate a strong Th1 T-cell response to an oral TB vaccine.

Although cellular immune responses are considered to be protective, the role that antibody responses play in controlling TB is currently under reevaluation (Attanasio, Pehler & McClure, 2000). Presence of Total IgG shows that a systemic immune response has been provoked (Roitt &, Delves, 2001). Clearly sero-conversion occurs with use of vaccine 1, 2 and 5 (Table 11). Sero-conversion was also observed for the probiotic control group when tested against STCF-WTB. There is the chance that soluble proteins found in TB may be conserved and found in other bacteria, and it is possible that these conserved proteins may be immunogenic. It is possible that these proteins occur in *P. jensenii* 702.

It was anticipated that a strong IgA response may provide a first line of defense, responding to intracellular infectious pathogens, such as TB (Falero-Diaz, 2000). It was expected that vaccine 5 after inducing a strong mucosal immune response, would also produce a strong IgA response, however this did not occur, and in fact, vaccine 4 and 5 had significantly lower IgA levels at the end of the study (Table 11). It is possible that the low IgA levels could be attributed to a problem with the preparation of faeces samples to maintain IgA levels, or with the transportation of samples between campuses, in which temperature fluctuations may have had an adverse effect on immunoglobulin levels. These specimens were tested at 1:10 dilution, which should be sufficient for IgA.

With vaccine 1 and 2, the fact that IgA levels did not increase (Table 35) is expected now that it is acknowledged that exposure time to *P. jensenii* 702 is critical. A final observation from this study involves an interesting pattern that can be noticed with regard to the deaths of five of the test animals during the vaccine trial. Autopsy revealed that the deaths of the mice were caused by presumptive mycoplasma infection. It is interesting to note that four of the five mice that died were from the vaccine groups receiving cholera toxin as the adjuvant, not the probiotic. The fact that the mice receiving *P. jensenii* 702 did not get sick, may be a further indication of the protective effect of this probiotic bacteria against respiratory infection. Literature shows that probiotics are known immune stimulating agents. They also protect the host against potential pathogens by competitive exclusion and through the production of bacteriocins (Matsuzaki & Chin, 2000). Consequently results from this study, combined with this observation indicate that the probiotic bacteria *P. jensenii* 702 has immune stimulating and adjuvant effects.

A study of a similar nature was conducted this year by Doherty et al (2002) involving orally administering a subunit TB vaccine concluded that oral immunisation does not efficiently prime immune responses and that IFN-γ levels in orally immunised test animals was no different to that of naïve animals (Doherty et al, 2002). It was also found that oral vaccination failed to induce significant immunity against *M. tuberculosis* either systemically or at mucosal surfaces, with the best they could achieve was to boost previously existing immune responses. The results described here contrast these findings to conclude that oral vaccination of the soluble secreted and intracellular proteins of *M. tuberculosis*, stimulate a strong systemic and mucosal immune response, shown by high T-cell proliferations in spleen lymphocytes and Peyer's patches respectively. In addition to this the immune response was of the desired Th1 type, indicated by high IFN-γ and low IL-4 levels.

Conclusion

It is clear from this research that the oral administration of the soluble proteins from *M. tuberculosis* can induce an immune response. This is shown by the results from T-cell proliferations, cytokine analysis and immunoglobulin levels. From this array of immunological testing techniques it was found that vaccines 1, 2 and 5 induced significant spleen cell T-cell proliferations. Only vaccine 5 produced significant proliferations in the Peyer's patches. These results indicate that the vaccines have potential to protect against tuberculosis infection.

The T-cell proliferation results highlighted the important role of the adjuvant in vaccine production. It is concluded that without *P. jensenii* 702, the likehood of successful oral vaccine production using the soluble *M. tuberculoisis* proteins would have been dubious. This conclusion is clearly evident when spleen cell proliferation results between vaccine 1 and 4 are compared. Both vaccines contained the same protein, however only vaccine 1, which had *P. jensenii* 702 as the adjuvant, had a T-cell proliferation response higher than the control (vaccine 3).

A difference was observed in the ability of the two adjuvants to elicit a mucosal immune response. Vaccine 2 contained the same antigens as vaccine 5, but had *P. jensenii* 702 as the adjuvant. Both produced high proliferations in the spleen, however vaccine 2 failed to produce significant proliferation in lymphocytes isolated from the Peyer's patches. This failure to induce a mucosal immune response can be attributed to the need for *P. jensenii* 702 to colonise thoroughly before it can exert its effect as an adjuvant on the mucosal immune system. The failure of *P. jensenii* 702 to adequately colonise within the short vaccine trial period was further verified by the low IgA levels in faeces and minimal colonisation in the first two weeks of the trial. The presence of *P. jensenii* 702 in the gastrointetinal tract of the mice was seen by day 7 of the study, however there was not a reduction of total anaerobe counts. This indicates that a longer colonisation time is in fact necessary, and should a longer period be allowed in the future for establishment in the gut, *P. jensenii* 702 is likely to be quite an effective mucosal adjuvant.

The desired Th1 type immune response was achieved by all vaccines tested in this study. This is a unique and valuable achievement as to date no other oral vaccines have been able to successfully induce a Th1 response to TB. In addition to this the potential of *P. jensenii* 702 as an oral adjuvant was again highlighted by its ability to induce a Th1 immune response. While Cholera toxin can induce a Th1 response, it along with its non-toxic subunits are not permitted for use in humans. *P. jensenii* 702 however has verified safety as a food borne/used organism.

Demonstration of *P. jensenii* 702 as an Immune Modulator

As described above in the vaccine experiment, *P. jensenii* 702 acts as an oral adjuvant. In so doing, it produces an immune response that is anti-allergy. In the immune system two types of T-cells exist; Th1 and Th2. The presence of one prohibits the production of the other. In allergy, a Th2 immune system predominates, however as demonstrated above, *P. jensenii* 702 produces a Th1 response, and in so doing reduces the Th2 and hence corrects the immunological cause of allergy.

EXAMPLE 5

Selection of Potential Proteins for Application in an Oral Vaccine Using *Propionibacterium Jensenii* 702 as an Adjuvant and Carrier The following is an example of the technology to be used to identify proteins for use in an oral vaccine. The technology is well defined in literature. Most infectious agents have well characterised immunogenic proteins (antigens), however in some cases an immunogenic response may vary according to the mode of delivery ie. oral versus parenteral, as well depending on the type of adjuvant used. As the concept of an oral vaccine in particular applications, such as tuberculosis, is novel, the following describes an example of how immunogenic proteins can be isolated and screened for efficacy. It is not meant to describe the only approach, but demonstrates that known technology and can be used to produce an oral vaccine using both known and novel antigens, that could previously could not have been done with the existing adjuvant technology.

In this case the example is for tuberculosis, but application to any infectious agent can be extrapolated.

Method.

Isolation and Identification of Immunogenic Proteins

Separation of protein fractions from sonicated whole *M. tuberculosis* or from short term culture filtrates can be used to provide antigens for the vaccines.

Sodium dodecyl sulfate-polyacrylamide gel electrophoresis (SDS-PAGE) separation of sonicated whole *M. tuberculosis* cells SDS-PAGE Equipment A Bio-Rad Protean II XI Cell electrophoresis unit is used for SDS-PAGE analysis in this experiment. A 16 cm×0.75 mm gel, consisting of a 12% separating gel, overlaid with a 4% stacking gel, is prepared according to manufacturer's instructions. A 15 well comb defines the wells in the stacking gel. The gels and running buffer are mounted in the electrophoresis cell, according to manufacturer's instructions.

SDS-PAGE Molecular Weight Standards

The choice of molecular weight standards depends on whether the gel is to be eluted or used for staining purposes. If the gel is to be eluted, a pre-stained low range SDS-PAGE standard (Bio-Rad) is used to indicate molecular weights. This standard does not require pre-treatment and 25 µl is added directly to the designated well. An unstained low range SDS-PAGE molecular weight standard (Bio-Rad) is used if the gel is to be stained for visualisation of protein bands. This standard is diluted 1 in 10 with sample buffer and heated at 95° C. for 4 minutes and cooled. 10 µl of treated standard is added to the designated well of the prepared SDS-PAGE gel.

Both the pre-stained and unstained standards, each contain 6 different proteins ranging in size from approximately 20-110 kDa.

Preparation of Sonicated *M. tuberculosis* for SDS-PAGE Separation

Samples are diluted 1 in 3 with sample buffer and heated to 95° C. for 4 minutes and cooled. 60 µl of treated sample is added to the designated wells of the prepared gel prior to electrophoresis.

Running Conditions for Separation of Sonicated *M. tuberculosis*

SDS-PAGE is performed at a constant current of 25 mA for approximately 8-12 hours, or until the dye front is approximately 1 cm from the bottom of the gel. After the gel is run it may be eluted to harvest the separated protein fractions or it can be stained for visualisation of protein bands.

Electroelution of Separated Protein Fractions (Based on Methods of Andersen & Heron, 1993)

Following electrophoresis, the gel is soaked in three changes of 2 mM phosphate buffer, pH6.8 on a Ratek rocker for a total of 20 minutes. This allowed the gel to swell prior to electro-elution and removes any excess SDS. The gel is then removed from the buffer, placed on a clean flat surface and trimmed, recording the position of the molecular weight markers in the process. The gel is then placed in a Bio-Rad Whole Gel Eluter and assembled according to manufacturer's instructions. The gel is electroeluted at 40V for 20 minutes, and then the current is reversed for 15 seconds to dislodge any proteins that may have bound to the cellophane membrane.

Harvesting of Fractions from the Bio-Rad Whole Gel Eluter

Following elution, the harvesting box is fitted to the Whole Gel Eluter (Bio-Rad) and thirty fractions harvested into separate test tubes. Individual fractions are pooled into the 5 designated size groups (Table 12) and stored at −80° C.

TABLE 36

Fractions of Sonicated *M. tuberculosis* (kDa)

| Fraction | Size Range (kDa) |
|---|---|
| A | <20 |
| B | 20-30 |
| C | 30-35 |
| D | 35-65 |
| E | >65 |

The fractions obtained are used as stimulating antigens in standard T-cell proliferation tests. Fractions yielding positive results according to this test may be further fractionated and the resulting subfractions used as stimulating antigens in standard T-cell proliferation tests to further refine the antigen.

Fractions may also be obtained using HPLC to generate greater yield.

Measurement of Immune Response

Immune response can be measured by the method described in example 4. Once the best immune response is determined a challenge study would be performed.

Media

| Reagent | Quantity | Supplier |
|---|---|---|
| Sodium Lactate Agar (SLA) | | |
| Double distilled water | 1 L | |
| Tryptone | 10 g | Oxoid |
| Yeast extract | 10 g | Oxoid |
| Sodium lactate (60%) | 16.5 Ml | Sigma |
| Di-potassium hydrogen phosphate | 0.25 g | AJAX |
| Manganes sulfate | 0.05 g | BDH |
| Bacteriological agar | 15 g | Oxoid |
| Preparation notes: Dissolve in water, adjust the pH to pH 7.0, then autoclave at 121° C. for 15 min. Store in cool room. | | |
| Sodium Lactate Broth (SLB) | | |
| Double distilled water | 1 L | |
| Tryptone | 10 g | Oxoid |
| Yeast extract | 10 g | Oxoid |
| Sodium lactate (60%) | 16.5 mL | Sigma |
| Di-potassium hydrogen phosphate | 0.25 g | AJAX |
| Manganese sulphate | 0.05 g | BDH |
| Preparation notes: Dissolve in water, adjust the pH to pH 7.0, then autoclave at 121° C. for 15 min. Store in cool room. | | |
| Yeast Extract Lactate Agar (YELA) | | |
| Double distilled water | 1 L | |
| Tryptone | 30 g | Oxoid |
| Yeast extract | 30 g | Oxoid |
| Sodium lactate (60%) | 20 mL | Sigma |
| Bacteriological agar | 15 g | Oxoid |
| Preparation notes: Dissolve in water, adjust the pH to pH 7.0, then autoclave at 121° C. for 15 min. Store in cool room. | | |
| Sodium Lactate Base (SL) | | |
| Double distilled water | 1 L | |
| Tryptone | 10 g | Oxoid |
| Yeast extract | 10 g | Oxoid |
| Potassium di-hydrogen phosphate | 5 g | BDH |
| Bromocresol purple | 0.025 g | |
| Preparation notes: Dissolve in water, adjust the pH to pH 7.0, then autoclave at 121° C. for 15 min. Store in cool room. | | |
| Fermentation Medium (FM) | | |
| Double distilled water | 1 L | |
| Glucose | 20 g | Sigma |
| Yeast Extract | 10 g | Oxoid |
| $KH_2PO_4$ | 1 g | BDH |
| $(NH_4)_2HPO_4$ | 2 g | Sigma |
| $FeSO_4.7H_2O$ | 5 mg | Chem Supply |
| $MgSO_4.7H_2O$ | 10 mg | Chem Supply |
| $MnSO_4.H_2O$ | 2.5 mg | Chem Supply |
| $CaCl_2.6H_2O$ | 10 mg | Chem Supply |
| NaCl | 10 mg | Chem Supply |
| $CoCl_2.6H_2O$ | 10 mg | Sigma |
| Preparation notes: Dissolve in water, adjust the pH to pH 7.0, then autoclave at 121° C. for 15 min. Store in cool room. | | |
| Supplemented RPMI 1640 | | |
| RPMI 1640 | 75.7 ml | Trace Biosciences |
| 200 mM L-glutamine | 2.5 mL | Sigma |
| 45% glucose | 0.8 mL | Sigma |
| 100 mM Sodium Pyruvate | 1 mL | Sigma |
| 20% fetal calf serum (heat inactivated) | 20 mL | HAPS |
| Preparation notes: Mix all of the reagent in Biohazard cabinet, store in cool room. Prewarmed to 37° C. before use. | | |

Buffer and Solutions

| Reagent | Quantity | Supplier |
|---|---|---|
| 12% acrylamide gel | | |
| Acrylamide/bis (30% T, 2.67% C) | 40.0 mL | Bio-Rad |
| Distilled Water | 33.5 mL | Bio-Rad |
| 1.5 M Tris-HCl, pH 8.8 | 25.0 mL | Bio-Rad |
| 10% (w/v) SDS | 1 mL | Bio-Rad |
| 10% ammonium persulfate (fresh) | 500 µl | Bio-Rad |
| TEMED | 50 µl | Bio-Rad |

Preparation notes: Prepare the monomer solution by combing all reagents except ammonium persulfate and TEMED. Deaerate the solution for 15 minutes. Add the two catalysts just prior to casting the gels.

4% acrylamide stacking gel

| Reagent | Quantity | Supplier |
|---|---|---|
| Acrylamide/bis (30% T, 2.67% C) | 1.3 mL | Bio-Rad |
| Distilled Water | 6.1 mL | Bio-Rad |
| 0.5 M Tris-HCl, pH 6.8 | 2.5 mL | Bio-Rad |
| 10% (w/v) SDS | 100 µl | Bio-Rad |
| 10% ammonium persulfate (fresh) | 50 µl | Bio-Rad |
| TEMED | 10 µl | Bio-Rad |

Preparation notes: Prepare the monomer solution by combing all reagents except ammonium persulfate and TEMED. Deaerate the solution for 15 minutes. Add the two catalysts just prior to casting the gels.

Acrylamide/Bis (30% T, 2.67% C)

| Reagent | Quantity | Supplier |
|---|---|---|
| Acrylamide | 146.0 g | Bio-Rad |
| N,N'-Methylene-bis Acrylamide | 4.0 g | Bio-Rad |
| Distilled water | 500 mL | |

Preparation notes: Add together. Filter and store at 4° C. in the dark. Maximum shelf life under these conditions is 30 days.

1.5 M Tris-HCl, pH 8.8

| Reagent | Quantity | Supplier |
|---|---|---|
| Tris base | 54.45 g | Bio-Rad |
| Distilled water | 300 mL | |

Preparation notes: Dissolve 54.45 g Tris base in 150 mL distilled water. Adjust to pH 8.8 with HCl. Add distilled water to 300 mL. Store at 4° C.

0.5 M Tris-HCl, pH 6.8

| Reagent | Quantity | Supplier |
|---|---|---|
| Tris base | 6 g | Bio-Rad |
| Distilled water | 100 mL | |

Preparation notes: Dissolve 6 g Tris base in 60 mL distilled water. Adjust to pH 6.8 with HCl. Add distilled water to 100 mL. Store at 4° C.

10% (w/v) SDS

| Reagent | Quantity | Supplier |
|---|---|---|
| SDS | 10 g | ICN |
| Distilled water | 100 mL | |

Preparation notes: Dissolve 10 g SDS (ICN) in 60 mL water with gentle stirring. Add distilled water to 100 mL. Store in room temperature.

10% Ammonium persulfate (w/v)

| Reagent | Quantity | Supplier |
|---|---|---|
| Ammonium Persulfate | 100 mg | Bio-Rad |
| Distilled water | 1 mL | |

Preparation notes: Dissolve 100 mg ammonium persulfate (Bio-Rad) in 1 mL distilled water. Use immediately.

Sample Buffer

| Reagent | Quantity | Supplier |
|---|---|---|
| 0.5 M Tris-HCl, pH 6.8 | 1.0 mL | |
| Glycerol | 1.6 mL | Sigma |
| 0.5% (w/v) bromophenol blue (in water) | 0.4 mL | |
| 10% SDS | 1.6 mL | |
| β-Mercaptoethanol | 0.4 mL | Bio-Rad |
| Distilled water | 3 mL | |

Preparation notes: Mix together. Store at 4° C.

5× Running Buffer (SDS-PAGE Electrode Buffer), pH 8.3

| Reagent | Quantity | Supplier |
|---|---|---|
| Tris-base | 45.0 g | Bio-Rad |
| Glycine | 216.0 g | Bio-Rad |
| SDS | 15.0 g | ICN |
| Distilled water | 3 L | |

Preparation notes: Added distilled water to 3 L. Do not adjust the pH with acid or base. Store at 4° C. Warm to 37° C. before use if precipitation occurs. Dilute 500 mL 5× stock with 2 L distilled water for one electrophoretic run.

Destaining Solution

| Reagent | Quantity | Supplier |
|---|---|---|
| Acetic acid | 800 mL | BDH |
| Methanol | 200 mL | Chem Supply |
| Distilled water | 1 L | |

Preparation notes: Mix together. Store at room temperature.

TE Buffer

| Reagent | Quantity | Supplier |
|---|---|---|
| Tris-HCL | 10 mM | Sigma |
| EDTA | 1 mM | Sigma |

Preparation notes: Adjust the pH to pH 7.5 with 1 M NaOH. Sterilized by filtering through 0.20 µm filter. Store at room temperature.

TES Buffer

| Reagent | Quantity | Supplier |
|---|---|---|
| Tris-HCL | 10 mM | Sigma |
| EDTA | 1 mM | Sigma |
| NaCl | 100 mM | Chem Supply |

Preparation notes: Adjust the pH to pH7.5 with 1 M NaOH. Store at 4° C.

PBS Buffer

| Reagent | Quantity | Supplier |
|---|---|---|
| KCl | 0.2 g | Chem Supply |
| $Na_2HPO_4$ | 1.44 g | Chem Supply |
| NaCl | 8 g | Chem Supply |
| $KH_2PO_4$ | 0.24 g | Chem Supply |
| Distilled water | 1 L | |

Preparation notes: Dissolve all the reagents in 800 mL distilled water. Adjust pH to pH 7.0 with HCl. Add distilled water to 1 L, then autoclave at 121° C. for 15 min. Store in cool room.

Simulated gastric juice (3 g/L pepsin in 0.5% NaCl)

| Reagent | Quantity | Supplier |
|---|---|---|
| Pepsin (1:10000) | 0.12 g | ICN |
| Sterile 0.5% NaCl | 40 mL | Chem Supply |

Preparation notes: Dissolve the pepsin in sterile 0.5% NaCl in a sterile container. Adjust pH aseptically to pH 2, pH 3 or pH 4 with concentrated HCl or sterile 0.1 M NaOH.

Simulated intestinal juice without bile salt (1 g/L pancreatin in 0.5% NaCl)

| Reagent | Quantity | Supplier |
|---|---|---|
| Pancreatin | 0.04 g | Sigma |
| Sterile 0.5% NaCl | 40 mL | Chem Supply |

Preparation notes: Dissolve the pancreatin in sterile 0.5% NaCl in a sterile container. Adjust pH aseptically to pH 8 using sterile 0.1 M NaOH.

Simulated intestinal juice with bile salt (1 g/L pancreatin, 0.45% bile salt in 0.5% NaCl)

| Reagent | Quantity | Supplier |
|---|---|---|
| Pancreatin | 0.04 g | Sigma |
| Bile salt | 0.18 g | Oxoid |
| Sterile 0.5% NaCl | 40 mL | Chem Supply |

Preparation notes: Dissolve 0.18 g of bile salt in 40 mL of 0.5% NaCl, sterilized by autoclaving at 121 C. for 15 min. After cooling, add 0.04 g pancreatin aseptically. Adjust pH aseptically to pH 8 using sterile 0.1 M NaOH.

Fixation Buffer (0.1 M cacodylate buffer containing 2.5% glutaraldehyde)

| Reagent | Quantity | Supplier |
|---|---|---|
| 0.4 M Cacodylic acid | 7 mL | Sigma |
| 70% glutaraldehyde | 1 mL | Sigma |
| 1 M NaOH | 1 mL | Chem Supply |
| Distilled water | 19 mL | |

Preparation notes: Store in cool room. Warm to room temperature before use.

0.1 M Cacodylate buffer (pH 7.2)

| Reagent | Quantity | Supplier |
|---|---|---|
| Cacodylic acid | 2.77 g | Sigma |
| Distilled water | 200 mL | |

Preparation notes: Dissolve 2.77 g cacodylic acid in 100 mL distilled water. Adjust pH to pH 7.2 using 1 M NaOH, then add distilled water to 200 mL. Store in cool room. Warm to room temperature before use.

-continued

| Reagent | Quantity | Supplier |
|---|---|---|
| 0.05 M Sodium Phosphate buffer (pH 7.0) | | |
| 0.05 M $Na_2HPO_4$ | 500 mL | Chem Supply |
| 0.05 M $NaH_2PO_4$ | 500 mL | Chem Supply |

Preparation notes: Add 0.05 M NaH2PO4 solution to 0.05 M $Na_2HPO_4$ till pH 7. Store in cool room.

β-Glucuronidase reaction mixture

| | | |
|---|---|---|
| 20 mM p-nitrophenyl-β-D-glucuronide | 2 mL | |
| 1 mM EDTA | 4 mL | Sigma |
| 40 mM potassium phosphate buffer | 20 mL | |
| Distilled water | 14 mL | |

Preparation notes: Mix and store in cool room.

20 mM p-nitrophenyl-β-D-glucuronide

| | | |
|---|---|---|
| p-nitrophenyl-β-D-glucuronide | 0.012 g | Sigma |
| 20 mM potassium phosphate buffer | 2 mL | |
| Distilled water | 14 mL | |

Preparation notes: Store in cool room.

40 mM potassium phosphate buffer (pH 6.8)

| | | |
|---|---|---|
| $K_2HPO_4$ | 0.544 g | Chem supply |
| $KH_2PO_4$ | 0.697 g | Chem supply |
| Distilled water | 200 mL | |

Preparation notes: Dissolve $K_2HPO_4$ or $KH_2PO_4$ in 100 ml distilled water respectively, mixed them together to pH 6.8

0.23 M glycine-NaOH—NaCl buffer (pH 10.4)

| | | |
|---|---|---|
| Glycine | 1.7266 g | Bio-Rad |
| NaCl | 1.344 g | Chem supply |
| Distilled water | 100 mL | |

Preparation notes: Dissolve glycine and NaCl in 70 ml distilled water. Adjust the pH to pH 10.4 with 1 M NaOH, add distilled water to 100 mL.

General Reagents

| Reagent | Quantity | Supplier |
|---|---|---|
| Phosphate Buffered Saline (PBS), pH 7.3 | | |
| Sodium chloride | 8.0 g | Sigma |
| Potassium chloride | 0.2 g | Sigma |
| Disodium hydrogen phosphate | 1.15 g | Fisons |
| Potassium dihydrogen phosphate | 0.2 g | BDH |

Dissolve all reagents in 1 L distilled water. Autoclave 15 minutes at 121° C.

70% Ethanol

| | | |
|---|---|---|
| Ethanol | 700 ml | Supplier |
| Distilled Water | 300 ml | Fronine |
| Mix well | | |

Mycobacterial Culture

Modified Sauton's Medium (MSM)

| Reagent | Quantity | Supplier |
|---|---|---|
| Asparagine | 8 g | Sigma |
| Tap Water | 500 ml | |

Dissolve asparagine in water (warm to 80° C. in water bath if necessary)

| | | |
|---|---|---|
| Magnesium sulfate heptahydrate | 1.0 g | Sigma |
| Citric acid | 3.66 g | |
| Potassium orthophosphate | 1.0 g | Sigma |
| Ferric ammonium citrate | 0.1 g | Fronine |
| D-glucose | 8.76 g | Sigma |
| Sodium pyruvate | 9.64 g | Sigma |

-continued

Modified Sauton's Medium (MSM)

| Reagent | Quantity | Supplier |
|---|---|---|
| Glycerol | 106 ml | Sigma |
| Tap water | 1420 ml | Sigma |

Add to dissolved asparagine. Adjust to pH 6.8 with concentrated ammonia (25-32%). Dispense into desired containers. Autoclave at 127° C. for 20 minutes. Allow to cool in autoclave for at least 2 hours. Store at 4° C. for up to 6 weeks. Caution: Explosive

Protein Analysis

| Reagent | Quantity | Supplier |
|---|---|---|
| Protein Reagent | | |
| Dye reagent concentrate | 4 ml | Bio-Rad |
| Distilled water | 16 ml | |

Mix well and filter through Whatman #1 filter. Store at room temperature for 2 weeks.

Stock Standard (1.43 mg/ml protein)

| | | |
|---|---|---|
| Lyophilized Bovine Serum Albumin(BSA) | 1 bottle | Bio-Rad |
| Distilled Water | 20 ml | |

Aliquot 50 μl quantities and store at −80° C.

Working Standards

| Standard | Protein Concentration (mg/ml) | Dilutions |
|---|---|---|
| Standard 1 (S1) | 0.050 | 50 μl S2 + 50 μL $dH_2O$ |
| Standard 2 (S2) | 0.100 | 50 μl S3 + 50 μL $dH_2O$ |
| Standard 3 (S3) | 0.200 | 50 μl S4 + 50 μL $dH_2O$ |
| Standard 4 (S4) | 0.400 | 28 μl Stock Standard + 72 μL $dH_2O$ |

Prepare the standards according to the above dilutions. Use immediately.

SDS-PAGE

Pre-stained low molecular weight standards

| Standard | Size (kDa) | Supplier |
|---|---|---|
| 1 | 21.4 | Bio-Rad |
| 2 | 29 | |
| 3 | 36.2 | |
| 4 | 51.2 | |
| 5 | 90 | |
| 6 | 110 | |

| Reagent | Quantity | Supplier |
|---|---|---|
| Acrylamide-Bis | | |
| Acrylamide | 146 g | Bio-Rad |
| N,N'-Methylene-bis Acrylamide | 4 g | Bio-Rad |

Add distilled water to 500 ml. Filter and store at 4° C. in the dark for up to 30 days.

1.5 M Tris-HCl, pH 8.8

| | | |
|---|---|---|
| Tris base | 54.45 g | Sigma |
| Distilled Water | 150 ml | |

Mix to dissolve. Adjust pH 8.8. Add distilled water to 300 ml. Store at 4° C.

-continued

| 0.5 M Tris-HCl, pH 6.8 | | |
|---|---|---|
| Tris-HCl | | |
| Distilled water | | |
| Mix to dissolve. Adjust to pH 6.8. Add distilled water to 100 ml. Store at 4° C. | | |
| 10% (w/v) SDS | | |
| SDS | 10 g | ICN |
| Distilled water | 60 ml | |
| Dissolve with gentle stirring. Add distilled water to 100 ml. | | |
| 10% (w/v) Ammonium persulfate | | |
| Ammonium persulfate | 100 mg | Bio-Rad |
| Distilled water | 1.0 ml | |
| Dissolve and use immediately. | | |
| 0.5% (w/v) Bromophenol Blue | | |
| Bromophenol Blue | 0.05 g | Bio-Rad |
| Distilled Water | 10.0 ml | |
| Mix and store in a dark place. | | |
| Sample Buffer, pH 6.8 | | |
| Distilled water | 3.0 ml | |
| 0.5 M Tris-HCl, pH 6.8 | 1.0 ml | |
| Glycerol | 1.6 ml | Sigma |
| 10% SDS | 1.6 ml | |
| 2-mercaptoethanol | 0.4 ml | Bio-Rad |
| 0.5% (w/v) bromophenol blue | 0.4 ml | |
| Mix well. Store 4° C. | | |
| 5× Electrode Buffer | | |
| Tris base | 45.0 g | Sigma |
| Glycine | 216.0 g | ICN |
| SDS | 15.0 g | ICN |
| Add distilled water to 3.0 L. Do not adjust the pH. Store at 4° C. Warm to 37° C. before use if precipitation occurs. | | |
| Running buffer | | |
| 5× Electrode buffer | 0.5 L | |
| Distilled water | 2.0 L | |
| Running buffer may be reused several times. Store at 4° C. | | |
| Separating Gel (12%, pH 8.8) | | |
| Acrylamide-bis | 40.0 ml | |
| Distilled water | 33.5 ml | |
| 1.5 M Tris-HCl, pH 8.8 | 25.0 ml | |
| 10% (w/v) SDS | 1.0 ml | |
| 10% (w/v) ammonium persulfate | 500 μm | |
| TEMED | 50 μm | Bio-Rad |
| Combine all reagents without frothing, except ammonium persulfate and TEMED. Allow to stand 15 mins. Add the two catalysts immediately prior to casting gel. | | |
| Stacking Gel (4%, pH 6.8) | | |
| Acrylamide-bis | 1.3 ml | |
| Distilled water | 6.1 ml | |
| 0.5 M Tris-HCl, pH 6.8 | 2.5 ml | |
| 10% (w/v) SDS | 100 μl | |
| 10% (w/v) ammonium persulfate | 50 μl | |
| TEMED | 10 μl | Bio-Rad |
| Combine all reagents without frothing, except ammonium persulfate and TEMED. Allow to stand 15 mins. Add the two catalysts immediately prior to casting gel. | | |
| Fixative I | | |
| Methanol | 800 ml | Fronine |
| Acetic Acid | 200 ml | BDH |
| Distilled Water | 1.0 L | |
| Mix together. Store at room temperature. | | |
| Phosphate Buffer (2 mM, pH 6.8) | | |
| Sodium orthophosphate | 0.48 g | BDH |
| Distilled Water | 1.8 L | |
| Dissolve and adjust to pH 6.79. Make up to 2.0 L with distilled water and store at 4° C. | | |

Immunisation

| Reagent | Quantity | Supplier |
|---|---|---|
| Protease Inhibitor ( Soybean Trypsin Inhibitor) | | |
| Soybean Trypsin inhibitor (100 mg/ml) | 3.0 mg | Sigma |
| PBS | 1 ml | |
| Autoclave 15 min at 121° C. Store at 4° C. | | |
| PMSF Solution | | |
| PMSF | 20 mg | Sigma |
| Absolute ethanol | 1 ml | RHONE-POULENC |
| Store at 4° C. | | |

Lymphocyte Culture and Analysis

| Reagent | Quantity | Supplier |
|---|---|---|
| RPMI Complete Medium | | |
| DMEM/RPMI | 500 ml | Trace |
| 10,000 U/ml Penicillin, 10 mg/ml Streptomycin | 5 ml | Trace |
| L-glutamine (200 mM) | 5 ml | Trace |
| 2-Mercaptoethanol (5 mM) | 5 ml | Trace |
| HEPES buffer (1 M) | 10 ml | Trace |
| Foetal Calf Serum (heat-inactivated*) | 50 ml | Trace |
| Combine all reagents under sterile conditions. Store at 4° C. | | |
| (*To heat inactivate FCS: place in 56° C. water bath for 45 mins) | | |
| Mouse Red Blood Cell (RBC) Lysis Buffer | | |
| $NH_4Cl$ | 4.15 g | BDH |
| $NaHCO_3$ | 0.5 g | BDH |
| Ethylene-diamine-tetra-acetic acid (EDTA) di-sodium salt | 0.0185 g | AJAX |
| Dissolve in approximately 400 ml sterile distilled water. Adjust pH to 7.35 and make up to 500 ml. Filter sterilise and store at 4° C. | | |
| Trypan Blue, 0.1% | | |
| Trypan Blue | 0.05 g | Sigma |
| PBS | 50 ml | |
| Store at room temperature. | | |
| Working Thymidine | | |
| [methyl-$^3$H]thymidine (1 mCi/ml) | 250 μl | Amersham |
| RPMI complete medium | 4.75 ml | |
| Store at 2° C. | | |

Probiotic Production

| Reagent | Quantity | Supplier |
|---|---|---|
| Sodium Lactate Broth (SLB) | | |
| Double distilled water | 1 L | |
| Tryptone | 10 g | Oxoid |
| Yeast extract | 10 g | Oxoid |
| Sodium lactate (60%) | 16.5 ml | Sigma |
| Di-potassium hydrogen phosphate | 0.25 g | AJAX |
| Manganese sulphate | 0.05 g | BDH |
| Make up to 1 L with distilled water. Autoclave at 121° C. for 15 mins. | | |
| Sodium Lactate Agar (SLA) | | |
| Double distilled water | 1 L | |
| Tryptone | 10 g | Oxoid |
| Yeast extract | 10 g | Oxoid |
| Sodium lactate (60%) | 16.5 ml | Sigma |
| Di-potassium hydrogen phosphate | 0.25 g | AJAX |
| Manganese sulfate | 0.05 g | BDH |
| Bacteriological agar | 15 g | Oxoid |

-continued

| Reagent | Quantity | Supplier |
|---|---|---|
| Dissolve in water, adjust to pH 7.0, then autoclave at 121° C. for 15 min. Store in cool room. | | |
| Diluted Wilken's Chalgren (WCAB) Broth | | |
| WCAB | 16.5 g | Oxoid |
| Distilled Water | 1 L | |
| Dissolve in water, adjust to pH 7.0, then autoclave at 121° C. for 15 minutes | | |

ELISA for IgG, IgG Subclasses and IgA

| Reagent | Quantity | Supplier |
|---|---|---|
| Bicarbonate Buffer | | |
| 15 mM $Na_2CO_3$ | 1.59 g/L | Sigma |
| 35 mM $NaHCO_3$ | 2.94 g/L | Sigma |
| Store at 4° C. | | |
| Wash Buffer (PBS/0.05% Tween 20) | | |
| PBS | 10 L | |
| Polyoxyethylenesorbitan Monolaurate (Tween 20) | 5 ml | Sigma |
| Store at 2-8° C. for up to 7 days. | | |
| 5% Foetal Calf Serum | | |
| Foetal calf serum (*heat inactivated) | 5 ml | Trace |
| PBS | 95 ml | |
| Store at 4° C for up to 7 days (*To heat inactivate FCS: place in 56° C. water bath for 45 mins) | | |
| Streptavidin Horseradish Peroxidase (SA-HRP) Conjugate | | |
| SA-HRP | 10 µl | Amersham |
| PBS (0.05% tween) | 9.99 ml | |
| Use immediately. | | |
| TMB Substrate Solution | | |
| Substrate A | 5 ml | Pharmingen |
| Substrate B | 5 ml | Pharmingen |
| Warm reagents to room temperature prior to use. Use substrate solution immediately. | | |
| Stop Solution (2 M) | | |
| Sulphuric Acid (3 M) | 33 ml | BDH |
| Distilled Water | 17 ml | |
| Mix together and store at room temperature. | | |

REFERENCES

References

Agger, E. M. & Andersen, P. 2001, 'Tuberculosis subunit vaccine development: on the role of interferon-γ', Vaccine, vol. 19, pp. 2298-2302.

Albert, M. J., Mathan, V. I. and Baker, S. J. (1980) Nature, 283, 781-782.

Allison, C., McFarlan, C. and Macfarlane, G. T. (1989) Applied and Environmental Microbiology, 55, 672-678.

Andersen, P. 2001, 'TB vaccines: progress and problems', Trends in Immunology, vol. 22, no. 3, pp. 160, 168.

Andersen, P. 1994, 'Effective vaccination of mice against Mycobacterium tuberculosis infection with a soluble mixture of secreted mycobacterial proteins', Infection and Immunity, vol. 62, pp. 2536-2544.

AOAC, I. (1995) In Official Methods of Analysis of AOAC International., Vol. II (Ed, Cunniff, P.) AOAC International, Gaithersburg, Md., pp. 44-45.

Attanasio, R., Pehler, K. & McClure H. M. 2000, 'Immunogenicity and safety of Mycobacterium tuberculosis culture filtrate proteins in non-human primates', Clinical and Experimental Immunology, vol. 119, pp. 84-91.

Baer, A. (1987) Milchwissenschaft, 7, 431-433.

Baik, H. W. and Russell, R. M. (1999) Annual Reviews of Nutrition, 19, 357-377.

Balaji, K. N., Boom, W. H. 1998, 'Processing of Mycobacterium tuberculosis bacilli by human monocytes for CD4+ alpha beta and gamma delta T cells role of particulate antigen', Infection and Immunity, vol. 66, pp. 98-106.

Ball, G. F. M. (1998) In Bioavailability and analysis of vitamins in foods. Chapman & Hall, London, Weinheim, New York, Tokyo, Melbourne, Madras, pp. 497-512.

Barnes, P. F., Abrams, J. S., Lu, S., Sieling, P. A., Rea, T. H. & Modlin, R. L. 1993, 'Patterns of cytokine production by Mycobacterium tuberculosis-reactive human T cell clone', Infection and Immunity, vol. 61, pp. 197-203.

Berry, E. C. and Bullerman, L. B. (1966) Applied Microbiology, 14, 356-357.

Bjorkergren, K. and Svardsudd, K. (2001) Journal of Internal Medicine, 249, 423-432.

Bougle, D., Roland, N., Lebeurrier, F. and Arhan, P. (1999) Scandinavian Journal of Gastroenterology, 144-148.

Britz, T. J. and Riedel, K. H. J. (1994) International Journal of Food Microbiology, 22, 257-267.

Brooker, B. E. and Fuller, R. (1975) Adhesion of Lactobacilli to the chicken crop epithelium. Journal of Ultrastructure Research 52: 21-31.

Bermudez, L. E. & Sangari, F. J. 2001, 'Cellular and molecular mechanisms of internalization of mycobacteria by host cells', Microbes and Infection, vol. 3, pp. 37-42.

Boom, H. W. 1999, 'γδ T cells and Mycobacterium tuberculosis', Microbes and Infection, vol. 1, pp. 187-195.

Bouvet, J. P., Decroix, N. & Pamonsinlapatham, P. 2002, 'Stimulation of local antibody production: parenteral or mucosal vaccination', Trends in Immunology, vol. 23, no. 4, pp. 209-213.

Brandt, L., Cunha, J. F., Olsen, A. W., Chilima, B., Hirsch, P., Appelberg, R., & Andersen, P. 2002, 'Failure of Mycobacterium bovis BCG vaccine: some species of environmental Mycobacteria block multiplication of BCG and Induction of protective immunity to Tuberculosis', Infection and Immunity, vol. 70, no. 2, pp. 672-678.

Brandtzaeg P. 1996, 'History of oral tolerance and mucosal immunity', Annals of the New York Academy of Sciences, vol. 778, pp. 1-27.

Brandtzaeg P. 1998, 'Development and basic mechanisms of human gut immunology', Nutrition Reviews, vol. 56, no. 1, pp S5-S18.

Broker, M, 1999, 'New approaches to vaccines against tuberculosis: where we stand and where we want to go', FEMS Immunology and Medical Microbiology, vol. 23, pp. 147-148.

Carmel, R. (2000) Annual Reviews of Medicine, 51, 357-375.

Casey, P. J., Speckman, K. R., Ebert, F. J. and Hobbs, W. E. (1982) Journal of Association of Official Analytic Chemistry, 65, 85-88.

Charteris, W. P., Kelly, P. M., Morelli, L. and Collins, J. K. (1998) Journal of Applied Microbiology, 84, 759-768.

Choi, S. (1999) Nutrition Reviews, 57, 250-260.

Chou, L. and Weimer, B. (1999) Journal of Dairy Science, 82, 23-31.

Chung, H. S., Kim, Y. B., Chun, S. L. and Ji, G. E. (1999) International Journal of Food Microbiology, 47, 25-32.

Clark, P. A., Cotton, L. N. and Martin, J. H. (1993) Cultured Dairy Products Journal, 28, 11-14.

Clark, P. A. and Martin, J. H. (1994) *Cultured Dairy Products Journal*, 29, 18-21.

Conway, P. L., Gorbach, S. L. and Goldin, B. R. (1987) *Journal of Dairy Science*, 70, 1-12.

Costas, M. (1990) *Electrophoresis*, 11, 382-391.

Costas, M., Pot, B., Vandamme, P., Kersters, K., Owen, R. J. and Hill, L. R. (1990) *Electrophoresis*, 11, 467-474.

Crociani, J., Grill, J. P., Huppert, M. and Ballongue, J. (1995) *Letters in Applied Microbiology*, 21, 146-148.

Cummins, C. S. and Johnson, J. (1986) In *Bergey's Manual of Systematic Bacteriology*, Vol. 2 (Eds, Sneath, P. H. A., Mair, N. S., Sharpe, M. E. and G., H. J.) Williams & Wilkins, Baltimore, HongKong, London, Munich, Philadephia, San Francisco, Sydney, Tokyo, pp. 1346-1353.

Caruso, A. M., Serbina, N., Klein, E., Triebold, K., Bloom B. R. & Flynn, J. L. 1999, 'Mice deficient in CD4 T cells have only transiently diminished levels of IFN-gamma, yet succumb to tuberculosis', *Journal of Immunology*, vol. 162, pp. 5407-5416.

Collins, D. M. 2000, 'New tuberculosis vaccines based on attenuated strains of the Mycobacterium tuberculosis complex', *Immunology and Cell Biology*, vol. 78, pp. 342-348.

Collins, H. L. & Kauffman, S. H. E. 2001, 'Prospects for better tuberculosis vaccines', *The Lancet: Infectious diseases*, vol. 1, August, pp. 21-28.

Cooper, A. M. Roberts, A. D. & Rhoades, E. R. 1995, 'The role of interleukin-12 in acquired immunity to Mycobacterium tuberculosis infection', *Immunology*, vol. 84, pp. 423-432.

Delva, M. D. (1997) *Canadian Family Physician*, 43, 917-922.

Donohue, D. C. and Salminen, S. (1996) *Asia Pacific Journal of Clinical Nutrition*, 5, 25-28.

Donohue, D. C., Salminen, S. and Marteau, P. (1998) In *Lactic Acid Bacteria: Microbiology and Functional Aspects* (Eds, Salminen, S. and Wright, A. v.) Marcel Dekker, New York, Basel, pp. 369-383.

Del Giudice, G., Podda, A., Rappuoli, R. 2002, 'What are the limits of adjuvanticity?', *Vaccine*, vol.20, pp. S38-S41.

Demangel, C. & Britton, W. 2000, 'Interaction of dendritic cells with mycobacteria: Where the action starts', *Immunology and Cell Biology*, vol. 78, pp. 318-324.

Doherty, M. T., Olsen, A. W., Van Pinxteren, L. & Andersen, P. 2002, 'Oral vaccination with subunit vaccines protects animals against aerosol infection with Mycobacterium tuberculosis', *Infection and Immunity*, vol. 70, no. 6, pp. 3111-3121.

Ehlers, S. 1999, 'Immunity to tuberculosis: a delicate balance between protection and pathology', *FEMS Immunology and Medical Microbiology*, vol. 23, pp. 149-158.

Elhay, M. J. & Andersen, P. 1997, 'Immunological requirements for a subunit vaccine against tuberculosis', *Immunology and Cell Biology*, vol. 75, pp. 595-603.

Erickson, K. L. & Hubbard, N. E. 2000, 'Probiotic immunomodulation in health and disease', *Journal of Nutrition*, vol. 130, pp. 403S-409S.

Fessler, D., Casey, M. G. and Puhan, Z. (1998) *Lait*, 78, 203-216.

Fessler, D., Casey, M. G. and Puhan, Z. (1999) *Lait*, 79, 201-209.

Finegold, S. M., Sulter, V. L. and Mathison, G. E. (1983) In *Human Intestinal Microflora in Health and Disease* (Ed, Hentges, D. J.) Academic Press, New York.

Fooks, L. J., Fuller R., Gibson, G. R. (1999) Prebiotics, probiotics and human gut microbiology. International Dairy Journal 9, 53-61.

Fujisawa, T. and Mori, M. (1996) *Letters in Applied Microbiology*, 22, 271-274.

Falero-Diaz, G., Challacombe, S., Banedjee, D., Douce, G., Boyd, A. & Ivanyi, J. 2000, 'Intranasal vaccination of mice against infection with Mycobacterium tuberculosis', *Vaccine*, vol. 18, pp. 3223-3229.

Famularo, G., Moretti, S., Marcellini, S. & De Simone, C. 1997, 'Stimulation of immunity by probiotics', in *Probiotics 2: Applications and practical aspects*, ed. R. Fuller, Chapman & Hall, London, pp. 133-161.

Fang, H., Tuomola, E., Heikki, A. & Seppo, S. 2000, 'Modulation of humoral immune response through probiotic intake', *FEMS Immunology and Medical Microbiology*, vol. 29, pp. 47-52.

Fatkenheuer, G., Taelman, H., Lepage, P., Schwenk, A. & Wenzel, R. 1999, 'The return of tuberculosis', *Diagnostic Microbiology and Infectious Disease*, vol. 34, pp. 139-146.

Feng, C. G., Bean, A. G. D. & Hooi H. 1999, 'Increase of gamma interferon-secreting CD8 (+), as well as CD4(+), T cells in lungs following aerosol infection with Mycobacterium Tuberculosis', *Infection and Immunity*, vol. 67, pp. 3242-3247.

Feng, C. G. & Britton, W. J. 2000, '$CD4^+$ and $CD8^+$ T cells mediate adoptive immunity to aerosol infection of Mycobacterium bovis Bacillus Calmette-Guerin', *Journal of Infectious Diseases*, vol. 181, pp. 1846-1849.

Flynn, J. L. 1999, 'Why is IFN-γ insufficient to control tuberculosis?', *Trends in Microbiology*, vol. 7, no. 12, pp. 1-2.

Gadelle, D., Raibaud, P. and Sacquet, E. (1985) *Applied and Environmental Microbiology*, 49, 682-685.

Gariballa, S. E. (2000) *British Journal of Nutrition*, 84, 5-17.

Gautier, M., de Carvalho, A. and Rouault, A. (1996) *Current Microbiology*, 32, 17-24.

Gilliland, S. E., Staley, T. E. and Bush, L. J. (1984) *Journal of Dairy Science*, 67, 3045-3051.

Grant, C. and Salminen, S. (1998) In *Lactic Acid Bacteria, Microbiology and Functional Aspects* (Eds, Salminen, S. and Wright, A. v.) Marcel Dekker, New York, Basel, pp. 589-601.

Gleeson, M., Hall, S., McDonald, W., Flanagan, A. J. & Clancy, R. L. 1999, 'Salivary. IgA subclasses and infection risk in elite swimmers', *Immunology and Cell Biology*, vol. 77, pp. 351-355.

Gleissberg, V. 1999, 'The threat of multidrug resistance: is tuberculosis ever untreatable or uncontrollable?', *The Lancet*, vol. 353, pp. 998-999.

Guerin, N. 1997, 'Evaluation of BCG and new vaccines against Tuberculosis', *Pediatric Pulmonology*, supplement 16, pp. 286-287.

Harrigan, W. F. (1998a) In *Laboratory Methods in Food Microbiology* Academic Press, San Diego, London, Boston, New York, Sydney, Tokyo, Toronto, pp. 266.

Harrigan, W. F. (1998b) In *Laboratory Methods in Food Microbiology* Academic Press, San Diego, London, Boston, New York, Sydney, Tokyo, Toronto, pp. 333-334.

Havenaar, R., Brink, N. G. and Huis In't Ved, J. H. J. (1992) In *Probiotics, The scientific basis* (Ed, Fuller, R.) Chapman & Hall, London, New York, Tokyo, Melbourne, Madras, pp. 210-224.

Hebbert, V. (1988) Vitamin B12: plant sources, requirements, and assay. *American Journal of Clinical Nutrition* 48: 852-858.

Hettinga, D. H. and Reinbold, G. W. (1972a) *Journal of Milk and Food Technology*, 35, 358-372.

Hettinga, D. H. and Reinbold, G. W. (1972b) *Journal of Milk and Food Technology*, 35, 436-447.

Hill, M. J. (1997) *European Journal of Cancer Prevention*, 6 (suppl 1), S43-S45.

Holt, J. G., Krieg, N. R., Sneath, P. H. A., Staley, J. T. and Williams, S. T. (1997) *Bergey's Manual of Determinative Bacteriology*.

Hood, S. K. and Zottola, E. A. (1988) *Journal of Food Science*, 53, 1514-1516.

Havlir, D. V., Wallis, R. S., Boom, W. H., Daniel, T. M., Chervenak, K. & Ellner, J. J. 1991, 'Human immune response to *Mycobacterium tuberculosis* antigens', *Infection and Immunity*, Vol. 59, pp. 665-670.

Hess, J. & Kaufmann, S. H. E. 1999, 'Live antigen carriers as tools for improved anti-tuberculosis vaccines', *FEMS Immunology and Medical Microbiology*, vol. 23, pp. 165-173.

Huang, Y. 2002, The isolation, characterization and selection of Vitamin B12-producing dairy *Propionibacterium* strains for probiotic use, PhD thesis, The University of Newcastle. (Submitted for examination)

Ibrahim, S. A. and Bezkorovainy, A. (1993) *Journal of the Science of Food and Agriculture.*, 62, 351-354.

Jan, G., Rouault, A. and Maubois, J. (2000) *Lait*, 80, 325-336.

Jones, D. and Collins, M. D. (1986) In *Bergey's Manual of Systematic Bacteriology.*, Vol. 2 (Eds, Sneath, P. H. A., Mair, N. S., Sharpe, M. E. and Holt, J. G.) Williams & Wilkins, Baltimore, HongKong, London, Munich, Philadelphia, San Francisco, Sydney, Tokyo, pp. 1263.

Jones, D. and Krieg, N. R. (1986) In *Bergey's Manual of Systematic Bacteriology*, Vol. 2 (Eds, Sneath, P. H. A., Mair, N. S., Sharpe, M. E. and Holt, J. G.) Williams & Wilkins, Baltimore, HongKong, London, Munich, Philadephia, San Francisco, Sydney, Tokyo, pp. 979-982.

Jones, J. (1986) In *Bergey's Manual of Systematic Bacteriology*, Vol. 2 (Eds, Sneath, P. H. A., Mair, N. S., Sharpe, M. E. and J. G., H.) Williams & Wilkins, Baltimore, HongKong, London, Munich, Philadephia, San Francisco, Sydney, Tokyo, pp. 972-975.

Julia, M., Flaminio, B. F., Rush, B. R. Shuman, W. (1998) Immunologic function in horses after non-specific immunostimulant administration. Veterinary Immunology and Immunopathology 63, 303-315

Kaneko, T., Mori, H., Iwata, M. and Meguro, S. (1994) *Journal of Dairy Science*, 77, 393-404.

Kankaapaa, P. E., Yang, B., Kallio, H. P., Isoluri, E. and Salminen, S. J. (2002) Influence of probiotic supplemented infant formula on composition of plasma lipids in atopic infants. *Journal of Nutritional Biochemistry* 13: 354-369

Kaur, I. P., Chopra K., Saini, A (2002) Probiotics: potential pharmaceutical applications. European Journal of Pharmaceutical Sciences. 15, 1-9.

Kawata, T., Tamiki, A., Tashiro, A., Suga, K., Kamioka, S., Yamada, K., Wada, M., Tanaka, N., Tadokoro, T. and Maekawa, A. (1997) *International Journal for Vitamin and Nutrition Research*, 67, 17-21.

Kawata, T., Tashiro, A., Tamiki, A., Suga, K., Kamioka, S., Yamada, K., Wada, M., Tadokoro, T. and Maekawa, A. (1995) *International Journal for Vitamin and Nutrition Research*, 65, 248-254.

Kitazawa, H., Matsumura, K., Itoh, T., Yamaguchi, T., (1992) Interferon induction inmurine peritoneal macrophage by stimulation with *Lactobacillus acidophilus*. Microbiol. Immunil. 36, 311-315

Kaufmann, S. H. E. & Andersen, P. 1998, 'Immunity to Mycobacteria with emphasis on tuberculosis: Implications for rational design of an effective tuberculosis vaccine', *Chemical Immunology*, vol. 70, pp. 21-59.

Kaufmann, S. H. E. & Hess, J. 2000, 'Immune response against *Mycobacterium tuberculosis*: implications for vaccine development', *Journal of Biotechnology*, vol. 83, pp. 13-17.

Kenney, R. T., Rabinovich, R. N., Pichyangkul, S., Price, V. L. & Engers, H. D. 2002, 'Meeting Report: 2$^{nd}$ Meeting on novel adjuvants currently in/close to human clinical testing. World Health Organisation-Organisation Mondiale de la Sante Foundation Merieux', *Vaccine*, vol. 20, pp. 2155-2163.

Lau, K. S., Gottlieg, C., Wasserman, L. R. and Herbert, V. (1965) *Blood*, 26, 202-214.

Lehto, E. M. and Salminen, S. (1997) *Bioscience Microflora*, 16, 13-17.

Lilly, D. M. and Stillwell, R. H. (1965) *Science*, 147, 747-748.

Langridge, W. H. R. 2000, 'Edible vaccines', *Scientific American*, available at URL: http://www.sciam.com/2000/0900issue/0900langridge.html [Date visited: Apr. 5, 2002] pp. 1-5.

Linblad, E. B., Elhay, M. J., Silva, R., Appelberg, R. & Andersen, P. 1997, 'Adjuvant modulation of immune responses to tuberculosis subunit vaccines', *Infection and Immunity*, vol. 65, pp. 623-629.

Lowrie, D. B., Silva, C. L. & Tascon, R. E. 1997, 'Genetic vaccination against tuberculosis', *Springer Seminars in Immunopathology*, vol. 19, pp 161-173.

Macfarlane, G., Cummings, J. H. and Allison, C. (1986) *Journal of General Microbiology*, 132, 1647-1656.

Mann, N. J., Li, D., Sinclair, A. J., Dudman, N. P. B., Guo, X. W., Elsworth, G. R., Wilson, A. K. and Kelly, F. D. (1999) *European Journal of Clinical Nutrition*, 53, 895-899.

Mantere-Alhonen, S. (1983) *Meijeritieteellinen Aikakauskirja*, XLI, 19-23.

Marteau, P., Minekus, M., Havenaar, R. and Huis In't Ved, J. H. J. (1997) *Journal of Dairy Science*, 80, 1031-1037.

Mayra-Makinen, A., Manninen, M. and Gyllenberg, H. (1983) *Journal of Applied Bacteriology*, 55, 241-245.

Meile, L., Dasen, G., Miescher, S., Stierli, M. and Teuber, M. (1999) *Lait*, 79, 71-78.

Muhammad, K., Briggs, D. and Jones, G. (1993a) *Food Chemistry*, 48, 423-425.

Muhammad, K., Briggs, D. and Jones, G. (1993b) *Food Chemistry*, 48, 427-429.

Muhammad, K., Briggs, D. and Jones, G. (1993c) *Food Chemistry*, 48, 431-434.

Mahairas, G. G., Sabo, P. J., Hickey, M. J., Singh, D. C. & Stover, C. K. 1996, 'Molecular analysis of genetic differences between *Mycobacterium bovis* BCG and Virulent *M. bovis*', *Journal of Bacteriology*, vol. 178, pp. 1274-1282.

Marth, T. & Strober, W. 1997, 'Oral tolerance and its modulation by anti-cytokines', 72$^{nd}$ *Forum in Immunology*, pp. 554-561.

Matsuzaki, T. & Chin, J. 2000, 'Modulating immune responses with probiotic bacteria', *Immunology and Cell Biology*, vol. 78, pp. 67-73.

Medina, E. & Guzman, C. A. 2000, 'Modulation of immune responses following antigen administration by mucosal route', *FEMS Immunology and Medical Microbiology*, vol. 27, pp. 305-311.

Miller, B. & Schieffelbein, C. 1998, 'Tuberculosis', *WHO Bulletin OMS*, vol. 76, sup. 2, pp. 141-143.

Mustafa, A. S. 2002, 'Development of new vaccines and diagnostic reagents against tuberculosis', *Molecular immunology*, vol. 1121, pp. 1-7.

Murray, C. J. L. & Salomon, J. A. 1998, 'Modeling the impact of global tuberculosis strategies', *Proceedings of the National Academy of Sciences USA*, vol. 95, pp. 13881-13886.

Nanno, M., Morotomi, M., Takayama, H., Kuroshima, T., Tanaka, R. and Mutai, M. (1986) *Journal of Medical Microbiology*, 22, 351-355.

National institute of Allergy and Infectious Disease (NIAID), 1999, 'Tuberculosis: fact sheet', available at URL: http://www.niaid.nih.gov/factsheets/tb.htm, [Date visited: Aug. 3, 2002], pp. 1-10.

National institute of Allergy and Infectious Disease (NIAID), 1996, 'Tuberculosis: news release', available at URL: http://www.niaid.nih.gov/newsroom/releases/tbtip.htm, [Date visited: Aug. 3, 2002], pp. 1-5.

National institute of Allergy and Infectious Disease (NIAID), 2000, 'Strategies for Developing Tuberculosis Vaccines' available at URL: hhtp://www.niaid.nih.gov/publications/blueprint/page4.htm, [Date visited: Aug. 3, 2002], pp. 1-6.

O'Sullivan, D. J. (1999) In *Probiotics: A Critical Review* (Ed, Tannock, G. W.) Horizon Scientific Press, Norfolk, pp. 23-44.

Ozkan, K., Ozkan, E and Simsek, B (2002) Plasma total homocysteine and cysteine levels as a cardiovascular risk factor in coronary heart disease. International Journal of Cardiology 82, 269-277.

Orme, I. M. 1999, 'Beyond BCG: the potential for a more effective TB vaccine', *Molecular Medicine Today*, vol. 5, pp. 487-492.

Perez-Chaia, A., Nader de Macias, M. E. and Oliver, G. (1995) *Lait*, 75, 435-445.

Perez-Chaia, A., Zarate, G. and Oliver, G. (1999) *Lait*, 79, 175-185.

Pinto, M., Robine-Leon, S., Appay, M., Kedinger, M., Triadou, N., Dussaulx, E., Lacroix, B., Simon-Assmann, P., Haffen, K., Fogh, J. and Zweibaum, A. (1983) *Biology of cell*, 47, 323-330.

Poston, J. M. and Hemmings, B. A. (1979) *Journal of Bacteriology*, 140, 1013-1016.

Pulverer, G., Ko, H. L., Tunggal, L., Beuth, J. and Jeljaszewicz, J. (1994) *Zentralblatt fur Bakteriologie*, 281, 491-494.

Pieters, J. & Gatfield, J. 2002, 'Hijacking the host: survival of pathogenic mycobacteria inside macrophages', *Trends in Microbiology*, vol. 10, no. 3, pp. 142-146.

Pizza, M., Giuliani, M. M., Fontana, M. R., Monaci, E., Douce, G., Dougan, G., Mills, K. H. G., Rappuoli, R. & Del Giudice, G. 2001, 'Mucosal vaccines: non toxic derivatives of LT and CT as mucosal adjuvants', *Vaccine*, vol. 19, pp. 2534-2541.

Pouwels, P. H., Leer, R. J., Shaw, M., Heijne den BakGlashouwer, M., Tielen, F. D., Smit, E., Martinez, B., Jore, J. & Conway, P. L. 1998, 'Lactic acid bacteria as antigen delivery vehicles for oral immunisation purposes', *International Journal of Food Microbiology*, vol. 41, pp. 155-167.

Quesada-Chanto, A., Afschar, A. S. and Wagner, F. (1994a) *Applied Microbiological Biotechnology*, 41, 378-383.

Quesada-Chanto, A., Afschar, A. S. and Wagner, F. (1994b) *Applied Microbiological Biotechnology*, 42, 16-21.

Quesada-Chanto, A., Silveira, M. M., Schmid-Meyer, A. C., Schroeder, A. G., da Costa, J. P. C. L., Lopez, J., Carvalho-Jonas, M. F., Artolozaga, M. J. and Jonas, R. (1998) *Applied Microbiological Biotechnology*, 49, 732-736.

Richardson, P. J., Favell, D. J., Gidley, G. C. and Jones, G. H. (1978) *Analyst*, 103, 865-868.

Riedel, K. H. J. and Britz, T. J. (1992) *Systematic and Applied Microbiology*, 15, 567-572.

Riedel, K. H. J., Wingfield, B. D. and Britz, T. J. (1994) *Systematic and Applied Microbiology*, 17, 536-542.

Riedel, K. H. J., Wingfield, B. D. and Britz, T. J. (1998) *Systematic and Applied Microbiology*, 21, 419-428.

Rossi, F., Torriani, S. and Dellaglio, F. (1998) *Journal of Applied Microbiology*, 85, 956-964.

Rossi, F., Torriani, S. and Dellaglio, F. (1999) *Applied and Environmental Microbiology*, 65, 4241-4244.

Rowland, I. R. (1992) In *Probiotics: The Scientific Basis* (Ed, Fuller, R.) Chapman & Hall, London, pp. 29-53.

Rowland, I. R., Mallet, A. K. and Wise, A. (1983) *Toxicology and Applied Pharmacology*, 69, 143-148.

Ravn, P., Boesen, H., Pedersen, B. K., & Andersen, P. 1997, 'Human T cell responses induced by vaccination with *Mycobacterium bovis Bacillus* Calmette-Guerin', *Journal of Immunology*, vol. 158, no. 4, pp. 1949-1955.

Richter, L. & Kipp, P. B. 1999, 'Transgenic plants as edible vaccines', *Current Topics in Microbiology and Immunology*, vol. 240, pp. 159-176.

Roitt, I. M. & Delves, P. J. 2001, *Roitt's Essential Immunology* $10^{th}$ ed., Blackwell Science, London.

Russell-Jones, G. J. 2000, 'Oral vaccine delivery', *Journal of Controlled Release*, vol. 65, pp. 49-54.

Salminen, S., Ouwehand, A., Benno, Y. and Lee, Y. K. (1999) *Trends in Food Science & Technology*, 10, 107-110

Salminen, S., von Wright, A., Morelli, L., Marteau, P., Brassart, D., de Vos, W. M., Fonden, R., Saxelin, M., Collins, K., Mogensen, G., Birkeland, S. and Mattila-Sandholm, T. (1998a) *International Journal of Food Microbiology*, 44, 93-106.

Salminen, s., Ouwehand, A, C., and Isolauri, E. (1998b). Clinical Applications of Probiotic Bacteria. International dairy Journal 563-572.

Sarem, F., Sarem-Damerdji, L. O. and Nicolas, J. P. (1996) *Letters in Applied Microbiology*, 22, 439-442.

Sarkar, S. and Misra, A. K. (1995) *Journal of Dairying, Foods & Home Science*, 14, 1-16.

Scheinbach, S. (1998) Probiotics: Functionality and Commercial Status. Biotechnology Advances 16, 581-608.

Scott, J. M. (1999) *Proceedings of the Nutrition Society*, 58, 441-448.

Shaw, J. T. E., McWinney, B., Tate, J. R., Kesting, J. B., Marczak, M., Purdie, D., Gibbs, H., Cameron, D. P. and Hickman, P. E. (1999) Plasma homocysteine levels in indigenous Australians. Medical Journal of Australia 170: 19-22

Somkuti, G. A. and Johnson, T. L. (1990) Cholesterol Uptake by *Propionibacterium freundenreichii*. Current Microbiology 20, 305-309.

Steffen, E. K. and Berg, R. D. (1983) *Infection and Immunity*, 39, 1215-1259.

Stine, K. E. and Brown, T. M. (1996) In *Principles of Toxicology* CRC Press Inc., Boca Raton, New York, London, Tokyo, pp. 1-10.

Sutter, V. L. (1984) *Reviews of Infectious Diseases*, 6, s62-s66.

Swift, J. A. and Marsh, M. N. (1968) Scanning electron microscopy of rat intestinal microvilli. *The Lancet*, II, 915

Sato, K., Akaki, T. & Tomioka, H. 1998, 'Differential potentiation of anti-mycobacterial activity and reactive nitrogen intermediate-producing ability of murine peritoneal macrophages activated by interferon-γ (IFN-γ) and tumour necrosis factor-α (TNF-α)', *Clinical and Experimental Immunology*, vol. 112, pp. 63-68.

Saunders, B. M. & Cooper, A. M. 2000, 'Restraining mycobacteria: Role of granulomas in mycobacterial infections', *Immunology and Cell Biology*, vol. 78, pp. 334-341.

Schaible, U. E., Collins, H. L. & Kaufmann, S. H. 1999, 'Confrontation between intracellular bacteria and the immune system', *Advances in Immunology*, vol. 71, pp. 267-377.

Sieling, P. A., Chatterjee, D., Porcelli, S. A., Prigozy, T. I., Mazzaccaro, R. J., Soriano, T., Bloom, B. R., Brenner, M. B., Kronenberg, M., Brennan, P. J. & Modlin, R. L. 1995, 'CD1-restricted T cell recognition of microbial lipoglycan antigens', *Science*, vol. 269, pp. 227-230.

Silva, C. L., Bonato, V. D. L., Lima, K. M., Coelho-Castelo, A. A. M., Faccioli, L. H., Sartori, A., DeSouza, A. O. & Leao, S. C. 2001, 'Cytotoxic T cells and mycobacteria', *FEMS Microbiology Letters*, vol. 197, pp. 11-18.

Stenger, S. & Modlin, R. L. 1999, 'T cell mediated immunity to *Mycobacterium tuberculosis*', *Current Opinion in Microbiology*, vol. 2, pp. 89-93.

Sun, J. B., Holmgren, J. & Czerkinsky, C. 1994, 'Cholera toxin B subunit: An efficient transmucosal carrier-delivery system for induction of peripheral immunological tolerance', *Immunology*, vol. 91, pp. 10795-10799.

Takeda, K., Saito, T., Kitazawa, t., Uemura, H., Itoh, T (1997). Mitogenic activity of whole cells and cell wall components of *Lactobacillus acidophilus* group lactic acid bacteria on murine spleen and peyer's patch cells. Milchwissenschaft 52, 21-25.

Taylor, G. R. J. and Williams, C. M. (1998) Effects of probiotics and prebiotics on blood lipids. British Journal of Nutrition 80, s2, 225-230.

Tsakalidou, E., Manolopoulou, E., Kabaraki, E., Zoidou, E., Pot, B., Kersters, K. and Kalantzopoulos, G. (1994) *Systematic and Applied Microbiology*, 17, 444-448.

Tuomola, E. M., Ouwehand, A. C. and Salminen, S. J. (1999) *Letters in Applied Microbiology*, 28, 159-163.

Tuomola, E. M. and Salminen, S. J. (1998) *International Journal of Food Microbiology*, 41, 45-51.

Tascon, R. E., Stravropoulos, E., Lukacs, K. V., Colston, M. J. 1998, 'Protection against *Mycobacterium tuberculosis* infection by CD8 T cells requires production of gamma interferon', *Infection and Immunity*, vol. 66, pp. 830-834.

Toy, L. S. & Mayer, L. 1996, 'Basic and clinical overview of the mucosal immune system', *Seminars in Gastrointestinal Disease*, vol. 7, pp. 2-11.

Tripathy, S. P. 1987, 'Fifteen year follow-up of the Indian BCG prevention trial', *Bulletin of the International Union Against Tuberculosis and Lung Disease*, vol. 62, pp. 69-72.

Tsuyuguchi, I. 1996, 'Regulation of the human immune response in tuberculosis', *Infectious Agents and Disease*, vol. 5, no. 2, pp. 82-97.

Van der Griend, R., Biesma, D. H. and Banga, J. D. (2000) Hyperhomocysteinaemia as a cardiovascular risk factor: an update. Netherlands Journal of Medicine 56, 119-130.

Wang, X., Brown, I. L., Evans, A. J. and Conway, P. L. (1999) *Journal of Applied Microbiology*, 87, 631-639.

Wilchen, D. E. I. and Wilckin, B. (1998) B vitamins and homocysteine in cardiovascular disease and aging. *Annals of the New York Academy of Sciences* 854: 361-370

Wynn, M. and Wynn, A. (1998) *Nutrition and Health*, 12, 215-226.

www.who.int/ncd/cvd/Date visited Feb. 4, 2002

Weldingh, K. & Andersen, P. 1999, 'Immunological evaluation of novel *Mycobacterium tuberculosis* culture filtrate proteins', *FEMS Immunology and Microbiology*, vol. 23, pp. 159-164.

World Health Organisation, 1992, 'Tuberculosis control and research strategies for the 1990's: memorandum from a WHO meeting', *Bulletin of the World Health Organisation*, vol. 70, pp. 17-21.

Ye, K., Shijo, M., Jin, S. and Shimizu, K. (1996) *Journal of Fermentation and Bioengineering*, 82, 484-491.

Zhou, J. S., Shu, Q., Rutherfund, K. J., Prasad, J., Gopal, P. K. and Gill, H. S. (2000) *Food and Chemical Toxicology*, 38, 153-161.

---

The invention claimed is:

1. An isolated *Propionibacterium* strain *Propionibacterium jensenii* 702.

2. A method of making a food preparation, medium or supplement comprising adding the strain of claim 1 to a food, medium or supplement.

3. The method of claim 2 wherein the food preparation is an animal food.

4. The method of claim 3 wherein the food preparation is milk.

5. The method of claim 3 wherein the food preparation is a vitamin $B_{12}$ fortified food.

6. The method of claim 2 wherein the preparation, medium or supplement contains other probiotic bacteria.

7. A supplement prepared by the method of claim 2 wherein the supplement is in the form selected from the group consisting of a capsule, a tablet, a powder, granules, a paste and a spray.

8. A method of making a formulation comprising adding the strain of claim 1 to a culture medium, storage medium excipient, carrier or diluent.

9. A method of making a mixed culture comprising adding the strain of claim 1 to a culture of one or more other probiotic bacteria.

* * * * *